US011866465B2

(12) United States Patent
Schmidt et al.

(10) Patent No.: US 11,866,465 B2
(45) Date of Patent: Jan. 9, 2024

(54) OLIGOMERIC PARTICLE REAGENTS AND METHODS OF USE THEREOF

(71) Applicant: Juno Therapeutics GmbH, Munich (DE)

(72) Inventors: Thomas Schmidt, Munich (DE); Christian Stemberger, Munich (DE); Tom Kowski, Seattle, WA (US); Ken Prentice, Seattle, WA (US)

(73) Assignee: Juno Therapeutics GmbH, Munich (DE)

( * ) Notice: Subject to any disclaimer, the term of this patent is extended or adjusted under 35 U.S.C. 154(b) by 911 days.

(21) Appl. No.: 16/608,796

(22) PCT Filed: Apr. 27, 2018

(86) PCT No.: PCT/IB2018/000507
§ 371 (c)(1),
(2) Date: Oct. 25, 2019

(87) PCT Pub. No.: WO2018/197949
PCT Pub. Date: Nov. 1, 2018

(65) Prior Publication Data
US 2021/0032297 A1 Feb. 4, 2021

Related U.S. Application Data

(60) Provisional application No. 62/491,245, filed on Apr. 27, 2017.

(51) Int. Cl.
| | | |
|---|---|---|
| *C07K 14/36* | (2006.01) | |
| *C07K 1/16* | (2006.01) | |
| *C07K 16/28* | (2006.01) | |
| *A61K 47/68* | (2017.01) | |
| *A61K 39/00* | (2006.01) | |

(52) U.S. Cl.
CPC .......... *C07K 14/36* (2013.01); *A61K 47/6898* (2017.08); *C07K 1/16* (2013.01); *C07K 16/2809* (2013.01); *C07K 16/2818* (2013.01); *A61K 2039/625* (2013.01); *C07K 2317/55* (2013.01)

(58) Field of Classification Search
CPC ...... C07K 14/36; C07K 1/16; C07K 16/2809; C07K 16/2818; C07K 2317/55; A61K 47/6898; A61K 2039/625
See application file for complete search history.

(56) References Cited

U.S. PATENT DOCUMENTS

| | | | |
|---|---|---|---|
| 2,467,434 A | 4/1949 | Kuplec | |
| 4,235,871 A | 11/1980 | Papahadjopoulos | |
| 4,361,549 A | 11/1982 | Kung | |
| 4,452,773 A | 6/1984 | Molday | |
| 4,501,728 A | 2/1985 | Geho | |
| 4,690,915 A | 9/1987 | Rosenberg | |
| 4,795,698 A | 1/1989 | Owen | |
| 4,816,567 A | 3/1989 | Cabilly et al. | |
| 4,837,028 A | 6/1989 | Allen | |
| 4,851,341 A | 7/1989 | Hopp | |
| 5,019,369 A | 5/1991 | Present | |
| 5,087,616 A | 2/1992 | Myers | |
| 5,168,049 A | 12/1992 | Meade | |
| 5,200,084 A | 4/1993 | Liberti | |
| 5,219,740 A | 6/1993 | Miller | |
| 5,506,121 A | 4/1996 | Skerra | |
| 5,629,205 A | 5/1997 | Lagosky | |
| 5,665,866 A | 9/1997 | Weir et al. | |
| 5,773,224 A | 6/1998 | Grandics et al. | |
| 5,849,576 A | 12/1998 | Skerra et al. | |
| 5,869,270 A | 2/1999 | Rhode et al. | |
| 5,985,658 A | 11/1999 | Colinas | |
| 6,022,951 A | 2/2000 | Sano | |

(Continued)

FOREIGN PATENT DOCUMENTS

| | | |
|---|---|---|
| CN | 101 226 118 A | 7/2008 |
| CN | 101 446 576 A | 6/2009 |

(Continued)

OTHER PUBLICATIONS

U.S. Appl. No. 14/234,463, filed May 2015, T. Schmidt.*
IBA, as cited in the IDS dated Jun. 17, 2020 (Year: 2014).*
Prospec, Streptavidin Protein, catalogue No. PRO-283, retrieved from: https://www.prospecbio.com/streptavidin [Dec. 28, 2022] (Year: 2016).*
Chai J, Wong LS, Giam L, Mirkin CA. Single-molecule protein arrays enabled by scanning probe block copolymer lithography. Proc Natl Acad Sci U S A. Dec. 6, 2011;108(49):19521-5. doi: 10.1073/pnas.1116099108. Epub Nov. 21, 2011. PMID: 22106270; PMCID: PMC3241798. (Year: 2011).*

(Continued)

*Primary Examiner* — Adam Weidner
*Assistant Examiner* — Ashley H. Gao
(74) *Attorney, Agent, or Firm* — Morrison & Foerster LLP

(57) ABSTRACT

Provided herein are oligomeric reagents, including oligomeric reagents of streptavidin or a streptavidin mutein, compositions thereof, and methods for manufacturing oligomeric reagents, including methods for reliably manufacturing oligomeric particle reagents of a desired size. In some cases, the reagents are oligomeric particle reagents containing a plurality of binding sites for agents, and thus the one or more agents are multimerized by reversibly binding to the oligomeric particle reagent, e.g., thereby creating a multimerized oligomeric particle reagent, having stimulatory agents multimerized thereon. Also provided are methods for using the oligomeric reagents for incubation or culturing, such as to induce stimulation of expansion, activation, and/or survival, of a composition of cells such as a population of lymphocytes. In some aspects, the disclosure provides methods and reagents for the stimulation, survival, persistence, activation, or other effect of cell populations that involve binding of agents to a molecule on the cell surface.

56 Claims, 15 Drawing Sheets

Specification includes a Sequence Listing.

(56) References Cited

U.S. PATENT DOCUMENTS

| | | | |
|---|---|---|---|
| 6,040,177 A | 3/2000 | Riddell | |
| 6,103,493 A | 8/2000 | Skerra | |
| 6,156,493 A | 12/2000 | Stayton | |
| 6,165,750 A | 12/2000 | Stayton | |
| 6,207,453 B1 | 3/2001 | Maass | |
| 6,232,445 B1 | 5/2001 | Rhode | |
| 6,270,772 B1 | 8/2001 | Burrows et al. | |
| 6,303,121 B1 | 10/2001 | Kwon | |
| 6,303,309 B1 | 10/2001 | Jurinke et al. | |
| 6,309,645 B1 | 10/2001 | Rhode et al. | |
| 6,312,916 B1 | 11/2001 | Kopetzki et al. | |
| 6,331,415 B1 | 12/2001 | Cabilly et al. | |
| 6,352,694 B1 | 3/2002 | June | |
| 6,368,813 B1 | 4/2002 | Reznik | |
| 6,391,571 B1 | 5/2002 | Kopetzki et al. | |
| 6,410,270 B1 | 6/2002 | Strittmater et al. | |
| 6,410,319 B1 | 6/2002 | Raubitschek | |
| 6,417,331 B1 | 7/2002 | Kopetzki et al. | |
| 6,451,995 B1 | 9/2002 | Cheung | |
| 6,534,055 B1 | 3/2003 | June et al. | |
| 6,569,997 B1 | 5/2003 | Kwon | |
| 6,638,728 B1 | 10/2003 | Desai et al. | |
| 6,716,602 B2 | 4/2004 | Andersen et al. | |
| 6,815,171 B2 | 11/2004 | Burrows et al. | |
| 6,849,185 B1 | 2/2005 | Wu et al. | |
| 6,979,556 B2 | 12/2005 | Simmons et al. | |
| 7,033,834 B2 | 4/2006 | Valerio | |
| 7,070,995 B2 | 7/2006 | Jensen | |
| 7,074,904 B2 | 7/2006 | Wong et al. | |
| 7,074,905 B2 | 7/2006 | Rhode et al. | |
| 7,094,579 B2 | 8/2006 | Gray et al. | |
| 7,112,439 B2 | 9/2006 | Johnson et al. | |
| 7,141,656 B2 | 11/2006 | Rhode et al. | |
| 7,189,322 B2 | 3/2007 | Wu et al. | |
| 7,202,349 B2 | 4/2007 | Davis et al. | |
| 7,265,209 B2 | 9/2007 | Jensen | |
| 7,265,218 B2 | 9/2007 | Burrows et al. | |
| 7,294,483 B2 | 11/2007 | Leung et al. | |
| 7,354,762 B2 | 4/2008 | Jensen | |
| 7,446,179 B2 | 11/2008 | Jensen | |
| 7,446,190 B2 | 11/2008 | Sadelain | |
| 7,446,191 B2 | 11/2008 | Jensen | |
| 7,482,000 B2 | 1/2009 | Devaux | |
| 7,494,656 B2 | 2/2009 | Bachmann | |
| 7,547,438 B2 | 6/2009 | Thomas | |
| 7,572,631 B2 | 8/2009 | Berenson | |
| 7,585,620 B2 | 9/2009 | Schutz et al. | |
| 7,618,799 B2 | 11/2009 | Coleman et al. | |
| 7,704,708 B2 | 4/2010 | Wu et al. | |
| 7,718,399 B2 | 5/2010 | Jung et al. | |
| 7,754,447 B2 | 7/2010 | Glover et al. | |
| 7,776,562 B2 | 8/2010 | Busch | |
| 7,837,871 B2 | 11/2010 | Gjerde et al. | |
| 7,906,327 B2 | 3/2011 | Sydnor et al. | |
| 7,923,221 B1 | 4/2011 | Cabilly et al. | |
| 7,981,632 B2 | 7/2011 | Schmidt | |
| 7,985,564 B2 | 7/2011 | Retallack et al. | |
| 8,148,494 B2 | 4/2012 | Leonhartsberger | |
| 8,216,573 B2 | 7/2012 | Wich et al. | |
| 8,268,964 B2 | 9/2012 | Scholler et al. | |
| 8,283,125 B2 | 10/2012 | Ramirez et al. | |
| 8,298,782 B2 | 10/2012 | Busch | |
| 8,324,353 B2 | 12/2012 | Jensen | |
| 8,339,645 B2 | 12/2012 | Nakawaki | |
| 8,361,744 B2 | 1/2013 | Marrichi et al. | |
| 8,389,282 B2 | 3/2013 | Sadelain | |
| 8,426,168 B2 | 4/2013 | Stempfer et al. | |
| 8,441,187 B2 | 5/2013 | Hunze et al. | |
| 8,449,874 B2 | 5/2013 | Bachmann | |
| 8,450,086 B2 | 5/2013 | Huang et al. | |
| 8,479,118 B2 | 7/2013 | Lyndersay | |
| RE44,512 E | 10/2013 | Glover et al. | |
| 8,735,098 B2 | 5/2014 | Marrichi et al. | |
| 8,735,330 B2 | 5/2014 | Geir | |
| 8,735,540 B2 | 5/2014 | Schmidt | |
| 8,828,379 B2 | 9/2014 | Loset et al. | |
| 9,023,604 B2 | 5/2015 | Schmidt | |
| 9,242,244 B2 | 1/2016 | Gjerde et al. | |
| 9,370,732 B2 | 6/2016 | Gjerde | |
| 9,637,719 B2 | 5/2017 | Gjerde | |
| 9,891,148 B2 | 2/2018 | Gjerde et al. | |
| 9,920,294 B2 | 3/2018 | Gjerde | |
| 10,107,729 B2 | 10/2018 | Gjerde | |
| 10,220,332 B2 | 3/2019 | Gjerde | |
| 10,228,312 B2 | 3/2019 | Stadler | |
| 10,307,693 B2 | 6/2019 | Gjerde | |
| 10,752,668 B2 | 8/2020 | Agaugue et al. | |
| 10,830,676 B2 | 11/2020 | Gjerde | |
| 11,077,389 B2 | 8/2021 | Gjerde | |
| 11,097,207 B2 | 8/2021 | Gjerde | |
| 11,137,327 B2 | 10/2021 | Gjerde | |
| 11,248,238 B2* | 2/2022 | Bashour | C07D 239/62 |
| 11,274,278 B2 | 3/2022 | Germeroth et al. | |
| 11,400,115 B2 | 8/2022 | Ramsborg et al. | |
| 11,466,253 B2 | 10/2022 | Germeroth et al. | |
| 2001/0026932 A1 | 10/2001 | Thomas | |
| 2002/0034513 A1 | 3/2002 | Rode et al. | |
| 2002/0091079 A1 | 7/2002 | Rhode et al. | |
| 2002/0131960 A1 | 9/2002 | Sadelain | |
| 2002/0142358 A1 | 10/2002 | Mikayama | |
| 2002/0176864 A1 | 11/2002 | Burrows et al. | |
| 2003/0077739 A1 | 4/2003 | Simmons et al. | |
| 2003/0162249 A1 | 8/2003 | Gray et al. | |
| 2003/0175850 A1 | 9/2003 | Ross | |
| 2003/0208783 A1 | 11/2003 | Hillen et al. | |
| 2003/0228660 A1 | 12/2003 | Gray et al. | |
| 2004/0082012 A1 | 4/2004 | Busch | |
| 2004/0209295 A1 | 10/2004 | Schwabe et al. | |
| 2005/0003431 A1 | 1/2005 | Wucherpfennig et al. | |
| 2005/0074848 A1 | 4/2005 | Schwebe | |
| 2005/0074853 A1 | 4/2005 | Burrows et al. | |
| 2006/0019319 A1 | 1/2006 | Billadeau | |
| 2006/0058226 A1 | 3/2006 | Ishikawa et al. | |
| 2006/0106199 A1 | 5/2006 | Erdmann | |
| 2006/0246542 A1 | 11/2006 | Simmons et al. | |
| 2006/0269990 A1 | 11/2006 | Stempfer et al. | |
| 2007/0015244 A1 | 1/2007 | Simmons et al. | |
| 2007/0077242 A1 | 4/2007 | Mikayama | |
| 2007/0224664 A1 | 9/2007 | Simmons et al. | |
| 2007/0241061 A1 | 10/2007 | Engstrom et al. | |
| 2008/0038282 A1 | 2/2008 | Napper et al. | |
| 2008/0064859 A1 | 3/2008 | Vandenbark et al. | |
| 2008/0076158 A1 | 3/2008 | Dassler et al. | |
| 2008/0085532 A1 | 4/2008 | Gorlach et al. | |
| 2008/0206818 A1 | 8/2008 | Wich et al. | |
| 2008/0254511 A1 | 10/2008 | Dassler et al. | |
| 2008/0255004 A1 | 10/2008 | Neurauter | |
| 2009/0104660 A1 | 4/2009 | Jung et al. | |
| 2009/0137472 A1 | 5/2009 | Schwabe et al. | |
| 2010/0068738 A1 | 3/2010 | Kawamura | |
| 2010/0168390 A1 | 7/2010 | Brix et al. | |
| 2010/0248257 A1 | 9/2010 | Jacobsen et al. | |
| 2010/0267057 A1 | 10/2010 | Rakestraw | |
| 2011/0003380 A1 | 1/2011 | Miltenyi | |
| 2011/0070581 A1 | 3/2011 | Gupta | |
| 2011/0236411 A1 | 9/2011 | Scholler et al. | |
| 2011/0244517 A1 | 10/2011 | Simmons et al. | |
| 2011/0318380 A1 | 12/2011 | Brix et al. | |
| 2012/0214187 A1 | 8/2012 | Lees | |
| 2012/0225453 A1 | 9/2012 | Withers et al. | |
| 2012/0264161 A1 | 10/2012 | Scholler et al. | |
| 2012/0321665 A1 | 12/2012 | Bollyky et al. | |
| 2013/0149337 A1 | 6/2013 | Cooper | |
| 2013/0184439 A1 | 7/2013 | Spitali et al. | |
| 2013/0196375 A1 | 8/2013 | Strobbe | |
| 2013/0287748 A1 | 10/2013 | June | |
| 2013/0289253 A1 | 10/2013 | Leuscher et al. | |
| 2014/0120580 A1 | 5/2014 | Simmons et al. | |
| 2014/0295458 A1 | 10/2014 | Schmidt | |
| 2014/0349315 A1 | 11/2014 | Loset et al. | |
| 2015/0024411 A1 | 1/2015 | Stadler | |
| 2015/0031566 A1 | 1/2015 | Napper et al. | |
| 2015/0301046 A1 | 10/2015 | Schmidt | |
| 2017/0037368 A1 | 2/2017 | Germeroth | |

(56) References Cited

U.S. PATENT DOCUMENTS

| | | | |
|---|---|---|---|
| 2017/0037369 A1 | 2/2017 | Ramsborg | |
| 2017/0037370 A1 | 2/2017 | Kaiser | |
| 2017/0052176 A1 | 2/2017 | Carl | |
| 2018/0178142 A1 | 6/2018 | Gjerde | |
| 2018/0296602 A1 | 10/2018 | Riddell | |
| 2019/0041306 A1 | 2/2019 | Gjerde | |
| 2019/0049351 A1 | 2/2019 | Gjerde | |
| 2019/0112576 A1 | 4/2019 | Germeroth | |
| 2019/0136186 A1 | 5/2019 | Germeroth | |
| 2019/0226951 A1 | 7/2019 | Stadler | |
| 2019/0232196 A1 | 8/2019 | Gjerde | |
| 2019/0234844 A1 | 8/2019 | Stadler | |
| 2019/0247846 A1 | 8/2019 | Suh et al. | |
| 2019/0358562 A1 | 11/2019 | Gjerde | |
| 2020/0017880 A1 | 1/2020 | Bashour | |
| 2021/0163893 A1 | 6/2021 | Westoby et al. | |
| 2022/0002669 A1 | 1/2022 | Germeroth et al. | |
| 2022/0195388 A1 | 6/2022 | Germeroth et al. | |
| 2022/0243223 A1 | 8/2022 | Bashour et al. | |
| 2023/0090176 A1 | 3/2023 | Ramsborg et al. | |

FOREIGN PATENT DOCUMENTS

| | | |
|---|---|---|
| CN | 101622340 A | 1/2010 |
| CN | 103305464 A | 9/2013 |
| CN | 103502438 A | 1/2014 |
| DE | 19641876 A1 | 4/1998 |
| EP | 0452342 B1 | 11/1994 |
| EP | 1054063 | 11/2000 |
| EP | 1669129 | 6/2006 |
| EP | 1882700 | 1/2008 |
| EP | 1908769 | 4/2008 |
| EP | 2537416 B1 | 11/2014 |
| JP | 2006516197 A | 6/2006 |
| JP | 2006525013 A | 11/2006 |
| JP | 2009531062 A | 9/2009 |
| JP | 2010075191 A | 4/2010 |
| JP | 2011-182702 | 9/2011 |
| JP | 2012-219062 | 11/2012 |
| RU | 2249039 C2 | 3/2005 |
| RU | 2469044 | 12/2012 |
| WO | WO8602077 A1 | 4/1986 |
| WO | WO9208796 A1 | 5/1992 |
| WO | WO9428143 A1 | 12/1994 |
| WO | WO-1996/004314 | 2/1996 |
| WO | WO9623879 A1 | 8/1996 |
| WO | WO9624606 A1 | 8/1996 |
| WO | WO-1996/036721 | 11/1996 |
| WO | WO-1997/028191 | 8/1997 |
| WO | WO-1998/006749 | 2/1998 |
| WO | WO9840396 A1 | 9/1998 |
| WO | WO-1999/014236 | 3/1999 |
| WO | WO-1999/021572 | 5/1999 |
| WO | WO-1999/042597 | 8/1999 |
| WO | WO9961065 A1 | 12/1999 |
| WO | WO0014257 A1 | 3/2000 |
| WO | WO-2000/069549 | 5/2000 |
| WO | WO 2000/043551 | 7/2000 |
| WO | WO0104144 A3 | 8/2001 |
| WO | WO0156603 A1 | 8/2001 |
| WO | WO0183755 A2 | 11/2001 |
| WO | WO-2002/040697 | 5/2002 |
| WO | WO 2002/055992 | 7/2002 |
| WO | WO02054065 A2 | 7/2002 |
| WO | WO-2002/061428 | 8/2002 |
| WO | WO02077018 A1 | 10/2002 |
| WO | WO 2003/018771 | 3/2003 |
| WO | WO03029462 A1 | 4/2003 |
| WO | WO-2003/068956 | 8/2003 |
| WO | WO-2003/090781 | 11/2003 |
| WO | WO-2004/001418 | 12/2003 |
| WO | WO-2004/018520 | 3/2004 |
| WO | WO2004029221 A2 | 4/2004 |
| WO | WO2004096975 A2 | 11/2004 |
| WO | WO-2004/104185 | 12/2004 |
| WO | WO-2005/017174 | 2/2005 |
| WO | WO-2005/019466 | 3/2005 |
| WO | WO-2005/024000 | 3/2005 |
| WO | WO-2005/035567 | 4/2005 |
| WO | WO-2005/038031 | 4/2005 |
| WO | WO-2005/050209 | 6/2005 |
| WO | WO 2005/087802 | 9/2005 |
| WO | WO-2006/044650 | 4/2006 |
| WO | WO-2006/058226 | 6/2006 |
| WO | WO2007117602 A2 | 10/2007 |
| WO | WO2007112012 A3 | 11/2007 |
| WO | WO-2008/011486 | 1/2008 |
| WO | WO 2008/100122 | 8/2008 |
| WO | WO-2008/116468 | 10/2008 |
| WO | WO2008140573 A2 | 11/2008 |
| WO | WO-2009/003492 | 1/2009 |
| WO | WO2009003493 A2 | 1/2009 |
| WO | WO-2009/039854 | 4/2009 |
| WO | WO2009072003 A2 | 6/2009 |
| WO | WO-2009/092068 | 7/2009 |
| WO | WO 2009/095447 | 8/2009 |
| WO | WO-2009/106073 | 9/2009 |
| WO | WO2010033140 A2 | 3/2010 |
| WO | WO-2010/037395 | 4/2010 |
| WO | WO2010080032 A2 | 7/2010 |
| WO | WO-2011/101681 | 8/2011 |
| WO | WO2011107489 A1 | 9/2011 |
| WO | WO-2012/013682 | 2/2012 |
| WO | WO-2012/017081 | 2/2012 |
| WO | WO-2012/044999 | 4/2012 |
| WO | WO-2012/058627 | 5/2012 |
| WO | WO2012129514 A1 | 9/2012 |
| WO | WO-2012/137538 | 10/2012 |
| WO | WO2013011011 A2 | 1/2013 |
| WO | WO 2013/038272 | 3/2013 |
| WO | WO2013071154 A1 | 5/2013 |
| WO | WO2013123061 A1 | 8/2013 |
| WO | WO2013124474 A2 | 8/2013 |
| WO | WO2013126726 A1 | 8/2013 |
| WO | WO2013166321 A1 | 11/2013 |
| WO | WO2014011489 A2 | 1/2014 |
| WO | WO2014011996 A1 | 1/2014 |
| WO | WO2014031687 A1 | 2/2014 |
| WO | WO2014039044 A1 | 3/2014 |
| WO | WO2014048920 A1 | 4/2014 |
| WO | WO2014055668 A1 | 4/2014 |
| WO | WO2014076277 A1 | 5/2014 | |
| WO | WO-2014076277 A1 * | 5/2014 | ............ C07K 14/36 |
| WO | WO-2014/118220 | 8/2014 | |
| WO | WO2015095895 A1 | 6/2015 | |
| WO | WO-2015158868 A2 * | 10/2015 | ......... A61K 39/0011 |
| WO | WO2015158868 A2 | 10/2015 | |
| WO | WO2015162211 A1 | 10/2015 | |
| WO | WO2015164675 A1 | 10/2015 | |
| WO | WO2016166568 A1 | 10/2016 | |
| WO | WO-2016166568 A1 * | 10/2016 | ......... A61K 39/0011 |
| WO | WO2017068421 A1 | 4/2017 | |
| WO | WO2017068425 A1 | 4/2017 | |
| WO | WO2017068419 A3 | 5/2017 | |
| WO | WO2017096329 A1 | 6/2017 | |
| WO | WO2018134691 A1 | 3/2018 | |
| WO | WO2018197949 A1 | 11/2018 | |
| WO | WO2020033927 A2 | 2/2020 | |
| WO | WO2020089343 A1 | 5/2020 | |
| WO | WO-2022/234009 | 11/2022 | |

OTHER PUBLICATIONS

Aleksandrova et al. "Functionality and Cell Senescence of CD4/CD8-Selected CD20 CAR T Cells Manufactured Using the Automated CliniMACS Prodigy® Platform." Transfus Med Hemother. (Feb. 2019) 46(1):47-54.

Bambauer et al., "LDL-apheresis: technical and clinical aspects," The Scientific World Journal (2012).

Brosseron et al. "Isolating peripheral lymphocytes by density gradient centrifugation and magnetic cell sorting" Methods Mol Biol (2015) 1295:33-42.

(56) References Cited

OTHER PUBLICATIONS

Corada et al., "Monoclonal antibodies directed to different regions of vascular endothelial cadherin extracellular domain affect adhesion and clustering of the protein and modulate endothelial permeability," Blood. (2001) 97(6):1679-84.
Depil et al., "Off-the-shelf' allogeneic CAR T cells: development and challenges." Nat Rev Drug Discov (2020) 3: 185-199.
Faraghat et al. "High-throughput, low-loss, low-cost, and label-free cell separation using electrophysiology-activated cell enrichment." Proc Natl Acad Sci U S A. (May 2, 2017) 114(18): 4591-4596.
Godawat et al., "Period counter-current chromatography—design and operational considerations for integrated and continuous purification of proteins," Biotechnology journal (2012) 7(12):1496-1508.
Grutzkau et al. "Small but mighty: how the MACS-technology based on nanosized superparamagnetic particles has helped to analyze the immune system within the last 20 years." Cytometry A. (Jul. 2010) 77(7): 643-647.
Guedan et al. "Emerging Cellular Therapies for Cancer." Annu Rev Immunol. (Apr. 26, 2019) 37:145-171.
Gunzer et al.,, "Two-step negative enrichment of CD4+ and CD8+ T cells from murine spleen via nylon wool adherence and an optimized antibody cocktail," J Immunol Methods. (2001) 258(1-2): 55-63.
HAN et a., "Chimeric antigen receptor T-cell therapy for cancer: a basic research-oriented perspective," Mar. 2018;10(3):221-234.
Hobson et al., "In situ transduction of target cells on solid surfaces by immobilized viral vectors," BMC Biotechnol (2003) 3(4):1-10.
Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese).
Invitrogen, "Healthy cells in—good data out," Cell isolation and Activation (2010) p. 1-12.
Isozaki et al. "Intelligent image-activated cell sorting 2.0." Lab Chip. (Jun. 30, 2020) 20(13): 2263-2273.
Kacherovsky et al. "Traceless aptamer-mediated isolation of CD8+ T cells for chimeric antigen receptor T-cell therapy." Nat Biomed Eng. (Oct. 2019) 3(10):783-795.
Kleymann et al. "Engineered Fv Fragments as a Tool for the One-Step Purification of Integral Multisubunit Membrane Protein Complexes." Nat Biotechnol (1995) 13: 155-160.
Kong et al., "Isolation of breast cancer stem cell and screening of specific polypeptide bonding to it," Chinese Journal of Cancer Prevention and Control (2013) 20(24):1892-1895.
Korndorfer et al., "Improved affinity of engineered streptavidin for the Strep-tag 11 peptide is due to a fixed open conformation of the lid-like loop at the binding site," Protein Sci (2002) 11:883-893.
Kubben et al. "Identification of differential protein interactors of lamin A and progerin," Nucleus (2010) 1(6): 513-525.
Kumar et al., "Integrated bioprocess for the production and isolation of urokinase from animal cell culture using supermacroporous cryogel matrices," Biotechnology and Bioengineering (2006) 93(4):636-646.
Matic et al., "Fine Tuning and Efficient T Cell Activation with Stimulatory aCD3 Nanoarrays," Nano Letters (2013) 13:5090-5097.
Milone et al., "Chimeric Receptors Containing CD137 Signal Transduction Domains Mediate Enhanced Survival of T Cells and Increased Antileukemic Efficacy In Vivo," Mol Ther (2009) 17(8):1453-64.
Mittal et al. "Biotin-4-fluorescein based fluorescence quenching assay for determination of biotin binding capacity of streptavidin conjugated quantum dots." Bioconjug Chem. (2011) 22(3):362-368.
Moeller et al., "Adoptive transfer of gene-engineered CD4+ helper T cells induces potent primary and secondary tumor rejection," Blood (2005) 106(9):2995-3003.
Mohr et al., "Minimally manipulated murine regulatory T cells purified by reversible Fab Multimers are potent suppressors for adoptive T-cell therapy." Eur. J. Immunol. (2017) 47: 2153-2162.
Murray et al. "Continuous and Quantitative Purification of T-Cell Subsets for Cell Therapy Manufacturing Using Magnetic Ratcheting Cytometry." SLAS Technol. (Aug. 2018) 23(4):326-337.
Nascimbeni et al., "Peripheral CD4+CD8+ T cells are differentiated effector memory cells with antiviral functions," Blood (2004) 104(2):478-86.
Padlan,"X-Ray Crystallography of Antibodies," Adv Prot Chem (1996) 49:57-133.
Poirier et al. "CD28-specific immunomodulating antibodies: what can be learned from experimental models?" American Journal of Transplantation. Jul. 2012;12(7):1682-90.
Poltorak et al., "Expamers: a new technology to control T cell activation." Sci. Rep. (2020) 10: 17832.
Pritchard et al. "Cell sorting actuated by a microfluidic inertial vortex." Lab Chip. (Jul. 9, 2019) 19(14): 2456-2465.
Purification Technical Handbook (2010 retrieved from https://at.vwr.com/assetsvc/asset/de AT/id/20551553/contents).
Qin et al. "Chimeric Antigen Receptor beyond CAR-T Cells." Cancers (Basel). (Jan. 22, 2021) 13(3):404.
Qureshi et al., "Development and characterization of a series of soluble tetrameric and monomeric streptavidin muteins with differential biotin binding affinities," The Journal of Biological Chemistry (2001) 276(49):46422-46428.
Roddie et al. "Manufacturing chimeric antigen receptor T cells: issues and challenges." Cytotherapy. (Mar. 2019) 21(3):327-340.
Sano et al., "A streptavidin-protein a chimera that allows one-step production of a variety of specific antibody conjugates," Nature (1991) 9:1378-1381.
Sawai et al., "A novel method of cell-specific mRNA transfection," Molecular Genetics of Metabolim (1998) 64:44-51.
Schroeder, Nach Zellen Angeln. Faszination Forschung Jun. 30, 2010:28-37 Retrieved from the Internet: URL:http://portal.mytum.de/pressestelle/faszination-forschung/2010nr6/index (Including English translation).
Singh et al. "CAR T cells: continuation in a revolution of immunotherapy." The Lancet Oncology (Mar. 2020) 21(3): e168-e178.
Skea et al., "The selective expansion of functional T cell subsets," J Hematother Stem Cell Res. (1999) 8(5): 525-38.
Sun et al., "Plug-and-go" strategy to manipulate streptavidin valencies, Bioconjugate Chem (2014) 25:1375-1380.
Tarantula, Explanatory Biotechnological Dictionary (English translation only).
Tsiotis et al. "Isolation and structural characterization of trimeric cyanobacterial photosystem I complex with the help of recombinant antibody fragments." Eur J Biochem. (Aug. 1, 1995) 231(3): 823-30.
Turka et al., "CD28 is an Inducible T Cell Surface Antigen That Transduces a Proliferative Signal in CD3+ Mature Thymocytes," J Immunol (1990) 144:1646-1653.
Vadakekolathu et al. "T-Cell Manipulation Strategies to Prevent Graft-Versus-Host Disease in Haploidentical Stem Cell Transplantation." Biomedicines. (Jun. 21, 2017) 5(2): 33.
Valle et al., "Heterogeneous CD3 Expression Levels in Differing T Cell Subsets Correlate with the In Vivo Anti-CD3-Mediated T Cell Modulation." J Immunol. (2015) 5: 2117-2127.
Walter et al., "Cutting edge: Predetermined Avidity of Human CD8 T cells expanded on calibrated MHC/Anti-CD28-Coated Microspheres," J Immunol (2003) 171:4973-4978.
Wang et al., "Open-tubular capillary cell affinity chromatography: single and tandem blood cell separation," Anal Chem (2008) 80(6):2118-2124.
Williams et al., "Affinity recovery of moloney murine leukaemia virus," J Chromatography B (2005) 820(1):111-119.
Woolridge et al. "Anti-CD8 antibodies can inhibit or enhance peptide-MHC class I (pMHCI) multimer binding: this is paralleled by their effects on CTL activation and occurs in the absence of an interaction between pMHCI and CD8 on the cell surface." The Journal of Immunology (2003)171. 12: 6650-6660.
Xia et al., "Enrichment of haploid spermatids in mice by flow sorting," Natl Journal of Andrology (2014) 20(2):106-110.
Zeiser et al., "Acute Graft-versus-Host Disease—Biologic Process, Prevention, and Therapy," N Engl J Med (2017) 377: 2167-2179.

(56) References Cited

OTHER PUBLICATIONS

Zhu et al. "Closed-system manufacturing of CD19 and dual-targeted CD20/19 chimeric antigen receptor T cells using the CliniMACS Prodigy device at an academic medical center." Cytotherapy. (Mar. 2018) 20(3):394-406.
Ahlers et al., "Memories That Last Forever: Strategies for Optimizing Vaccine T-Cell Memory", Blood (2010) 115(9):1678-1689.
Aksoy et al., "Human primary T cells: A practical guide," Published on Jun. 19, 2018. Retrieved on Jan. 7, 2020. Retrieved from https://peerj.com/preprints/26993/.
Al-Aghbar et al., "High-Affinity Ligands Can Trigger T Cell Receptor Signaling Without CD45 Segregation." Front Immunol. (2018); 9: 713.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Amstutz et al., "In vitro Display Technologies: Novel Developments and Applications," Curr Opin Biotechnol. (2001) 12(4): 400-405.
Anonymous, "Cross-linking reagents introduction to cross-linking single step vs. multi-step reactions," Published on Jan. 1, 2005. Retrieved from http://www.korambiotech.com/upload/bbs/2/Cross-LinkingTechHB.pdf. Retrieved on Nov. 30, 2018.
Anonymous, "Optimization of Human T Cell Expansion Protocol: Effects of Early Cell Dilution," Published Oct. 2018. Retrieved on Jan. 7, 2020. Retrieved on https://cdn.stemcell.com/media/files/techbulletin/TB27143-Optimization_of_Human_T_Cell_Expansion_Protocol.pdf?_ga=2.128430788.931468903.1578439383-852611746.1578439383.
Anonymous, "SMCC and Sulfo-SMCC," Published Jan. 1, 2018. Retrieved on https://assets.thermofisher.com/TFSAssets/LSG/manuals/MAN0011295_SMCC_SulfoSMCC_UG.pdf. Retrieved on Dec. 3, 2018.
Anonymous, "Traut's reagent," Published on Jan. 1, 2012. Retrieved from https://assets.thermofisher.com/TFS-Assets/LSG/manuals/MAN0011238_Trauts_Reag_UG.pdf. Retrieved on Dec. 3, 2018.
Arakawa et al. "Cloning and sequencing of the VH and V kappa genes of an anti-CD3 monoclonal antibody, and construction of a mouse/human chimeric antibody," J Biochem. (1996) 120(3): 657-662.
Argarana et al. "Molecular cloning and nucleotide sequence of the streptavidin gene," Nucleic Acids Res. (1996) 14(4): 1871-1882.
Arndt et al., "Analysis of TCR activation kinetics in primary human T cells upon focal or soluble stimulation," J Immunol Methods. (2013) 387(1-2): 276-283.
Ashouri et al., "Endogenous Nur77 Is a Specific Indicator of Antigen Receptor Signaling in Human T and B Cells." J. Immunol. (2017) 198(2); 657-668.
Barrett et al., "Chimeric antigen receptor therapy for cancer," Annu Rev Med. (2014); 65: 333-347.
Barrett et al., "The length and mode of termination of individual muscle fibers in the human Sartorius and posterior femoral muscles," Cell Tissues Organs (1962) 48(3): 242-257.
Bashour et al., "Functional Characterization of a T Cell Stimulation Reagent for the Production of Therapeutic Chimeric Antigen Receptor T Cells," Abstract of Poster, presented at American Societyof Hematology Annual Meeting, Orlando, FL (Dec. 5, 2015) 1 page.
Bashour et al., "Functional Characterization of a T Cell Stimulation Reagent for the Production of Therapeutic Chimeric Antigen Receptor T Cells," Presentation of Poster, presented at AmericanSociety of Hematology Annual Meeting, Orlando, FL (Dec. 5, 2015).
Battaglia et al., "Interleukin-21 (IL-21) synergizes with IL-2 to enhance T-cell receptor-induced human T-cell proliferation and counteracts IL-2/transforming growth factor-β-induced regulatory Tcell development," Immunology. May 2013;139(1):109-120.
Baum et al., "Retrovirus vectors: toward the plentivirus?," Molecular Therapy: The Journal of the American Society of Gene Therapy (2006) 13(6): 1050-1063.
Bazdar et al. "Interleukin-7 enhances proliferation responses to T-cell receptor stimulation in naïve CD4+ T cells from human immunodeficiency virus-infected persons," J Virol. (2007) 81(22): 12670-12674.
Berg et al., "Sustained TCRsignaling is required for mitogen-activated protein kinase activation anddegranulation by cytotoxic T lymphocytes." 1998. J. Immunol. 161(6); 2919-2924.
Berger et al., "Adoptive transfer of effector CD8 T cells derived from central memory cells establishes persistent T cell memory in primates." J Clin Invest (2008) 118(1): 294-305.
Bes, C. et al. (2003). "Mapping the Paratope of Anti-CD4 Recombinant Fab 13B8.2 by Combining Parallel Peptide Synthesis and Site-directed Mutagenesis", The Journal of Biological Chemistry (2003) 278(16):14266-14273.
Beste et al., "Small antibody-like proteins with prescribed ligand specificities derived from the lipocalin fold," Proc Natl Acad Sci U S A. (1999) 96(5): 1898-1903.
Birnbaum et al., "Molecular architecture of the αβ T cell receptor-CD3 complex." Proc Natl Acad Sci U S A. (2014) 111(49): 17576-17581.
Blair, "Cd40 Ligand (Cd154) Triggers a Short-Term Cd4+ T Cell Activation Response That Results in Secretion of Immunomodulatory Cytokines and Apoptosis", J Exp Med. (2000) 191(4): 651-660.
Boerman et al., "Pretargeted radioimmunotherapy of cancer: progress step by step." J Nucl Med. (2003) 44(3); 400-411.
Boris-Lawrie et al., "Recent advances in retrovirus vector technology," Cur. Opin. Genet. Develop. (1993) 3:102-109.
Brash et al., "Strontium phosphate transfection of human cells in primary culture: stable expression of the simian virus 40 large-T-antigen gene in primary human bronchial epithelial cells," Mol. Cell Biol. (1987) 7(5): 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Buckle et al., "Integrating Experiment and Theory to Understand TCR-pMHC Dynamics," Front Immunol. (2018) 9:2898.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90(17): 8033-8037.
Busch et al., "Differing roles of inflammation and antigen in T cell proliferation and memory generation." J Immunol. (2000) 164(8); 4063-4070.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Carpentier et al., "T-cell artificial focal triggering tools: linking surface interactions with cell response." PLoS One (2009) 4(3), e4784.
Casalegno-Garduno et al., Multimer technologies for detection and adoptive transfer of antigen-specific T cells. Cancer Immunol Immunother (2010) 59(2):195-202.
Casati et al., "Enrichment, stimulation, and viral transduction of naive and central memory CD8+ Tcells under GMP conditions for translational research towards the development of adoptive celltherapy of cancer patients," MACS&more (2013) 15: 20-24.
Cavalieri et al., "Human T lymphocytes transduced by lentiviral vectors in the absence of TCR activation maintain an intact immune competence," Blood (2003) 102(2): 497-505.
Chang et al., "Identification and selective expansion of functionally superior T cells expressing chimeric antigen receptors," J Transl Med (2015) 13(1): 161.
Cheadle et al., "Chimeric antigen receptors for T-cell based therapy," Methods Mol Biol. (2012);907:645-66.
Chen et al., "Biotin IgM Antibodies in Human Blood: A Previously Unknown Factor Eliciting False Results in Biotinylation-Based Immunoassays," Plos One (2012); 7(8); e42376, pp. 1-8.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.

(56) References Cited

OTHER PUBLICATIONS

Choudhuri et al., "Signaling microdomains in T cells." FEBS Lett. (2010) 584(24): 4823-4831.
Church et al., "Tumor-specific CD4+ T cells maintain effector and memory tumor-specific CD8+ T cells," Eur J Immunol (2013) 44(1):69-79.
Cieri et al., "Generation of human memory stem T cells after haploidentical T-replete hematopoietic stem cell transplantation", Blood (2015) 125(8): 2865-2874.
Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.
Clement et al., "Analysis of the monocyte Fc receptors and antibody-mediated cellular interactions required for the Induction of T cell proliferation by anti-T3 antibodies." J Immunol. (1985) 135(1): 165-171.
Cohen et al., "Recognition of fresh human tumor by human peripheral blood lymphocytes transduced with a bicistronic retroviral vector encoding a murine anti-p53 TCR," J Immunol. (2005) 175(9): 5799-5808.
Cooper et al., "T-cell clones can be rendered specific for CD19: toward the selective augmentation of the graft-versus-B-lineage leukemia effect," Blood (2003) 101(4): 1637-1644.
Cornish et al., "Differential regulation of T-cell growth by IL-2 and IL-15," Blood. (2006) 108(2): 600-608.
Dainiak et al., Methods in Cell Separations. Adv Biochem Eng Biotechnol. 2007;106:1-18.
Daniels et al., "Thymic Selection Threshold Defined by Compartmentalization of Ras/MAPK Signalling," Nature. (2006) 444(7120): 724-729.
Davila et al., "CD19 CAR-targeted T cells induce long-term remission and B Cell Aplasia in an immunocompetent mouse model of B cell acute lymphoblastic leukemia," PLoS ONE (2013) 8(4):e61338.
Davis et al., "The kinetic-segregation model: TCR triggering and beyond." Nat. Immunol. (2006) 7(8); 803-809.
Dienz et al., "The induction of antibody production by IL-6 is indirectly mediated by IL-21 produced by CD4+ T cells," J Exp Med. (2009) 206(1): 69-78.
Dubel et al., "Bifunctional and multimeric complexes of streptavidin fused to single chain antibodies (scFv)," J Immunol Methods (1995) 178(2): 201-209.
Effenberger et al., "FLEXamers: A Double Tag for Universal Generation of Versatile Peptide-MHC Multimers." J Immunol. (2019) 202(7): 2164-2171.
Fairhead, M. et al., "Plug-and-Play Pairing via Defined Divalent Streptavidins", J Mol Biol. (2014) 426(1): 199-214.
Fedorov et al., "PD-1-and CTLA-4-Based Inhibitory Chimeric Antigen Receptors (iCARs) Divert Off-Target Immunotherapy Responses," Science Translational Medicine (2013) 5(215):215ra172.
Flynn, K.J. et al. "Stem memory T cells (TSCM)-their role in cancer and HIV immunotherapies", Clinical & Translational Immunology (2014) 3(e20): 1-7.
Fontaine et al., "Long-Term Stabilization of Maleimide-Thiol Conjugates," Bioconjug Chem (2015) 26(1):145-152 (Pub Date: Dec. 2014).
Frecha et al., "Advances in the field of lentivector-based transduction of T and B lymphocytes for gene therapy," Molecular Therapy: The Journal of the American Society of Gene Therapy (2010) 18: 1748-1757.
Gao, "Instability of thiol/maleimide conjugation and strategies for mitigation," 7th World ADC San Diego (Linker design—Workshop F), Presentation, Oct. 10, 2016.
Garlie et al., "T cells coactivated with immobilized anti-CD3 and anti-CD28 as potential immunotherapy for cancer." J. Immunother. (1999) 22(4); 336-345.
Gattinoni et al., "Paths to stemness: building the ultimate antitumour T cell," Nat Rev Cancer. (2012) 12(10): 671-84.
Gattinoni, L. et al. (2012). "A human memory T-cell subset with stem cell-like properties", Nat Med 17(10): 1290-1297.

Germeroth "IBA T-catch cell isolation in pipette tips" Apr. 23, 2014Retrieved from the internet:URL:http: / /x.ymcdn.com /sites /www.celltherapysociety. org/ resource /resmgr /2014_ AnnualMtgPresent ations/T2_L.Germeroth.pdf [Retrieved on Jan. 23, 2017].
Ghassemi et al., "Reducing Ex Vivo Culture Improves the Antileukemic Activity of Chimeric Antigen Receptor (CAR) T Cells," Cancer Immunology Research (2018) 6(9):1100-1109.
Ghassemi S., "Ultra-Short Manufacturing of Quiescent Chimeric Antigen Receptor T Cells for Adoptive Immunotherapy," Molecular Therapy (2019) 27(4S1); 86.
Gill et al., "Biopharmaceutical drug discovery using novel protein scaffolds," Curr Opin Biotechnol. (2006) 17(6): 653-658.
Godin et al., "Microfluidics and photonics for Bio-System-on-a-Chip: a review of advancements in technology towards a microfluidic flow cytometry chip," J Biophoton. (2008) 1(5): 355-376.
Goyette et al., "How does T cell receptor clustering impact on signal transduction?" J Cell Sci. (2019) 132(4); ics226423.
Hackett et al., "A transposon and transposase system for human application," Molecular Therapy: The Journal of the American Society of Gene Therapy (2010) 18: 674-683.
Hermans et al., "The VITAL assay: a versatile fluorometric technique for assessing CTL-and NKT-mediated cytotoxicity against multiple targets in vitro and in vivo," J. Immunological Methods (2004) 285(1): 25-40.
Holliger, P. et al. (Jul. 1993). ""Diabodies": Small Bivalent and Bispecific Antibody Fragments," Proceedings of the National Academy of Sciences USA 90:6444-6448.
Holt, L. et al. (Nov. 2003) "Domain Antibodies: Proteins For Therapy," TRENDS in Biotechnology 21(11): 484-490.
Hoshino et al., "Activation via the CD3 and CD16 pathway mediates interleukin-2-dependent autocrine proliferation of granular lymphocytes in patients with granular lymphocyte proliferative disorders," Blood. (1991) 78(12): 3232-3240.
Howarth, M. et al. (Apr. 2006). "A monovalent streptavidin with a single femtomolar biotin binding site," Nat Methods 3(4): 267-273.
Huang et al., "DNA transposons for modification of human primary T lymphocytes," Methods Mol Biol (2009) 506: 115-126.
Hudson et al., "Engineered Antibodies," Nature Medicine (2003) 9(1):129-133.
Hunziker et al., "Exhaustion of cytotoxic T cells during adoptiveimmunotherapy of virus carrier mice can be prevented by B cells or CD4+ T cells," Eur J Immunol (2002) 32(2):374-382.
Huppa et al., "T-cell-antigen recognition and the immunological synapse," Nat. Rev. Immunol. (2003) 3(12); 973-983.
Hutten et al., New magnetic nanoparticles for biotechnology. J Biotechnol. Aug. 26, 2004; 112(1-2):47-63.
Ill et al., "Design and construction of a hybrid immunoglobulin domain with properties of both heavy and light chain variable regions," Protein Eng. (1997) 10(8): 949-957.
Iliades et al., "Triabodies: single chain Fv fragments without a linker form trivalent trimers," FEBS Lett. (1997) 409(3): 437-441.
Johnston, "Biolistic transformation: microbes to mice," Nature (1990) 346:776-777.
Kato et al., "Development of Rous Sarcoma Virus-like Particles Displaying hCC49 scFv for Specific Targeted Drug Delivery to Human Colon Carcinoma Cells," Pharm Res (2015) 32(11): 3699-3707.
Kim et al., "The ABCs of Artificial Antigen Presentation," Nat Biotechnol Apr. 2004;22(4): 403-410.
Klebanoff et al., "Sorting through subsets: which T-cell populations mediate highly effective adoptive immunotherapy?," J Immunother. (2012) 35(9): 651-660.
Knabel et al., "Reversible MHC multimer staining for functional isolation of T-cell populations and effective adoptive transfer," Nat Med. (2002( 8(6): 631-637.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nature Reviews Clinical Oncology (2013) 10(5); 267-276.

(56) References Cited

OTHER PUBLICATIONS

Kohanski et al., "Monovalent avidin affinity columns" Methods Enzymol. (1990) 184: 194-200.
Koste et al., "T-cell receptor transfer into human T cells with ecotropic retroviral vectors," Gene Therapy (2014) 21: 533-538.
Kumar et al., "Affinity binding of cells to cryogel adsorbents with immobilized specific ligands: effect of ligand coupling and matrix architecture." J Mol Recognit. (2005) 18(1): 84-93.
Kumar et al., "Cell separation using cryogel-basedaffinity chromatography",Nature Protocols, Nature Publishing Group, GB, vol. 5, No. 11, Nov. 1, 2010, pp. 1737-1747.
Kwon et al., "Quantitative evaluation of the relative cell permeability of peptoids and peptides," J Am Chem Soc. Feb. 14, 2007;129(6):1508-1509.
Lada et al., "Quantitation of Integrated HIV Provirus by Pulsed-Field Gel Electrophoresis and Droplet Digital PCR," J Clin Microbiol (2018) 56(12): e01158-18.
Larvor et al., Measurement of the dissociation rate constant of antigen/antibody complexes in solution by enzyme-linked immunosorbent assay. J Immunol Methods. Apr. 15, 1994;170(2):167-175.
Lenschow, D.J. et al. (1996). "CD28/B7 System of T Cell Costimulation," Ann. Rev. Immunol. 14:233-258.
Levin et al., "Optimizing the affinity and specificity of proteins with molecular display," Mol BioSyst (2006) 2: 49-57.
Levine et al., 1997. "Effects of CD28 costimulation on long-term proliferation of CD4+ T cells in the absence of exogenous feeder cells." J. Immunol. (1997) 159(12), 5921-5930.
Li et al., "Comparison of anti-CD3 and anti-CD28-coated beads with soluble anti-CD3 for expanding human T cells: Differing impact on CD8 T cell phenotype and responsiveness to restimulation," J Transl Med., (2010) 8:104.
Li et al., "Comparison of inlet geomery in microfluidic cell affinity chromatography," Analytical chemistry (2011) 83(3):774-781.
Li et al., "Directed evolution of human T-cell receptors with picomolar affinities by phage display", Nat Biotechnol. (2005) 23(3):349-354.
Li et al., "Multiparameter cell affinity chromatography: Separation and analysis in a single microfluidic channel," Anal Chem (2012) 84(19):8140-8148.
Li et al., "Negative enrichment of target cells by microfluidic affinity chromatography," Analytical Chemistry (2011) 83(20):7863-7869.
Li et al.. "T cell receptor signalling in the control of regulatory T cell differentiation and function." Nat Rev Immunol. (2016) 16(4): 220-233.
Li, G. et al. (Jun. 27, 2013). "T-Bet and Eomes Regulate the Balance between the Effector/Central Memory T Cells versus Memory Stem Like T Cells", Plos One 8(6):e67401, 1-10.
Lim et al. "Engineered Streptavidin Monomer and Dimer with Improved Stability and Function," Biochemistry (2010), 50:8682-91.
Liu et al., "Building Potent Chimeric Antigen Receptor T Cells with CRISPR Genome Editing," Front Immunol. (2019) 10: 456. doi: 10.3389/fimmu.2019.00456.
Liu et al., "Characterization of TectoRNA Assembly with Cationic Conjugated Polymers," J Am Chem Soc (2004) 126(13):4076-4077.
Lowman, "Bacteriophage display and discovery of peptide leads for drug development," Annu Rev Biophy Biomol Struct (1997) 26; 401-424.
Lu et al., "A rapid cell expansion process for production of engineered autologous CAR-T cell therapies," Human Gene Therapy Methods (2016) 27(6): 209-218.
Lupton et al., "Dominant positive and negative selection using a hygromycin phosphotransferase-thymidine kinase fusion gene," Mol and Cell Biol (1991) 11(6):3374-3378.
Lyon, R.P. et al. (Oct. 2014, e-pub. Sep. 7, 2014). "Self-hydrolyzing Maleimides Improve the Stability and Pharmacological Properties of Antibody-Drug Conjugates," Nat Biotechnol 32(10): 1059-1062.

Manuri et al., "piggyBac transposon/transposase system to generate CD19-specific T cells for the treatment of B-lineage malignancies," Hum Gene Ther (2010) 21(4): 427-437.
Martin et al., "The affinity-selection of a minibody polypeptide inhibitor of human interleukin-6," EMBO J. (1994) 13(22): 5303-5309.
Mehlhop-Williams et al., "Memory CD8+ T cells exhibit increased antigen threshold requirements for recall proliferation." J Exp Med. (2014) 211(2): 345-56.
Meyer et al., "Biodegradable nanoellipsoidal artificial antigen presenting cells for antigen specific T-cell activation." Small. (2015) 11(13): 1519-1525.
Miller et al., "Improved retroviral vectors for gene transfer and expression," Biotechniques (1989) 7(9):980-982.
Miller et al., "Retrovirus packaging cells," Human Gene Therapy (1990) 1:5-14.
Miltenyi et al., High Gradient Magnetic Cell Separation With MACS. Cytometry. 1990;11(2):231-238.
Mittler, R.S. et al. "Anti-CD137 antibodies in the treatment of autoimmune disease and cancer", Immunol. Res. (2004) 29(1-3): 197-208.
Mohr et al., "Efficient immunoaffinity chromatography of lymphocytes directly from whole blood." Sci Rep. 2018 8(1):16731.
Morizono et al., "A versatile targeting system with lentiviral vectors bearing the biotin-adaptor peptide," J Gene Med. 2009 11(8): 655-663.
Mosavi et al., "The ankyrin repeat as molecular architecture for protein recognition," Protein Sci. (2004) 13(6) :1435-1448.
Mullen et al., "Transfer of the bacterial gene for cytosine deaminase to mammalian cells confers lethal sensitivity to 5-fluorocytosine: a negative selection system," Proc. Natl. Acad. Sci. USA (1992)89(1):33-37.
Nauerth et al., "Flow cytometry-based TCR-ligand Koff-rate assay for fast avidity screening of even very small antigen-specific T cell populations ex vivo." Cytometry A. (2016) 89(9): 816-825.
Neeson et al., "Ex Vivo Culture of Chimeric Antigen Receptor T Cells Generates Functional CD8+ T Cells With Effector and Central Memory-Like Phenotype," Gene Ther (2010) 17(9): 1105-1116.
Neuenhahn et al., "Transfer of minimally manipulated CMV-specific T cells from stem cell or third-party donors to treat CMV infection after alloHSCT." Leukemia (2017) 31(10): 2161-2171.
Noguchi et al., Preparation and Properties of the Immunoconjugate Composed of Anti-Human Colon Cancer Monoclonal Antibody and Mitomycin C-Dextran Conjugate. Bioconjug Chem. (1992) 3(2): 132-137.
Okamoto et al., "A Promising Vector for TCR Gene Therapy: Differential Effect of siRNA, 2A Peptide, and Disulfide Bond on the Introduced TCR Expression," Mol Ther Nucleic Acids. (2012) 1(12): e63. 11 pages.
Padmanabhan et al., Purification of Transiently Transfected Cells by Magnetic Affinity Cell Sorting. J Immunogenet. Apr. 1989;16(2): 91-102.
Palmer et al., "Affinity Threshold for Thymic Selection Through a T-cell Receptor-Co-Receptor Zipper," Nat Rev Immunol (2009) 9(3): 207-213.
Park et al., "Treating cancer with genetically engineered T cells," Trends Biotechnol. (2011) 29(11): 550-557.
Parkhurst et al., "Characterization of genetically modified T-cell receptors that recognize the CEA:691-699 peptide in the context of HLA-A2.1 on human colorectal cancer cells," Clin Cancer Res. (2009) 15:169-180.
Paulsen, M. et al. "Modulation of CD4+ T-cell activation by CD95 co-stimulation", Cell Death Differ. (2011) 18(4): 619-631.
Pearce EL. "Metabolism in T cell activation and differentiation," Curr. Opin. Immunol. (2010) 22(3), 314-320.
Plieva et al., "Characterization of supermacroporous monolithic polyacrylamide based matrices designed for chromatography of bioparticles," Journal of Chromatography (2004) 807(1): 129-137.
Poltorak et al., "TCR activation kinetics and feeDynaBeads™ ack regulation in primary human T cells." Cell Commun Signal. (2013) 11:4.
Pozarowski et al., "Analysis of Cell Cycle by Flow Cytometry," Methods Mol Biol. (2004) 281: 301-311.

(56) References Cited

OTHER PUBLICATIONS

Pullagurla et al., "Parallel affinity-based isolation of leukocyte subsets using microfluidics: application for stroke diagnosis," Analytical chemistry (2014) 86(8):4058-4065.
Qiagen: "Strep-tagged Protein Purification Handbook For expressing, purifying, and detecting proteins carrying a Strep-tag II or a 6xHis tag and a Strep-tag II Two-step protein purificationsystem His. Strep pQE-TriSystem Vector Set pQE-TriSystem Strep Vector Strep-Tactin Superflow and Superflow Cartridge", Apr. 1, 2007 (Apr. 1, 2007).
Rapoport et al., "Restoration of immunity in lymphopenic individuals with cancer by vaccination and adoptive T-cell transfer." Nat Med. (2005) 11(11):1230-1237.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Riddell et al., "The use of anti-CD3 and anti-CD28 monoclonal antibodies to clone and expand human antigen-specific T cells." J Immunol Methods. (1990) 128(2): 189-201.
Rodi et al., "Phage-display technology—finding a needle in a vast molecular haystack," Curr Opin Biotechnol (1999) 10(1): 87-93.
Rosenberg, et al., "Cell transfer immunotherapy for metastatic solid cancer—what clinicians need to know," Nat Rev Clin Oncol. (2011) 8(10):577-585.
Rossy et al., "How Does the Kinase Lck Phosphorylate the T Cell Receptor? Spatial Organization as a Regulatory Mechanism," Front Immunol. (2012) 3: 167.
Rudd et al.,"CD28 and CTLA-4 coreceptor expression and signal transduction." Immunol Rev. (2009) 229(1); 12-26.
Rybak et al., "Purification of biotinylated proteins on streptavidin resin: a protocol for quantitative elution," Proteomics. 2004 4(8): 2296-2299.
Sabatino et al., "Generation of clinical-grade CD19-specific CAR-modified CD8+ memory stem cells for the treatment of human B-cell malignancies," Blood. (2016) 128(4): 519-528.
Sadelain et al., "The basic principles of chimeric antigen receptor design," Cancer Discov. (2013) 3(4): 388-398.
Sanchez-Paulete et al., "Deciphering CD137 (4-1BB) signaling in T-cell costimulation for translation into successful cancer immunotherapy." Eur. J. Immunol. (2016) 46(3); 513-522.
Scarpa et al., "Characterization of recombinant helper retroviruses from Moloneybased vectors in ecotropic and amphotropic packaging cell lines," Virology (1991) 180: 849-852.
Schmidt and Skerra, The Strep-tag system for one step purification and high-affinity detection or capturing of proteins. Nat Protoc. 2007;2(6):1528-1535.
Schmidt et al., "Development of the Twin-Strep-tag and its application for purification of recombinant proteins from cell culture supernatants." Protein Expression and Purification (2013) 92(1); 54-61.
Schmidt et al., "Molecular Interaction Between the Strep-tag Affinity Peptide and its Cognate Target, Streptavidin." Mol. Biol. (1996) 255(5); 753-766.
Schmidt et al., "The random peptide library-assisted engineering of a C-terminal affinity peptide, useful for the detection and purification of a functional Ig Fv fragment." Protein Eng. (1993) 6(1); 109-122.
Schmitt et al., "Adoptive transfer and selective reconstitution of streptamer-selected cytomegalovirus-specific CD8+ T cells leads to virus clearance in patients after allogeneic peripheral blood stem cell transplantation," Transfusion. (2011) 51(3): 591-599.
Schober et al., "Orthotopic replacement of T-cell receptor α-and β-chains with preservation of near-physiological T-cell function." Nat Biomed Eng. (2019) 3(12): 974-984.
Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]-p. 34-p. 37 (English translation provided).
Sharma et al., "Efficient sleeping beauty DNA transposition from DNA minicircles," Molec Ther Nucl Acids (2013) 2: e74.
Silverman et al., "Multivalent avimer proteins evolved by exon shuffling of a family of human receptor domains," Nat Biotechnol. (2005) 23(12): 1556-61.
Singh et al., "Formation of N-substituted 2-iminothiolanes When Amino Groups in Proteins and Peptides Are Modified by 2-iminothiolane," Anal Biochem (1996) 236(1): 114-125.
Skerra et al., "Applications of a peptide ligand for streptavidin: the Strep-tag," Biomolecular Engineer (1999) 16 (1-4):79-86.
Skerra, "A general vector, pASK84, for cloning, bacterial production, and single-step purification of antibody Fab fragments," Gene. (1994) 141(1): 79-84.
Skerra, "Engineered protein scaffolds for molecular recognition," J Mol Recognit. (2000) 13(4): 167-187.
Stemberger et al., Novel Serial Positive Enrichment Technology Enables Clinical Multiparameter Cell Sorting. PLoS One. 2012;7(4):e35798 (11 pp).
Stone et al., "The assembly of single domain antibodies into bispecific decavalent molecules," J Immunol Methods. (2007) 318(1-2): 88-94.
Szoka et al., "Comparative properties and methods of preparation of lipid vesicles (liposomes)," Ann. Rev. Biophys. Bioeng. (1980) 9: 467-508.
Taraban et al. (Dec. 2002, e-pub. ). "Expression and costimulatory effects of the TNF receptor superfamily members CD134 (OX40) and CD137 (4-1BB), and their role in the generationof anti-tumor immune responses", Eur J Immunol. 32(12): 3617-3627.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
ThermoFisher Scientific, Avidin-Biotein Interaction, retrieved fromhttps://www.thermofisher.com/us/en/home/life-science/protein-biology/protein-biology-learningcenter/protein-biology-resource-library/pierce-protein-methods/avidin-biotin-interaction.html on Apr. 9, 2019, pp. 1-7.
Traunecker et al., "Bispecific single chain molecules (Janusins) target cytotoxic lymphocytes on HIV infected cells," EMBO j. (1991) 10(12):3655-3659.
Traunecker et al., "Janusin: new molecular design for bispecific reagents," Int J Cancer Suppl. (1992);7:51-2.
Trickett et al., "T cell stimulation and expansion using anti-CD3/CD28 beads" J. Immunol Methods (2003) 275(102): 251-255.
Tsukahara et al., "CD19 target-engineered T-cells accumulate at tumor lesions in human B-cell lymphoma xenograft mouse models," Biochem Biophys Res Commun (2013) 438(1): 84-89.
Tumaini et al., "Simplified process for the production of anti-CD19-CAR-engineered T cells," Cytotherapy. (2013) 15(11): 1406-1415.
Tumey et al., "Mild Method for Succinimide Hydrolysis on ADCs: Impact on ADC Potency, Stability, Exposure, and Efficacy," Bioconjug Chem. (2014) 25(10): 1871-1880.
Turtle et al., "Engineered T cells for anti-cancer therapy," Curr. Opin. Immunol. (2012) 24(5): 633-639.
Turtle et al., "Genetically retargeting CD8+ lymphocyte subsets for cancer immunotherapy." Curr Opin Immunol. (2011) 23(2); 299-305.
Van Panhuys et al., "T-cell-receptor-dependent signal intensity dominantly controls CD4(+) T cell polarization In Vivo." Immunity. (2014) 41(1): 63-74.
Van Stipdonk et al., "Naïve CTLs require a single brief period of antigenic stimulation for clonal expansion and differentiation." Nat Immunol. (2001) 2(5): 423-429.
Van Tendeloo et al., "High-level transgene expression in primary human T lymphocytes and adult bone marrow CD34+ cells via electroporation-mediated gene delivery," Gene Therapy (2000) 7(16): 1431-1437.
Vanhove et al., "Selective blockade of CD28 and not CTLA-4 with a single-chain Fv-alpha1-antitrypsin fusion antibody," Blood. (2003) 102(2): 564-570.

(56) References Cited

OTHER PUBLICATIONS

Varela-Rohena et al., "Control of HIV-1 immune escape by CD8 T cellsexpressing enhanced T-cell receptor," Nat Med. (2008) 14: 1390-1395.
Verhoeyen et al., "Lentiviral vector gene transfer into human T cells," Methods Mol Biol. (2009) 506: 97-114.
Vitale et al., "NK-active cytokines IL-2, IL-12, and IL-15 selectively modulate specific protein kinase C (PKC) isoforms in primary human NK cells," Anat Rec. (2002) 266(2): 87-92.
Vormittag et al., "A Guide to Manufacturing CAR T Cell Therapies," Curr Opin Biotechnol (2018) 53: 164-181.
Voss et al. "Mutagenesis of a flexible loop in Streptavidin Leads to Higher Affinity for the Strep-tag II Peptide and Improved Performance in Recombinant Protein Purification", ProteinEngineering (1997) 10(8): 975-982.
Wadhwa et al., "Receptor mediated glycotargeting," J. Drug Targeting (1995) 3(2):111-127.
Wang et al., "A transgene-encoded cell surface polypeptide for selection, in vivo tracking, and ablation of engineered cells," Blood (2011) 118(5):1255-1263.
Wang et al., "Clinical manufacturing of CAR T cells: foundation of a promising therapy," Mol Ther Oncolytics (2016) 3:16015.
Wang et al., "Dynamics of proximal signaling events after TCR/CD8-mediated induction of proliferation or apoptosis in mature CD8+ T cells." J. Immunol. (2008) 180(10); 6703-6712.
Wang et al., "Phenotypic and functional attributes of lentivirus-modified CD19-specific human CD8+ central memory T cells manufactured at clinical scale," J Immunother (2012) 35(9):689-701.
Wang et al., Database Biosis. Database accession No. PREV200900325303.Abstract Only Mar. 2009: 1 page.
Wang et al., Generation of leukaemia antigen-specific donor lymphocyte infusions powered by streptamer-based selection. Bone Marrow Transplantation Mar. 2009;43 (Suppl1):S73.
Wang et al., Open-Tubular Capillary Cell Affinity Chromatography: Single and Tandem Blood Cell Separation. Anal Chem. Mar. 15, 2008;80(6):2118-2124.
Wang et al: "Streptamer-based selection of VVT1-specific CD8+ T cells for specific donor lymphocyte infusions", Experimental Hematology, vol. 38, No. 11, Nov. 1, 2010 (Nov. 1, 2010 ), pp. 1066-1073.
Wigler et al., "Transfer of purified herpes virus thymidine kinase gene to cultured mouse cells," Cell (1977) 11: 223-232.
Wilson et al. "The Use of mRNA Display to Select High-Affinity Protein-Binding Peptides," Proc Natl Acad Sci USA (2001) 98(7): 3750-3755.
Wu et al., "Adoptive T-cell therapy using autologous tumor-infiltrating lymphocytes for metastatic melanoma: current status and future outlook," Cancer (2012) 18(2): 160-175.
Wu et al., "Engineering soluble monomeric streptavidin with reversible biotin binding capability", J. Biol. Chem.(2005) 280(24): 23225-23231.
Xu et al., "Closely related T-memory stem cells correlate with in vivo expansion of CAR.CD19-T cells and are preserved by IL-7 and IL-15," Blood (2014) 123(24): 3750-3759.
Xu et al., "Multiparameter comparative analysis reveals differential impacts of various cytokines on CART cell phenotypes and function ex vivo and in vivo," Oncotarget (2016) 7(50): 82354-82368.
Xu et al., Aptamer-Based Microfluidic Device for Enrichment, Sorting, and Detection of Multiple Cancer Cells. Anal Chem. Sep. 1, 2009;81(17):7436-7442.
Yang et al., "In vitro generated anti-tumor T lymphocytes exhibit distinct subsets mimicking in vivo antigen-experienced cells." Cancer Immunol Immunother (2011) 60(5): 739-749.
Yang et al., "Targeting lentiviral vectors to specific cell types in vivo," PNAS USA (2006) 103(31): 11479-11484.

Yarilin, "Immunology principles," M. Medicine (1999) 184-195, 339-347 (English Translation included).
Zhang et al., "A novel approach to make homogeneous protease-stable monovalent streptavidin", Biochem Biophys Res Commun. (2015) 463(4): 1059-1063.
Zhang et al., "CD137 promotes proliferation and survival of human B cells," J Immunol. (2010) 184(2): 787-795.
Zhang et al., "LAT: the ZAP-70 tyrosine kinase substrate that links T cell receptor to cellular activation," Cell (1998) 92(1):83-92.
Zhao et al., "Development of the First World Health Organization Lentiviral Vector Standard: Toward the Production Control and Standardization of Lentivirus-Based Gene Therapy Products," Hum Gene Ther Methods (2017) 28 (4): 205-214.
Zhou X et al., "Lentivirus-mediated gene transfer and expression in established human tumor antigen-specific cytotoxic T cells and primary unstimulated T cells," Hum Gene Ther. (2003) 14(11): 1089-1105.
Zufferey et al. "Self-Inactivating Lentivirus Vector for Safe and Efficient In Vivo Gene Delivery," J. Viral (1998) 72 (12):9873-9880.
Zufferey et al., "Woodchuck Hepatitis Virus Posttranscriptional Regulatory Element Enhances Expression of Transgenes Delivered by Retroviral Vectors," J Viral (1999) 73(4):2886-2892.
U.S. Appl. No. 18/045,137, filed Oct. 7, 2022, by Germeroth et al. (Copy not provided). (Copy not submitted herewith pursuant to the waiver of 37 C.F. R. § 1.98(a)(2)(iii) issued by the Office on Sep. 21, 2004).
Bostrom et al., "High affinity antigen recognition of the dual specific variants of herceptin is entropy-driven in spite of structural plasticity," PLoS One. (2011) 6(4):e17887.
Braun et al., "Rapid separation of T cell subpopulations with monoclonal antibodies and affinity chromatography," J Immunol Methods. (1982) 54(2):251-8.
Casati et al., "Clinical-scale selection and viral transduction of human naïve and central memory CD8+ T cells for adoptive cell therapy of cancer patients," Cancer Immunology (2013) 62(10): 1563- 1573.
Davis et al., "Assessment of a positive selection technique using an avidin column to isolate human peripheral blood T cell subsets," J Immunol Methods. (1994) 175(2):247-57.
Fernandes et al., "Kinetics of class II MHC expression on cytotoxic T cells generated by skin allograft," Tissue Antigens. (1990) 36(3):93-9.
Iyer et al., "Industrializing Autologous Adoptive Immunotherapies: Manufacturing Advances and Challenges," Front Med (Lausanne). (2018) 5:150.
Jethwa et al., "Use of gene-modified regulatory T-cells to control autoimmune and alloimmune pathology: Is now the right time?" Clin Immunology (2014) 150:51-63.
Kaikkonen et al., "(Strept)avidin-displaying lentiviruses as versatile tools for targeting and dual imaging of gene delivery," Gene Ther (2009) 16:894-904.
Katz et al., "Therapeutic targeting of CD19 in hematological malignancies: past, present, future and beyond," Leukemia & Lymphoma (2014) 55:999-1006.
Medvec et al., "Improved Expansion and In Vivo Function of Patient T Cells by a Serum-free Medium," Mol Ther Methods Clin Dev. (2017) 8:65-74.
Mei et al., "Rationale of anti-CD 19 immunotherapy: an option to target autoreactive plasma cells in autoimmunity," Arthritis Research & Therapy (2012) 14(Suppl 5):S1. p. 1-16.
Nesbeth et al., "Metabolic Biotinylation of Lentiviral Pseudotypes for Scalable Paramagnetic Microparticle-Dependent Manipulation," Mol Ther (2006) 13(4):814-822.
Smith et al., "Redirected infection of directly biotinylated recombinant adenovirus vectors through cell surface receptors and antigens," Proc Natl Acad Sci USA (1999) 8855-8860.

\* cited by examiner

FIG. 7
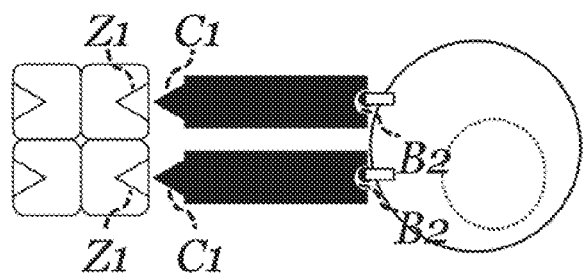
FIG. 7A
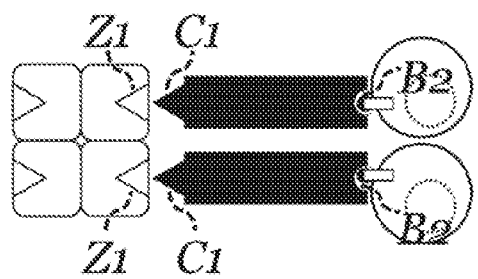
FIG. 7B
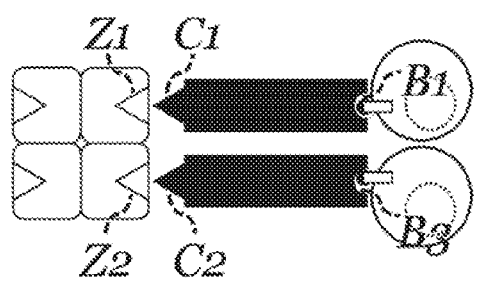
FIG. 7C
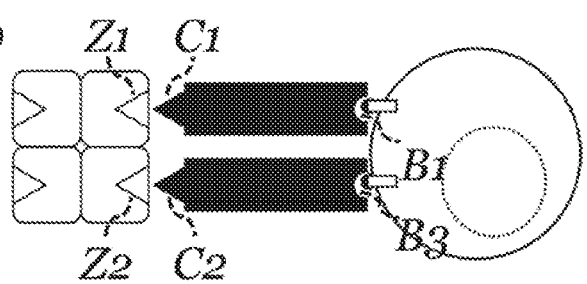
FIG. 7D
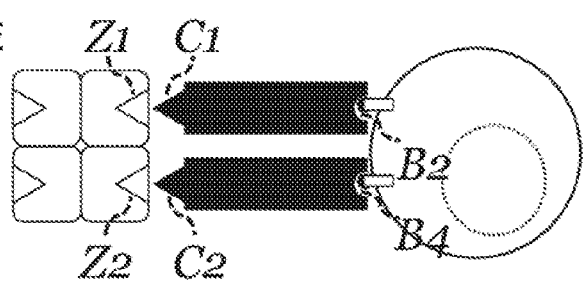
FIG. 7E

FIG. 8
FIG. 8A
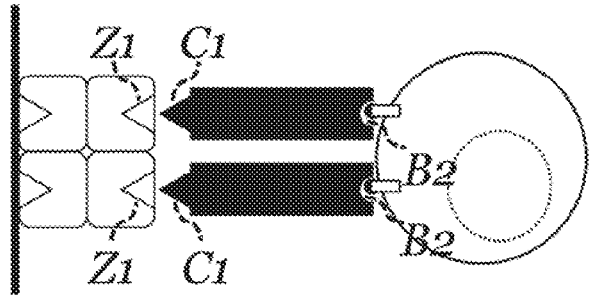
FIG. 8B
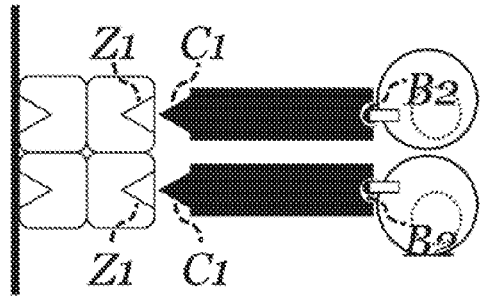
FIG. 8C
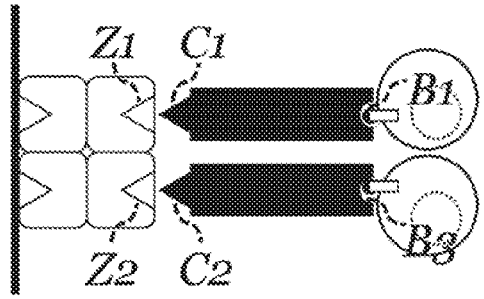
FIG. 8D
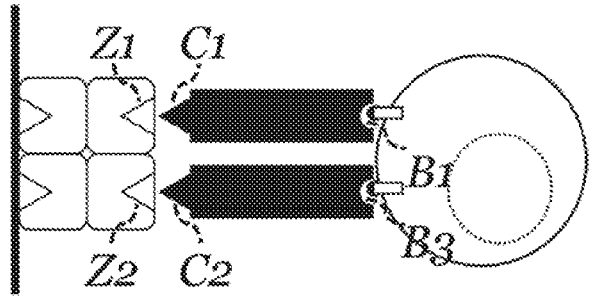
FIG. 8E
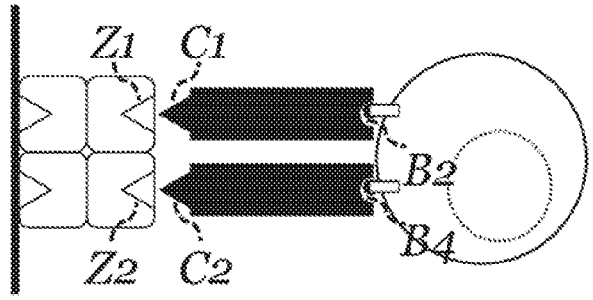

SEQUENCE LISTING

<160> NUMBER OF SEQ ID NOS: 63

<210> SEQ ID NO 1
<211> LENGTH: 159
<212> TYPE: PRT
<213> ORGANISM: Streptomyces avidinii
<220> FEATURE:
<223> OTHER INFORMATION: Streptavidin

<400> SEQUENCE: 1

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 2
<211> LENGTH: 126
<212> TYPE: PRT
<213> ORGANISM: Streptomyces avidinii
<220> FEATURE:
<223> OTHER INFORMATION: Minimal streptavidin

<400> SEQUENCE: 2

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

```
Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 3
<211> LENGTH: 159
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 3

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 4
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 4

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
```

```
                100             105               110
Gly His Asp Thr Phe Thr Lys Val Lys Pro Ser Ala Ala Ser
        115             120             125

<210> SEQ ID NO 5
<211> LENGTH: 159
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 5

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Ile Gly Ala Arg Gly
        35                  40                  45

Asn Ala Glu Ser Arg Tyr Val Leu Thr Gly Arg Tyr Asp Ser Ala Pro
50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 6
<211> LENGTH: 126
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 6

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ile Gly
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125
```

```
<210> SEQ ID NO 7
<211> LENGTH: 8
<212> TYPE: PRT
<213> ORGANISM: Artificial Sequence
<220> FEATURE:
<223> OTHER INFORMATION: Streptavidin binding peptide, Strep-tag

<400> SEQUENCE: 7

Trp Arg His Pro Gln Phe Gly Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Strep-tag

<400> SEQUENCE: 8

Trp Ser His Pro Gln Phe Glu Lys
1               5

<210> SEQ ID NO 9
<211> LENGTH: 3
<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: (3)...(3)
<223> OTHER INFORMATION: Xaa is selected from glutamine, asparagine and
      methionine

<400> SEQUENCE: 9

His Pro Xaa
1

<210> SEQ ID NO 10
<211> LENGTH: 4
<212> TYPE: PRT
<213> ORGANISM: Artificial Sequence
<220> FEATURE:
<223> OTHER INFORMATION: Streptavidin-binding peptide

<400> SEQUENCE: 10

His Pro Gln Phe
1

<210> SEQ ID NO 11
<211> LENGTH: 8
<212> TYPE: PRT
<213> ORGANISM: Artificial Sequence
<220> FEATURE:
<223> OTHER INFORMATION: Streptavidin-binding peptide
<220> FEATURE:
<221> NAME/KEY: VARIANT
<222> LOCATION: (1)...(1)
<223> OTHER INFORMATION: Xaa is Trp, Lys or Arg
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
```

```
<223> OTHER INFORMATION: Xaa is Gly, Lys or Arg

<400> SEQUENCE: 11

Xaa Xaa His Pro Gln Phe Xaa Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: Streptavidin-binding peptide
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg

<400> SEQUENCE: 12

Trp Xaa His Pro Gln Phe Xaa Xaa
1               5

<210> SEQ ID NO 13
<211> LENGTH: 17
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: VARIANT
<222> LOCATION: (9)...(9)
<223> OTHER INFORMATION: Xaa is any amino acid
<220> FEATURE:
<221> NAME/KEY: REPEAT
<222> LOCATION: (9)...(9)
<223> OTHER INFORMATION: Xaa is repeated 8 or 12 times

<400> SEQUENCE: 13

Trp Ser His Pro Gln Phe Glu Lys Xaa Trp Ser His Pro Gln Phe Glu
1               5                   10                  15

Lys

<210> SEQ ID NO 14
<211> LENGTH: 20
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: REPEAT
<222> LOCATION: (9)...(12)
<223> OTHER INFORMATION: repeated 2 or 3 times

<400> SEQUENCE: 14

Trp Ser His Pro Gln Phe Glu Lys Gly Gly Gly Ser Trp Ser His Pro
1               5                   10                  15

Gln Phe Glu Lys
            20

<210> SEQ ID NO 15
```

```
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 15

Ser Ala Trp Ser His Pro Gln Phe Glu Lys Gly Gly Gly Ser Gly Gly
1               5                   10                  15

Gly Ser Gly Gly Gly Ser Trp Ser His Pro Gln Phe Glu Lys
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 16

Ser Ala Trp Ser His Pro Gln Phe Glu Lys Gly Gly Gly Ser Gly Gly
1               5                   10                  15

Gly Ser Gly Gly Ser Ala Trp Ser His Pro Gln Phe Glu Lys
            20                  25                  30

<210> SEQ ID NO 17
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 17

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 18
<211> LENGTH: 24
<212> TYPE: PRT
<213> ORGANISM: Artificial Sequence
<220> FEATURE:
<223> OTHER INFORMATION: Twin-Strep-tag

<400> SEQUENCE: 18

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 19
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 19

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25
```

```
<210> SEQ ID NO 20
<211> LENGTH: 9
<212> TYPE: PRT
<213> ORGANISM: Artificial Sequence
<220> FEATURE:
<223> OTHER INFORMATION: HA-tag

<400> SEQUENCE: 20

Tyr Pro Tyr Asp Val Pro Asp Tyr Ala
1               5

<210> SEQ ID NO 21
<211> LENGTH: 11
<212> TYPE: PRT
<213> ORGANISM: Artificial Sequence
<220> FEATURE:
<223> OTHER INFORMATION: VSV-G-tag

<400> SEQUENCE: 21

Tyr Thr Asp Ile Glu Met Asn Arg Leu Gly Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: HSV-tag

<400> SEQUENCE: 22

Gln Pro Glu Leu Ala Pro Glu Asp Pro Glu Asp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: T7 epitope

<400> SEQUENCE: 23

Ala Ser Met Thr Gly Gly Gln Gln Met Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: HSV epitope

<400> SEQUENCE: 24

Glu Gln Lys Leu Ile Ser Glu Glu Asp Leu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Myc epitope

<400> SEQUENCE: 25

Glu Gln Lys Leu Ile Ser Glu Glu Asp Leu
1               5                   10

<210> SEQ ID NO 26
```

```
<211> LENGTH: 14
<212> TYPE: PRT
<213> ORGANISM: Artificial Sequence
<220> FEATURE:
<223> OTHER INFORMATION: V5-tag

<400> SEQUENCE: 26

Gly Lys Pro Ile Pro Asn Pro Leu Leu Gly Leu Asp Ser Thr
1               5                   10

<210> SEQ ID NO 27
<211> LENGTH: 126
<212> TYPE: PRT
<213> ORGANISM: Streptomyces avidinii
<220> FEATURE:
<223> OTHER INFORMATION: Mutein Streptavidin Ile44-Gly45-Ala-46-Arg47
      and Glu117, Gly120, Try121 (mutein m1-9)

<400> SEQUENCE: 27

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Tyr Ser Thr Leu Val
            100                 105                 110

Gly His Asp Thr Phe Thr Lys Val Lys Pro Ser Ala Ala Ser
        115                 120                 125

<210> SEQ ID NO 28
<211> LENGTH: 139
<212> TYPE: PRT
<213> ORGANISM: Streptomyces avidinii
<220> FEATURE:
<223> OTHER INFORMATION: Mutein Streptavidin Ile44-Gly45-Ala-46-Arg47
      and Glu117, Gly120, Try121 (mutein m1-9)

<400> SEQUENCE: 28

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Glu Asn Ala Gly Tyr Ser Thr Leu Val Gly His Asp
```

```
              115                 120                 125
Thr Phe Thr Lys Val Lys Pro Ser Ala Ala Ser
        130                 135

<210> SEQ ID NO 29
<211> LENGTH: 253
<212> TYPE: PRT
<213> ORGANISM: Artificial Sequence
<220> FEATURE:
<223> OTHER INFORMATION: Variable Heavy chain of Fab fragment m13B8.2

<400> SEQUENCE: 29

Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
            20                  25                  30

Thr Phe Gly Val His Trp Val Arg Gln Ser Pro Gly Lys Gly Leu Glu
        35                  40                  45

Trp Leu Gly Val Ile Trp Ala Ser Gly Ile Thr Asp Tyr Asn Val Pro
    50                  55                  60

Phe Met Ser Arg Leu Ser Ile Thr Lys Asp Asn Ser Lys Ser Gln Val
65                  70                  75                  80

Phe Phe Lys Leu Asn Ser Leu Gln Pro Asp Asp Thr Ala Ile Tyr Tyr
                85                  90                  95

Cys Ala Lys Asn Asp Pro Gly Thr Gly Phe Ala Tyr Trp Gly Gln Gly
            100                 105                 110

Thr Leu Val Thr Val Ser Ala Gly Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Ser
    210                 215                 220

Ala Trp Ser His Pro Gln Phe Glu Lys Gly Gly Gly Ser Gly Gly Gly
225                 230                 235                 240

Ser Gly Gly Ser Ala Trp Ser His Pro Gln Phe Glu Lys
                245                 250

<210> SEQ ID NO 30
<211> LENGTH: 218
<212> TYPE: PRT
<213> ORGANISM: Artificial Sequence
<220> FEATURE:
<223> OTHER INFORMATION: Variable Light chain of Fab Fragment m13B8.2

<400> SEQUENCE: 30

Ala Met Asp Ile Gln Met Thr Gln Ser Pro Ala Ser Leu Ser Ala Ser
1               5                   10                  15

Val Gly Glu Thr Val Thr Phe Cys Arg Ala Ser Glu Met Ile Tyr
            20                  25                  30
```

-continued

```
Ser Tyr Leu Ala Trp Tyr Gln Gln Lys Gln Lys Ser Pro Gln Leu
        35                  40                  45

Leu Val His Asp Ala Lys Thr Leu Ala Glu Gly Val Pro Ser Arg Phe
 50                  55                  60

Ser Gly Gly Ser Gly Thr Gln Phe Ser Leu Lys Ile Asn Thr Leu
 65                  70                  75                  80

Gln Pro Glu Asp Phe Gly Thr Tyr Tyr Cys Gln Ala His Tyr Gly Asn
                85                  90                  95

Pro Pro Thr Phe Gly Gly Gly Thr Lys Leu Glu Ile Lys Arg Gly Ile
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
            195                 200                 205

Lys Ser Phe Asn Arg Gly Glu Cys Gly Ser
            210                 215

<210> SEQ ID NO 31
<211> LENGTH: 119
<212> TYPE: PRT
<213> ORGANISM: Artificial Sequence
<220> FEATURE:
<223> OTHER INFORMATION: Variable Heavy chain of anti-CD3 antibody OKT3

<400> SEQUENCE: 31

Gln Val Gln Leu Gln Gln Ser Gly Ala Glu Leu Ala Arg Pro Gly Ala
 1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser
            115

<210> SEQ ID NO 32
<211> LENGTH: 106
<212> TYPE: PRT
<213> ORGANISM: Artificial Sequence
<220> FEATURE:
<223> OTHER INFORMATION: Variable Light chain of anti-CD3 antibody OKT3

<400> SEQUENCE: 32
```

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65              70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105
```

<210> SEQ ID NO 33
<211> LENGTH: 116
<212> TYPE: PRT
<213> ORGANISM: Artificial Sequence
<220> FEATURE:
<223> OTHER INFORMATION: Variable Heavy chain of anti-CD28 antibody
      CD28.3

<400> SEQUENCE: 33

```
Leu Gln Gln Ser Gly Ala Glu Leu Val Lys Pro Gly Ala Ser Val Arg
1               5                   10                  15

Leu Ser Cys Lys Ala Ser Gly Tyr Thr Phe Thr Glu Tyr Ile Ile His
                20                  25                  30

Trp Ile Lys Leu Arg Ser Gly Gln Gly Leu Glu Trp Ile Gly Trp Phe
            35                  40                  45

Tyr Pro Gly Ser Asn Asp Ile Gln Tyr Asn Ala Lys Phe Lys Gly Lys
        50                  55                  60

Ala Thr Leu Thr Ala Asp Lys Ser Ser Ser Thr Val Tyr Met Glu Leu
65              70                  75                  80

Thr Gly Leu Thr Ser Glu Asp Ser Ala Val Tyr Phe Cys Ala Arg Arg
                85                  90                  95

Asp Asp Phe Ser Gly Tyr Asp Ala Leu Pro Tyr Trp Gly Gln Gly Thr
            100                 105                 110

Met Val Thr Val
        115
```

<210> SEQ ID NO 34
<211> LENGTH: 108
<212> TYPE: PRT
<213> ORGANISM: Artificial Sequence
<220> FEATURE:
<223> OTHER INFORMATION: Variable Light chain of anti-CD28 antibody
      CD28.3

<400> SEQUENCE: 34

```
Asp Ile Gln Met Thr Gln Ser Pro Ala Ser Leu Ser Val Ser Val Gly
1               5                   10                  15

Glu Thr Val Thr Ile Thr Cys Arg Thr Asn Glu Asn Ile Tyr Ser Asn
                20                  25                  30

Leu Ala Trp Tyr Gln Gln Lys Gln Gly Lys Ser Pro Gln Leu Leu Ile
            35                  40                  45

Tyr Ala Ala Thr His Leu Val Glu Gly Val Pro Ser Arg Phe Ser Gly
        50                  55                  60
```

```
Ser Gly Ser Gly Thr Gln Tyr Ser Leu Lys Ile Thr Ser Leu Gln Ser
 65                  70                  75                  80

Glu Asp Phe Gly Asn Tyr Tyr Cys Gln His Phe Trp Gly Thr Pro Cys
                 85                  90                  95

Thr Phe Gly Gly Gly Thr Lys Leu Glu Ile Lys Arg
            100                 105
```

<210> SEQ ID NO 35
<211> LENGTH: 11
<212> TYPE: PRT
<213> ORGANISM: Artificial Sequence
<220> FEATURE:
<223> OTHER INFORMATION: MAT tag

<400> SEQUENCE: 35

```
His Asn His Arg His Lys His Gly Gly Gly Cys
 1               5                  10
```

<210> SEQ ID NO 36
<211> LENGTH: 1145
<212> TYPE: PRT
<213> ORGANISM: Homo sapiens
<220> FEATURE:
<223> OTHER INFORMATION: LFA-1alpha

<400> SEQUENCE: 36

```
Tyr Asn Leu Asp Val Arg Gly Ala Arg Ser Phe Ser Pro Pro Arg Ala
 1               5                  10                  15

Gly Arg His Phe Gly Tyr Arg Val Leu Gln Val Gly Asn Gly Val Ile
                 20                  25                  30

Val Gly Ala Pro Gly Glu Gly Asn Ser Thr Gly Ser Leu Tyr Gln Cys
             35                  40                  45

Gln Ser Gly Thr Gly His Cys Leu Pro Val Thr Leu Arg Gly Ser Asn
 50                  55                  60

Tyr Thr Ser Lys Tyr Leu Gly Met Thr Leu Ala Thr Asp Pro Thr Asp
 65                  70                  75                  80

Gly Ser Ile Leu Ala Cys Asp Pro Gly Leu Ser Arg Thr Cys Asp Gln
                 85                  90                  95

Asn Thr Tyr Leu Ser Gly Leu Cys Tyr Leu Phe Arg Gln Asn Leu Gln
                100                 105                 110

Gly Pro Met Leu Gln Gly Arg Pro Gly Phe Gln Glu Cys Ile Lys Gly
            115                 120                 125

Asn Val Asp Leu Val Phe Leu Phe Asp Gly Ser Met Ser Leu Gln Pro
130                 135                 140

Asp Glu Phe Gln Lys Ile Leu Asp Phe Met Lys Asp Val Met Lys Lys
145                 150                 155                 160

Leu Ser Asn Thr Ser Tyr Gln Phe Ala Ala Val Gln Phe Ser Thr Ser
                165                 170                 175

Tyr Lys Thr Glu Phe Asp Phe Ser Asp Tyr Val Lys Arg Lys Asp Pro
            180                 185                 190

Asp Ala Leu Leu Lys His Val Lys His Met Leu Leu Leu Thr Asn Thr
        195                 200                 205

Phe Gly Ala Ile Asn Tyr Val Ala Thr Glu Val Phe Arg Glu Glu Leu
    210                 215                 220

Gly Ala Arg Pro Asp Ala Thr Lys Val Leu Ile Ile Ile Thr Asp Gly
225                 230                 235                 240

Glu Ala Thr Asp Ser Gly Asn Ile Asp Ala Ala Lys Asp Ile Ile Arg
```

```
                    245                 250                 255
Tyr Ile Ile Gly Ile Gly Lys His Phe Gln Thr Lys Glu Ser Gln Glu
                260                 265                 270

Thr Leu His Lys Phe Ala Ser Lys Pro Ala Ser Glu Phe Val Lys Ile
                275                 280                 285

Leu Asp Thr Phe Glu Lys Leu Lys Asp Leu Phe Thr Glu Leu Gln Lys
            290                 295                 300

Lys Ile Tyr Val Ile Glu Gly Thr Ser Lys Gln Asp Leu Thr Ser Phe
305                 310                 315                 320

Asn Met Glu Leu Ser Ser Gly Ile Ser Ala Asp Leu Ser Arg Gly
                325                 330                 335

His Ala Val Val Gly Ala Val Gly Ala Lys Asp Trp Ala Gly Gly Phe
                340                 345                 350

Leu Asp Leu Lys Ala Asp Leu Gln Asp Thr Phe Ile Gly Asn Glu
            355                 360                 365

Pro Leu Thr Pro Glu Val Arg Ala Gly Tyr Leu Gly Tyr Thr Val Thr
        370                 375                 380

Trp Leu Pro Ser Arg Gln Lys Thr Ser Leu Leu Ala Ser Gly Ala Pro
385                 390                 395                 400

Arg Tyr Gln His Met Gly Arg Val Leu Leu Phe Gln Glu Pro Gln Gly
                    405                 410                 415

Gly Gly His Trp Ser Gln Val Gln Thr Ile His Gly Thr Gln Ile Gly
                420                 425                 430

Ser Tyr Phe Gly Gly Glu Leu Cys Gly Val Asp Val Asp Gln Asp Gly
            435                 440                 445

Glu Thr Glu Leu Leu Leu Ile Gly Ala Pro Leu Phe Tyr Gly Glu Gln
        450                 455                 460

Arg Gly Gly Arg Val Phe Ile Tyr Gln Arg Arg Gln Leu Gly Phe Glu
465                 470                 475                 480

Glu Val Ser Glu Leu Gln Gly Asp Pro Gly Tyr Pro Leu Gly Arg Phe
                485                 490                 495

Gly Glu Ala Ile Thr Ala Leu Thr Asp Ile Asn Gly Asp Gly Leu Val
                500                 505                 510

Asp Val Ala Val Gly Ala Pro Leu Glu Glu Gln Gly Ala Val Tyr Ile
            515                 520                 525

Phe Asn Gly Arg His Gly Gly Leu Ser Pro Gln Pro Ser Gln Arg Ile
        530                 535                 540

Glu Gly Thr Gln Val Leu Ser Gly Ile Gln Trp Phe Gly Arg Ser Ile
545                 550                 555                 560

His Gly Val Lys Asp Leu Glu Gly Asp Gly Leu Ala Asp Val Ala Val
                565                 570                 575

Gly Ala Glu Ser Gln Met Ile Val Leu Ser Ser Arg Pro Val Val Asp
                580                 585                 590

Met Val Thr Leu Met Ser Phe Ser Pro Ala Glu Ile Pro Val His Glu
            595                 600                 605

Val Glu Cys Ser Tyr Ser Thr Ser Asn Lys Met Lys Glu Gly Val Asn
        610                 615                 620

Ile Thr Ile Cys Phe Gln Ile Lys Ser Leu Ile Pro Gln Phe Gln Gly
625                 630                 635                 640

Arg Leu Val Ala Asn Leu Thr Tyr Thr Leu Gln Leu Asp Gly His Arg
                645                 650                 655

Thr Arg Arg Arg Gly Leu Phe Pro Gly Gly Arg His Glu Leu Arg Arg
                660                 665                 670
```

```
Asn Ile Ala Val Thr Thr Ser Met Ser Cys Thr Asp Phe Ser Phe His
            675                 680                 685

Phe Pro Val Cys Val Gln Asp Leu Ile Ser Pro Ile Asn Val Ser Leu
690                 695                 700

Asn Phe Ser Leu Trp Glu Glu Gly Thr Pro Arg Asp Gln Arg Ala
705                 710                 715                 720

Gln Gly Lys Asp Ile Pro Pro Ile Leu Arg Pro Ser Leu His Ser Glu
                725                 730                 735

Thr Trp Glu Ile Pro Phe Glu Lys Asn Cys Gly Glu Asp Lys Lys Cys
                740                 745                 750

Glu Ala Asn Leu Arg Val Ser Phe Ser Pro Ala Arg Ser Arg Ala Leu
            755                 760                 765

Arg Leu Thr Ala Phe Ala Ser Leu Ser Val Glu Leu Ser Leu Ser Asn
            770                 775                 780

Leu Glu Glu Asp Ala Tyr Trp Val Gln Leu Asp Leu His Phe Pro Pro
785                 790                 795                 800

Gly Leu Ser Phe Arg Lys Val Glu Met Leu Lys Pro His Ser Gln Ile
                805                 810                 815

Pro Val Ser Cys Glu Glu Leu Pro Glu Glu Ser Arg Leu Leu Ser Arg
                820                 825                 830

Ala Leu Ser Cys Asn Val Ser Ser Pro Ile Phe Lys Ala Gly His Ser
            835                 840                 845

Val Ala Leu Gln Met Met Phe Asn Thr Leu Val Asn Ser Ser Trp Gly
850                 855                 860

Asp Ser Val Glu Leu His Ala Asn Val Thr Cys Asn Asn Glu Asp Ser
865                 870                 875                 880

Asp Leu Leu Glu Asp Asn Ser Ala Thr Thr Ile Ile Pro Ile Leu Tyr
                885                 890                 895

Pro Ile Asn Ile Leu Ile Gln Asp Gln Glu Asp Ser Thr Leu Tyr Val
                900                 905                 910

Ser Phe Thr Pro Lys Gly Pro Lys Ile His Gln Val Lys His Met Tyr
            915                 920                 925

Gln Val Arg Ile Gln Pro Ser Ile His Asp His Asn Ile Pro Thr Leu
            930                 935                 940

Glu Ala Val Val Gly Val Pro Gln Pro Pro Ser Glu Gly Pro Ile Thr
945                 950                 955                 960

His Gln Trp Ser Val Gln Met Glu Pro Pro Val Pro Cys His Tyr Glu
                965                 970                 975

Asp Leu Glu Arg Leu Pro Asp Ala Ala Glu Pro Cys Leu Pro Gly Ala
                980                 985                 990

Leu Phe Arg Cys Pro Val Val Phe Arg Gln Glu Ile Leu Val Gln Val
            995                 1000                1005

Ile Gly Thr Leu Glu Leu Val Gly Glu Ile Glu Ala Ser Ser Met Phe
    1010                1015                1020

Ser Leu Cys Ser Ser Leu Ser Ile Ser Phe Asn Ser Ser Lys His Phe
1025                1030                1035                1040

His Leu Tyr Gly Ser Asn Ala Ser Leu Ala Gln Val Val Met Lys Val
            1045                1050                1055

Asp Val Val Tyr Glu Lys Gln Met Leu Tyr Leu Tyr Val Leu Ser Gly
            1060                1065                1070

Ile Gly Gly Leu Leu Leu Leu Leu Leu Ile Phe Ile Val Leu Tyr Lys
    1075                1080                1085
```

```
Val Gly Phe Phe Lys Arg Asn Leu Lys Glu Lys Met Glu Ala Gly Arg
    1090                1095                1100

Gly Val Pro Asn Gly Ile Pro Ala Glu Asp Ser Glu Gln Leu Ala Ser
1105                1110                1115                1120

Gly Gln Glu Ala Gly Asp Pro Gly Cys Leu Lys Pro Leu His Glu Lys
            1125                1130                1135

Asp Ser Glu Ser Gly Gly Gly Lys Asp
            1140                1145

<210> SEQ ID NO 37
<211> LENGTH: 747
<212> TYPE: PRT
<213> ORGANISM: Homo sapiens
<220> FEATURE:
<223> OTHER INFORMATION: LFA-1beta

<400> SEQUENCE: 37

Gln Glu Cys Thr Lys Phe Lys Val Ser Ser Cys Arg Glu Cys Ile Glu
1               5                   10                  15

Ser Gly Pro Gly Cys Thr Trp Cys Gln Lys Leu Asn Phe Thr Gly Pro
            20                  25                  30

Gly Asp Pro Asp Ser Ile Arg Cys Asp Thr Arg Pro Gln Leu Leu Met
        35                  40                  45

Arg Gly Cys Ala Ala Asp Asp Ile Met Asp Pro Thr Ser Leu Ala Glu
    50                  55                  60

Thr Gln Glu Asp His Asn Gly Gly Gln Lys Gln Leu Ser Pro Gln Lys
65                  70                  75                  80

Val Thr Leu Tyr Leu Arg Pro Gly Gln Ala Ala Ala Phe Asn Val Thr
                85                  90                  95

Phe Arg Arg Ala Lys Gly Tyr Pro Ile Asp Leu Tyr Tyr Leu Met Asp
            100                 105                 110

Leu Ser Tyr Ser Met Leu Asp Asp Leu Arg Asn Val Lys Lys Leu Gly
        115                 120                 125

Gly Asp Leu Leu Arg Ala Leu Asn Glu Ile Thr Glu Ser Gly Arg Ile
    130                 135                 140

Gly Phe Gly Ser Phe Val Asp Lys Thr Val Leu Pro Phe Val Asn Thr
145                 150                 155                 160

His Pro Asp Lys Leu Arg Asn Pro Cys Pro Asn Lys Glu Lys Glu Cys
                165                 170                 175

Gln Pro Pro Phe Ala Phe Arg His Val Leu Lys Leu Thr Asn Asn Ser
            180                 185                 190

Asn Gln Phe Gln Thr Glu Val Gly Lys Gln Leu Ile Ser Gly Asn Leu
        195                 200                 205

Asp Ala Pro Glu Gly Gly Leu Asp Ala Met Met Gln Val Ala Ala Cys
    210                 215                 220

Pro Glu Glu Ile Gly Trp Arg Asn Val Thr Arg Leu Leu Val Phe Ala
225                 230                 235                 240

Thr Asp Asp Gly Phe His Phe Ala Gly Asp Gly Lys Leu Gly Ala Ile
                245                 250                 255

Leu Thr Pro Asn Asp Gly Arg Cys His Leu Glu Asp Asn Leu Tyr Lys
            260                 265                 270

Arg Ser Asn Glu Phe Asp Tyr Pro Ser Val Gly Gln Leu Ala His Lys
        275                 280                 285

Leu Ala Glu Asn Asn Ile Gln Pro Ile Phe Ala Val Thr Ser Arg Met
    290                 295                 300
```

-continued

```
Val Lys Thr Tyr Glu Lys Leu Thr Glu Ile Ile Pro Lys Ser Ala Val
305                 310                 315                 320

Gly Glu Leu Ser Glu Asp Ser Ser Asn Val Val Gln Leu Ile Lys Asn
                325                 330                 335

Ala Tyr Asn Lys Leu Ser Ser Arg Val Phe Leu Asp His Asn Ala Leu
            340                 345                 350

Pro Asp Thr Leu Lys Val Thr Tyr Asp Ser Phe Cys Ser Asn Gly Val
        355                 360                 365

Thr His Arg Asn Gln Pro Arg Gly Asp Cys Asp Gly Val Gln Ile Asn
    370                 375                 380

Val Pro Ile Thr Phe Gln Val Lys Val Thr Ala Thr Glu Cys Ile Gln
385                 390                 395                 400

Glu Gln Ser Phe Val Ile Arg Ala Leu Gly Phe Thr Asp Ile Val Thr
                405                 410                 415

Val Gln Val Leu Pro Gln Cys Glu Cys Arg Cys Arg Asp Gln Ser Arg
            420                 425                 430

Asp Arg Ser Leu Cys His Gly Lys Gly Phe Leu Glu Cys Gly Ile Cys
        435                 440                 445

Arg Cys Asp Thr Gly Tyr Ile Gly Lys Asn Cys Glu Cys Gln Thr Gln
    450                 455                 460

Gly Arg Ser Ser Gln Glu Leu Glu Gly Ser Cys Arg Lys Asp Asn Asn
465                 470                 475                 480

Ser Ile Ile Cys Ser Gly Leu Gly Asp Cys Val Cys Gly Gln Cys Leu
                485                 490                 495

Cys His Thr Ser Asp Val Pro Gly Lys Leu Ile Tyr Gly Gln Tyr Cys
            500                 505                 510

Glu Cys Asp Thr Ile Asn Cys Glu Arg Tyr Asn Gly Gln Val Cys Gly
        515                 520                 525

Gly Pro Gly Arg Gly Leu Cys Phe Cys Gly Lys Cys Arg Cys His Pro
    530                 535                 540

Gly Phe Glu Gly Ser Ala Cys Gln Cys Glu Arg Thr Thr Glu Gly Cys
545                 550                 555                 560

Leu Asn Pro Arg Arg Val Glu Cys Ser Gly Arg Gly Arg Cys Arg Cys
                565                 570                 575

Asn Val Cys Glu Cys His Ser Gly Tyr Gln Leu Pro Leu Cys Gln Glu
            580                 585                 590

Cys Pro Gly Cys Pro Ser Pro Cys Gly Lys Tyr Ile Ser Cys Ala Glu
        595                 600                 605

Cys Leu Lys Phe Glu Lys Gly Pro Phe Gly Lys Asn Cys Ser Ala Ala
    610                 615                 620

Cys Pro Gly Leu Gln Leu Ser Asn Asn Pro Val Lys Gly Arg Thr Cys
625                 630                 635                 640

Lys Glu Arg Asp Ser Glu Gly Cys Trp Val Ala Tyr Thr Leu Glu Gln
                645                 650                 655

Gln Asp Gly Met Asp Arg Tyr Leu Ile Tyr Val Asp Glu Ser Arg Glu
            660                 665                 670

Cys Val Ala Gly Pro Asn Ile Ala Ala Ile Val Gly Gly Thr Val Ala
        675                 680                 685

Gly Ile Val Leu Ile Gly Ile Leu Leu Leu Val Ile Trp Lys Ala Leu
    690                 695                 700

Ile His Leu Ser Asp Leu Arg Glu Tyr Arg Arg Phe Glu Lys Glu Lys
705                 710                 715                 720

Leu Lys Ser Gln Trp Asn Asn Asp Asn Pro Leu Phe Lys Ser Ala Thr
```

725                 730                 735
Thr Thr Val Met Asn Pro Lys Phe Ala Glu Ser
            740                 745

<210> SEQ ID NO 38
<211> LENGTH: 344
<212> TYPE: PRT
<213> ORGANISM: Homo sapiens
<220> FEATURE:
<223> OTHER INFORMATION: L-selectin

<400> SEQUENCE: 38

Asp Phe Leu Ala His His Gly Thr Asp Cys Trp Thr Tyr His Tyr Ser
1               5                   10                  15

Glu Lys Pro Met Asn Trp Gln Arg Ala Arg Arg Phe Cys Arg Asp Asn
            20                  25                  30

Tyr Thr Asp Leu Val Ala Ile Gln Asn Lys Ala Glu Ile Glu Tyr Leu
        35                  40                  45

Glu Lys Thr Leu Pro Phe Ser Arg Ser Tyr Tyr Trp Ile Gly Ile Arg
    50                  55                  60

Lys Ile Gly Gly Ile Trp Thr Trp Val Gly Thr Asn Lys Ser Leu Thr
65                  70                  75                  80

Glu Glu Ala Glu Asn Trp Gly Asp Gly Glu Pro Asn Asn Lys Lys Asn
                85                  90                  95

Lys Glu Asp Cys Val Glu Ile Tyr Ile Lys Arg Asn Lys Asp Ala Gly
            100                 105                 110

Lys Trp Asn Asp Asp Ala Cys His Lys Leu Lys Ala Ala Leu Cys Tyr
        115                 120                 125

Thr Ala Ser Cys Gln Pro Trp Ser Cys Ser Gly His Gly Glu Cys Val
    130                 135                 140

Glu Ile Ile Asn Asn Tyr Thr Cys Asn Cys Asp Val Gly Tyr Tyr Gly
145                 150                 155                 160

Pro Gln Cys Gln Phe Val Ile Gln Cys Glu Pro Leu Glu Ala Pro Glu
                165                 170                 175

Leu Gly Thr Met Asp Cys Thr His Pro Leu Gly Asn Phe Ser Phe Ser
            180                 185                 190

Ser Gln Cys Ala Phe Ser Cys Ser Glu Gly Thr Asn Leu Thr Gly Ile
        195                 200                 205

Glu Glu Thr Thr Cys Gly Pro Phe Gly Asn Trp Ser Ser Pro Glu Pro
    210                 215                 220

Thr Cys Gln Val Ile Gln Cys Glu Pro Leu Ser Ala Pro Asp Leu Gly
225                 230                 235                 240

Ile Met Asn Cys Ser His Pro Leu Ala Ser Phe Ser Phe Thr Ser Ala
                245                 250                 255

Cys Thr Phe Ile Cys Ser Glu Gly Thr Glu Leu Ile Gly Lys Lys Lys
            260                 265                 270

Thr Ile Cys Glu Ser Ser Gly Ile Trp Ser Asn Pro Ser Pro Ile Cys
        275                 280                 285

Gln Lys Leu Asp Lys Ser Phe Ser Met Ile Lys Glu Gly Asp Tyr Asn
    290                 295                 300

Pro Leu Phe Ile Pro Val Ala Val Met Val Thr Ala Phe Ser Gly Leu
305                 310                 315                 320

Ala Phe Ile Ile Trp Leu Ala Arg Arg Leu Lys Lys Gly Lys Lys Ser
                325                 330                 335

Lys Arg Ser Met Asn Asp Pro Tyr

<210> SEQ ID NO 39
<211> LENGTH: 715
<212> TYPE: PRT
<213> ORGANISM: Homo sapiens
<220> FEATURE:
<223> OTHER INFORMATION: VCAM-1

<400> SEQUENCE: 39

```
Phe Lys Ile Glu Thr Thr Pro Glu Ser Arg Tyr Leu Ala Gln Ile Gly
1               5                   10                  15

Asp Ser Val Ser Leu Thr Cys Ser Thr Thr Gly Cys Glu Ser Pro Phe
            20                  25                  30

Phe Ser Trp Arg Thr Gln Ile Asp Ser Pro Leu Asn Gly Lys Val Thr
        35                  40                  45

Asn Glu Gly Thr Thr Ser Thr Leu Thr Met Asn Pro Val Ser Phe Gly
    50                  55                  60

Asn Glu His Ser Tyr Leu Cys Thr Ala Thr Cys Glu Ser Arg Lys Leu
65                  70                  75                  80

Glu Lys Gly Ile Gln Val Glu Ile Tyr Ser Phe Pro Lys Asp Pro Glu
                85                  90                  95

Ile His Leu Ser Gly Pro Leu Glu Ala Gly Lys Pro Ile Thr Val Lys
            100                 105                 110

Cys Ser Val Ala Asp Val Tyr Pro Phe Asp Arg Leu Glu Ile Asp Leu
        115                 120                 125

Leu Lys Gly Asp His Leu Met Lys Ser Gln Glu Phe Leu Glu Asp Ala
    130                 135                 140

Asp Arg Lys Ser Leu Glu Thr Lys Ser Leu Glu Val Thr Phe Thr Pro
145                 150                 155                 160

Val Ile Glu Asp Ile Gly Lys Val Leu Val Cys Arg Ala Lys Leu His
                165                 170                 175

Ile Asp Glu Met Asp Ser Val Pro Thr Val Arg Gln Ala Val Lys Glu
            180                 185                 190

Leu Gln Val Tyr Ile Ser Pro Lys Asn Thr Val Ile Ser Val Asn Pro
        195                 200                 205

Ser Thr Lys Leu Gln Glu Gly Gly Ser Val Thr Met Thr Cys Ser Ser
    210                 215                 220

Glu Gly Leu Pro Ala Pro Glu Ile Phe Trp Ser Lys Lys Leu Asp Asn
225                 230                 235                 240

Gly Asn Leu Gln His Leu Ser Gly Asn Ala Thr Leu Thr Leu Ile Ala
                245                 250                 255

Met Arg Met Glu Asp Ser Gly Ile Tyr Val Cys Glu Gly Val Asn Leu
            260                 265                 270

Ile Gly Lys Asn Arg Lys Glu Val Glu Leu Ile Val Gln Glu Lys Pro
        275                 280                 285

Phe Thr Val Glu Ile Ser Pro Gly Pro Arg Ile Ala Ala Gln Ile Gly
    290                 295                 300

Asp Ser Val Met Leu Thr Cys Ser Val Met Gly Cys Glu Ser Pro Ser
305                 310                 315                 320

Phe Ser Trp Arg Thr Gln Ile Asp Ser Pro Leu Ser Gly Lys Val Arg
                325                 330                 335

Ser Glu Gly Thr Asn Ser Thr Leu Thr Leu Ser Pro Val Ser Phe Glu
            340                 345                 350

Asn Glu His Ser Tyr Leu Cys Thr Val Thr Cys Gly His Lys Lys Leu
```

```
                355                 360                 365
Glu Lys Gly Ile Gln Val Glu Leu Tyr Ser Phe Pro Arg Asp Pro Glu
        370                 375                 380

Ile Glu Met Ser Gly Gly Leu Val Asn Gly Ser Ser Val Thr Val Ser
385                 390                 395                 400

Cys Lys Val Pro Ser Val Tyr Pro Leu Asp Arg Leu Glu Ile Glu Leu
                405                 410                 415

Leu Lys Gly Glu Thr Ile Leu Glu Asn Ile Glu Phe Leu Glu Asp Thr
            420                 425                 430

Asp Met Lys Ser Leu Glu Asn Lys Ser Leu Glu Met Thr Phe Ile Pro
        435                 440                 445

Thr Ile Glu Asp Thr Gly Lys Ala Leu Val Cys Gln Ala Lys Leu His
    450                 455                 460

Ile Asp Asp Met Glu Phe Glu Pro Lys Gln Arg Gln Ser Thr Gln Thr
465                 470                 475                 480

Leu Tyr Val Asn Val Ala Pro Arg Asp Thr Thr Val Leu Val Ser Pro
                485                 490                 495

Ser Ser Ile Leu Glu Glu Gly Ser Ser Val Asn Met Thr Cys Leu Ser
            500                 505                 510

Gln Gly Phe Pro Ala Pro Lys Ile Leu Trp Ser Arg Gln Leu Pro Asn
        515                 520                 525

Gly Glu Leu Gln Pro Leu Ser Glu Asn Ala Thr Leu Thr Leu Ile Ser
    530                 535                 540

Thr Lys Met Glu Asp Ser Gly Val Tyr Leu Cys Glu Gly Ile Asn Gln
545                 550                 555                 560

Ala Gly Arg Ser Arg Lys Glu Val Glu Leu Ile Ile Gln Val Thr Pro
                565                 570                 575

Lys Asp Ile Lys Leu Thr Ala Phe Pro Ser Glu Ser Val Lys Glu Gly
            580                 585                 590

Asp Thr Val Ile Ile Ser Cys Thr Cys Gly Asn Val Pro Glu Thr Trp
        595                 600                 605

Ile Ile Leu Lys Lys Lys Ala Glu Thr Gly Asp Thr Val Leu Lys Ser
    610                 615                 620

Ile Asp Gly Ala Tyr Thr Ile Arg Lys Ala Gln Leu Lys Asp Ala Gly
625                 630                 635                 640

Val Tyr Glu Cys Glu Ser Lys Asn Lys Val Gly Ser Gln Leu Arg Ser
                645                 650                 655

Leu Thr Leu Asp Val Gln Gly Arg Glu Asn Asn Lys Asp Tyr Phe Ser
            660                 665                 670

Pro Glu Leu Leu Val Leu Tyr Phe Ala Ser Ser Leu Ile Ile Pro Ala
        675                 680                 685

Ile Gly Met Ile Ile Tyr Phe Ala Arg Lys Ala Asn Met Lys Gly Ser
    690                 695                 700

Tyr Ser Leu Val Glu Ala Gln Lys Ser Lys Val
705                 710                 715

<210> SEQ ID NO 40
<211> LENGTH: 999
<212> TYPE: PRT
<213> ORGANISM: Homo sapiens
<220> FEATURE:
<223> OTHER INFORMATION: VLA-4

<400> SEQUENCE: 40

Tyr Asn Val Asp Thr Glu Ser Ala Leu Leu Tyr Gln Gly Pro His Asn
```

-continued

```
1               5                   10                  15
Thr Leu Phe Gly Tyr Ser Val Val Leu His Ser His Gly Ala Asn Arg
                20                  25                  30

Trp Leu Val Gly Ala Pro Thr Ala Asn Trp Leu Ala Asn Ala Ser
        35                  40                  45

Val Ile Asn Pro Gly Ala Ile Tyr Arg Cys Arg Ile Gly Lys Asn Pro
            50                  55                  60

Gly Gln Thr Cys Glu Gln Leu Gln Leu Gly Ser Pro Asn Gly Glu Pro
65                  70                  75                  80

Cys Gly Lys Thr Cys Leu Glu Glu Arg Asp Asn Gln Trp Leu Gly Val
                85                  90                  95

Thr Leu Ser Arg Gln Pro Gly Glu Asn Gly Ser Ile Val Thr Cys Gly
                100                 105                 110

His Arg Trp Lys Asn Ile Phe Tyr Ile Lys Asn Glu Asn Lys Leu Pro
            115                 120                 125

Thr Gly Gly Cys Tyr Gly Val Pro Pro Asp Leu Arg Thr Glu Leu Ser
        130                 135                 140

Lys Arg Ile Ala Pro Cys Tyr Gln Asp Tyr Val Lys Lys Phe Gly Glu
145                 150                 155                 160

Asn Phe Ala Ser Cys Gln Ala Gly Ile Ser Ser Phe Tyr Thr Lys Asp
                165                 170                 175

Leu Ile Val Met Gly Ala Pro Gly Ser Ser Tyr Trp Thr Gly Ser Leu
                180                 185                 190

Phe Val Tyr Asn Ile Thr Thr Asn Lys Tyr Lys Ala Phe Leu Asp Lys
            195                 200                 205

Gln Asn Gln Val Lys Phe Gly Ser Tyr Leu Gly Tyr Ser Val Gly Ala
        210                 215                 220

Gly His Phe Arg Ser Gln His Thr Thr Glu Val Val Gly Gly Ala Pro
225                 230                 235                 240

Gln His Glu Gln Ile Gly Lys Ala Tyr Ile Phe Ser Ile Asp Glu Lys
                245                 250                 255

Glu Leu Asn Ile Leu His Glu Met Lys Gly Lys Lys Leu Gly Ser Tyr
                260                 265                 270

Phe Gly Ala Ser Val Cys Ala Val Asp Leu Asn Ala Asp Gly Phe Ser
            275                 280                 285

Asp Leu Leu Val Gly Ala Pro Met Gln Ser Thr Ile Arg Glu Glu Gly
        290                 295                 300

Arg Val Phe Val Tyr Ile Asn Ser Gly Ser Gly Ala Val Met Asn Ala
305                 310                 315                 320

Met Glu Thr Asn Leu Val Gly Ser Asp Lys Tyr Ala Ala Arg Phe Gly
                325                 330                 335

Glu Ser Ile Val Asn Leu Gly Asp Ile Asp Asn Asp Gly Phe Glu Asp
                340                 345                 350

Val Ala Ile Gly Ala Pro Gln Glu Asp Asp Leu Gln Gly Ala Ile Tyr
            355                 360                 365

Ile Tyr Asn Gly Arg Ala Asp Gly Ile Ser Ser Thr Phe Ser Gln Arg
        370                 375                 380

Ile Glu Gly Leu Gln Ile Ser Lys Ser Leu Ser Met Phe Gly Gln Ser
385                 390                 395                 400

Ile Ser Gly Gln Ile Asp Ala Asp Asn Asn Gly Tyr Val Asp Val Ala
                405                 410                 415

Val Gly Ala Phe Arg Ser Asp Ser Ala Val Leu Leu Arg Thr Arg Pro
            420                 425                 430
```

```
Val Val Ile Val Asp Ala Ser Leu Ser His Pro Glu Ser Val Asn Arg
            435                 440                 445

Thr Lys Phe Asp Cys Val Glu Asn Gly Trp Pro Ser Val Cys Ile Asp
    450                 455                 460

Leu Thr Leu Cys Phe Ser Tyr Lys Gly Lys Glu Val Pro Gly Tyr Ile
465                 470                 475                 480

Val Leu Phe Tyr Asn Met Ser Leu Asp Val Asn Arg Lys Ala Glu Ser
                485                 490                 495

Pro Pro Arg Phe Tyr Phe Ser Ser Asn Gly Thr Ser Asp Val Ile Thr
                500                 505                 510

Gly Ser Ile Gln Val Ser Ser Arg Glu Ala Asn Cys Arg Thr His Gln
            515                 520                 525

Ala Phe Met Arg Lys Asp Val Arg Asp Ile Leu Thr Pro Ile Gln Ile
            530                 535                 540

Glu Ala Ala Tyr His Leu Gly Pro His Val Ile Ser Lys Arg Ser Thr
545                 550                 555                 560

Glu Glu Phe Pro Pro Leu Gln Pro Ile Leu Gln Gln Lys Lys Glu Lys
                565                 570                 575

Asp Ile Met Lys Lys Thr Ile Asn Phe Ala Arg Phe Cys Ala His Glu
                580                 585                 590

Asn Cys Ser Ala Asp Leu Gln Val Ser Ala Lys Ile Gly Phe Leu Lys
            595                 600                 605

Pro His Glu Asn Lys Thr Tyr Leu Ala Val Gly Ser Met Lys Thr Leu
            610                 615                 620

Met Leu Asn Val Ser Leu Phe Asn Ala Gly Asp Asp Ala Tyr Glu Thr
625                 630                 635                 640

Thr Leu His Val Lys Leu Pro Val Gly Leu Tyr Phe Ile Lys Ile Leu
                645                 650                 655

Glu Leu Glu Glu Lys Gln Ile Asn Cys Glu Val Thr Asp Asn Ser Gly
                660                 665                 670

Val Val Gln Leu Asp Cys Ser Ile Gly Tyr Ile Tyr Val Asp His Leu
            675                 680                 685

Ser Arg Ile Asp Ile Ser Phe Leu Leu Asp Val Ser Ser Leu Ser Arg
            690                 695                 700

Ala Glu Glu Asp Leu Ser Ile Thr Val His Ala Thr Cys Glu Asn Glu
705                 710                 715                 720

Glu Glu Met Asp Asn Leu Lys His Ser Arg Val Thr Val Ala Ile Pro
                725                 730                 735

Leu Lys Tyr Glu Val Lys Leu Thr Val His Gly Phe Val Asn Pro Thr
                740                 745                 750

Ser Phe Val Tyr Gly Ser Asn Asp Glu Asn Glu Pro Glu Thr Cys Met
            755                 760                 765

Val Glu Lys Met Asn Leu Thr Phe His Val Ile Asn Thr Gly Asn Ser
            770                 775                 780

Met Ala Pro Asn Val Ser Val Glu Ile Met Val Pro Asn Ser Phe Ser
785                 790                 795                 800

Pro Gln Thr Asp Lys Leu Phe Asn Ile Leu Asp Val Gln Thr Thr Thr
                805                 810                 815

Gly Glu Cys His Phe Glu Asn Tyr Gln Arg Val Cys Ala Leu Glu Gln
                820                 825                 830

Gln Lys Ser Ala Met Gln Thr Leu Lys Gly Ile Val Arg Phe Leu Ser
            835                 840                 845
```

```
Lys Thr Asp Lys Arg Leu Leu Tyr Cys Ile Lys Ala Asp Pro His Cys
    850                 855                 860

Leu Asn Phe Leu Cys Asn Phe Gly Lys Met Glu Ser Gly Lys Glu Ala
865                 870                 875                 880

Ser Val His Ile Gln Leu Glu Gly Arg Pro Ser Ile Leu Glu Met Asp
                885                 890                 895

Glu Thr Ser Ala Leu Lys Phe Glu Ile Arg Ala Thr Gly Phe Pro Glu
            900                 905                 910

Pro Asn Pro Arg Val Ile Glu Leu Asn Lys Asp Glu Asn Val Ala His
        915                 920                 925

Val Leu Leu Glu Gly Leu His His Gln Arg Pro Lys Arg Tyr Phe Thr
    930                 935                 940

Ile Val Ile Ile Ser Ser Leu Leu Leu Gly Leu Ile Val Leu Leu
945                 950                 955                 960

Leu Ile Ser Tyr Val Met Trp Lys Ala Gly Phe Phe Lys Arg Gln Tyr
                965                 970                 975

Lys Ser Ile Leu Gln Glu Glu Asn Arg Arg Asp Ser Trp Ser Tyr Ile
            980                 985                 990

Asn Ser Lys Ser Asn Asp Asp
        995
```

<210> SEQ ID NO 41
<211> LENGTH: 133
<212> TYPE: PRT
<213> ORGANISM: Homo sapiens
<220> FEATURE:
<223> OTHER INFORMATION: IL-2

<400> SEQUENCE: 41

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 42
<211> LENGTH: 129
<212> TYPE: PRT
<213> ORGANISM: Homo sapiens
<220> FEATURE:
<223> OTHER INFORMATION: IL-4

<400> SEQUENCE: 42

```
His Lys Cys Asp Ile Thr Leu Gln Glu Ile Ile Lys Thr Leu Asn Ser
1               5                   10                  15
```

```
Leu Thr Glu Gln Lys Thr Leu Cys Thr Glu Leu Thr Val Thr Asp Ile
             20                  25                  30

Phe Ala Ala Ser Lys Asn Thr Thr Glu Lys Glu Thr Phe Cys Arg Ala
         35                  40                  45

Ala Thr Val Leu Arg Gln Phe Tyr Ser His His Glu Lys Asp Thr Arg
     50                  55                  60

Cys Leu Gly Ala Thr Ala Gln Gln Phe His Arg His Lys Gln Leu Ile
 65                  70                  75                  80

Arg Phe Leu Lys Arg Leu Asp Arg Asn Leu Trp Gly Leu Ala Gly Leu
                 85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser
```

<210> SEQ ID NO 43
<211> LENGTH: 152
<212> TYPE: PRT
<213> ORGANISM: Homo sapiens
<220> FEATURE:
<223> OTHER INFORMATION: IL-7

<400> SEQUENCE: 43

```
Asp Cys Asp Ile Glu Gly Lys Asp Gly Lys Gln Tyr Glu Ser Val Leu
  1               5                  10                  15

Met Val Ser Ile Asp Gln Leu Leu Asp Ser Met Lys Glu Ile Gly Ser
             20                  25                  30

Asn Cys Leu Asn Asn Glu Phe Asn Phe Phe Lys Arg His Ile Cys Asp
         35                  40                  45

Ala Asn Lys Glu Gly Met Phe Leu Phe Arg Ala Ala Arg Lys Leu Arg
     50                  55                  60

Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 44
<211> LENGTH: 160
<212> TYPE: PRT
<213> ORGANISM: Homo sapiens
<220> FEATURE:
<223> OTHER INFORMATION: IL-10

<400> SEQUENCE: 44

```
Ser Pro Gly Gln Gly Thr Gln Ser Glu Asn Ser Cys Thr His Phe Pro
  1               5                  10                  15

Gly Asn Leu Pro Asn Met Leu Arg Asp Leu Arg Asp Ala Phe Ser Arg
             20                  25                  30
```

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
             100                 105                 110

Pro Cys Glu Asn Lys Ser Lys Ala Val Glu Gln Val Lys Asn Ala Phe
         115                 120                 125

Asn Lys Leu Gln Glu Lys Gly Ile Tyr Lys Ala Met Ser Glu Phe Asp
 130                 135                 140

Ile Phe Ile Asn Tyr Ile Glu Ala Tyr Met Thr Met Lys Ile Arg Asn
145                 150                 155                 160

<210> SEQ ID NO 45
<211> LENGTH: 133
<212> TYPE: PRT
<213> ORGANISM: Homo sapiens
<220> FEATURE:
<223> OTHER INFORMATION: IL-15

<400> SEQUENCE: 45

Gly Ile His Val Phe Ile Leu Gly Cys Phe Ser Ala Gly Leu Pro Lys
 1               5                  10                  15

Thr Glu Ala Asn Trp Val Asn Val Ile Ser Asp Leu Lys Lys Ile Glu
             20                  25                  30

Asp Leu Ile Gln Ser Met His Ile Asp Ala Thr Leu Tyr Thr Glu Ser
         35                  40                  45

Asp Val His Pro Ser Cys Lys Val Thr Ala Met Lys Cys Phe Leu Leu
 50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                 85                  90                  95

Gly Asn Val Thr Glu Ser Gly Cys Lys Glu Cys Glu Glu Leu Glu Glu
             100                 105                 110

Lys Asn Ile Lys Glu Phe Leu Gln Ser Phe Val His Ile Val Gln Met
         115                 120                 125

Phe Ile Asn Thr Ser
 130

<210> SEQ ID NO 46
<211> LENGTH: 132
<212> TYPE: PRT
<213> ORGANISM: Homo sapiens
<220> FEATURE:
<223> OTHER INFORMATION: IL-17

<400> SEQUENCE: 46

Gly Ile Thr Ile Pro Arg Asn Pro Gly Cys Pro Asn Ser Glu Asp Lys
 1               5                  10                  15

Asn Phe Pro Arg Thr Val Met Val Asn Leu Asn Ile His Asn Arg Asn
             20                  25                  30

Thr Asn Thr Asn Pro Lys Arg Ser Ser Asp Tyr Tyr Asn Arg Ser Thr

```
                    35                  40                  45

Ser Pro Trp Asn Leu His Arg Asn Glu Asp Pro Glu Arg Tyr Pro Ser
 50                  55                  60

Val Ile Trp Glu Ala Lys Cys Arg His Leu Gly Cys Ile Asn Ala Asp
 65                  70                  75                  80

Gly Asn Val Asp Tyr His Met Asn Ser Val Pro Ile Gln Gln Glu Ile
                     85                  90                  95

Leu Val Leu Arg Arg Glu Pro Pro His Cys Pro Asn Ser Phe Arg Leu
             100                 105                 110

Glu Lys Ile Leu Val Ser Val Gly Cys Thr Cys Val Thr Pro Ile Val
             115                 120                 125

His His Val Ala
        130

<210> SEQ ID NO 47
<211> LENGTH: 103
<212> TYPE: PRT
<213> ORGANISM: Homo sapiens
<220> FEATURE:
<223> OTHER INFORMATION: CXCL9

<400> SEQUENCE: 47

Thr Pro Val Val Arg Lys Gly Arg Cys Ser Cys Ile Ser Thr Asn Gln
 1                   5                  10                  15

Gly Thr Ile His Leu Gln Ser Leu Lys Asp Leu Lys Gln Phe Ala Pro
                     20                  25                  30

Ser Pro Ser Cys Glu Lys Ile Glu Ile Ile Ala Thr Leu Lys Asn Gly
             35                  40                  45

Val Gln Thr Cys Leu Asn Pro Asp Ser Ala Asp Val Lys Glu Leu Ile
 50                  55                  60

Lys Lys Trp Glu Lys Gln Val Ser Gln Lys Lys Lys Gln Lys Asn Gly
 65                  70                  75                  80

Lys Lys His Gln Lys Lys Val Leu Lys Val Arg Lys Ser Gln Arg
                     85                  90                  95

Ser Arg Gln Lys Lys Thr Thr
            100

<210> SEQ ID NO 48
<211> LENGTH: 77
<212> TYPE: PRT
<213> ORGANISM: Homo sapiens
<220> FEATURE:
<223> OTHER INFORMATION: CXCL10

<400> SEQUENCE: 48

Val Pro Leu Ser Arg Thr Val Arg Cys Thr Cys Ile Ser Ile Ser Asn
 1                   5                  10                  15

Gln Pro Val Asn Pro Arg Ser Leu Glu Lys Leu Glu Ile Ile Pro Ala
                     20                  25                  30

Ser Gln Phe Cys Pro Arg Val Glu Ile Ile Ala Thr Met Lys Lys Lys
             35                  40                  45

Gly Glu Lys Arg Cys Leu Asn Pro Glu Ser Lys Ala Ile Lys Asn Leu
 50                  55                  60

Leu Lys Ala Val Ser Lys Glu Arg Ser Lys Arg Ser Pro
 65                  70                  75

<210> SEQ ID NO 49
<211> LENGTH: 77
```

```
<212> TYPE: PRT
<213> ORGANISM: Homo sapiens
<220> FEATURE:
<223> OTHER INFORMATION: CCL19

<400> SEQUENCE: 49

Gly Thr Asn Asp Ala Glu Asp Cys Cys Leu Ser Val Thr Gln Lys Pro
1               5                   10                  15

Ile Pro Gly Tyr Ile Val Arg Asn Phe His Tyr Leu Leu Ile Lys Asp
            20                  25                  30

Gly Cys Arg Val Pro Ala Val Val Phe Thr Thr Leu Arg Gly Arg Gln
        35                  40                  45

Leu Cys Ala Pro Pro Asp Gln Pro Trp Val Glu Arg Ile Ile Gln Arg
50                  55                  60

Leu Gln Arg Thr Ser Ala Lys Met Lys Arg Arg Ser Ser
65                  70                  75

<210> SEQ ID NO 50
<211> LENGTH: 111
<212> TYPE: PRT
<213> ORGANISM: Homo sapiens
<220> FEATURE:
<223> OTHER INFORMATION: CCL21

<400> SEQUENCE: 50

Ser Asp Gly Gly Ala Gln Asp Cys Cys Leu Lys Tyr Ser Gln Arg Lys
1               5                   10                  15

Ile Pro Ala Lys Val Val Arg Ser Tyr Arg Lys Gln Glu Pro Ser Leu
            20                  25                  30

Gly Cys Ser Ile Pro Ala Ile Leu Phe Leu Pro Arg Lys Arg Ser Gln
        35                  40                  45

Ala Glu Leu Cys Ala Asp Pro Lys Glu Leu Trp Val Gln Gln Leu Met
50                  55                  60

Gln His Leu Asp Lys Thr Pro Ser Pro Gln Lys Pro Ala Gln Gly Cys
65                  70                  75                  80

Arg Lys Asp Arg Gly Ala Ser Lys Thr Gly Lys Lys Gly Lys Gly Ser
                85                  90                  95

Lys Gly Cys Lys Arg Thr Glu Arg Ser Gln Thr Pro Lys Gly Pro
            100                 105                 110

<210> SEQ ID NO 51
<211> LENGTH: 127
<212> TYPE: PRT
<213> ORGANISM: Homo sapiens
<220> FEATURE:
<223> OTHER INFORMATION: CCL25

<400> SEQUENCE: 51

Gln Gly Val Phe Glu Asp Cys Cys Leu Ala Tyr His Tyr Pro Ile Gly
1               5                   10                  15

Trp Ala Val Leu Arg Arg Ala Trp Thr Tyr Arg Ile Gln Glu Val Ser
            20                  25                  30

Gly Ser Cys Asn Leu Pro Ala Ala Ile Phe Tyr Leu Pro Lys Arg His
        35                  40                  45

Arg Lys Val Cys Gly Asn Pro Lys Ser Arg Glu Val Gln Arg Ala Met
        50                  55                  60

Lys Leu Leu Asp Ala Arg Asn Lys Val Phe Ala Lys Leu His His Asn
65                  70                  75                  80

Thr Gln Thr Phe Gln Ala Gly Pro His Ala Val Lys Lys Leu Ser Ser
```

85                  90                  95

Gly Asn Ser Lys Leu Ser Ser Lys Phe Ser Asn Pro Ile Ser Ser
                100                 105                 110

Ser Lys Arg Asn Val Ser Leu Leu Ile Ser Ala Asn Ser Gly Leu
        115                 120                 125

<210> SEQ ID NO 52
<211> LENGTH: 118
<212> TYPE: PRT
<213> ORGANISM: Artificial Sequence
<220> FEATURE:
<223> OTHER INFORMATION: anti-CD16 antibody 3G8 VH

<400> SEQUENCE: 52

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Arg Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ser
        115

<210> SEQ ID NO 53
<211> LENGTH: 111
<212> TYPE: PRT
<213> ORGANISM: Artificial Sequence
<220> FEATURE:
<223> OTHER INFORMATION: anti-CD16 antibody 3G8 VL

<400> SEQUENCE: 53

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110

<210> SEQ ID NO 54
<211> LENGTH: 1065
<212> TYPE: PRT
<213> ORGANISM: Artificial Sequence
<220> FEATURE:

<223> OTHER INFORMATION: LFA-1alpha Extracellular Domain (ECD)

<400> SEQUENCE: 54

```
Tyr Asn Leu Asp Val Arg Gly Ala Arg Ser Phe Ser Pro Pro Arg Ala
1               5                   10                  15

Gly Arg His Phe Gly Tyr Arg Val Leu Gln Val Gly Asn Gly Val Ile
            20                  25                  30

Val Gly Ala Pro Gly Glu Gly Asn Ser Thr Gly Ser Leu Tyr Gln Cys
        35                  40                  45

Gln Ser Gly Thr Gly His Cys Leu Pro Val Thr Leu Arg Gly Ser Asn
    50                  55                  60

Tyr Thr Ser Lys Tyr Leu Gly Met Thr Leu Ala Thr Asp Pro Thr Asp
65                  70                  75                  80

Gly Ser Ile Leu Ala Cys Asp Pro Gly Leu Ser Arg Thr Cys Asp Gln
                85                  90                  95

Asn Thr Tyr Leu Ser Gly Leu Cys Tyr Leu Phe Arg Gln Asn Leu Gln
            100                 105                 110

Gly Pro Met Leu Gln Gly Arg Pro Gly Phe Gln Glu Cys Ile Lys Gly
        115                 120                 125

Asn Val Asp Leu Val Phe Leu Phe Asp Gly Ser Met Ser Leu Gln Pro
130                 135                 140

Asp Glu Phe Gln Lys Ile Leu Asp Phe Met Lys Asp Val Met Lys Lys
145                 150                 155                 160

Leu Ser Asn Thr Ser Tyr Gln Phe Ala Ala Val Gln Phe Ser Thr Ser
                165                 170                 175

Tyr Lys Thr Glu Phe Asp Phe Ser Asp Tyr Val Lys Arg Lys Asp Pro
            180                 185                 190

Asp Ala Leu Leu Lys His Val Lys His Met Leu Leu Leu Thr Asn Thr
        195                 200                 205

Phe Gly Ala Ile Asn Tyr Val Ala Thr Glu Val Phe Arg Glu Glu Leu
    210                 215                 220

Gly Ala Arg Pro Asp Ala Thr Lys Val Leu Ile Ile Ile Thr Asp Gly
225                 230                 235                 240

Glu Ala Thr Asp Ser Gly Asn Ile Asp Ala Ala Lys Asp Ile Ile Arg
                245                 250                 255

Tyr Ile Ile Gly Ile Gly Lys His Phe Gln Thr Lys Glu Ser Gln Glu
            260                 265                 270

Thr Leu His Lys Phe Ala Ser Lys Pro Ala Ser Glu Phe Val Lys Ile
        275                 280                 285

Leu Asp Thr Phe Glu Lys Leu Lys Asp Leu Phe Thr Glu Leu Gln Lys
    290                 295                 300

Lys Ile Tyr Val Ile Glu Gly Thr Ser Lys Gln Asp Leu Thr Ser Phe
305                 310                 315                 320

Asn Met Glu Leu Ser Ser Ser Gly Ile Ser Ala Asp Leu Ser Arg Gly
                325                 330                 335

His Ala Val Val Gly Ala Val Gly Ala Lys Asp Trp Ala Gly Gly Phe
            340                 345                 350

Leu Asp Leu Lys Ala Asp Leu Gln Asp Asp Thr Phe Ile Gly Asn Glu
        355                 360                 365

Pro Leu Thr Pro Glu Val Arg Ala Gly Tyr Leu Gly Tyr Thr Val Thr
    370                 375                 380

Trp Leu Pro Ser Arg Gln Lys Thr Ser Leu Leu Ala Ser Gly Ala Pro
385                 390                 395                 400
```

-continued

```
Arg Tyr Gln His Met Gly Arg Val Leu Leu Phe Gln Glu Pro Gln Gly
            405                 410                 415

Gly Gly His Trp Ser Gln Val Gln Thr Ile His Gly Thr Gln Ile Gly
        420                 425                 430

Ser Tyr Phe Gly Gly Glu Leu Cys Gly Val Asp Val Asp Gln Asp Gly
        435                 440                 445

Glu Thr Glu Leu Leu Leu Ile Gly Ala Pro Leu Phe Tyr Gly Glu Gln
    450                 455                 460

Arg Gly Gly Arg Val Phe Ile Tyr Gln Arg Gln Leu Gly Phe Glu
465                 470                 475                 480

Glu Val Ser Glu Leu Gln Gly Asp Pro Gly Tyr Pro Leu Gly Arg Phe
            485                 490                 495

Gly Glu Ala Ile Thr Ala Leu Thr Asp Ile Asn Gly Asp Gly Leu Val
            500                 505                 510

Asp Val Ala Val Gly Ala Pro Leu Glu Glu Gln Gly Ala Val Tyr Ile
        515                 520                 525

Phe Asn Gly Arg His Gly Gly Leu Ser Pro Gln Pro Ser Gln Arg Ile
    530                 535                 540

Glu Gly Thr Gln Val Leu Ser Gly Ile Gln Trp Phe Gly Arg Ser Ile
545                 550                 555                 560

His Gly Val Lys Asp Leu Glu Gly Asp Gly Leu Ala Asp Val Ala Val
            565                 570                 575

Gly Ala Glu Ser Gln Met Ile Val Leu Ser Ser Arg Pro Val Val Asp
            580                 585                 590

Met Val Thr Leu Met Ser Phe Ser Pro Ala Glu Ile Pro Val His Glu
        595                 600                 605

Val Glu Cys Ser Tyr Ser Thr Ser Asn Lys Met Lys Glu Gly Val Asn
        610                 615                 620

Ile Thr Ile Cys Phe Gln Ile Lys Ser Leu Ile Pro Gln Phe Gln Gly
625                 630                 635                 640

Arg Leu Val Ala Asn Leu Thr Tyr Thr Leu Gln Leu Asp Gly His Arg
            645                 650                 655

Thr Arg Arg Arg Gly Leu Phe Pro Gly Gly Arg His Glu Leu Arg Arg
            660                 665                 670

Asn Ile Ala Val Thr Thr Ser Met Ser Cys Thr Asp Phe Ser Phe His
        675                 680                 685

Phe Pro Val Cys Val Gln Asp Leu Ile Ser Pro Ile Asn Val Ser Leu
    690                 695                 700

Asn Phe Ser Leu Trp Glu Glu Glu Gly Thr Pro Arg Asp Gln Arg Ala
705                 710                 715                 720

Gln Gly Lys Asp Ile Pro Pro Ile Leu Arg Pro Ser Leu His Ser Glu
            725                 730                 735

Thr Trp Glu Ile Pro Phe Glu Lys Asn Cys Gly Glu Asp Lys Lys Cys
        740                 745                 750

Glu Ala Asn Leu Arg Val Ser Phe Ser Pro Ala Arg Ser Arg Ala Leu
        755                 760                 765

Arg Leu Thr Ala Phe Ala Ser Leu Ser Val Glu Leu Ser Leu Ser Asn
    770                 775                 780

Leu Glu Glu Asp Ala Tyr Trp Val Gln Leu Asp Leu His Phe Pro Pro
785                 790                 795                 800

Gly Leu Ser Phe Arg Lys Val Glu Met Leu Lys Pro His Ser Gln Ile
            805                 810                 815

Pro Val Ser Cys Glu Glu Leu Pro Glu Glu Ser Arg Leu Leu Ser Arg
```

```
                820                 825                 830

Ala Leu Ser Cys Asn Val Ser Ser Pro Ile Phe Lys Ala Gly His Ser
            835                 840                 845

Val Ala Leu Gln Met Met Phe Asn Thr Leu Val Asn Ser Ser Trp Gly
850                 855                 860

Asp Ser Val Glu Leu His Ala Asn Val Thr Cys Asn Asn Glu Asp Ser
865                 870                 875                 880

Asp Leu Leu Glu Asp Asn Ser Ala Thr Thr Ile Ile Pro Ile Leu Tyr
            885                 890                 895

Pro Ile Asn Ile Leu Ile Gln Asp Gln Glu Asp Ser Thr Leu Tyr Val
            900                 905                 910

Ser Phe Thr Pro Lys Gly Pro Lys Ile His Gln Val Lys His Met Tyr
        915                 920                 925

Gln Val Arg Ile Gln Pro Ser Ile His Asp His Asn Ile Pro Thr Leu
    930                 935                 940

Glu Ala Val Val Gly Val Pro Gln Pro Pro Ser Glu Gly Pro Ile Thr
945                 950                 955                 960

His Gln Trp Ser Val Gln Met Glu Pro Pro Val Pro Cys His Tyr Glu
            965                 970                 975

Asp Leu Glu Arg Leu Pro Asp Ala Ala Glu Pro Cys Leu Pro Gly Ala
            980                 985                 990

Leu Phe Arg Cys Pro Val Val Phe Arg Gln Glu Ile Leu Val Gln Val
        995                1000                1005

Ile Gly Thr Leu Glu Leu Val Gly Glu Ile Glu Ala Ser Ser Met Phe
    1010                1015                1020

Ser Leu Cys Ser Ser Leu Ser Ile Ser Phe Asn Ser Ser Lys His Phe
1025                1030                1035                1040

His Leu Tyr Gly Ser Asn Ala Ser Leu Ala Gln Val Val Met Lys Val
            1045                1050                1055

Asp Val Val Tyr Glu Lys Gln Met Leu
            1060                1065

<210> SEQ ID NO 55
<211> LENGTH: 678
<212> TYPE: PRT
<213> ORGANISM: Artificial Sequence
<220> FEATURE:
<223> OTHER INFORMATION: LFA-1beta Extracellular Domain (ECD)

<400> SEQUENCE: 55

Gln Glu Cys Thr Lys Phe Lys Val Ser Ser Cys Arg Glu Cys Ile Glu
1               5                  10                  15

Ser Gly Pro Gly Cys Thr Trp Cys Gln Lys Leu Asn Phe Thr Gly Pro
            20                  25                  30

Gly Asp Pro Asp Ser Ile Arg Cys Asp Thr Arg Pro Gln Leu Leu Met
        35                  40                  45

Arg Gly Cys Ala Ala Asp Asp Ile Met Asp Pro Thr Ser Leu Ala Glu
    50                  55                  60

Thr Gln Glu Asp His Asn Gly Gly Gln Lys Gln Leu Ser Pro Gln Lys
65                  70                  75                  80

Val Thr Leu Tyr Leu Arg Pro Gly Gln Ala Ala Ala Phe Asn Val Thr
                85                  90                  95

Phe Arg Arg Ala Lys Gly Tyr Pro Ile Asp Leu Tyr Tyr Leu Met Asp
            100                 105                 110

Leu Ser Tyr Ser Met Leu Asp Asp Leu Arg Asn Val Lys Lys Leu Gly
```

-continued

```
            115                 120                 125
Gly Asp Leu Leu Arg Ala Leu Asn Glu Ile Thr Glu Ser Gly Arg Ile
    130                 135                 140

Gly Phe Gly Ser Phe Val Asp Lys Thr Val Leu Pro Phe Val Asn Thr
145                 150                 155                 160

His Pro Asp Lys Leu Arg Asn Pro Cys Pro Asn Lys Glu Lys Glu Cys
                165                 170                 175

Gln Pro Pro Phe Ala Phe Arg His Val Leu Lys Leu Thr Asn Asn Ser
            180                 185                 190

Asn Gln Phe Gln Thr Glu Val Gly Lys Gln Leu Ile Ser Gly Asn Leu
        195                 200                 205

Asp Ala Pro Glu Gly Gly Leu Asp Ala Met Met Gln Val Ala Ala Cys
    210                 215                 220

Pro Glu Glu Ile Gly Trp Arg Asn Val Thr Arg Leu Leu Val Phe Ala
225                 230                 235                 240

Thr Asp Asp Gly Phe His Phe Ala Gly Asp Gly Lys Leu Gly Ala Ile
                245                 250                 255

Leu Thr Pro Asn Asp Gly Arg Cys His Leu Glu Asp Asn Leu Tyr Lys
            260                 265                 270

Arg Ser Asn Glu Phe Asp Tyr Pro Ser Val Gly Gln Leu Ala His Lys
        275                 280                 285

Leu Ala Glu Asn Asn Ile Gln Pro Ile Phe Ala Val Thr Ser Arg Met
    290                 295                 300

Val Lys Thr Tyr Glu Lys Leu Thr Glu Ile Ile Pro Lys Ser Ala Val
305                 310                 315                 320

Gly Glu Leu Ser Glu Asp Ser Ser Asn Val Val Gln Leu Ile Lys Asn
                325                 330                 335

Ala Tyr Asn Lys Leu Ser Ser Arg Val Phe Leu Asp His Asn Ala Leu
            340                 345                 350

Pro Asp Thr Leu Lys Val Thr Tyr Asp Ser Phe Cys Ser Asn Gly Val
        355                 360                 365

Thr His Arg Asn Gln Pro Arg Gly Asp Cys Asp Gly Val Gln Ile Asn
    370                 375                 380

Val Pro Ile Thr Phe Gln Val Lys Val Thr Ala Thr Glu Cys Ile Gln
385                 390                 395                 400

Glu Gln Ser Phe Val Ile Arg Ala Leu Gly Phe Thr Asp Ile Val Thr
                405                 410                 415

Val Gln Val Leu Pro Gln Cys Glu Cys Arg Cys Arg Asp Gln Ser Arg
            420                 425                 430

Asp Arg Ser Leu Cys His Gly Lys Gly Phe Leu Glu Cys Gly Ile Cys
        435                 440                 445

Arg Cys Asp Thr Gly Tyr Ile Gly Lys Asn Cys Glu Cys Gln Thr Gln
    450                 455                 460

Gly Arg Ser Ser Gln Glu Leu Glu Gly Ser Cys Arg Lys Asp Asn Asn
465                 470                 475                 480

Ser Ile Ile Cys Ser Gly Leu Gly Asp Cys Val Cys Gly Gln Cys Leu
                485                 490                 495

Cys His Thr Ser Asp Val Pro Gly Lys Leu Ile Tyr Gly Gln Tyr Cys
            500                 505                 510

Glu Cys Asp Thr Ile Asn Cys Glu Arg Tyr Asn Gly Gln Val Cys Gly
        515                 520                 525

Gly Pro Gly Arg Gly Leu Cys Phe Cys Gly Lys Cys Arg Cys His Pro
    530                 535                 540
```

```
Gly Phe Glu Gly Ser Ala Cys Gln Cys Glu Arg Thr Thr Glu Gly Cys
545                 550                 555                 560

Leu Asn Pro Arg Arg Val Glu Cys Ser Gly Arg Gly Arg Cys Arg Cys
                565                 570                 575

Asn Val Cys Glu Cys His Ser Gly Tyr Gln Leu Pro Leu Cys Gln Glu
            580                 585                 590

Cys Pro Gly Cys Pro Ser Pro Cys Gly Lys Tyr Ile Ser Cys Ala Glu
        595                 600                 605

Cys Leu Lys Phe Glu Lys Gly Pro Phe Gly Lys Asn Cys Ser Ala Ala
    610                 615                 620

Cys Pro Gly Leu Gln Leu Ser Asn Asn Pro Val Lys Gly Arg Thr Cys
625                 630                 635                 640

Lys Glu Arg Asp Ser Glu Gly Cys Trp Val Ala Tyr Thr Leu Glu Gln
                645                 650                 655

Gln Asp Gly Met Asp Arg Tyr Leu Ile Tyr Val Asp Glu Ser Arg Glu
            660                 665                 670

Cys Val Ala Gly Pro Asn
        675

<210> SEQ ID NO 56
<211> LENGTH: 674
<212> TYPE: PRT
<213> ORGANISM: Artificial Sequence
<220> FEATURE:
<223> OTHER INFORMATION: VCAM-1 Extracellular Domain (ECD)

<400> SEQUENCE: 56

Phe Lys Ile Glu Thr Thr Pro Glu Ser Arg Tyr Leu Ala Gln Ile Gly
1               5                   10                  15

Asp Ser Val Ser Leu Thr Cys Ser Thr Thr Gly Cys Glu Ser Pro Phe
            20                  25                  30

Phe Ser Trp Arg Thr Gln Ile Asp Ser Pro Leu Asn Gly Lys Val Thr
        35                  40                  45

Asn Glu Gly Thr Thr Ser Thr Leu Thr Met Asn Pro Val Ser Phe Gly
50                  55                  60

Asn Glu His Ser Tyr Leu Cys Thr Ala Thr Cys Glu Ser Arg Lys Leu
65                  70                  75                  80

Glu Lys Gly Ile Gln Val Glu Ile Tyr Ser Phe Pro Lys Asp Pro Glu
                85                  90                  95

Ile His Leu Ser Gly Pro Leu Glu Ala Gly Lys Pro Ile Thr Val Lys
            100                 105                 110

Cys Ser Val Ala Asp Val Tyr Pro Phe Asp Arg Leu Glu Ile Asp Leu
        115                 120                 125

Leu Lys Gly Asp His Leu Met Lys Ser Gln Glu Phe Leu Glu Asp Ala
    130                 135                 140

Asp Arg Lys Ser Leu Glu Thr Lys Ser Leu Glu Val Thr Phe Thr Pro
145                 150                 155                 160

Val Ile Glu Asp Ile Gly Lys Val Leu Val Cys Arg Ala Lys Leu His
                165                 170                 175

Ile Asp Glu Met Asp Ser Val Pro Thr Val Arg Gln Ala Val Lys Glu
            180                 185                 190

Leu Gln Val Tyr Ile Ser Pro Lys Asn Thr Val Ile Ser Val Asn Pro
        195                 200                 205

Ser Thr Lys Leu Gln Glu Gly Gly Ser Val Thr Met Thr Cys Ser Ser
    210                 215                 220
```

```
Glu Gly Leu Pro Ala Pro Glu Ile Phe Trp Ser Lys Lys Leu Asp Asn
225                 230                 235                 240

Gly Asn Leu Gln His Leu Ser Gly Asn Ala Thr Leu Thr Leu Ile Ala
                245                 250                 255

Met Arg Met Glu Asp Ser Gly Ile Tyr Val Cys Glu Gly Val Asn Leu
            260                 265                 270

Ile Gly Lys Asn Arg Lys Glu Val Glu Leu Ile Val Gln Glu Lys Pro
        275                 280                 285

Phe Thr Val Glu Ile Ser Pro Gly Pro Arg Ile Ala Ala Gln Ile Gly
    290                 295                 300

Asp Ser Val Met Leu Thr Cys Ser Val Met Gly Cys Glu Ser Pro Ser
305                 310                 315                 320

Phe Ser Trp Arg Thr Gln Ile Asp Ser Pro Leu Ser Gly Lys Val Arg
                325                 330                 335

Ser Glu Gly Thr Asn Ser Thr Leu Thr Leu Ser Pro Val Ser Phe Glu
                340                 345                 350

Asn Glu His Ser Tyr Leu Cys Thr Val Thr Cys Gly His Lys Lys Leu
                355                 360                 365

Glu Lys Gly Ile Gln Val Glu Leu Tyr Ser Phe Pro Arg Asp Pro Glu
370                 375                 380

Ile Glu Met Ser Gly Gly Leu Val Asn Gly Ser Ser Val Thr Val Ser
385                 390                 395                 400

Cys Lys Val Pro Ser Val Tyr Pro Leu Asp Arg Leu Glu Ile Glu Leu
                405                 410                 415

Leu Lys Gly Glu Thr Ile Leu Glu Asn Ile Glu Phe Leu Glu Asp Thr
                420                 425                 430

Asp Met Lys Ser Leu Glu Asn Lys Ser Leu Glu Met Thr Phe Ile Pro
                435                 440                 445

Thr Ile Glu Asp Thr Gly Lys Ala Leu Val Cys Gln Ala Lys Leu His
    450                 455                 460

Ile Asp Asp Met Glu Phe Glu Pro Lys Gln Arg Gln Ser Thr Gln Thr
465                 470                 475                 480

Leu Tyr Val Asn Val Ala Pro Arg Asp Thr Thr Val Leu Val Ser Pro
                485                 490                 495

Ser Ser Ile Leu Glu Glu Gly Ser Ser Val Asn Met Thr Cys Leu Ser
                500                 505                 510

Gln Gly Phe Pro Ala Pro Lys Ile Leu Trp Ser Arg Gln Leu Pro Asn
                515                 520                 525

Gly Glu Leu Gln Pro Leu Ser Glu Asn Ala Thr Leu Thr Leu Ile Ser
                530                 535                 540

Thr Lys Met Glu Asp Ser Gly Val Tyr Leu Cys Glu Gly Ile Asn Gln
545                 550                 555                 560

Ala Gly Arg Ser Arg Lys Glu Val Glu Leu Ile Ile Gln Val Thr Pro
                565                 570                 575

Lys Asp Ile Lys Leu Thr Ala Phe Pro Ser Glu Ser Val Lys Glu Gly
                580                 585                 590

Asp Thr Val Ile Ile Ser Cys Thr Cys Gly Asn Val Pro Glu Thr Trp
                595                 600                 605

Ile Ile Leu Lys Lys Lys Ala Glu Thr Gly Asp Thr Val Leu Lys Ser
                610                 615                 620

Ile Asp Gly Ala Tyr Thr Ile Arg Lys Ala Gln Leu Lys Asp Ala Gly
625                 630                 635                 640
```

```
Val Tyr Glu Cys Glu Ser Lys Asn Lys Val Gly Ser Gln Leu Arg Ser
                645                 650                 655

Leu Thr Leu Asp Val Gln Gly Arg Glu Asn Asn Lys Asp Tyr Phe Ser
            660                 665                 670

Pro Glu

<210> SEQ ID NO 57
<211> LENGTH: 294
<212> TYPE: PRT
<213> ORGANISM: Artificial Sequence
<220> FEATURE:
<223> OTHER INFORMATION: L-selectin Extracellular Domain (ECD)

<400> SEQUENCE: 57

Trp Thr Tyr His Tyr Ser Glu Lys Pro Met Asn Trp Gln Arg Ala Arg
1               5                   10                  15

Arg Phe Cys Arg Asp Asn Tyr Thr Asp Leu Val Ala Ile Gln Asn Lys
                20                  25                  30

Ala Glu Ile Glu Tyr Leu Glu Lys Thr Leu Pro Phe Ser Arg Ser Tyr
            35                  40                  45

Tyr Trp Ile Gly Ile Arg Lys Ile Gly Gly Ile Trp Thr Trp Val Gly
50                  55                  60

Thr Asn Lys Ser Leu Thr Glu Glu Ala Glu Asn Trp Gly Asp Gly Glu
65                  70                  75                  80

Pro Asn Asn Lys Lys Asn Lys Glu Asp Cys Val Glu Ile Tyr Ile Lys
                85                  90                  95

Arg Asn Lys Asp Ala Gly Lys Trp Asn Asp Asp Ala Cys His Lys Leu
            100                 105                 110

Lys Ala Ala Leu Cys Tyr Thr Ala Ser Cys Gln Pro Trp Ser Cys Ser
        115                 120                 125

Gly His Gly Glu Cys Val Glu Ile Ile Asn Asn Tyr Thr Cys Asn Cys
    130                 135                 140

Asp Val Gly Tyr Tyr Gly Pro Gln Cys Gln Phe Val Ile Gln Cys Glu
145                 150                 155                 160

Pro Leu Glu Ala Pro Glu Leu Gly Thr Met Asp Cys Thr His Pro Leu
                165                 170                 175

Gly Asn Phe Ser Phe Ser Ser Gln Cys Ala Phe Ser Cys Ser Glu Gly
            180                 185                 190

Thr Asn Leu Thr Gly Ile Glu Glu Thr Thr Cys Gly Pro Phe Gly Asn
        195                 200                 205

Trp Ser Ser Pro Glu Pro Thr Cys Gln Val Ile Gln Cys Glu Pro Leu
    210                 215                 220

Ser Ala Pro Asp Leu Gly Ile Met Asn Cys Ser His Pro Leu Ala Ser
225                 230                 235                 240

Phe Ser Phe Thr Ser Ala Cys Thr Phe Ile Cys Ser Glu Gly Thr Glu
                245                 250                 255

Leu Ile Gly Lys Lys Lys Thr Ile Cys Glu Ser Ser Gly Ile Trp Ser
            260                 265                 270

Asn Pro Ser Pro Ile Cys Gln Lys Leu Asp Lys Ser Phe Ser Met Ile
        275                 280                 285

Lys Glu Gly Asp Tyr Asn
    290

<210> SEQ ID NO 58
<211> LENGTH: 943
<212> TYPE: PRT
```

<213> ORGANISM: Artificial Sequence
<220> FEATURE:
<223> OTHER INFORMATION: VLA-4 Extracellular Domain (ECD)

<400> SEQUENCE: 58

```
Asn Val Asp Thr Glu Ser Ala Leu Leu Tyr Gln Gly Pro His Asn Thr
1               5                   10                  15

Leu Phe Gly Tyr Ser Val Val Leu His Ser His Gly Ala Asn Arg Trp
            20                  25                  30

Leu Leu Val Gly Ala Pro Thr Ala Asn Trp Leu Ala Asn Ala Ser Val
        35                  40                  45

Ile Asn Pro Gly Ala Ile Tyr Arg Cys Arg Ile Gly Lys Asn Pro Gly
50                  55                  60

Gln Thr Cys Glu Gln Leu Gln Leu Gly Ser Pro Asn Gly Glu Pro Cys
65                  70                  75                  80

Gly Lys Thr Cys Leu Glu Arg Asp Asn Gln Trp Leu Gly Val Thr
                85                  90                  95

Leu Ser Arg Gln Pro Gly Glu Asn Gly Ser Ile Val Thr Cys Gly His
            100                 105                 110

Arg Trp Lys Asn Ile Phe Tyr Ile Lys Asn Glu Asn Lys Leu Pro Thr
        115                 120                 125

Gly Gly Cys Tyr Gly Val Pro Pro Asp Leu Arg Thr Glu Leu Ser Lys
130                 135                 140

Arg Ile Ala Pro Cys Tyr Gln Asp Tyr Val Lys Lys Phe Gly Glu Asn
145                 150                 155                 160

Phe Ala Ser Cys Gln Ala Gly Ile Ser Ser Phe Tyr Thr Lys Asp Leu
                165                 170                 175

Ile Val Met Gly Ala Pro Gly Ser Ser Tyr Trp Thr Gly Ser Leu Phe
            180                 185                 190

Val Tyr Asn Ile Thr Thr Asn Lys Tyr Lys Ala Phe Leu Asp Lys Gln
        195                 200                 205

Asn Gln Val Lys Phe Gly Ser Tyr Leu Gly Tyr Ser Val Gly Ala Gly
210                 215                 220

His Phe Arg Ser Gln His Thr Thr Glu Val Val Gly Gly Ala Pro Gln
225                 230                 235                 240

His Glu Gln Ile Gly Lys Ala Tyr Ile Phe Ser Ile Asp Glu Lys Glu
                245                 250                 255

Leu Asn Ile Leu His Glu Met Lys Gly Lys Lys Leu Gly Ser Tyr Phe
            260                 265                 270

Gly Ala Ser Val Cys Ala Val Asp Leu Asn Ala Asp Gly Phe Ser Asp
        275                 280                 285

Leu Leu Val Gly Ala Pro Met Gln Ser Thr Ile Arg Glu Glu Gly Arg
290                 295                 300

Val Phe Val Tyr Ile Asn Ser Gly Ser Gly Ala Val Met Asn Ala Met
305                 310                 315                 320

Glu Thr Asn Leu Val Gly Ser Asp Lys Tyr Ala Ala Arg Phe Gly Glu
                325                 330                 335

Ser Ile Val Asn Leu Gly Asp Ile Asp Asn Asp Gly Phe Glu Asp Val
            340                 345                 350

Ala Ile Gly Ala Pro Gln Glu Asp Asp Leu Gln Gly Ala Ile Tyr Ile
        355                 360                 365

Tyr Asn Gly Arg Ala Asp Gly Ile Ser Ser Thr Phe Ser Gln Arg Ile
370                 375                 380

Glu Gly Leu Gln Ile Ser Lys Ser Leu Ser Met Phe Gly Gln Ser Ile
```

```
                385              390              395              400
        Ser Gly Gln Ile Asp Ala Asp Asn Asn Gly Tyr Val Asp Val Ala Val
                        405              410              415

Gly Ala Phe Arg Ser Asp Ser Ala Val Leu Leu Arg Thr Arg Pro Val
                        420              425              430

Val Ile Val Asp Ala Ser Leu Ser His Pro Glu Ser Val Asn Arg Thr
                        435              440              445

Lys Phe Asp Cys Val Glu Asn Gly Trp Pro Ser Val Cys Ile Asp Leu
                        450              455              460

Thr Leu Cys Phe Ser Tyr Lys Gly Lys Glu Val Pro Gly Tyr Ile Val
        465              470              475              480

Leu Phe Tyr Asn Met Ser Leu Asp Val Asn Arg Lys Ala Glu Ser Pro
                        485              490              495

Pro Arg Phe Tyr Phe Ser Ser Asn Gly Thr Ser Asp Val Ile Thr Gly
                        500              505              510

Ser Ile Gln Val Ser Ser Arg Glu Ala Asn Cys Arg Thr His Gln Ala
                        515              520              525

Phe Met Arg Lys Asp Val Arg Asp Ile Leu Thr Pro Ile Gln Ile Glu
                        530              535              540

Ala Ala Tyr His Leu Gly Pro His Val Ile Ser Lys Arg Ser Thr Glu
        545              550              555              560

Glu Phe Pro Pro Leu Gln Pro Ile Leu Gln Gln Lys Lys Glu Lys Asp
                        565              570              575

Ile Met Lys Lys Thr Ile Asn Phe Ala Arg Phe Cys Ala His Glu Asn
                        580              585              590

Cys Ser Ala Asp Leu Gln Val Ser Ala Lys Ile Gly Phe Leu Lys Pro
                        595              600              605

His Glu Asn Lys Thr Tyr Leu Ala Val Gly Ser Met Lys Thr Leu Met
                        610              615              620

Leu Asn Val Ser Leu Phe Asn Ala Gly Asp Asp Ala Tyr Glu Thr Thr
        625              630              635              640

Leu His Val Lys Leu Pro Val Gly Leu Tyr Phe Ile Lys Ile Leu Glu
                        645              650              655

Leu Glu Glu Lys Gln Ile Asn Cys Glu Val Thr Asp Asn Ser Gly Val
                        660              665              670

Val Gln Leu Asp Cys Ser Ile Gly Tyr Ile Tyr Val Asp His Leu Ser
                        675              680              685

Arg Ile Asp Ile Ser Phe Leu Leu Asp Val Ser Ser Leu Ser Arg Ala
        690              695              700

Glu Glu Asp Leu Ser Ile Thr Val His Ala Thr Cys Glu Asn Glu Glu
        705              710              715              720

Glu Met Asp Asn Leu Lys His Ser Arg Val Thr Val Ala Ile Pro Leu
                        725              730              735

Lys Tyr Glu Val Lys Leu Thr Val His Gly Phe Val Asn Pro Thr Ser
                        740              745              750

Phe Val Tyr Gly Ser Asn Asp Glu Asn Glu Pro Glu Thr Cys Met Val
                        755              760              765

Glu Lys Met Asn Leu Thr Phe His Val Ile Asn Thr Gly Asn Ser Met
                        770              775              780

Ala Pro Asn Val Ser Val Glu Ile Met Val Pro Asn Ser Phe Ser Pro
        785              790              795              800

Gln Thr Asp Lys Leu Phe Asn Ile Leu Asp Val Gln Thr Thr Thr Gly
                        805              810              815
```

-continued

```
Glu Cys His Phe Glu Asn Tyr Gln Arg Val Cys Ala Leu Glu Gln Gln
            820                 825                 830

Lys Ser Ala Met Gln Thr Leu Lys Gly Ile Val Arg Phe Leu Ser Lys
        835                 840                 845

Thr Asp Lys Arg Leu Leu Tyr Cys Ile Lys Ala Asp Pro His Cys Leu
    850                 855                 860

Asn Phe Leu Cys Asn Phe Gly Lys Met Glu Ser Gly Lys Glu Ala Ser
865                 870                 875                 880

Val His Ile Gln Leu Glu Gly Arg Pro Ser Ile Leu Glu Met Asp Glu
                885                 890                 895

Thr Ser Ala Leu Lys Phe Glu Ile Arg Ala Thr Gly Phe Pro Glu Pro
            900                 905                 910

Asn Pro Arg Val Ile Glu Leu Asn Lys Asp Glu Asn Val Ala His Val
        915                 920                 925

Leu Leu Glu Gly Leu His His Gln Arg Pro Lys Arg Tyr Phe Thr
    930                 935                 940

<210> SEQ ID NO 59
<211> LENGTH: 127
<212> TYPE: PRT
<213> ORGANISM: Streptomyces avidinii
<220> FEATURE:
<223> OTHER INFORMATION: Minimal streptavidin

<400> SEQUENCE: 59

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 60
<211> LENGTH: 127
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 60

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Val
            20                  25                  30

Thr Ala Arg Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
```

```
                    50                  55                  60
Val Ala Trp Lys Asn Asn Tyr Arg Asn Ala His Ser Ala Thr Thr Trp
 65                  70                  75                  80

Ser Gly Gln Tyr Val Gly Gly Ala Glu Ala Arg Ile Asn Thr Gln Trp
                 85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 61
<211> LENGTH: 126
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 61

Glu Ala Gly Ile Thr Gly Thr Trp Tyr Asn Gln Leu Gly Ser Thr Phe
 1               5                  10                  15

Ile Val Thr Ala Gly Ala Asp Gly Ala Leu Thr Gly Thr Tyr Ile Gly
             20                  25                  30

Ala Arg Gly Asn Ala Glu Ser Arg Tyr Val Leu Thr Gly Arg Tyr Asp
         35                  40                  45

Ser Ala Pro Ala Thr Asp Gly Ser Gly Thr Ala Leu Gly Trp Thr Val
     50                  55                  60

Ala Trp Lys Asn Asn Tyr Arg Asn Ala His Ser Ala Thr Thr Trp Ser
 65                  70                  75                  80

Gly Gln Tyr Val Gly Gly Ala Glu Ala Arg Ile Asn Thr Gln Trp Leu
                 85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 62
<211> LENGTH: 4
<212> TYPE: PRT
<213> ORGANISM: Artificial Sequence
<220> FEATURE:
<223> OTHER INFORMATION: Streptavidin Mutein Residues

<400> SEQUENCE: 62

Val Thr Ala Arg
 1

<210> SEQ ID NO 63
<211> LENGTH: 4
<212> TYPE: PRT
<213> ORGANISM: Artificial Sequence
<220> FEATURE:
<223> OTHER INFORMATION: Streptavidin Mutein Residues

<400> SEQUENCE: 63

Ile Gly Ala Arg
 1
```

OLIGOMERIC PARTICLE REAGENTS AND METHODS OF USE THEREOF

CROSS-REFERENCE TO RELATED APPLICATIONS

This application is a U.S. National Stage of International Application No. PCT/IB2018/000507 filed Apr. 27, 2018, which claims the benefit of priority to U.S. provisional patent application 62/491,245, entitled "OLIGOMERIC PARTICLE REAGENTS AND METHODS OF USE THEREOF" filed on Apr. 27, 2017, the content of each of which is incorporated by reference in its entirety.

INCORPORATION BY REFERENCE OF SEQUENCE LISTING

The present application is being filed along with a Sequence Listing in electronic format. The Sequence Listing is provided as a file entitled 735042008500SeqList.txt, created May 10, 2023, which is 106,132 bytes in size. The information in the electronic format of the Sequence Listing is incorporated by reference in its entirety.

FIELD

The present disclosure provides oligomeric reagents, including oligomeric reagents of streptavidin or a streptavidin mutein, and compositions thereof and methods for manufacturing oligomeric reagents, including methods for reliably manufacturing oligomeric particle reagents of a desired size. In some cases, the reagents are oligomeric particle reagents containing a plurality of binding sites for agents, and thus the one or more agents, e.g., one or more selection agents or stimulatory reagents, are multimerized by reversibly binding to the oligomeric particle reagent, e.g., thereby creating a multimerized oligomeric particle reagent, having stimulatory or selection agents multimerized thereon. The present disclosure also provides methods for using the oligomeric reagents for incubation or culturing, such as to induce stimulation of expansion (proliferation), activation, costimulation and/or survival, of a composition of cells such as a population of lymphocytes. In some aspects, the disclosure provides methods and reagents for the stimulation, e.g., of expansion (proliferation), survival or persistence, activation, costimulation, or other effect (e.g. affinity selection), of cell populations that involve binding of agents to a molecule on the surface of the cells, thereby providing one or more signals to the cells.

BACKGROUND

Various strategies are available for stimulating T cell populations in vitro, including for expanding antigen-specific T cells in vitro for use in adoptive cellular immunotherapy or cancer therapy in which infusions of such T cells have been shown to have anti-tumor reactivity in a tumor-bearing host or for use to treat viral infections. Improved strategies are needed for expanding cell populations in vitro, including for research, diagnostic and therapeutic purposes.

SUMMARY

Provided herein are an oligomeric particle reagents comprising a plurality of streptavidin or streptavidin mutein molecules, wherein the size of the oligomeric particle reagent comprises i) a radius, e.g., a hydrodynamic radius, of greater than 25 nm, ii) a molecular weight of at least $5 \times 10^6$ g/mol; and/or (iii) at least 100 streptavidin or streptavidin mutein tetramers per oligomeric particle reagent.

In particular embodiments of any of the oligomeric particle reagents provided herein, the streptavidin or streptavidin mutein molecules bind to or are capable of binding to biotin, a biotin analog (e.g. desthiobiotin, iminobiotin) or to a streptavidin binding peptide (e.g. Strep-tagII (WSHPQFEK, SEQ ID NO:8)). In certain embodiments of any of the oligomeric particle reagents provided herein, the streptavidin or streptavidin mutein molecules reversibly bind to or are capable of reversibly binding to biotin, a biotin analog or to a streptavidin binding peptide (e.g. Strep-tagII (WSHPQFEK, SEQ ID NO:8)). In some embodiments of any of the oligomeric particle reagents provided herein, the oligomeric particle reagent comprises a plurality of streptavidin mutein molecules, wherein the streptavidin mutein molecules comprise the amino acid sequence $Val^{44}$-$Thr^{45}$-$Ala^{46}$-$Arg^{47}$ (SEQ ID NO: 62) or $Ile^{44}$-$Gly^{45}$-$Ala^{46}$-$Arg^{47}$ (SEQ ID NO: 63) at sequence positions corresponding to positions 44 to 47 with reference to positions in streptavidin in the sequence of amino acids set forth in SEQ ID NO: 1.

In particular embodiments of any of the oligomeric particle reagents provided herein, the streptavidin or streptavidin mutein molecules bind to or are capable of binding to biotin, avidin, a biotin analog or mutein, an avidin analog or mutein, and/or a biologically active fragment thereof. In certain embodiments of any of the oligomeric particle reagents provided herein, the streptavidin or streptavidin mutein molecules reversibly bind to or are capable of reversibly binding to biotin, avidin, a biotin analog or mutein, an avidin analog or mutein, and/or a biologically active fragment thereof. In some embodiments of any of the oligomeric particle reagents provided herein, the oligomeric particle reagent comprises a plurality of streptavidin mutein molecules, wherein the streptavidin mutein molecules comprise the amino acid sequence $Val^{44}$-$Thr^{45}$-$Ala^{46}$-$Arg^{47}$ (SEQ ID NO: 62) or $Ile^{44}$-$Gly^{45}$-$Ala^{46}$-$Arg^{47}$ (SEQ ID NO: 63) at sequence positions corresponding to positions 44 to 47 with reference to positions in streptavidin in the sequence of amino acids set forth in SEQ ID NO: 1.

In particular embodiments of any of the oligomeric particle reagents provided herein, the oligomeric particle reagent comprises a plurality of streptavidin mutein molecules that comprise: a) the sequence of amino acids set forth in any of SEQ ID NOS: 3-6, 27, 28, 60, or 61; b) a sequence of amino acids that exhibit at least 85%, 86%, 87%, 88%, 89%, 89%, 90%, 91%, 92%, 93%, 94%, 95%, 96%, 97%, 98%, 99% or more sequence identity to any of SEQ ID NOS: 3-6, 27, 28, 60, or 61 and contain the amino acid sequence corresponding to $Val^{4}$-$Thr^{45}$-$Ala^{46}$-$Ag^{47}$ (SEQ ID NO: 62) or $Ile^{44}$-$Gly^{45}$-$Ala^{46}$-$Ag^{47}$ (SEQ ID NO: 63) and/or reversibly bind to biotin, a biotin analog or a streptavidin-binding peptide; or and/or a sequence of amino acids that exhibit at least 85%, 86%, 87%, 88%, 89%, 89%, 90%, 91%, 92%, 93%, 94%, 95%, 96%, 97%, 98%, 99% or more sequence identity to any of SEQ ID NOS: 3-6, 27, 28, 60, or 61 and contain the amino acid sequence corresponding to $Val^{44}$-$Thr^{45}$-$Ala^{46}$-$Arg^{47}$ (SEQ ID NO: 62) or $Ile^{44}$-$Gly^{45}$-$Ala^{46}$-$Ag^{47}$ (SEQ ID NO: 63) and/or binds to biotin or a biologically active form thereof, a biotin analog or mutein or a biologically active fragment thereof or a streptavidin-binding peptide) a functional fragment of a) or b) that binds to biotin or a biologically active form thereof, a biotin analog or mutein or a biologically active fragment thereof or a streptavidin-binding peptide and/or reversibly bind to biotin, a biotin analog or a streptavidin-binding peptide; or c) a functional fragment of a) or b) that binds to biotin, a biotin analog or a streptavidin-binding peptide.. In certain embodiments of any of the oligomeric particle reagents provided herein, wherein the oligomeric particle reagent comprises a plurality of streptavidin mutein molecules that comprise the sequence of amino acids set forth in SEQ ID NO: 6 or 61. In some embodiments of any of the oligomeric particle reagents provided herein, the streptavidin mutein molecule further comprises an amino acid replacement or replacements at a position corresponding to 117, 120 and/or 121 with reference to positions in streptavidin in the sequence of amino acids set forth in SEQ ID NO: 1.

In particular embodiments of any of the oligomeric particle reagents provided herein: the amino acid replacement or replacements are selected from among Glu117, Asp117, Arg117, Ser120, Ala120, Gly120, Trp121, Tyr121 or Phe121; or the amino acid replacement or replacements are selected from one or more of Glu117, Gly120 or Tyr121; or the amino acid replacements are selected from Glu117, Gly120 or Tyr121. In certain embodiments of any of the oligomeric particle reagents provided herein, the oligomeric particle reagent comprises a plurality of streptavidin mutein molecules that comprise: a) the sequence of amino acids set forth in SEQ ID NO: 27 or 28; b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NO: 28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and/or binds to biotin or a biologically active fragment, a biotin analog or mutein or a biologically active fragment thereof or a streptavidin-binding peptide; or c) a functional fragment of a) or b) that binds to biotin or a biologically active fragment, a biotin analog or mutein or a biologically active fragment thereof or a streptavidin-binding peptide.

In particular embodiments of any of the oligomeric particle reagents provided herein: the amino acid replacement or replacements are selected from among Glu117, Asp117, Arg117, Ser120, Ala120, Gly120, Trp121, Tyr121 or Phe121; or the amino acid replacement or replacements are selected from one or more of Glu117, Gly120 or Tyr121; or the amino acid replacements are selected from Glu117, Gly120 or Tyr121. In certain embodiments of any of the oligomeric particle reagents provided herein, the oligomeric particle reagent comprises a plurality of streptavidin mutein molecules that comprise: a) the sequence of amino acids set forth in SEQ ID NO: 27 or 28; b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NO: 28 and contains the amino acid sequence corresponding to Val$^{44}$, Thr$^{45}$, Ala$^{46}$, Arg$^{47}$, Glu$^{117}$, Gly$^{120}$ and Tyr$^{121}$ and/or reversibly binds to biotin, a biotin analog or a streptavidin-binding peptide; or c) a functional fragment of a) or b) that reversibly binds to biotin, a biotin analog or a streptavidin-binding peptide.

In some embodiments of any of the oligomeric particle reagents provided herein, the oligomeric particle reagent is bound to or is capable of binding to one or more agents via a binding partner, in which the one or more agents comprise the binding partner, such as biotin, a biotin analog or a streptavidin binding peptide. In particular embodiments of any of the oligomeric particle reagents provided herein, the one or more agents comprise a binding partner, wherein the binding partner is capable of binding to one or more binding site on the oligomeric particle reagent. In certain embodiments of any of the oligomeric particle reagents provided herein, the binding partner comprises a streptavidin-binding peptide or biotin or a biotin analog. In some embodiments of any of the oligomeric particle reagents provided herein, the binding partner comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19). In particular embodiments of any of the oligomeric particle reagents provided herein, the one or more agents binds or is further capable of binding to a molecule expressed on the surface of a target cell. In certain embodiments of any of the oligomeric particle reagents provided herein, the one or more agents comprises an antibody, optionally a Fab or a nanobody®, for example a single domain antibody (sdAb).

In some embodiments of any of the oligomeric particle reagents provided herein, the one or more agents is a receptor binding agent that binds to or is capable of binding to a receptor expressed on the surface of a target cell. In particular embodiments of any of the oligomeric particle reagents provided herein, the receptor binding agent is or comprises a stimulatory agent capable of binding to a molecule on the surface of a target cell, thereby inducing or modulating a signal in the target cell. In certain embodiments of any of the oligomeric particle reagents provided herein, the receptor-binding agent is capable of initiating a TCR/CD3 complex-associated signal in T cells, binds to a member of a TCR/CD3 complex; and/or specifically binds to CD3. In some embodiments of any of the oligomeric particle reagents provided herein, the stimulatory agent is a first receptor-binding agent and the oligomeric particle reagent comprises a second receptor-binding agent, wherein the second receptor-binding agent is capable of specifically binding to a second molecule on the surface of the target cell, which binding to the second molecule is optionally capable of inducing or modulating a signal in the target cells.

In particular embodiments of any of the oligomeric particle reagents provided herein, the second receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule. In certain embodiments of any of the oligomeric particle reagents provided herein, the receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

In some embodiments of any of the oligomeric particle reagents provided herein, the receptor-binding agent (second receptor-binding agent) binds to a costimulatory or accessory molecule and the costimulatory or accessory molecule is selected from CD28, CD90 (Thy-1), CD95 (Apo-/Fas), CD137 (4-1BB), CD154 (CD40L), ICOS, LAT, CD27, OX40 or HVEM.

In particular embodiments of any of the oligomeric particle reagents provided herein, the receptor-binding agent (second receptor-binding agent) specifically binds to a cytokine receptor and the cytokine receptor is selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2. In certain embodiments of any of the oligomeric particle reagents provided herein, the receptor-binding agent (second receptor-binding agent) specifically binds to a chemokine receptor and the chemokine receptor is selected from among CCR1, CCR2, CCR3, CCR4, CCR5, CCR7, CCR9, CXCR1, CXCR3 and CXCR4.

In some embodiments of any of the oligomeric particle reagents provided herein, the receptor-binding agent (second receptor-binding agent) is a factor that induces cytokine or chemokine production and the factor is a ligand that specifically binds to a cytokine or chemokine receptor.

In particular embodiments of any of the oligomeric particle reagents provided herein, the receptor-binding agent (second receptor-binding agent) is a ligand that specifically binds to a cytokine receptor, wherein the ligand specifically binds IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the ligand is selected from among IL-2, IL-1, IL-15, IFN-gamma, TNF-alpha, IL-4, IL-10, IL-12, IL-15, IL-17 and TNF, or is a biologically active fragment thereof.

In certain embodiments of any of the oligomeric particle reagents provided herein, the receptor-binding agent (second receptor-binding agent) is a ligand that specifically binds to a chemokine receptor, wherein the ligand specifically binds to a chemokine receptor selected from among CCR1, CCR2, CCR3, CCR4, CCR5, CCR7, CCR9, CXCR1, CXCR3 and CXCR4; or the ligand is selected from among CXCL9, CXCL10, CCL19, CCL21 and CCL25 or is a biologically active fragment thereof. In some embodiments of any of the oligomeric particle reagents provided herein, the receptor-binding agent (second receptor-binding agent) is an adhesion molecule and the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof.

In particular embodiments of any of the oligomeric particle reagents provided herein, the one or more agents comprises a selection agent, wherein the selection agent binds to or is capable of binding to a selection marker that is expressed on the surface of a target cell. In certain embodiments of any of the oligomeric particle reagents provided herein, the target cell is an immune cell. In some embodiments of any of the oligomeric particle reagents provided herein, the target cell is a lymphocyte or an antigen-presenting cell. In particular embodiments of any of the oligomeric particle reagents provided herein, the target cell is a T cell, B cell, NK cell, macrophage or dendritic cell. In certain embodiments of any of the oligomeric particle reagents provided herein, the target cell is a T cell. In some embodiments of any of the oligomeric particle reagents provided herein, the selection marker is CD25, CD28, CD62L, CCR7, CD27, CD127, CD3, CD4, CD8, CD45RA, and/or CD45RO.

In particular embodiments of any of the oligomeric particle reagents provided herein, the oligomeric particle reagent comprises a radius of greater than 25 nm, greater than 50 nm, greater than 60 nm, greater than 70 nm, greater than 80 nm, or greater than 90 nm. In certain embodiments of any of the oligomeric particle reagents provided herein, the oligomeric particle reagent comprises a radius of between 25 nm and 150 nm, between 50 nm and 150 nm, between 75 nm and 125 nm, between 80 nm and 115 nm, or between 90 nm and 110 nm, inclusive, or 90 nm±15 nm, or 95 nm±20-25 nm. In some embodiments of any of the oligomeric particle reagents provided herein, the oligomeric particle reagent has a radius of less than 150 nm. In particular embodiments, the radius is a hydrodynamic radius.

In particular embodiments of any of the oligomeric particle reagents provided herein, the oligomeric particle reagent comprises a molecular weight of at least $1\times10^7$ g/mol, at least $5\times10^7$ g/mol, or at least $1\times10^8$ g/mol. In certain embodiments of any of the oligomeric particle reagents provided herein, the oligomeric particle reagent comprises a molecular weight of between $1\times10^6$ g/mol and $1\times10^{10}$ g/mol, between $1\times10^7$ g/mol and $1\times10^9$ g/mol, between $5\times10^7$ g/mol and $5\times10^8$ g/mol, between $1\times10^8$ g/mol and $5\times10^8$ g/mol, or between $1\times10^8$ g/mol and $2\times10^8$ g/mol. In some embodiments of any of the oligomeric particle reagents provided herein, the oligomeric particle reagent comprises at least 100 streptavidin or streptavidin mutein tetramers, at least 500 streptavidin or streptavidin mutein tetramers, at least 1,000 streptavidin or streptavidin mutein tetramers, at least 1,500 streptavidin or streptavidin mutein tetramers, or at least 2,000 streptavidin or streptavidin mutein tetramers.

In particular embodiments of any of the oligomeric particle reagents provided herein, the oligomeric particle reagent comprises between 100 and 50,000 streptavidin or streptavidin mutein tetramers, between 1,000 and 20,000 streptavidin or streptavidin mutein tetramers, between 1,000 and 10,000 streptavidin or streptavidin mutein tetramers, or between 2,000 and 5,000 streptavidin or streptavidin mutein tetramers. In certain embodiments of any of the oligomeric particle reagents provided herein, the plurality of streptavidin or streptavidin muteins comprise lysine residues, wherein less than 20%, 10%, 5%, 1%, of the lysine residues comprise N-substituted iminothiolane.

Provided herein is a composition comprising one or more oligomeric particle reagents. In some embodiments of any of the compositions provided herein, the one or more oligomeric particle reagents is a plurality of oligomeric particle reagents. In particular embodiments of any of the compositions provided herein, the plurality of oligomeric particle reagents comprises i) an average radius of greater than 70 nm; ii) an average molecular weight of at least $1\times10^8$ g/mol; and/or iii) an average number of streptavidin or streptavidin tetramers per oligomeric particle reagent of at least 2,000 and/or iv) a radius size distribution wherein at least 95% of the plurality of oligomeric particle reagents comprise a radius of between 10 nm to 150 nm. In certain embodiments, the radius size distribution is a hydrodynamic radius size distribution.

In certain embodiments of any of the compositions provided herein, the plurality of oligomeric particle reagents comprises an average radius of greater than 25 nm, greater than 50 nm, greater than 60 nm, greater than 70 nm, greater than 80 nm, greater than 90 nm, or greater than 100 nm. In some embodiments of any of the compositions provided herein, the plurality of oligomeric particle reagents comprise an average radius of between 25 nm and 150 nm, between 50 nm and 150 nm, between 75 nm and 125 nm, between 80 nm and 110 nm, or between 90 nm and 110 nm, inclusive, or 90 nm±15 nm, or 95 nm±20-25 nm. In particular embodiments of any of the compositions provided herein, at least 95% of the plurality of oligomeric particle reagents comprise a radius of between 50 and 150 nm, between 70 nm and 140 nm, between 80 nm and 120 nm, between 80 nm and 115 nm, between 80 nm and 100 nm, between 90 nm and 110 nm, and/or between 100 nm and 120 nm.

In certain embodiments of any of the compositions provided herein, at least 95% of the oligomeric particle reagents comprise a radius between ±50%, ±25%, ±20%, ±15%, ±10%, and/or ±5% of the average and/or the median radius of the plurality of oligomeric particle reagents. In some embodiments of any of the compositions provided herein, the plurality of oligomeric particle reagents comprising an average radius of between 80 nm and 115 nm and wherein at least 95% of the oligomeric particle reagents comprise a radius between ±25% of the average radius. In particular embodiments of any of the compositions provided herein, the plurality of particles comprise an average molecular weight of between $1\times10^8$ g/mol and $5\times10^8$ g/mol, or between $1\times10^8$ g/mol and $2\times10^8$ g/mol, inclusive.

In certain embodiments of any of the compositions provided herein, the plurality of oligomeric particle reagents comprises an average number of streptavidin or streptavidin tetramers per oligomeric particle reagent of at least 100, at least 500, at least 1,000, at least 1,500, or at least 2,000. In some embodiments of any of the compositions provided herein, the plurality of oligomeric particle reagents comprises an average number of streptavidin or streptavidin tetramers per oligomeric particle reagent of between 100 and 50,000, between 1,000 and 20,000, between 1,000 and 10,000, or between 2,000 and 5,000, each inclusive.

In particular embodiments of any of the compositions provided herein, the average radius of the plurality the oligomer particles does not increase by more than 25% when stored at about or below −80° C., at about or below −20° C., and/or at about or below 4° C. for at least 1 week. In certain embodiments of any of the compositions provided herein, the average radius of the plurality the oligomer particles does not increase by more than 10% when stored at about or below 4° C. for at least one week. In some embodiments of any of the compositions provided herein, the average radius of the plurality of the oligomer particles does not increase by more than 10% when stored at about or below 4° C. for at least 3 weeks. In particular embodiments of any of the compositions provided herein, the average radius of the plurality of the oligomer particles does not increase by more than 10% when stored at about or below 4° C. for at least 9 weeks, at least 27 weeks, or at least 46 weeks. In particular embodiments, the average radius of the plurality of the oligomer particles does not increase by more than 10% when stored at, at about, or below −20° C., −30° C., −40° C., −50° C., −60° C., −70° C., or −80° C., for at least 1 week, 3 weeks, 9 weeks, 27 weeks, or 46 weeks.

Provided herein are methods for producing an oligomeric particle reagent comprising streptavidin or a streptavidin mutein, the method comprising: incubating a plurality of activated streptavidin or streptavidin mutein molecules comprising a thiol-reactive functional group capable of reacting with a thiol functional group and a plurality of thiolated streptavidin or streptavidin mutein molecules comprising one or more thiol functional group, thereby generating oligomeric streptavidin or streptavidin mutein particles; separating the oligomeric particles from monomer and/or smaller oligomeric molecules; and contacting the oligomeric particle with a stabilizing agent, thereby producing the oligomeric particle reagent.

In some embodiments of any of the methods provided herein, the plurality of activated streptavidin or streptavidin mutein molecules is generated by incubating a first plurality of streptavidin or streptavidin mutein molecules with an activation agent that is capable of converting one or more amines to a thiol-reactive functional group. In particular embodiments of any of the methods provided herein, the plurality of thiolated streptavidin or streptavidin mutein molecules is generated by incubation of a second plurality of streptavidin or streptavidin mutein molecules with a thiolating agent that adds or is capable of adding a thiol functional group to one or more lysine residue.

Also provided herein is a method for producing oligomeric particle reagents, the method comprising: (a) incubating a first plurality of streptavidin or streptavidin mutein molecules with an activation agent under conditions to convert one or more amines to a thiol-reactive group capable of reacting with a thiol functional group, thereby generating a plurality of activated streptavidin or streptavidin mutein molecules; (b) incubating a second plurality of streptavidin or streptavidin mutein molecules with a thiolating agent that adds or is capable of adding a thiol functional group to one or more lysine residue, thereby generating a plurality of thiolated streptavidin or streptavidin mutein molecules; and (c) incubating the plurality of activated streptavidin or streptavidin mutein molecules with the plurality of thiolated streptavidin or streptavidin mutein molecules, thereby generating particle composition comprising the oligomeric particle reagents; wherein the method is carried out under conditions in which, at the time of initiation of the incubation in (c), the plurality of thiolated streptavidin or streptavidin mutein molecules are such that at least 60% of the lysines, on average, comprise a thiol functional group, and/or at least 10 lysines, on average, per thiolated streptavidin or streptavidin mutein tetramer comprise a thiol functional group.

Certain embodiments further comprise separating the oligomeric particle reagents from monomer and/or smaller oligomeric streptavidin or streptavidin mutein molecules. In certain embodiments of any of the methods provided herein, the incubation of the first plurality of streptavidin or streptavidin mutein molecules with the activation agent is performed at a molar ratio of between 1:1 and 1:10 of streptavidin or streptavidin mutein to the activation reagent. In some embodiments of any of the methods provided herein, the incubation of the first plurality of streptavidin or streptavidin mutein molecules with the activation agent is performed at a molar ratio of 1:2±2% of streptavidin or streptavidin mutein to the activation reagent. In particular embodiments of any of the methods provided herein, the activation agent comprises a heterobifunctional crosslinker. In certain embodiments of any of the methods provided herein, the activation agent comprises sulfosuccinimidyl 4-(N-maleimidomethyl)cyclohexane-1-carboxylate (sulfo SMCC) and/or Succinimidyl-6-[(β-maleimidopropionamido)hexanoate (SMPH). In some embodiments of any of the methods provided herein, the thiol-reactive functional group is a haloacetyl group, a maleimide group, an aziridine group, an acryloyl group, an arylating agent, a vinylsulfone group, a pyridyl disulfide, a TNB-thiol or a disulfide reducing agent. In particular embodiments of any of the methods provided herein, the thiol-reactive functional group is a maleimide group. In certain embodiments of any of the methods provided herein, the first plurality of streptavidin or streptavidin mutein molecules and the activation agent are incubated at a neutral pH.

In some embodiments of any of the methods provided herein, the first plurality of streptavidin or streptavidin mutein molecules and the activation agent are incubated at a pH of between 6.8 and 7.5. In particular embodiments of any of the methods provided herein, the first plurality of streptavidin or streptavidin mutein molecules and the activation agent are incubated at a pH of between 7.0 and 7.4, optionally of or about 7.2. In certain embodiments of any of the methods provided herein, the first plurality of streptavidin or streptavidin mutein molecules and the activation agent are incubated at a temperature between 4° C. and 39° C. In some embodiments of any of the methods provided herein, the first plurality of streptavidin or streptavidin mutein molecules and the activation agent are incubated at room temperature, optionally between 20° C. and 25° C., optionally about 23° C. or about 24° C.

In particular embodiments of any of the methods provided herein, the first plurality of streptavidin or streptavidin mutein molecules and the activation agent are incubated for between 15 minutes and 6 hours or 30 minutes and 2 hours, each inclusive. In certain embodiments of any of the methods provided herein, the first plurality of streptavidin or streptavidin mutein molecules and the activation agent are incubated for between 45 minutes and 1.5 hours, inclusive, optionally for or for about 1 hour.

In some embodiments of any of the methods provided herein, the incubation of the second plurality of streptavidin or streptavidin mutein molecules with the thiolating agent is performed at a molar ratio of between 10:1 and 1:1, inclusive, of the thiolating reagent to each primary amine per streptavidin or streptavidin mutein molecule. In particular embodiments of any of the methods provided herein, the incubation of the second plurality of streptavidin or streptavidin mutein molecules with the thiolating agent is performed at a molar ratio of between 1:50 and 1:500, inclusive, of streptavidin or streptavidin mutein to the thiolating agent. In certain embodiments of any of the methods provided herein, the incubation of the second plurality of streptavidin or streptavidin mutein molecules with the thiolating agent is performed at a molar ratio of or about 1:100 of streptavidin or streptavidin mutein to the activation reagent. In some embodiments of any of the methods provided herein, the thiolating agent is or comprises 2-iminothiolane.

In particular embodiments of any of the methods provided herein, the second plurality of streptavidin or streptavidin mutein molecules and the thiolating agent are incubated at a pH of 7.0 or greater, optionally between 7.0 and 8.0, inclusive. In certain embodiments of any of the methods provided herein, the second plurality of streptavidin or streptavidin mutein molecules and the thiolating agent are incubated at a pH of about 7.7. In some embodiments of any of the methods provided herein, the incubation of the second plurality of streptavidin or streptavidin mutein molecules and the thiolating agent is initiated in the presence of a buffer with a pH of 8.0 or greater, optionally between 8.0 and 9.0, inclusive. In particular embodiments of any of the methods provided herein, the incubation of the second plurality of streptavidin or streptavidin mutein molecules and the thiolating agent is initiated in the presence of a buffer with a pH of or about 8.5. In certain embodiments of any of the methods provided herein, the buffer comprises borate. In some embodiments of any of the methods provided herein, the buffer comprises 10 mM to 200 mM borate or 50 mM to 100 mM borate, each inclusive, optionally about 100 mM borate.

In particular embodiments of any of the methods provided herein, the second plurality of streptavidin or streptavidin mutein molecules and the thiolating agent are incubated at a temperature between 4° C. and 39° C. In certain embodiments of any of the methods provided herein, the second plurality of streptavidin or streptavidin mutein molecules and the thiolating agent are incubated at room temperature, optionally between 20° C. and 25° C., optionally at or about 23° C. or at or about 24° C. In some embodiments of any of the methods provided herein, the second plurality of strepta- vidin or streptavidin mutein molecules and the thiolating agent are incubated for between 15 minutes and 2 hours or 15 minutes and 1.5 hours. In particular embodiments of any of the methods provided herein the second plurality of streptavidin or streptavidin mutein molecules and the thiolating agent are incubated for between 15 minutes and 2 hours or 25 minutes and 1 hour, each inclusive. In certain embodiments of any of the methods provided herein the second plurality of streptavidin molecules and the thiolating agent are incubated for or for about 1 hour.

In some embodiments of any of the methods provided herein the second plurality of streptavidin or streptavidin mutein molecules and the thiolating agent are incubated for or for about 25 minutes. In particular embodiments of any of the methods provided herein the plurality of activated streptavidin or streptavidin mutein molecules to the plurality of thiolated streptavidin or streptavidin mutein molecules during the incubation is at a molar ratio of X:1, wherein X is the number of lysine residues available to be thiolated per molecule of streptavidin or streptavidin mutein. In certain embodiments of any of the methods provided herein the molar ratio is from 1:1 to 8:1 or 2:1 to 6:1, optionally of or about 4:1. In certain embodiments, the molar ratio is from 1:1 to 1:8 or 1:2 to 1:6, optionally of or about 1:4.

In some embodiments of any of the methods provided herein the plurality of activated streptavidin or streptavidin mutein molecules and the plurality of thiolated streptavidin or streptavidin mutein molecules, are incubated at a pH of between 6.8 and 7.5, inclusive. In particular embodiments of any of the methods provided herein the plurality of activated streptavidin or streptavidin mutein molecules and the plurality of thiolated streptavidin or streptavidin mutein molecules, are incubated at a pH of between 7.0 and 7.4, inclusive. In certain embodiments of any of the methods provided herein the plurality of activated streptavidin or streptavidin mutein molecules and the plurality of thiolated streptavidin or streptavidin mutein molecules, are incubated at a pH of or about 7.2.

In some embodiments of any of the methods provided herein the plurality of activated streptavidin or streptavidin mutein molecules and the plurality of thiolated streptavidin or streptavidin mutein molecules, are incubated at a temperature between 4° C. and 39° C., inclusive. In particular embodiments of any of the methods provided herein the plurality of activated streptavidin or streptavidin mutein molecules and the plurality of thiolated streptavidin or streptavidin mutein molecules, are incubated at room temperature, optionally between 20° C. and 25° C., inclusive, optionally at or about 23° C. or at or about 24° C. In certain embodiments of any of the methods provided herein the plurality of activated streptavidin molecules and the plurality of thiolated streptavidin molecules, are incubated for between 15 minutes and 6 hours or 30 minutes and 2 hours, each inclusive. In some embodiments of any of the methods provided herein the plurality of activated streptavidin molecules and the plurality of thiolated streptavidin molecules, are incubated for between 45 minutes and 1.5 hours, inclusive, optionally for or for about 1 hour. In particular embodiments of any of the methods provided herein the incubation of activated streptavidin or streptavidin mutein molecules and the thiolated streptavidin or streptavidin mutein molecules is ended by contacting the molecules with N-ethylmaleimide (NEM).

In certain embodiments of any of the methods provided herein at least a portion of the incubating of the first plurality of streptavidin or streptavidin mutein molecules with the activation agent and at least a portion of the incubating of the second plurality of streptavidin or streptavidin mutein molecules with the thiolating agent are carried out separately at the same time. In some embodiments of any of the methods provided herein the incubating of the first plurality of streptavidin or streptavidin mutein molecules with the activation agent and the incubating of the second plurality of streptavidin or streptavidin mutein molecules with the thiolating agent are carried out for substantially the same amount of time and/or are completed at substantially the same time. In particular embodiments of any of the methods provided herein, wherein, prior to incubating the thiolated streptavidin or streptavidin mutein molecules and the activated streptavidin or streptavidin mutein molecules, the method comprises (i) removing the activation agent from the composition comprising the activated streptavidin or streptavidin mutein molecules; and/or (ii) removing the thiolating agent from the composition comprising the thiolated streptavidin or streptavidin mutein molecules..

In certain embodiments of any of the methods provided herein wherein the incubation of the plurality of activated streptavidin or streptavidin mutein molecules and the plurality of thiolated streptavidin or streptavidin mutein molecules is initiated within 15 minutes after the incubating of the second plurality of streptavidin molecules with the thiolating agent is ended and/or after the removing of the thiolating agent from composition comprising the thiolated streptavidin or streptavidin mutein molecules..

Provided herein are methods producing oligomeric particle reagents, comprising: incubating a first plurality of streptavidin or streptavidin mutein molecules with Succinimidyl-6-[(β-maleimidopropionamido)hexanoate (SMPH) for or for about 1 hour at a pH of or of about 7.2, thereby generating a plurality of activated streptavidin or streptavidin mutein molecules comprising a maleimide thiol-reacting functional group; incubating a second plurality of streptavidin or streptavidin mutein molecules with 2-iminothiolane for or for about 1 hour at a pH of between 7.5 and 8.5, inclusive, thereby generating a plurality of thiolated streptavidin molecules comprising one or more thiol functional groups; and incubating the plurality of activated streptavidin or streptavidin mutein molecules with the plurality of thiolated streptavidin molecules for or for about 1 hour at a pH of or of about 7.2, thereby generating a composition comprising the oligomeric particle reagents; wherein the incubating of the plurality of activated streptavidin molecules with the plurality of thiolated streptavidin molecules is initiated within 10 minutes after the incubation of the second plurality of streptavidin molecules with 2-iminothiolane ends.

In some embodiments of any of the methods provided herein the method further comprises contacting the oligomeric particle reagents with a stabilization agent. In particular embodiments of any of the methods provided herein the stabilization agent reduces an amount of N-substituted iminothiolane present on lysine residues of the oligomeric particle reagents. In certain embodiments of any of the methods provided herein the stabilization agent reduces an amount of N-substituted iminothiolane present on lysine residues of the oligomeric particle reagents by at least 25%, at least 50%, at least 60%, at least 70%, at least 80%, at least 90%, or at least 95%. In some embodiments of any of the methods provided herein the stabilization agent comprises hydroxylamine.

In particular embodiments of any of the methods provided herein the oligomeric particle reagents have a radius of less than 150 nm. Certain embodiments of any of the methods provided herein further comprise filter sterilizing the oligomeric particle reagents. In some embodiments of any of the methods provided herein the oligomeric particle reagents are separated from the monomer or smaller oligomeric streptavidin or streptavidin mutein molecules by size exclusion chromatography. In particular embodiments of any of the methods provided herein, the size exclusion limit is greater than or greater than about 100 kDa, 500 kDa, 750 kDa, 1000 kDa or 2000 kDa. In certain embodiments of any of the methods provided herein, the size exclusion limit is from or from about 500 kDa to 1000 kDa. In some embodiments of any of the methods provided herein, the size exclusion limit is or is about 750 kDa.

Particular embodiments of any of the methods provided herein comprise collecting one or more fractions comprising the void volume, thereby separating oligomeric particle reagents from the monomer or smaller oligomeric streptavidin or streptavidin mutein molecules. In certain embodiments the methods further comprise storing the oligomeric particle reagents at a temperature at about or below 4° C., at about or below −20° C., or about or below −80° C. In some embodiments the methods further comprise mixing the oligomeric particle reagents with one or more agents under conditions to reversibly bind the one or more agents to the oligomeric particle reagents.

Also provided herein are methods of multimerizing one or more agents to an oligomeric particle reagent, the method comprising mixing an oligomeric particle reagent produced by the methods provided herein with one or more agents under conditions to reversibly bind the one or more agents to the oligomeric particle reagents. In particular embodiments of any of the methods provided herein, the one or more agents comprise a binding partner, wherein the binding partner is capable of binding to one or more binding site on the oligomeric particle reagent. In certain embodiments of any of the methods provided herein, the binding partner comprises a streptavidin-binding peptide.

In some embodiments of any of the methods provided herein, the binding partner comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

In particular embodiments of any of the methods provided herein, the one or more agents binds or is capable of binding to a molecule expressed on the surface of a target cell. In certain embodiments of any of the methods provided herein, the one or more agents comprise an antibody, optionally a Fab. In some embodiments of any of the methods provided herein, the one or more agents is a receptor binding-agent that binds to or is capable of binding to a receptor expressed on the surface of a target cell. In particular embodiments of any of the methods provided herein, the receptor binding agent is or comprises a stimulatory agent capable of binding to a molecule on the surface of a target cell, thereby inducing or modulating a signal in the target cell.

In certain embodiments of any of the methods provided herein, the receptor-binding agent is capable of initiating a TCR/CD3 complex-associated signal in T cells, binds to a member of a TCR/CD3 complex; and/or specifically binds to CD3. In some embodiments of any of the methods provided herein, the stimulatory agent is a first receptor-binding agent and the method further comprises reversibly binding to the oligomeric particle reagent a second receptor-binding agent, wherein the second receptor-binding agent is capable of specifically binding to a second molecule on the surface of the target cell, which binding to the second molecule is optionally capable of inducing or modulating a signal in the target cells.

In particular embodiments of any of the methods provided herein, the second receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule. In certain embodiments of any of the methods provided herein, the receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

In some embodiments of any of the methods provided herein, the receptor-binding agent (second receptor-binding agent) binds to a costimulatory or accessory molecule and the costimulatory or accessory molecule is selected fromCD28, CD90 (Thy-1), CD95 (Apo-/Fas), CD137 (4-1BB), CD154 (CD40L), ICOS, LAT, CD27, OX40 or HVEM. In particular embodiments of any of the methods provided herein, the receptor-binding agent (second receptor-binding agent) specifically binds to a cytokine receptor and the cytokine receptor is selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2. In certain embodiments of any of the methods provided herein, the receptor-binding agent (second receptor-binding agent) specifically binds to a chemokine receptor and the chemokine receptor is selected from among CCR1, CCR2, CCR3, CCR4, CCR5, CCR7, CCR9, CXCR1, CXCR3 and CXCR4.

In some embodiments of any of the methods provided herein, the receptor-binding agent (second receptor-binding agent) is a factor that induces cytokine or chemokine production and the factor is a ligand that specifically binds to a cytokine or chemokine receptor. In particular embodiments of any of the methods provided herein, the receptor-binding agent (second receptor-binding agent) is a ligand that specifically binds to a cytokine receptor, wherein the ligand specifically binds IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the ligand is selected from among IL-2, IL-1, IL-15, IFN-gamma, TNF-alpha, IL-4, IL-10, IL-12, IL-15, IL-17 and TNF, or is a biologically active fragment thereof.

In certain embodiments of any of the methods provided herein, the receptor-binding agent (second receptor-binding agent) is a ligand that specifically binds to a chemokine receptor, wherein the ligand specifically binds to a chemokine receptor selected from among CCR1, CCR2, CCR3, CCR4, CCR5, CCR7, CCR9, CXCR1, CXCR3 and CXCR4; or the ligand is selected from among CXCL9, CXCL10, CCL19, CCL21 and CCL25 or is a biologically active fragment thereof. In some embodiments of any of the methods provided herein, the receptor-binding agent (second receptor-binding agent) is an adhesion molecule and the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof.

In particular embodiments of any of the methods provided herein, the one or more agents comprises a selection agent, wherein the selection agent binds to or is capable of binding to a selection marker that is expressed on the surface of a target cell. In certain embodiments of any of the methods provided herein, the target cell is an immune cell. In some embodiments of any of the methods provided herein, the target cell is a lymphocyte or an antigen-presenting cell. In particular embodiments of any of the methods provided herein, the target cell is a T cell, B cell, NK cell, macrophage or dendritic cell. In certain embodiments of any of the methods provided herein, the target cell is a T cell. In some embodiments of any of the methods provided herein, the selection marker is CD25, CD28, CD62L, CCR7, CD27, CD127, CD3, CD4, CD8, CD45RA, and/or CD45RO.

Particular embodiments are directed to a composition comprising oligomeric particle reagents produced by the method of any of embodiment provided herein. Particular embodiments are directed to a composition comprising a plurality of the oligomeric particle reagents produced by the method of any of embodiment provided herein. Certain embodiments are directed to an article of manufacture, comprising the oligomeric particle reagent of any of embodiments provided herein or the composition of any of embodiments provided herein.

Provided herein are methods for modulating cells, the method comprising incubating a cell composition comprising target cells in the presence of the oligomeric particle reagent of any of embodiments provided herein or in the presence of the composition of any of embodiments provided herein, thereby modulating the target cells. In some embodiments of any of the methods provided herein, modulating the target cells comprises activating, enriching, and/or expanding the target cells.

Provided herein are methods for culturing cells, the method comprising incubating a cell composition comprising target cells in the presence of the oligomeric particle reagent of any of embodiments provided herein or in the presence of the composition of any of embodiments provided herein. In certain embodiments of any of the methods provided herein, the oligomeric particle reagent comprises are reversibly bound to one or more agents. In particular embodiments of any of the methods provided herein, the one or more agents binds or is capable of binding to a molecule expressed on the surface of a target cell. In some embodiments of any of the methods provided herein, the one or more agents comprise an antibody, optionally a Fab.

In certain embodiments of any of the methods provided herein, the one or more agents is a receptor binding-agent that binds to or is capable of binding to a receptor expressed on the surface of a target cell. In particular embodiments of any of the methods provided herein, the receptor binding agent is or comprises a stimulatory agent capable of binding to a molecule on the surface of a target cell, thereby inducing or modulating a signal in the target cell.

In some embodiments of any of the methods provided herein, the receptor-binding agent is capable of initiating a TCR/CD3 complex-associated signal in T cells, binds to a member of a TCR/CD3 complex; and/or specifically binds to CD3. In certain embodiments of any of the methods provided herein, the stimulatory agent is a first receptor-binding agent and the method further comprises reversibly binding to the oligomeric particle reagent a second receptor-binding agent, wherein the second receptor-binding agent is capable of specifically binding to a second molecule on the surface of the target cell, which binding to the second molecule is optionally capable of inducing or modulating a signal in the target cells.

In particular embodiments of any of the methods provided herein, the second receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule. In some embodiments of any of the methods provided herein, the receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

In certain embodiments of any of the methods provided herein, the receptor-binding agent (second receptor-binding agent) binds to a costimulatory or accessory molecule and the costimulatory or accessory molecule is selected from CD28, CD90 (Thy-1), CD95 (Apo-/Fas), CD137 (4-1BB), CD154 (CD40L), ICOS, LAT, CD27, OX40 or HVEM. In particular embodiments of any of the methods provided herein, the receptor-binding agent (second receptor-binding agent) specifically binds to a cytokine receptor and the cytokine receptor is selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2. In some embodiments of any of the methods provided herein, the receptor-binding agent (second receptor-binding agent) specifically binds to a chemokine receptor and the chemokine receptor is selected from among CCR1, CCR2, CCR3, CCR4, CCR5, CCR7, CCR9, CXCR1, CXCR3 and CXCR4.

In certain embodiments of any of the methods provided herein, the receptor-binding agent (second receptor-binding agent) is a factor that induces cytokine or chemokine production and the factor is a ligand that specifically binds to a cytokine or chemokine receptor. In particular embodiments of any of the methods provided herein, the receptor-binding agent (second receptor-binding agent) is a ligand that specifically binds to a cytokine receptor, wherein the ligand specifically binds IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the ligand is selected from among IL-2, IL-1, IL-15, IFN-gamma, TNF-alpha, IL-4, IL-10, IL-12, IL-15, IL-17 and TNF, or is a biologically active fragment thereof.

In some embodiments of any of the methods provided herein, the receptor-binding agent (second receptor-binding agent) is a ligand that specifically binds to a chemokine receptor, wherein the ligand specifically binds to a chemokine receptor selected from among CCR1, CCR2, CCR3, CCR4, CCR5, CCR7, CCR9, CXCR1, CXCR3 and CXCR4; or the ligand is selected from among CXCL9, CXCL10, CCL19, CCL21 and CCL25 or is a biologically active fragment thereof.

In certain embodiments of any of the methods provided herein, the receptor-binding agent (second receptor-binding agent) is an adhesion molecule and the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof.

In particular embodiments of any of the methods provided herein, the one or more agents comprises a selection agent, wherein the selection agent binds to or is capable of binding to a selection marker that is expressed on the surface of a target cell. In some embodiments of any of the methods provided herein, the target cell is an immune cell. In certain embodiments of any of the methods provided herein, the target cell is a lymphocyte or an antigen-presenting cell. In particular embodiments of any of the methods provided herein, the target cell is a T cell, B cell, NK cell, macrophage or dendritic cell. In some embodiments of any of the methods provided herein, the target cell is a T cell. In certain embodiments of any of the methods provided herein, the selection marker is CD25, CD28, CD62L, CCR7, CD27, CD127, CD3, CD4, CD8, CD45RA, and/or CD45RO. In certain embodiments, the target cells comprise blood cells, leukocytes, lymphocytes, B cells, a population of B cells, T cells, a population of T cells, NK cells, dendritic cells and/or macrophages. In particular embodiments of any of the methods provided herein, the target cells express a recombinant receptor. In some embodiments of any of the methods provided herein, the target cells express a recombinant T cell receptor and/or a chimeric antigen receptor (CAR).

In certain embodiments of any of the methods provided herein, the target cells express a CAR that binds to an antigen associated with a disease and/or a cancer. In particular embodiments of any of the methods provided herein, the antigen is αvβ6 integrin (avb6 integrin), B cell maturation antigen (BCMA), B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), G Protein Coupled Receptor 5D (GPCR5D), Her2/neu (receptor tyrosine kinase erbB2), Her3 (erb-B3), Her4 (erb-B4), erbB dimers, human high molecular weight-melanoma-associated antigen (HMW-MAA), hepatitis B surface antigen, Human leukocyte antigen A1 (HLA-AI), human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, preferentially expressed antigen of melanoma (PRAME), progesterone receptor, a prostate specific antigen, prostate stem cell antigen (PSCA), prostate specific membrane antigen (PSMA), receptor tyrosine kinase like orphan receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms tumor 1 (WT-1), a pathogen-specific antigen or an antigen associated with a universal tag, and/or biotinylated molecules, and/or molecules expressed by HIV, HCV, HBV or other pathogens.

Some embodiments of any of the methods provided herein further comprise disrupting the reversible binding between the one or more agent and the oligomeric particle reagent. In certain embodiments of any of the methods provided herein, said disruption comprises introducing to the target cells a composition comprising a substance capable of reversing the bond between the one or more agent and the oligomeric particle reagent. In particular embodiments of any of the methods provided herein, the substance is a free binding partner and/or is a competition agent.

In some embodiments of any of the methods provided herein, said disruption terminates or lessens the signal induced or modulated by the one or more agent in the target cells, optionally T cells. In certain embodiments of any of the methods provided herein, the substance comprises a streptavidin-binding peptide, biotin or a biologically active fragment, optionally a D-biotin, or a biotin analog (or biologically active fragment)

In particular embodiments of any of the methods provided herein, the substance is a streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19). In some embodiments of any of the methods provided herein, the disruption is carried out within 5 days after initiation of said incubation.

BRIEF DESCRIPTION OF THE DRAWINGS

FIG. 6A summarizes WST metabolic activity for all tested batches (pooled) compared to reference batches containing anti-CD3/anti-CD28 multimerized on an oligomeric backbone with an average hydrodynamic radius of 36 nm or 101 nm. The average WST metabolic activity among T cells from the different donors for individual tested batches and reference reagents is shown in FIG. 6B.

FIG. 7, which includes FIGS. 7A-7E, provides schematic representations of exemplary embodiments.

FIG. 7A shows a schematic representation of a reagent (or representative portion thereof), such as a streptavidin or streptavidin mutein oligomeric reagent, with a plurality of binding sites for reversible binding to agents. In this case, the reagent is shown as capable of reversibly binding to two agents, each of which is capable of specifically binding to a molecule on a cell. The reagent has a plurality of binding sites, including a plurality of the binding site, Z1, each capable of reversibly binding to the agents. The first and second agents, which, in some cases, can be the same, in the schematic representation shown each contain at least one binding partner C1. Binding partner C1 reversibly binds to binding site Z1. The first and second agents each also contain a binding site, B2, which can specifically bind to a molecule on the surface of a cell, which, in some cases, can be on the same cell. Here, the first and second agents are shown specifically binding to molecules on the same cell.

FIG. 7B shows a schematic representation of a reagent, such as a streptavidin or streptavidin mutein oligomeric reagent, with a plurality of binding sites, capable of reversibly binding to a first and second agent, which agents are each capable of specifically binding to a molecule on a first and second cell, respectively. The reagent has a plurality of binding sites Z1, each capable of reversibly binding to an agent. The first and second agents, which, in some cases, can be the same, each contain a binding partner C1, which reversibly binds to binding site Z1. The first and second agents each contain a binding site B2, which can specifically bind to a molecule on the surface of a cell, which, in some cases, can be on the same cell or a different cell. Here, the first agent is bound to a molecule on the surface of a first cell and the second agent is bound to a molecule on the surface of a second cell.

FIG. 7C shows a reagent, such as a streptavidin or streptavidin mutein oligomeric reagent, capable of reversibly binding to a first and second agents, which agents are each capable of specifically binding to a molecule on a first and second cell, respectively. The reagent has a plurality of binding sites Z1 and Z2, which can be the same or different, each capable of reversibly binding to one or both of the agents. The first agent contains a binding partner C1, which reversibly binds to Z1; the second agent contains a binding partner C2, which can reversibly bind to Z2. In some cases, C1 and C2 are different. In some cases, C1 and C2 are the same or substantially the same. The first agent contains a binding site B1, which can specifically bind to a molecule on the surface of a cell and the second agent contains at least one binding site B3, which can specifically bind to a molecule on the surface of a cell. Binding sites B1 and B3 in some cases bind to two different cell surface molecules, or different epitopes on a single molecule, or the same or different molecules on the surface of different cells. Here, the first agent is shown as being bound, via B1, to a molecule on the surface of a first cell, and the second agent is bound to a molecule on the surface of a second cell.

FIG. 7D shows a reagent, such as a streptavidin or streptavidin mutein oligomeric reagent, capable of reversibly binding to a first and second agent, such as selection agents, which are each capable of specifically binding to a molecule on a cell. The reagent has a plurality of binding sites, including Z1 and Z2, which can be the same or different, each capable of reversibly binding to an agent. The first agent contains a binding partner C1 that can specifically bind to binding site Z1 and the second agent contains at least one binding partner C2 that can specifically bind to binding site Z2. In some cases, C1 and C2 are different. In some cases, C1 and C2 are the same or substantially the same. The first agent contains a binding site B1, which can specifically bind to a molecule on the surface of a cell and the second agent contains a binding site B3, which can specifically bind to a molecule on the surface of a cell. In some embodiments, the first agent and second agent can be a selection agent. Binding sites B1and B3 can bind the same or different molecules (e.g. receptor) on the surface of a cell, the same or different epitopes on a molecule, or the same or different molecules on the surface of different cells. Here, the first agent is bound to a first molecule on the surface of a cell and the second agent is bound to a second molecule on the surface of the same cell.

FIG. 7E shows a reagent, such as a streptavidin or streptavidin mutein oligomeric reagent, reversibly bound to a first and second agent, which agents are each capable of specifically binding to a molecule on a cell. The reagent has a plurality of binding sites, including Z1 and Z2, which can be the same or different, each capable of reversibly binding to an agent. The first agent contains a binding partner C1 that can reversibly bind to Z1 of the reagent and the second agent contains a binding partner C2 that can reversibly bind to Z2. In some cases, C1 and C2 are different. In some cases, C1 and C2 are the same or substantially the same. The first agent contains at least one binding site B2, which can specifically bind to a molecule on the surface of a cell and the second agent contains at least one binding site B4, which can specifically bind to a molecule on the surface of a cell. In some embodiments, the first agent and second agent can be stimulatory agents. Binding sites B2 and B4 can bind the same or different molecules on the surface of a cell, the same or different epitopes on a molecule, or the same or different molecules on the surface of different cells. Here, the first agent is bound to a first molecule on the surface of a cell and the second agent is bound to a second molecule on the surface of the same cell.

FIG. 8, which includes FIGS. 8A-8E, provide schematic representations of exemplary embodiments as shown in FIGS. 7A-7E, respectively, except that the depicted reagents, such as a streptavidin or streptavidin mutein oligomeric reagent, are shown as being immobilized on a support, such as a stationary phase.

DETAILED DESCRIPTION

Figure 1:
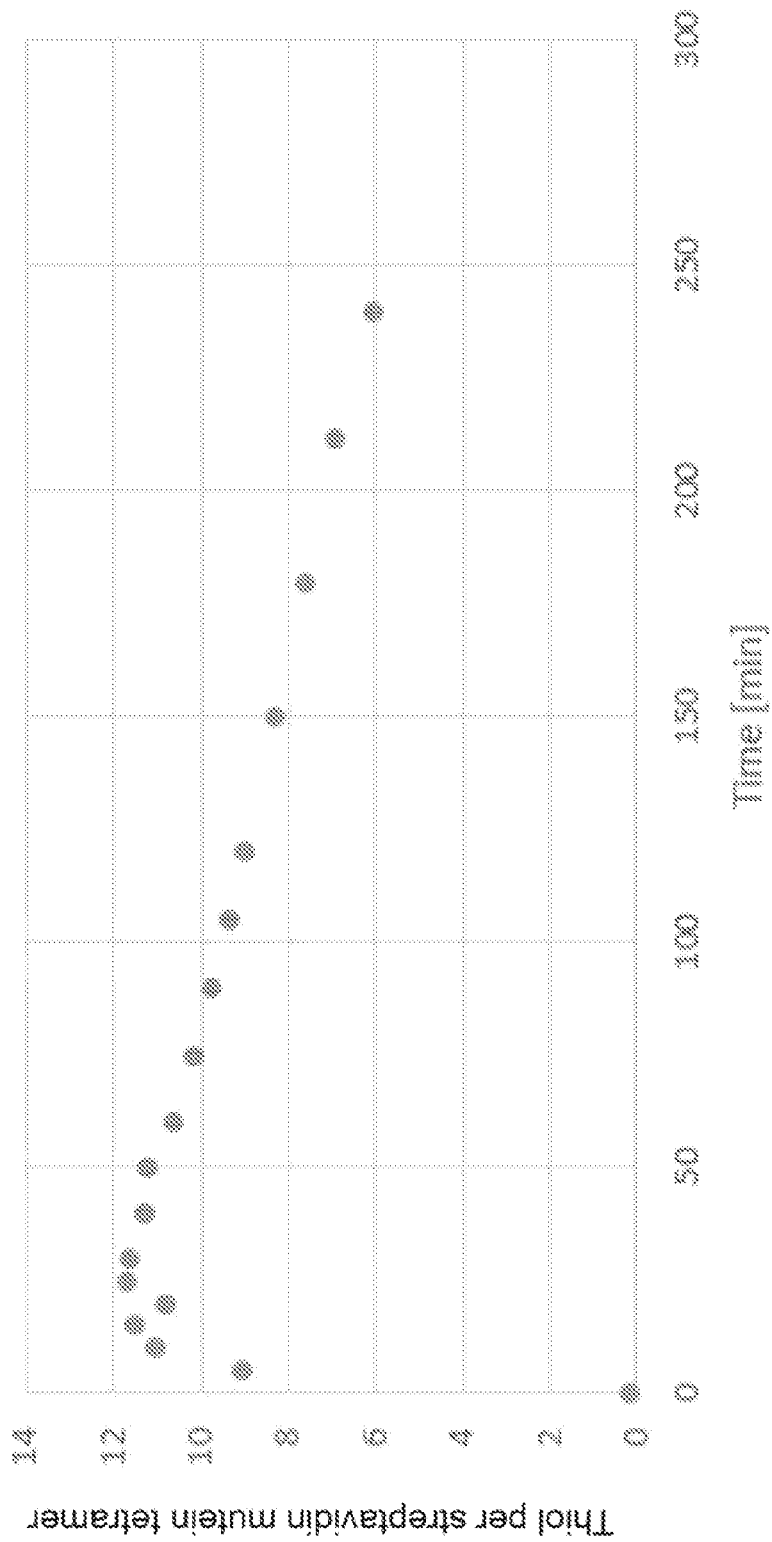
FIG. 1 depicts levels of thiol functional groups attached to streptavidin mutein tetramers during a time course incubation of the exemplary streptavidin mutein STREP-TACTIN® M2 with 2-iminothiolane in the presence of 100 mM borate.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Provided herein are methods for manufacturing, producing, and/or generating oligomeric particle reagents. In some embodiments, the methods provided herein are useful to oligomerize molecules into oligomer particle reagents ranging from 1 million Da to 100 million Da, 1 million Da to 1 billion Da, 1 million Da to 10 billion Da, and/or 1 million Da to 100 billion Da. Particular embodiments contemplate that the size distribution of the oligomeric particle reagents produced by the provided methods is affected by changing distinct reaction conditions of one or more of the various steps. Thus, in some embodiments, conditions such as timing, concentrations and molar ratios of reagents, and pH of solutions, are controlled and kept constant with precision. In some embodiment, the methods provided herein are useful to derive oligomeric particle reagents with consistent sizes between batches or lots. In some embodiments, the conditions of one or more steps or stages of the methods provided herein may be adjusted to manufacture, produce, or generate oligomeric particle reagents of one or more different desired sizes.

In some embodiments, the methods provided herein for manufacturing, producing, and/or generating oligomeric particle reagents crosslink molecules, e.g., streptavidin or streptavidin mutein tetramers, by reacting a plurality of the molecules having attached thiol functional groups (also referred to as thiolated molecules, e.g. thiolated streptavidin or streptavidin mutein molecules) with a plurality of the molecules having attached a thiol-reactive functional group (e.g. activated molecules, e.g. streptavidin or streptavidin mutein molecules), such as a maleimide functional group.

Particular embodiments contemplate that multimerization reagents and/or oligomeric particle reagents of one or more particular sizes may be particularly effective for use in modulating cells. For example, in some embodiments, oligomeric particle reagents of a certain size, when reversibly bound to one or more stimulatory agent, are particularly effective for expanding, activating, and/or enriching a population of cells. As found herein, oligomeric particle reagents of a particular larger size, e.g. having an average radius, e.g., hydrodynamic radius, larger than 32 nm, and generally an average radius greater than 60 nm, such as an average radius greater than or greater than about 90 nm, 95 nm or 100 nm that are reversibly bound to stimulatory agents activate cells to a greater degree than oligomeric particles of a smaller size, e.g. FIG. 6. Thus, in some embodiments, oligomeric particle reagents of defined sizes and size distributions, and methods for consistently manufacturing oligomeric particle reagents with a desired sizes and size distributions, are provided herein.

In some embodiments, the provided methods of manufacturing oligomeric particle reagents result in reduced variability and generally consistent generation of oligomeric reagents of larger size while minimizing the size distribution of oligomers in a composition. In some embodiments, the reactive thiol groups for the oligomerization reaction are added to the molecules by an iminothiolane activation of amines present on lysine residues and at the N-terminus of the molecules. In some embodiments, the timing of the thiolation reaction, and the time between the end of the thiolation reaction and the start of the oligomerization reaction, is kept constant from reaction to reaction, in some cases, because the free thiols can be lost due to isomerization, i.e. formation of N-substituted iminothiolane. In some aspects, the timing should minimize loss of thiols and generation of the N-substituted iminothiolane form, which, in some cases, is a hidden source of SH functions upon re-isomerization that can lead to postsynthetic growth of oligomers. In some embodiments, controlling the availability of thiol groups for reaction with maleimide-containing molecules, and minimizing the accumulation of N-substituted iminothiolane, is a parameter that can influence consistency of oligomer size.

Moreover, in some embodiments, the kinetics of thiol activation and also of the other chemical reactions can, in some cases, be pH dependent. In some embodiments, the pH of one or more buffers for chemical reactions (activation and coupling buffers), and in particular the pH of the buffer for the thiolating agent, are within a predetermined range or level and generally are measured and adjusted with precision. Furthermore, in some embodiments, the stoichiometry between the thiolating and activation agents and the molecules are adjusted with high precision by adjusting concentrations within small tolerances (±2%) to get reproducible average sizes of the multimers.

Also provided herein are such oligomeric reagents as described herein. In some embodiments, one or more agents can be reversibly or irreversibly bound to the oligomeric reagents, which, in some cases, is a multimerization agent in which the one or more agents are multimerized on the oligomeric particle reagents. The oligomeric reagents having bound thereto one or more agents, such as the multimerization agents, can be used in methods involving culturing or incubation with target cells, including primary cells, such as T cells.

In some aspects, provided herein are oligomeric particle reagents that are bound or reversibly bound (e.g., multimerized) to one or more agents, such as receptor-binding reagents and/or stimulatory reagents. In particular embodiments, the provided oligomeric particles are composed of oligomerized molecules, e.g., crosslinked streptavidin muteins, and are bound to stimulatory and/or receptor-binding agents, that bind to and/or are capable of binding to the surface of a cell. In some aspects, the agents are or include anti-CD3 and/or anti-CD28 antibody or antigen binding fragements thereof having a binding partner, e.g., a streptavidin binding peptide, such as Strep-tagII. In particular embodiments, the oligomerized particle reagents have a radius between 50 nm and 150 nm, 75 nm and 125 nm, 80 nm and 115 nm, or a radius of or of about 80 nm, 85 nm, 90 nm, 95 nm, 100 nm, 105 nm, 110 nm, 115 nm±25%, ±20%, ±15%, ±10%, ±5%, ±2%, ±1%, or ±0.1%. In some aspects, a composition containing a plurality of oligomeric particle reagents, such as those bound or reversibly bound (e.g. multimerized) to one or more agents, are provided in which the average radius of the oligomeric particle reagents among the plurality is between 50 nm and 150 nm, 75 nm and 125 nm, 80 nm and 115 nm, or a radius of or of about 80 nm, 85 nm, 90 nm, 95 nm, 100 nm, 105 nm, 110 nm, 115 nm±25%, ±20%, ±15%, ±10%, ±5%, ±2%, ±1%, or±0.1%, In some aspects, the oligomerized particle reagents are particularly useful for selecting and/or stimulating cells, such as via binding of the selection agent or stimulatory agent, respectively, to a cell surface molecule on target cells. In some instances, the presence or addition of a competition reagent results in a dissociation between oligomeric particle reagent and the agents, e.g., receptor binding reagents, which in some instances, may quickly terminate, end, or disrupt stimulation of the cells by the oligomeric particle reagents.

Provided herein is a method for expanding a composition of target cells, such as T cells, using the provided oligomeric reagents. In some embodiments, the methods relate to reversible reagent systems capable of binding to molecules on the surface of a target cells, such as a receptor binding molecule, thereby providing a signal to the cells, which, in some cases, can be a primary activation signal. In some embodiments, the oligomeric particle reagents employed in the methods are multimerization reagents and/or oligomeric particle reagents having bound thereon one or more agents, e.g. a first agent, second agent, etc. that provides a signal to the cells, such as a primary activation signal and/or an accessory or costimulatory signal. In some embodiments, the primary activation signal may as such be sufficient to activate the cells to expand/proliferate. This first agent can either be bound reversibly or also irreversibly to the multimerization reagent and/or oligomeric particle reagents. The multimerization reagent and/or oligomeric particle reagents may have bound thereto also a second agent that stimulates an accessory molecule on the surface of the cells. The second agent, when binding to the accessory molecule on the surface on the surface of the cells, may thereby stimulate the activated cells to expand. Also this second agent can either be bound reversibly or also irreversibly to the multimerization reagent and/or oligomeric particle reagent. The multimerization reagent and/or oligomerized particle reagent may either be immobilized on a solid support or soluble. In one aspect, the method disclosed herein is a serial expansion of a population of cells in which a complete population of lymphocytes is stimulated/expanded, the reagents necessary for the expansion are then removed by chromatography on a suitable stationary phase. In some embodiments, the expanded/stimulated cells, which are the cultured cells, are optionally transfected with e.g. a T cell receptor or a chimeric antigen receptor (CAR) and, in some aspects, can be subjected to a second stimulation expansion with a different stimulatory molecule that binds to the introduced T cell receptor or the chimeric antigen receptor.

Provided herein is a method for expanding a composition of target cells, such as T cells. In some embodiments, the methods relates to reversible reagent systems capable of binding to molecules on the surface of a target cells, such as a receptor binding molecule, thereby providing a signal to the cells, which, in some cases, can be a primary activation signal. In some embodiments, the methods employ reagents, such as oligomeric particle reagents, which can be multimerization reagents and/or oligomeric particle reagent having bound thereon one or more agents, e.g. a first agent, second agent, etc. that provides a signal to the cells, such as a primary activation signal and/or an accessory or costimulatory signal. In some embodiments, the primary activation signal may as such be sufficient to activate the cells to expand/proliferate. This first agent can either be bound reversibly or also irreversibly to the multimerization reagent and/or oligomeric particle reagent. The multimerization reagent and/or oligomeric particle reagent may have bound thereto also a second agent that stimulates an accessory molecule on the surface of the cells. The second agent, when binding to the accessory molecule on the surface of the cells, may thereby stimulate the activated cells to expand. Also this second agent can either be bound reversibly or also irreversibly to the multimerization reagent and/or oligomeric particle reagent. The multimerization agent may either be immobilized on a solid support or soluble. In one aspect, the method disclosed herein is a serial expansion of a population of cells in which a complete population of lymphocytes is stimulated/expanded, the reagents necessary for the expansion are then removed by chromatography on a suitable stationary phase. In some embodiments, the expanded/stimulated cells, which are the cultured cells, are optionally transfected with e.g. a T cell receptor or a chimeric antigen receptor (CAR) and, in some aspects, can be subjected to a second stimulation expansion with a different stimulatory molecule that binds to the introduced T cell receptor or the chimeric antigen receptor.

Methods of expanding T cell populations in vitro in the absence of exogenous growth factors or low amounts of exogenous growth factors are known in the art (see e.g. U.S. Pat. No. 6,352,694 B1 and European Patent EP 0 700 430 B1). In general, such methods employ a solid phase surfaces of greater than 1 µm in diameter to which various binding agents (e.g. anti-CD3 antibody and/or anti-CD28 antibody) are immobilized. For example, Dynabeads® CD3/CD28 (Invitrogen) are commercially available reagents for T cell expansion, which are uniform, 4.5 µm in diameter, super-paramagnetic, sterile, non-pyrogenic polystyrene beads coated with a mixture of affinity purified monoclonal antibodies against the CD3 and CD28 cell surface molecules on human T cells. However, in some cases, such magnetic beads are, for example, difficult to integrate into a method to expand cells under conditions required for clinical trials or therapeutic purposes since it has to be made sure that these magnetic beads are completely removed before administering the expanded T cells to a patient.

In some embodiments, the methods provided herein address these concerns. In some aspects, the provided reagents are reversible, such that the stimulating agents can be removed from the cell composition. Also, in some aspects, the reagent, e.g. multimerization reagent or an oligomeric particle regeagent, to which the stimulating agents are bound is not immobilized on a support, such as not immobilized on a solid support or surface. Thus, in some aspects, the reagent, e.g. multimerization reagent and/or oligomeric particle reagent, is flexible and not rigid. In some embodiments, the reagent can adapt or conform to the cell surface. In some embodiments, it is possible to immobilize the reagent on a support, such as a solid support, including a stationary phase. In some embodiments, such methods can be used in concert with selection methods using similar selection agents in which one or more target cells can be selected and, simultaneously or sequentially, exposed to the stimulatory agents. Hence, in some aspects, the stimulation of particular cells or subsets of cells can be biased by selection and isolation in together with stimulation.

Figure 10:
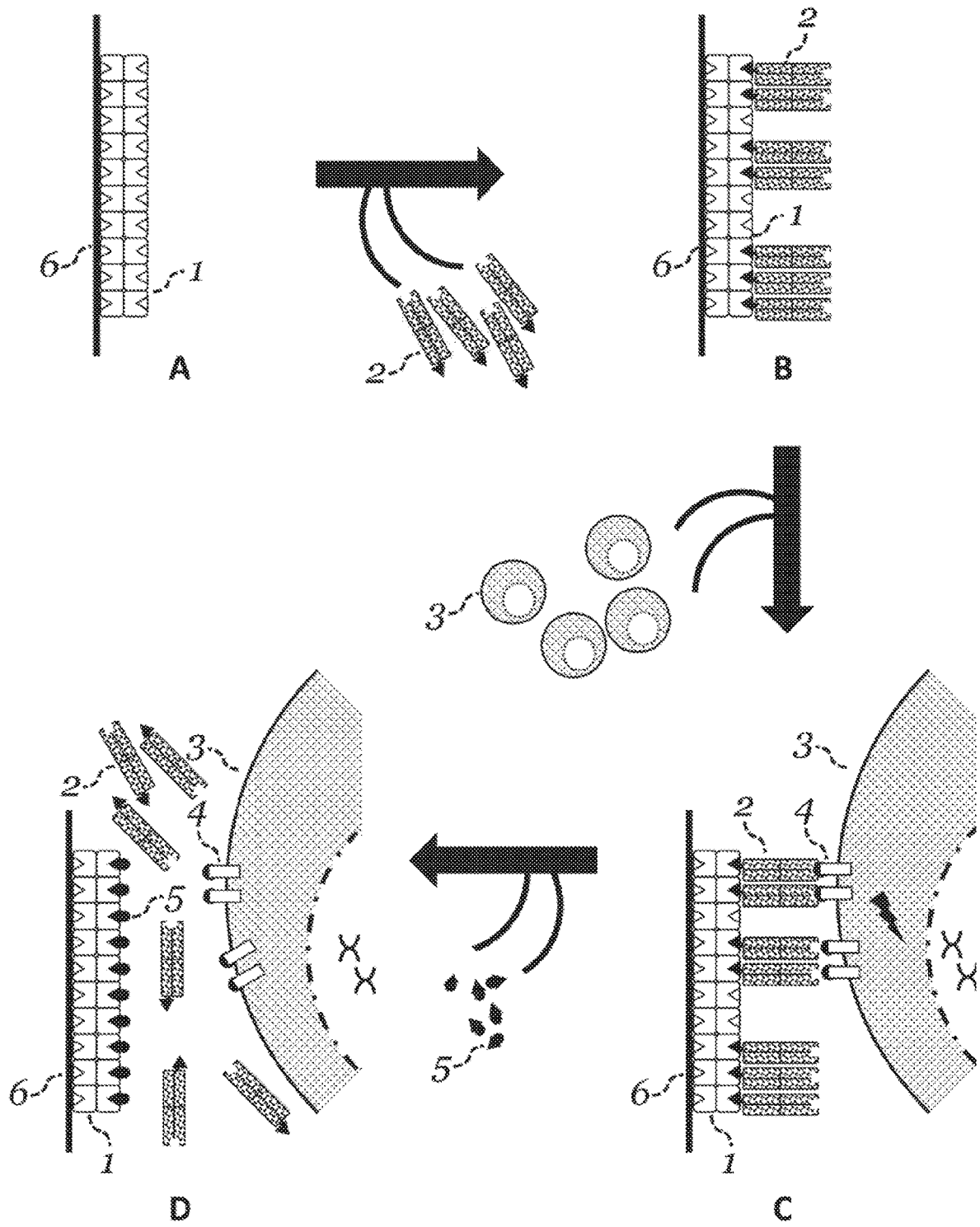
FIG. 10 provides a schematic representation of exemplary embodiments of a reversible system involving oligomeric reagents, such as a streptavidin or streptavidin mutein oligomeric reagent, attached to a support, such as a solid support or a surface, including a stationary phase. Panel A shows a support 6 containing the reagent 1. Agents 2, such as Fab fragments, that are capable of specifically binding to a molecule on the surface of a cell are added to the system. The agents 2, such as Fab fragments, comprise a binding partner (e.g. binding partner C) that is capable of reversibly binding to a binding site (e.g. binding site Z) on the reagent. Panel B depicts the binding partner reversibly binding to a binding site on the reagent. Cells 3 are added to the system. Panel C depicts the agents 2, e.g. Fab fragments, binding to the molecules 4 on the surface of a cell 3. In some embodiments, the scFvs comprise a receptor-binding agent or a selection agent. In some embodiments, the agents, e.g. Fab fragments, can be a receptor-binding agent or a selection agent. Panel C depicts an exemplary receptor-binding agent or agents (e.g. a first receptor-binding agent and/or a second receptor-binding agent), which can induce or modulate a signal in a cell upon binding of the agent, e.g. Fab fragment, to the molecule on the cell. A substance 5, such as a competitive reagent (e.g. biotin), is added, which can be a substance that exhibits a higher binding affinity for the binding site on the reagent than for the binding partner on the agent, e.g. Fab fragment, thereby disrupting binding between the reagent and the agent. Panel D depicts disruption of the binding between the agent 2, e.g. Fab fragment, and the reagent, thereby resulting in dissociation of the reagent from the agent, and thereby the cell. In some cases, the agent, e.g. Fab fragment, also can dissociate from its interaction with the molecule 4 on the cell 3. In some cases, this can disrupt, lessen and/or terminate the signaling in the cell.

In some embodiments, the provided methods involve culturing, e.g. contacting, a composition of cells with a reagent, e.g. multimerization reagent or oligomeric particle reagent, to which is bound one or more receptor-binding agents (e.g. stimulatory agents) (see e.g. FIGS. 10A and 10B). In some embodiments, after contacting the cell composition with the multimerization reagent and/or oligomeric particle reagent with one or more bound receptor-binding agents and usually incubating the cell population with the multimerization reagent and/or oligomeric particle reagent with one or more bound receptor-binding agents, the population of cells forms complexes/is bound to the multimerization agent via the first agent. The other cell populations contained in the initial sample that lack the specific cell surface molecule do not bind to the multimerization reagent and/or oligomeric particle reagent with one or more bound receptor-binding agents. In this respect, it is noted that the cell population usually has multiple copies of the cell surface molecule on its surface and binding of these multiple copies is typically needed for stimulation or activation.

Thus, the multimerization agent provide typically more than one binding site, e.g. Z1, in which, in some cases, a plurality of agents can be reversibly bound, such as via binding of a binding partner, e.g. C1, of the one or more agent to the one or more binding site, e.g. Z1. In some such aspects, this presents the first agent, second agent and/or other agents in a sufficient density to the population of cells. In this respect, it is noted that a multimerization agent can as such have multiple binding sites, e.g., Z1, for example, a streptavidin mutein (being a homo-tetramer) in its native state has four such binding sites, e.g. Z1, and can further be oligomerized. In some cases, a reagent may have only one binding site, e.g. Z1, for the reversible binding of a binding partner, e.g. C1. Such an example is multimeric calmodulin.

Calmodulin as such has only one binding site for calmodulin binding peptides. However, calmodulin can be biotinylated and then reacted with streptavidin-oligomers (see also below), thereby providing a multimerization reagent in which multiple calmodulin molecules are presented in high density on a "scaffold", thereby providing multimeric calmodulin.

In some embodiments, after incubation or other suitable time at which stimulation is desired to be disrupted, the binding between the binding partner, also referred to herein as binding partner C, e.g. C1 of a reversibly bound agent, and the binding site Z, e.g. Z1, of the multimerization reagent and/or oligomeric particle reagent is disrupted by disrupting the respective reversible bond. In some cases, the disruption may be achieved by adding a competitor to the incubation/reaction mixture containing the population of cells being bound to the multimerization reagent and/or oligomeric particle reagents. For competitive disruption (which can be understood as being a competitive elution) of the reversible bond between the binding partner C, e.g. C1, of a reversibly bound agent and the binding site Z, e.g. Z1 of the multimerization reagent and/or oligomeric particle reagents, the incubation mixture/population of cells can be contacted with a free first binding partner C, e.g. C1, or an analog of said first binding partner C that is capable of disrupting the bond between the first binding partner and the binding site Z, e.g. Z1. In the example of the binding partner C, e.g. C1, being a streptavidin binding peptide that binds to biotin binding site of streptavidin, the first free partner may be the corresponding free streptavidin binding peptide or an analogue that binds competitively. Such an analogue can, for example, be biotin or a biotin derivate or analog such as desthiobiotin.

In some embodiments, the addition of the free partner or the analog thereof results in displacement of the binding partner C, e.g. C1, from the multimerization reagent and/or oligomeric particle reagent and thus, since the binding partner is comprised in the reversibly bound agent, displacement of such agent from the multimerization reagent and/or oligomeric particle reagent is achieved. This displacement of the agent in turn results in a dissociation of the first agent from the cell surface molecule, in particular if the binding affinity of the bond between the first agent and the cell surface receptor has a dissociation constant ($K_d$) in the range of $10^{-2}$ M to $10^{-13}$ M and is thus also reversible. Due to this dissociation, in some aspects, the stimulation of the cell population is also terminated.

In some embodiments, the binding affinity of antibody molecules towards their antigen, including for example, a cell surface receptor molecule is usually in the affinity range of the $K_d$ of $10^{-7}$ M to $10^{-13}$ M. Thus, conventional monoclonal antibodies can be used as an agent (first or second, receptor-binding, e.g. stimulatory agent, or selection agent). In some embodiments, in order to avoid any unwanted avidity effects that lead to a stronger binding, monoclonal antibodies can also be used in form of their monovalent antibody fragments such as Fab-fragments or single chain Fv fragments.

In some embodiments, due to the dissociation of the reversibly bound agent or agents from the cell surface molecule, the provided method has the added advantage that the stimulated cell population is free of stimulating agents at the end of the stimulation period. Also, in some embodiments, all other reagents used in the method, namely the agents (e.g. first or second, receptor-binding agents, e.g. stimulatory agents, or selection agents) as well as the competition reagent of the binding partner C, e.g. C1, or the analog thereof can be easily removed from the stimulated cell population via a "removal cartridge" (see e.g. described in International patent application WO 2013/124474). In some cases, for example in which the multimerization reagent and/or oligomeric particle reagent is immobilized on a solid support, such as a bioreactor surface or a magnetic bead, it is being held back. Thus, the use of a removal cartridge for removal of the free agent and the competition reagent, can include loading the elution sample (e.g. sample obtained after disruption of the reversible binding or bond) onto a second chromatography column.

In some embodiments, this chromatography column has a suitable stationary phase that is both an affinity chromatography matrix and, at the same time, can act as gel permeation matrix. In some aspects, this affinity chromatography matrix has an affinity reagent immobilized thereon. In some embodiments, the affinity reagent may, for instance, be streptavidin, a streptavidin mutein, avidin, an avidin mutein or a mixture thereof. In some embodiments the agent (e.g. first or second, receptor-binding agents, e.g. stimulatory agents, or selection agents), the competition reagent of the binding partner C, C1, bind to the affinity reagent, thereby being immobilized on the chromatography matrix. As a result the elution sample containing the isolated and expanded cell population is being depleted of the agent (e.g. first or second, receptor-binding agents, e.g. stimulatory agents, or selection agents) and the competition reagent. In some embodiments, the cultured composition is free of any reactants, which in some aspects is an advantageous for use in connection with diagnostic applications (for example, further FACS™ sorting) or for any cell based therapeutic application.

In some embodiments, the ability to remove the reagent and other components form the composition has the further advantage of being able to avoid any solid support such as magnetic beads. In some embodiments, this means there is no risk or minimal risk of contamination of the activated T cells by such magnetic beads. In some embodiments, this also means that a process that is compliant with GMP standards can be more easily established compared to other methods, such as the use of Dynabeads® in which additional measures have to be taken to ensure that the final expanded T cell population is free of magnetic beads. Furthermore, in some embodiments, the use of a soluble multimerization agent makes it much easier to remove the same from the activated cell population (T cells, B cells or also natural killer cells) since the cells can be simply sedimented by centrifugation and the supernatant, including the soluble multimerization agent can be discarded. Alternatively, the soluble multimerization agent can be removed from the expanded cell population in a gel permeations matrix of the removal cartridge, such as described above (e.g. International patent application WO 2013/124474). In some embodiments, since no solid phase (e.g. magnetic beads) are present, the present invention also provides for an automated closed system for expansion of the cells that can be integrated into known cell expansion systems such as the Xuri Cell Expansion System W25 and WAVE Bioreactor 2/10 System, available from GE Healthcare (Little Chalfont, Buckinghamshire, United Kingdom) or the QUANTUM® Cell Expansion System, available from TerumoBCT Inc. (Lakewood, CO, USA).

In some aspects, the methods provided herein can include a population of cells that carry at least two specific cell surface molecules. In some embodiments, a first cell surface molecule is involved in a primary activation signal to the cell population, while the second cell surface molecule is an accessory molecule on the cell surface that is involved in providing a stimulus to the cells. In particular embodiments, the cell population is contacted with a multimerization reagent and/or oligomeric particle reagents in which is reversibly or non-reversibly bound a first agent that provides a primary activation signal to the cells and a second agent that induces or modulates an additional signal, such as stimulates an accessory molecule on the surface of the cells. In some embodiments, the cell population is contacted with a multimerization reagent and/or oligomeric particle reagent in which is reversibly bound a first agent that provides a primary activation signal to the cells and a second agent that induces or modulates an additional signal, such as stimulates an accessory molecule on the surface of the cells. The population of cells may, for example, be a T cell population in which the cell surface molecule is a TCR/CD3 complex and the cell surface molecule is the accessory molecule CD28. In some aspects, stimulation through such other accessory molecules can result in an increase in a less-differentiated, and, in some cases, a long-lived population T cells such as long-lived memory T cells as compared to conventional stimulation through CD28. In some embodiments, binding of both the TCR/CD3 complex as the primary activation signal and binding of the accessory molecule (e.g. CD28 or other accessory molecule) can be necessary for expansion/proliferation of T cells.

In some embodiments, the methods provided herein also can be further combined to include at least one selection agent reversibly bound to the same reagent, e.g. same multimerization reagent and/or oligomeric particle reagents, as either or both of the first or second receptor-binding agent (e.g. stimulatory agent). In some cases, it is possible to enhance or increase one or more features resulting from the incubation or culture, such as stimulation of expansion (proliferation), activation, costimulation, and/or survival, in a subset of T cells which can be reversibly selected in the presence of the at least one or more selection agent in an incubation or culture that occurs also in the presence of the one or more stimulatory agents. For example, as shown in examples herein, the degree of expansion in a composition of T cells was selectively increased in CD8+ cells when such cells were incubated with a multimerized agent to which was reversibly bound an anti-CD8 antibody in addition to the anti-CD3 antibody and anti-CD28 antibody stimulatory agents. In some embodiments, one or more features resulting from the incubation or culture, such as stimulation of expansion (proliferation), activation, costimulation, and/or survival, can be increased at least 1.5-fold, at least 2.0-fold, at least 3.0-fold, at least 4.0-fold, at least 5.0-fold, at least 6.0-fold, at least 7.0-fold, at least 8.0-fold, at least 9.0-fold, at least 10-fold or more in a subset of T cell in the cultured composition that are positive for a selection marker when incubated in the presence of the one or more stimulatory agents and the selection agent that specifically binds to the selection marker compared to the incubation only in the presence of the one of more stimulatory agents but not the selection agent. This biasing or selectivity of cell, such as T cell, features permits one to control the end points features of specific subsets or populations of T cells. In some embodiments, the selection marker can be any selection marker as described herein. In some embodiments, the selection marker is selected from among CD25, CD28, CD62L, CCR7, CD27, CD127, CD3, CD4, CD8, CD45RA, and/or CD45RO.

In some embodiments, the multimerization reagent and/or oligomeric particle reagent comprises at least one binding site Z, e.g. Z1, for the reversible binding of the first agent and the first agent also comprises at least one binding partner C, e.g. C1, wherein the binding partner C, e.g. C1, is able of reversibly or non-reversibly binding to the binding site Z, e.g. Z1, of the multimerization reagent and/or oligomeric particle reagent. Thus, the first agent, when contacted or incubated with the multimerization agent, can be reversibly bound to the multimerization reagent and/or oligomeric particle reagent via the reversible bond formed between the binding partner C, e.g. C1, and the binding site Z, e.g. Z1. In addition, the second agent can comprises a binding partner C, e.g. C2, wherein the binding partner C2 is able of being reversibly bound to a binding site Z, e.g. Z2, respectively, of the multimerization reagent and/or oligomeric particle reagent. In some embodiments, the second agent, when it is contacted or incubated with the multimerization agent, is reversibly bound to the multimerization reagent and/or oligomeric particle reagents via the reversible bond formed between the binding partner C, e.g. C1 and the binding site Z, e.g. Z2. In some cases, C1 and C2 can be the same or substantially the same and/or comprise the same or substantially the same moiety. In some cases, Z1 and Z2 can be the same or substantially the same and/or comprise the same or substantially the same moiety.

In some embodiments, using as binding partners C1 and C2, moieties that bind to the same binding site of the multimerization agent has the advantage that the same competition reagent (of the first binding partner C1 and also of the second binding partner C2) or analog thereof can be used to disrupt, and in some cases terminate, the expansion of the population of target cells (e.g. T cells) and to release this population of target cells (e.g. T cells) from the multimerization agent.

In some cases for producing the binding agents (e.g. e.g. first or second, receptor-binding agents, e.g. stimulatory agents, or selection agents) to comprise a binding partner C, the binding partner C, e.g. C1 or C2, can be provided by the respective expression vector used for the recombinant production of the agent (e.g. antibody fragment) so that the binding partner C, e.g. C1 or C2, is part of a fusion peptide with the agent at either the N-terminus or C-terminus. In some embodiments, in the context of an agent that is an antibody or antigen-binding fragment, the binding partner C, e.g. C1 or C2, can be present at the C-terminus of either the light or the heavy chain. Also this methodology of cloning a recombinant protein, such as the variable domains of an antibody molecule, and recombinantly producing a respective protein, e.g. antibody fragment, is well known to the person skilled in the art, see for example, Skerra, A. (1994). In some embodiments, an antibody molecule can be generated of artificial binding molecules with antibody like properties against a given target, such as CD3 or CD28 or other accessory or stimulatory agent molecules as described, such as by well-known evolutive methods such as phage display (reviewed, e.g., in Kay, B. K. et al. (1996) Phage Display of Peptides and Proteins—A Laboratory Manual, 1$^{st}$ Ed., Academic Press, New York NY; Lowman, H. B. (1997) Annu. Rev. Biophys. Biomol. Struct. 26, 401-424, or Rodi, D. J., and Makowski, L. (1999) Curr. Opin. Biotechnol. 10, 87-93), ribosome display (reviewed in Amstutz, P. et al. (2001) Curr. Opin. Biotechnol. 12, 400-405) or mRNA display as reported in Wilson, D. S. et al. (2001) Proc. Natl. Acad. Sci. USA 98, 3750-3755.

II. Reversible Reagent Systems and Related Uses

In some embodiments, the methods employ reversible systems in which at least one agent (e.g., a receptor-binding agent or selection agent) capable of binding to a molecule on the surface of a cell (cell surface molecule), is associated, e.g., reversibly associated, with a reagent. In some cases, the reagent contains a plurality of binding sites capable of binding, e.g., reversibly binding to the agent (e.g., receptor-binding agent or selection agent). In some cases, the reagent is a multimerization reagent and/or oligomeric particle reagent having bound thereto the at least one agent. In some embodiments, the at least one agent (e.g., receptor-binding agent or selection agent) contains at least one binding site B that can specifically bind an epitope or region of the molecule and also contains a binding partner, also referred to herein as a binding partner C, that specifically binds to at least one binding site Z of the reagent. In some cases, the binding interaction between the binding partner C and the at least one binding site Z is a non-covalent interaction. In some cases, the binding interaction between the binding partner C and the at least one binding site Z is a covalent interaction. In some embodiments, the binding interaction, such as non-covalent interaction, between the binding partner C and the at least one binding site Z is reversible.

In some embodiments, the reversible association can be mediated in the presence of a substance, such as a competition reagent (also called an eluent reagent), that is or contains a binding site that also is able to bind to the at least one binding site Z. Generally, the substance (e.g. competition reagent) can act as a competitor. For example, in some embodiments, binding partner C dissociates from the at least one binding site Z as a consequence of its off-rate. In certain aspects, following the dissociation binding partner C may (i) bind again to the at least one binding site Z, or, in some aspects, (ii) will be prevented from binding again to the at least one binding site Z if the substance, e.g., the competition reagent, binds to the one or more binding site Z first. In some aspects, the substance may have a higher binding affinity and/or be present at a high and/or sufficient concentration for the binding site Z present in the reagent and/or due to being present at higher concentrations than the binding partner C, thereby reducing the amount of attached and/or associated binding partner C from the one or more binding partner C. In some embodiments, the affinity of the substance (e.g. competition reagent) for the at least one binding site Z is greater than the affinity of the binding partner C of the agent (e.g., receptor-binding agent or selection agent) for the at least one binding site Z. In certain embodiments, the, the bonds between the binding site Z of the reagent and the binding partner C of the agent (e.g., receptor-binding agent or selection agent) can be reduced or decreased by addition of the substance (e.g. competition reagent), thereby in some aspects rendering the association of the agent (e.g., receptor-binding agent or selection agent) and reagent effectively reversible.

Reagents that can be used in such reversible systems are described and known in the art, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277. Non-limiting examples of reagents and binding partners capable of forming a reversible interaction, as well as substances (e.g. competition reagents) capable of reversing such binding, are described below.

A. Reagent

In some embodiments, the reagent contains one or a plurality of binding sites Z that are capable of reversibly binding to a binding partners C comprised by the agent (e.g., receptor-binding agent or selection agent). In some embodiments, the reagent contains a plurality of binding sites Z, which each are able to specifically bind to the binding partner C that is included in the agent (e.g., receptor-binding agent or selection agent), such that the reagent is capable of reversibly binding to a plurality of agents (e.g., receptor-binding agent or selection agent), e.g., is a multimerization reagent and/or oligomeric particle reagent with one or more bound reagent. In some embodiments, the reagent is an oligomer or polymer of individual molecules (e.g. monomers) or complexes that make up an individual molecule (e.g. tetramer), each containing at least one binding site Z. In some embodiments, the reagent contains at least two binding sites Z, at least three binding sites Z, at least four binding sites Z, such as at least 5, 6, 7, 8, 9, 10, 11, 12, 13, 14, 15, 16, 17, 18, 19, 20, 24, 28, 32, 36, 40, 44, 48, 52, 56, 60, 64, 68, 72 or more binding sites Z. The binding sites can all be the same or the plurality of binding sites can contain one or more different binding sites (e.g., Z1, Z2, Z3, etc.). In some embodiments, the reagent is an oligomeric particle reagent, and contains at least 72, 120, 140, 200, 240, 280, 320, 360, 400, 440, 480, 520, 560, 600, 640, 680, 720, 760, 800, 900, 1,000, 2000, 3000, 4000, 5000, 6000, 7000, 8000, 9000, 10,000, or at least 100,000 binding sites Z.

In some embodiments, one or more agents (e.g., receptor-binding agents or selection agents) associate with, such as are reversibly bound to, the reagent, such as via the one or plurality of binding sites Z present on the reagent. In some cases, this results in the agents (e.g., receptor-binding agents or selection agents) being closely arranged to each other such that an avidity effect can take place if a target cell having (at least two copies of) a cell surface molecule is brought into contact with the agent (e.g., receptor-binding agent or selection agent) that has one or more binding sites B able to bind the particular molecule.

In some embodiments, two or more different agents (e.g., receptor-binding agents or selection agents) that are the same, i.e. containing the same binding site B, can be reversibly bound to the reagent. In some embodiments, the two or more different agents containing the same binding site B are reversibly bound to the oligomeric particle reagent. In some embodiments, it is possible to use at least two different (kinds of) agents (e.g., receptor-binding agents or selection agents), and in some cases, three or four different (kinds of) agents, e.g. two or more different receptor-binding agents and/or selection agent. For example, in some embodiments, the reagent can be reversibly bound to a first agent (e.g., receptor-binding agent or selection agent) containing a binding site B1, B2, B3 or B4, etc. and a second agent (e.g., receptor-binding agent or selection agent) containing another binding site, e.g. another of a binding site B1, B2, B3 or B4. In some cases, the binding site of the first agent and the second agent can be the same. For example, in some aspects, each of the at least two agents (e.g. receptor-binding agent or selection agent) can bind to the same molecule. In some cases, the binding site of the first agent and the second agent can be different. In some aspects, each of the at least two agents (e.g. receptor-binding agent or selection agent) can bind to a different molecule, such as a first molecule, second molecule and so on. In some cases, the different molecules, such as cell surface molecules, can be present on the same target cell. In other cases, the different molecules, such as cell surface molecules, can be present on different target cells that are present in the same population of cells. In some case, a third, fourth and so on agent (e.g., receptor-binding agent or selection agent) can be associated with the same reagent, each containing a further different binding site.

In some embodiments, the two or more different agents (e.g., receptor-binding agents or selection agents) contain the same binding partner C. In some embodiments, the two or more different agents (e.g., receptor-binding agents or selection agents) contain different binding partners. In some aspects, a first agent (e.g., receptor-binding agent or selection agent) can have a binding partner C1 that can specifically bind to a binding site Z1 present on the reagent and a second agent (e.g., receptor-binding agents or selection agent) can have a binding partner C2 that can specifically bind to the binding site Z1 or to a binding site Z2 present on the reagent. Thus, in some instances, the plurality of binding sites Z comprised by the reagent includes binding sites Z1 and Z2, which are capable of reversibly binding to binding partners C1 and C2, respectively, comprised by the agent (e.g., receptor-binding agent or selection agent). In some embodiments, C1 and C2 are the same, and/or Z1 and Z2 are the same. In other aspects, one or more of the plurality of binding sites Z can be different. In other instances, one or more of the plurality of binding partners C may be different. It is within a level of a skilled artisan to choose any combination of different binding partners C that are compatible with a reagent containing the binding sites Z, as long as each of the binding partners C are able to interact, such as specifically bind, with one of the binding sites Z.

In some embodiments, the reagent is a streptavidin, a streptavidin mutein or analog, avidin, an avidin mutein or analog (such as neutravidin) or a mixture thereof, in which such reagent contains one or more binding sites Z for reversible association with a binding partner C. In some embodiments, the binding partner C can be a biotin, a biotin derivative or analog, or a streptavidin-binding peptide or other molecule that is able to specifically bind to streptavidin, a streptavidin mutein or analog, avidin or an avidin mutein or analog. In some embodiments, the reagent is or contains streptavidin, avidin, an analog or mutein of streptavidin, or an analog or mutein or avidin that reversibly binds biotin, a biotin analog or a biologically active fragment thereof. In some embodiments, the reagent is or contains an analog or mutein of streptavidin or an analog or mutein of avidin that reversibly binds a streptavidin-binding peptide. In some embodiments, the substance (e.g. competitive reagent) can be a biotin, a biotin derivative or analog or a streptavidin-binding peptide capable of competing for binding with the binding partner C for the one or more binding sites Z. In some embodiments, the binding partner C and the substance (e.g. competitive reagent) are different, and the substance (e.g. competitive reagent) exhibits a higher binding affinity for the one or more binding sites Z compared to the affinity of the binding partner.

In some embodiments, the streptavidin can be wild-type streptavidin, streptavidin muteins or analogs, such as streptavidin-like polypeptides. Likewise, avidin, in some aspects, includes wild-type avidin or muteins or analogs of avidin such as neutravidin, a deglycosylated avidin with modified arginines that typically exhibits a more neutral pi and is available as an alternative to native avidin. Generally, deglycosylated, neutral forms of avidin include those commercially available forms such as "Extravidin", available through Sigma Aldrich, or "NeutrAvidin" available from Thermo Scientific or Invitrogen, for example.

In some embodiments, the reagent is a streptavidin or a streptavidin mutein or analog. In some embodiments, wild-type streptavidin (wt-streptavidin) has the amino acid sequence disclosed by Argarana et al, Nucleic Acids Res. 14 (1986) 1871-1882 (SEQ ID NO: 1). In general, streptavidin naturally occurs as a tetramer of four identical subunits, i.e.

it is a homo-tetramer, where each subunit contains a single binding site for biotin, a biotin derivative or analog or a biotin mimic. An exemplary sequence of a streptavidin subunit is the sequence of amino acids set forth in SEQ ID NO: 1, but such a sequence also can include a sequence present in homologs thereof from other *Streptomyces* species. In particular, each subunit of streptavidin may exhibit a strong binding affinity for biotin with a dissociation constant ($K_d$) on the order of about $10^{-14}$ M. In some cases, streptavidin can exist as a monovalent tetramer in which only one of the four binding sites is functional (Howarth et al. (2006) *Nat. Methods*, 3:267-73; Zhang et al. (2015) *Biochem. Biophys. Res. Commun.*, 463:1059-63)), a divalent tetramer in which two of the four binding sites are functional (Fairhead et al. (2013) *J. Mol. Biol.*, 426:199-214), or can be present in monomeric or dimeric form (Wu et al. (2005) *J. Biol. Chem.*, 280:23225-31; Lim et al. (2010) *Biochemistry*, 50:8682-91).

In some embodiments, streptavidin may be in any form, such as wild-type or unmodified streptavidin, such as a streptavidin from a *Streptomyces* species or a functionally active fragment thereof that includes at least one functional subunit containing a binding site for biotin, a biotin derivative or analog or a biotin mimic, such as generally contains at least one functional subunit of a wild-type streptavidin from *Streptomyces avidinii* set forth in SEQ ID NO: 1 or a functionally active fragment thereof. For example, in some embodiments, streptavidin can include a fragment of wild-type streptavidin, which is shortened at the N-and/or C-terminus. Such minimal streptavidins include any that begin N-terminally in the region of amino acid positions 10 to 16 of SEQ ID NO: 1 and terminate C-terminally in the region of amino acid positions 133 to 142 of SEQ ID NO: 1. In some embodiments, a functionally active fragment of streptavidin contains the sequence of amino acids set forth in SEQ ID NO: 2. In some embodiments, streptavidin, such as set forth in SEQ ID NO: 2, can further contain an N-terminal methionine at a position corresponding to Ala13 with numbering set forth in SEQ ID NO: 1. Reference to the position of residues in streptavidin or streptavidin muteins is with reference to numbering of residues in SEQ ID NO: 1.

In some aspects, streptavidin muteins include polypeptides that are distinguished from the sequence of an unmodified or wild-type streptavidin by one or more amino acid substitutions, deletions, or additions, but that include at least one functional subunit containing a binding site for biotin, a biotin derivative or analog or a streptavidin-binding peptide. In some aspects, streptavidin-like polypeptides and streptavidin muteins can be polypeptides which essentially are immunologically equivalent to wild-type streptavidin and are in particular capable of binding biotin, biotin derivatives or biotin analogues with the same or different affinity as wt-streptavidin. In some cases, streptavidin-like polypeptides or streptavidin muteins may contain amino acids which are not part of wild-type streptavidin or they may include only a part of wild-type streptavidin. In some embodiments, streptavidin-like polypeptides are polypeptides which are not identical to wild-type streptavidin, since the host does not have the enzymes which are required in order to transform the host-produced polypeptide into the structure of wild-type streptavidin. In some embodiments, streptavidin also may be present as streptavidin tetramers and streptavidin dimers, in particular streptavidin homotetramers, streptavidin homodimers, streptavidin heterotetramers and streptavidin heterodimers. Generally, each subunit normally has a binding site for biotin or biotin analogues or for streptavidin-binding peptides. Examples of streptavidins or streptavidin muteins are mentioned, for example, in WO 86/02077, DE 19641876 A1, U.S. Pat. No. 6,022,951, WO 98/40396 or WO 96/24606.

In some emobdiments, the biotin is generally employed in its natural d-sterioisomeric form, i.e., D-biotin. In some embodiments, the biotin is D-biotin. In particular embodiments, examples of biotin analogs and/or derivatives include, but are not limited to, D-biotin, N-ketone biotin analog, a ketone biotin analog, an N-azide biotin analog, an azide biotin analog, an N-acyl azide biotin analog, an NBD-GABA biotin analog, a 1,2-diamine biotin analog, an N-alkyne biotin analog, a tetrathiol biotin analog, N-hydroxysuccinimide-iminobiotin, iminobiotin, amidobiotin N-hydroxysuccinimide-iminobiotin, amidobiotins, desthiobiotin, biotin sulfone, caproylamidobiotin and biocytin. In some aspects, biotin analogs are or include biotin sulfone, 2'-thiobiotin, 2'-iminobiotin, d-desthiobiotin, dl-desthiobiotin, dl-desthiobiotin methyl ester and other imidazolidone derivatives and those described in Green, N. M., (1975) in Advances in Protein Chemistry (Anson, M. L. and Edsell, J. T., Eds), Vol. 29, pp. 85-133, Academic Press, New York. In certain embodiments, the biotin anolog or derivative is D-biotin, desthiobiotin, and/or iminobiotin.

In some embodiments, a streptavidin mutein can contain amino acids that are not part of an unmodified or wild-type streptavidin or can include only a part of a wild-type or unmodified streptavidin. In some embodiments, a streptavidin mutein contains at least one subunit that can have one or more amino acid substitutions (replacements) compared to a subunit of an unmodified or wild-type streptavidin, such as compared to the wild-type streptavidin subunit set forth in SEQ ID NO: 1 or a functionally active fragment thereof, e.g. set forth in SEQ ID NO: 2. In some embodiments, at least one subunit of a streptavidin mutein can have at least 1, 2, 3, 4, 5, 6, 7, 8, 9, 10, 11, 12, 13, 14, 15, 16, 17, 18, 19 or 20 amino acid differences compared to a wild-type or unmodified streptavidin and/or contains at least one subunit that comprising an amino acid sequence that exhibits at least 85%, 86%, 87%, 88%, 89%, 90%, 91%, 92%, 93%, 94%, 95%, 96%, 97%, 98%, 99% or more sequence identity to the sequence of amino acids set forth in SEQ ID NO: 1, 2 or 59, where such streptavidin mutein exhibits functional activity to bind biotin, a biotin derivative or analog or biotin mimic. In some embodiments, the amino acid replacements (substitutions) are conservative or non-conservative mutations. Examples of streptavidin muteins are known in the art, see e.g., U.S. Pat. Nos. 5,168,049; 5,506,121; 6,022,951; 6,156, 493; 6,165,750; 6,103,493; or 6,368,813; or International published PCT App. No. WO2014/076277.

In some embodiments, streptavidin or a streptavidin mutein includes proteins containing one or more than one functional subunit containing one or more binding sites Z for biotin, a biotin derivative or analog or a streptavidin-binding peptide, such as two or more, three or more, four or more, and, in some cases, 5, 6, 7, 8, 9, 10, 11, 12 or more functional subunits. In some embodiments, streptavidin or streptavidin mutein can include a monomer; a dimer, including a heterodimer or a homodimer; a tetramer, including a homotetramer, a heterotetramer, a monovalent tetramer or a divalent tetramer; or can include higher ordered multimers or oligomers thereof.

In some embodiments, the binding affinity, such as dissociation constant ($K_d$), of streptavidin or a streptavidin mutein for a peptide ligand binding partner is less than $1 \times 10^{-4}$ M, $5 \times 10^{-4}$ M, $1 \times 10^{-5}$ M, $5 \times 10^{-5}$ M, $1 \times 10^{-6}$ M, $5 \times 10^{-6}$ M or $1 \times 10^{-7}$ M, but generally greater than $1 \times 10^{-13}$ M, $1 \times 10^{-12}$ M or $1 \times 10^{-11}$ M. For example, peptide sequences (Strep-tags), such as disclosed in U.S. Pat. No. 5,506,121, can act as biotin mimics and demonstrate a binding affinity for streptavidin, e.g., with a $K_d$ of approximately between $10^{-4}$ and $10^{-5}$ M. In some cases, the binding affinity can be further improved by making a mutation within the streptavidin molecule, see e.g. U.S. Pat. No. 6,103,493 or International published PCT App. No. WO2014/076277. In some embodiments, binding affinity can be determined by methods known in the art, such as any described herein.

In some embodiments, the reagent, such as a streptavidin or streptavidin mutein, exhibits binding affinity for a peptide ligand binding partner, which peptide ligand binding partner can be the binding partner C present in the agent (e.g., receptor-binding agent or selection agent). In some embodiments, the peptide sequence contains a sequence with the general formula set forth in SEQ ID NO: 9, such as contains the sequence set forth in SEQ ID NO: 10. In some embodiments, the peptide sequence has the general formula set forth in SEQ ID NO: 11, such as set forth in SEQ ID NO: 12. In one example, the peptide sequence is Trp-Arg-His-Pro-Gln-Phe-Gly-Gly (also called Strep-tag®, set forth in SEQ ID NO: 7). In one example, the peptide sequence is Trp-Ser-His-Pro-Gln-Phe-Glu-Lys (also called Strep-tag® II, set forth in SEQ ID NO: 8). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa (SEQ ID NO: 9), where Xaa is glutamine, asparagine, or methionine, and wherein the other binding module has the same or different streptavidin peptide ligand, such as set forth in SEQ ID NO: 11 (see e.g. International Published PCT Appl. No. WO02/077018; U.S. Pat. No. 7,981,632). In some embodiments, the peptide ligand contains a sequence having the formula set forth in any of SEQ ID NO: 13 or 14. In some embodiments, the peptide ligand has the sequence of amino acids set forth in any of SEQ ID NOS: 15-19. In most cases, all these streptavidin binding peptides bind to the same binding site, namely the biotin binding site of streptavidin. If one or more of such streptavidin binding peptides is used as binding partners C, e.g. C1 and C2, the multimerization reagent and/or oligomeric particle reagents bound to the one or more agents via the binding partner C is typically composed of one or more streptavidin muteins.

Figure 9:
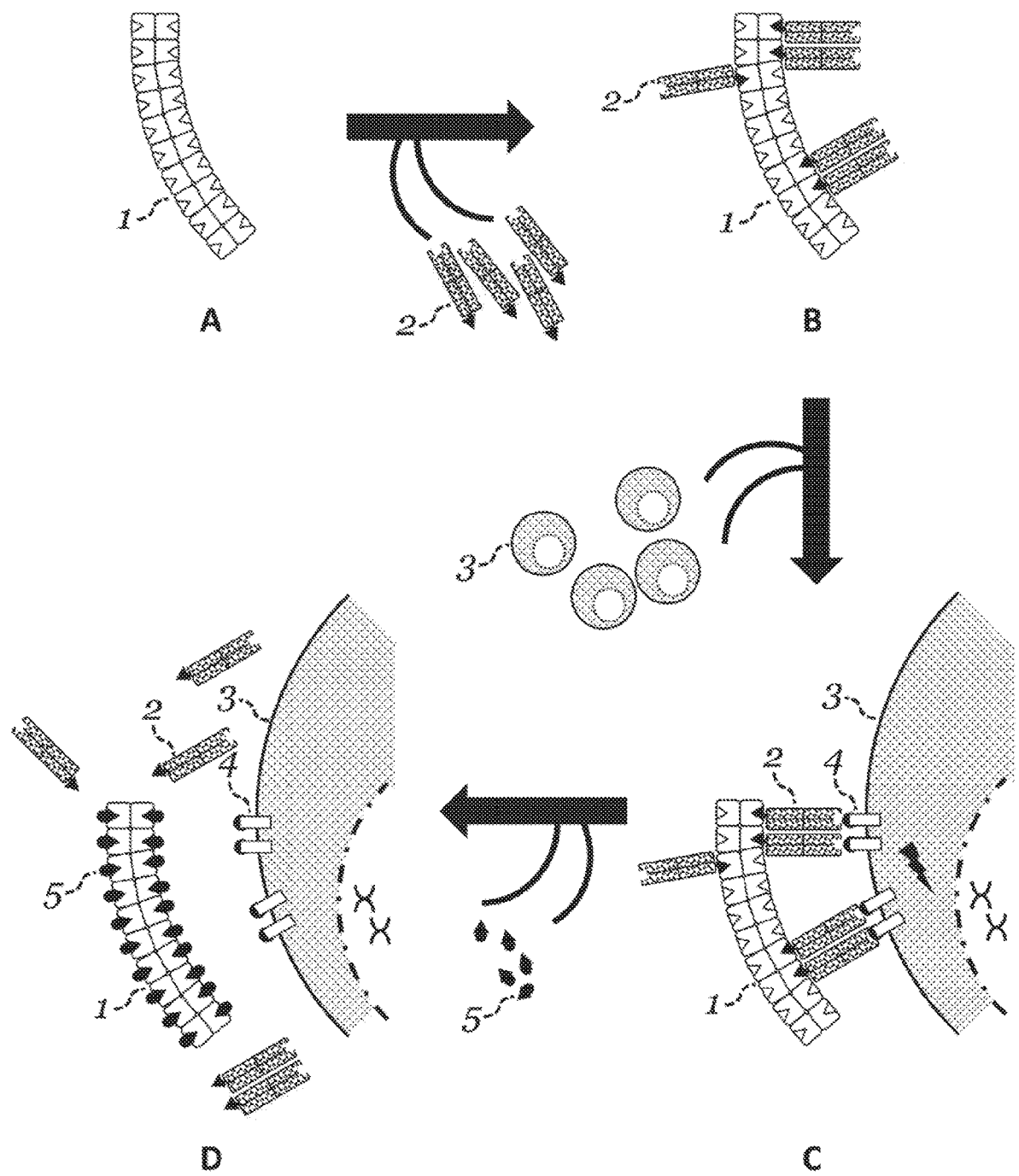
FIG. 9 provides a schematic representation of exemplary embodiments in which oligomeric reagents, such as a streptavidin or streptavidin mutein oligomeric reagent, are used to multimerize stimulatory agents and the resulting complexes incubated with cells to deliver signals to the cells, followed by reversal of the binding. Panel A shows an oligomeric reagent 1, which is shown as not bound to any support and as being flexible. Stimulatory agents 2, which are shown here as Fab fragments and are capable of specifically binding to a molecule on the surface of a cell, are combined with the reagent. The agents comprise a binding partner (e.g. binding partner C) that is capable of reversibly binding to a binding site (e.g. binding site Z) on the reagent, multimerizing the agents. Panel B depicts the binding partner reversibly binding to a binding site on the reagent. Cells 3 are added to the system. Panel C depicts the multimerized agents (Fab fragments) specifically binding to the molecules 4 on the surface of a cell 3. In Panel C, the depicted agents are stimulatory receptor-binding agents, (e.g. a first receptor-binding agent and/or a second receptor-binding agent), which can induce or modulate a signal in a cell upon binding of the agent, to the molecule on the cell. As shown in panel D, a substance 5, such as a competitive reagent (e.g. biotin), is added to the composition, which can be a substance that exhibits a higher binding affinity for the binding site on the reagent than for the binding partner on the agent, thereby disrupting the reversible binding between the reagent 1 and the agent 2. In some cases, the agent, e.g., Fab fragment also can dissociate from its interaction with the molecule 4 on the cell 3. In some cases, this can disrupt, lessen and/or terminate the signaling in the cell.

In some embodiments, the reagent is or contains a streptavidin mutein. In some embodiments, the streptavidin muteins contain one or more mutations (e.g. amino acid replacements) compared to wild-type streptavidin set forth in SEQ ID NO: 1 or a biologically active portion thereof. For example, biologically active portions of streptavidin can include streptavidin variants that are shortened at the N- and/or the C-terminus, which in some cases is called a minimal streptavidin. In some embodiments, an N-terminally shortened minimal streptavidin, to which any of the mutations can be made, begins N-terminally in the region of the amino acid positions 10 to 16 and terminates C-terminally in the region of the amino acid positions 133 to 142 compared to the sequence set forth in SEQ ID NO: 1. In some embodiments, an N-terminally shortened streptavidin, to which any of the mutations can be made, contains the amino acid sequence set forth in SEQ ID NO: 2 or 59. In some embodiments, the minimal streptavidin contains an amino acid sequence from position Ala13 to Ser139 and optionally has an N-terminal methionine residue instead of Ala13. For purposes herein, the numbering of amino acid positions refers throughout to the numbering of wt-streptavidin set forth in SEQ ID NO: 1 (e.g. Argarana et al., Nucleic Acids Res. 14 (1986), 1871-1882, cf. also FIG. 9).

In some embodiments, the streptavidin mutein is a mutant as described in U.S. Pat. No. 6,103,493. In some embodiments, the streptavidin mutein contains at least one mutation within the region of amino acid positions 44 to 53, based on the amino acid sequence of wild-type streptavidin, such as set forth in SEQ ID NO: 1. In some embodiments, the streptavidin mutein contains a mutation at one or more residues 44, 45, 46, and/or 47. In some embodiments, the streptavidin mutein contains a replacement of Glu at position 44 of wild-type streptavidin with a hydrophobic aliphatic amino acid, e.g. Val, Ala, Ile or Leu, any amino acid at position 45, an aliphatic amino acid, such as a hydrophobic aliphatic amino acid at position 46 and/or a replacement of Val at position 47 with a basic amino acid, e.g. Arg or Lys, such as generally Arg. In some embodiments, Ala is at position 46 and/or Arg is at position 47 and/or Val or Ile is at position 44. In some embodiments, the streptavidin mutant contains residues $Val^{44}$-$Thr^{45}$-$Ala^{46}$-$Arg^{47}$ (SEQ ID NO: 62), such as set forth in exemplary streptavidin muteins containing the sequence of amino acids set forth in SEQ ID NO: 3 or SEQ ID NO: 4 or 60 (also known as streptavidin mutant 1, SAM1). In some embodiments, the streptavidin mutein contains residues $Ile^{44}$-$Gly^{45}$-$Ala^{46}$-$Arg^{47}$ (SEQ ID NO: 63), such as set forth in exemplary streptavidin muteins containing the sequence of amino acids set forth in SEQ ID NO: 5, 6, or 61 (also known as SAM2). In some cases, such streptavidin mutein are described, for example, in U.S. Pat. No. 6,103,493, and are commercially available under the trademark Strep-Tactin®.

In some embodiment, the streptavidin mutein is a mutant as described in International Published PCT Appl. Nos. WO 2014/076277. In some embodiments, the streptavidin mutein contains at least two cysteine residues in the region of amino acid positions 44 to 53 with reference to amino acid positions set forth in SEQ ID NO: 1. In some embodiments, cysteine residues are present at positions 45 and 52 to create a disulfide bridge connecting these amino acids. In such an embodiment, amino acid 44 is typically glycine or alanine and amino acid 46 is typically alanine or glycine and amino acid 47 is typically arginine. In some embodiments, the streptavidin mutein contains at least one mutation or amino acid difference in the region of amino acids residues 115 to 121 with reference to amino acid positions set forth in SEQ ID NO: 1. In some embodiments, the streptavidin mutein contains at least one mutation at amino acid position 117, 120 and 121 and/or a deletion of amino acids 118 and 119 and substitution of at least amino acid position 121.

In some embodiments, the streptavidin mutein contains a mutation at a position corresponding to position 117, which mutation can be to a large hydrophobic residue like Trp, Tyr or Phe or a charged residue like Glu, Asp or Arg or a hydrophilic residue like Asn or Gln, or, in some cases, the hydrophobic residues Leu, Met or Ala, or the polar residues Thr, Ser or His. In some embodiments, the mutation at position 117 is combined with a mutation at a position corresponding to position 120, which mutation can be to a small residue like Ser or Ala or Gly, and a mutation at a position corresponding to position 121, which mutation can be to a hydrophobic residue, such as a bulky hydrophobic residue like Trp, Tyr or Phe. In some embodiments, the mutation at position 117 is combined with a mutation at a position corresponding to position 120 of wildtype streptavidin set forth in SEQ ID NO:1 or a biologically active fragment thereof, which mutation can be a hydrophobic residue such as Leu, Ile, Met, or Val or, generally, Tyr or Phe, and a mutation at a position corresponding to position 121 compared to positions of wildtype streptavidin set forth in SEQ ID NO:1 or a biologically active fragment thereof, which mutation can be to a small residue like Gly, Ala, or Ser, or with Gln, or with a hydrophobic residue like Leu, Val, Ile, Trp, Tyr, Phe, or Met. In some embodiments, such muteins also can contain residues Val44-Thr45-Ala46-Arg47 (SEQ ID NO: 62) or residues Ile44-Gly45-Ala46-Arg47 (SEQ ID NO: 63). In some embodiments, the streptavidin mutein contains the residues Val44, Thr45, Ala46, Arg47, Glu117, Gly120 and Tyr121. In some embodiments, the mutein streptavidin contains the sequence of amino acids set forth in SEQ ID NO:27 or SEQ ID NO:28, or a sequence of amino acids that exhibits at least 85%, 86%, 87%, 88%, 89%, 90%, 91%, 92%, 93%, 94%, 95%, 96%, 97%, 98%, 99% or more sequence identity to the sequence of amino acids set forth in SEQ ID NO: 27 or SEQ ID NO: 28, contains the residues Val44, Thr45, Ala46, Arg47, Glu117, Gly120 and Tyr121 and exhibits functional activity to bind to biotin, a biotin analog or a streptavidin-binding peptide.

In some embodiments, the molecule, e.g. streptavidin or streptavidin mutein has about 5 to 30 primary amines, which, in some cases, can include an N-terminal amine and/or one or more lysine residues. In particular embodiments, the molecule is a tetramer of streptavidin or a streptavidin mutein, including any of the described streptavidin muteins, which, as a tetramer, contains greater than 5 primary amines, such as generally 5 to 40 or 15 to 35, such as generally about 15, 16, 17, 18, 19, 20, 21, 22, 23, 14, 25, 26, 27, 28, 29, 30, 31, 32 or more primary amines. In some embodiments, the molecule is streptavidin or a streptavidin mutein or a truncated fragment thereof, such as any of such described molecules. In particular embodiments, the molecule is a tetramer of streptavidin or a streptavidin mutein comprising a sequence set forth in any of SEQ ID NOS:2, 4, 6, 27, 59, 60 or 61, which, as a tetramer, is a molecule that contains 20 primary amines, including 1 N-terminal amine and 4 lysines per monomer.

In some embodiments, a streptavidin mutein can contain any of the above mutations in any combination, and the resulting streptavidin mutein may exhibit a binding affinity characterized by a dissociation constant ($K_d$) that is or is less than $3.7\times10^{-5}$ M for the peptide ligand (Trp-Arg-His-Pro-Gln-Phe-Gly-Gly; also called Strep-tag®, set forth in SEQ ID NO: 7) and/or that is or is less than $7.1\times10^{-5}$ M for the peptide ligand (Trp-Ser-His-Pro-Gln-Phe-Glu-Lys; also called Strep-tag® II, set forth in SEQ ID NO: 8) and/or that is or is less than $7.0\times10^{-5}$ M, $6.0\times10^{-5}$ M, $5.0\times10^{-5}$ M, $4.0\times10^{-5}$ M, $3.0\times10^{-5}$ M, $2.0\times10^{-5}$ M, $1.0\times10^{-5}$ M, $9.0\times10^{-6}$ M, $8.0\times10^{-6}$ M, $7.0\times10^{-6}$ M, $6.0\times10^{-6}$ M, $5.0\times10^{-6}$ M, $4.0\times10^{-6}$ M, $3.0\times10^{-6}$ M, $2.0\times10^{-6}$ M, $1.0\times10^{-6}$ M, $9.0\times10^{-7}$ M, $8.0\times10^{-7}$ M, $7.0\times10^{-7}$ M, $6.0\times10^{-7}$ M, $5.0\times10^{-7}$ M, $4.0\times10^{-7}$ M, $3.0\times10^{-7}$ M, $2.0\times10^{-7}$ M or $1.0\times10^{-7}$ M,, but generally greater than $1\times10^{-13}$ M, $1\times10^{-12}$ M or $1\times10^{-11}$ M for any of the peptide ligands set forth in any of SEQ ID NOS:7-19.

In some embodiments, a streptavidin mutein can contain any of the above mutations in any combination, and the resulting streptavidin mutein may exhibit a binding affinity characterized by an association constant ($K_a$) that is or is greater than $2.7\times10^4$ M$^{-1}$ for the peptide ligand (Trp-Arg-His-Pro-Gln-Phe-Gly-Gly; also called Strep-tag®, set forth in SEQ ID NO: 7) and/or that is or is greater than $1.4\times10^4$ M$^{-1}$ for the peptide ligand (Trp-Ser-His-Pro-Gln-Phe-Glu-Lys; also called Strep-tag® II, set forth in SEQ ID NO: 8) and/or that is or is greater than $1.43\times10^4$ M$^{-1}$, $1.67\times10^4$ M$^{-1}$, $2\times10^4$ M$^{-1}$, $3.33\times10^4$ M$^{-1}$, $5\times10^4$ M$^{-1}$, $1\times10^5$ M$^{-1}$, $1.11\times10^5$ M$^{-1}$, $1.25\times10^5$ M$^{-1}$, $1.43\times10^5$ M$^{-1}$, $1.67\times10^5$ M$^{-1}$, $2\times10^5$ M$^{-1}$, $3.33\times10^5$ M$^{-1}$, $5\times10^5$ M$^{-1}$, $1\times10^6$ M$^{-1}$, $1.11\times10^6$ M$^{-1}$, $1.25\times10^6$ M$^{-1}$, $1.43\times10^6$ M$^{-1}$, $1.67\times10^6$ M$^{-1}$, $2\times10^6$ M$^{-1}$, $3.33\times10^6$ M$^{-1}$, $5\times10^6$ M$^{-1}$, $1\times10^7$ M$^{-1}$, but generally less than $1\times10^{13}$ M$^{-1}$, $1\times10^{12}$ M$^{-1}$ or $1\times10^{11}$ M$^{-1}$ for any of the peptide ligands set forth in any of SEQ ID NOS:7-19.

In some embodiments, the streptavidin mutein exhibits the sequence of amino acids set forth in any of SEQ ID NOs: 3-6, 27, 28, 60, or 61 or a sequence of amino acids that exhibits at least 90%, 91%, 92%, 93%, 94%, 95%, 96%, 97%, 98%, 99% or more sequence identity to the sequence of amino acids set forth in any of SEQ ID NO: 3-6, 27, 28, 60, or 61, and exhibits a binding affinity characterized by a dissociation constant ($K_d$) that is or that is less than $3.7\times10^{-5}$ M for the peptide ligand (Trp-Arg-His-Pro-Gln-Phe-Gly-Gly; also called STREP-TAG @, set forth in SEQ ID NO: 7) and/or that is or is less than $7.1\times10^{-5}$ M for the peptide ligand (Trp-Ser-His-Pro-Gln-Phe-Glu-Lys; also called STREP-TAG® II, set forth in SEQ ID NO: 8) and/or that is or is less than $7.0\times10^{-5}$ M, $6.0\times10^{-5}$ M, $5.0\times10^{-5}$ M, $4.0\times10^{-5}$ M, $3.0\times10^{-5}$ M, $2.0\times10^{-5}$ M, $1.0\times10^{-5}$ M, $9.0\times10^{-6}$ M, $8.0\times10^{-6}$ M, $7.0\times10^{-6}$ M, $6.0\times10^{-6}$ M, $5.0\times10^{-6}$ M, $4.0\times10^{-6}$ M, $3.0\times10^{-6}$ M, $2.0\times10^{-6}$ M, $1.0\times10^{-6}$ M, $9.0\times10^{-7}$ M, $8.0\times10^{-7}$ M, $7.0\times10^{-7}$ M, $6.0\times10^{-7}$ M, $5.0\times10^{-7}$ M, $4.0\times10^{-7}$ M, $3.0\times10^{-7}$ M, $2.0\times10^{-7}$ M or $1.0\times10^{-7}$ M, but generally greater than $1\times10^{-13}$ M, $1\times10^{-12}$ M or $1\times10^{-11}$ M for any of the peptide ligands set forth in any of SEQ ID NOS:7-19.

In some embodiments, the streptavidin mutein also exhibits binding to other streptavidin ligands, such as but not limited to, biotin, iminobiotin, lipoic acid, desthiobiotin, diaminobiotin, HABA (hydroxyazobenzene-benzoic acid) and/or dimethyl-HABA. In some embodiments, the streptavidin mutein exhibits a binding affinity for another streptavidin ligand, such as biotin or desthiobiotin, that is greater than the binding affinity of the streptavidin mutein for a biotin mimic peptide ligand, such as set forth in any of SEQ ID NOS: 7-19. In some embodiments, the streptavidin mutein exhibits a binding affinity for another streptavidin ligand, such as biotin or desthiobiotin, that is the same, about the same, or lower than the binding affinity of the streptavidin mutein for a biotin mimic peptide ligand, such as set forth in any of SEQ ID NOS: 7-19. In some embodiments, biotin or a biotin analog or derivative (e.g. desthiobiotin) can be employed as a competition reagent in the provided methods. For example, as an example, the interaction of a mutein streptavidin designated Strep-tactin® (e.g. containing the sequence set forth in SEQ ID NO: 4 or 60) with the peptide ligand designated STREP-TAG® II (e.g. set forth in SEQ ID NO: 8) is characterized by a binding affinity with a $K_d$ of approximately $10^{-6}$ M compared to approximately $10^{-13}$ M for the biotin-streptavidin interaction. In some cases, biotin, which can bind with high affinity to the Strep-Tactin® with a $K_d$ of between or between about $10^{-10}$ and $10^{-13}$ M, can compete with STREP-TAG® II for the binding site.

In some cases, the reagent contains at least two chelating groups K that may be capable of binding to a transition metal ion. In some embodiments, the reagent may be capable of binding to an oligohistidine affinity tag, a glutathione-S-transferase, calmodulin or an analog thereof, calmodulin binding peptide (CBP), a FLAG-peptide, an HA-tag, maltose binding protein (MBP), an HSV epitope, a myc epitope, and/or a biotinylated carrier protein.

In some embodiments, the reagent is an oligomer or polymer. In some embodiments, the oligomer or polymer can be generated by linking directly or indirectly individual molecules of the protein as it exists naturally, either by linking directly or indirectly individual molecules of a monomer or a complex of subunits that make up an individual molecule (e.g. linking directly or indirectly dimers, trimers, tetramers, etc. of a protein as it exists naturally). For example, in some embodiments, tetrameric streptavidin or avidin may be referred to as an individual molecule or smallest building block of a respective oligomer or polymer. In particular embodiments, a tetrameric homodimer or heterodimer of streptavidin or avidin may be referred to as an individual molecule or smallest building block of a respective oligomer or polymer. In some embodiments, the oligomer or polymer can contain linkage of at least 2 individual molecules of the protein (e.g. is a 2-mer), or can be at least a 3-mer, 4-mer, 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, 25-mer, 30-mer, 35-mer, 40-mer, 45-mer or 50-mer of individual molecules of the protein (e.g., monomers, tetramers). In certain embodiments, the oligomer can be at least a 100-mer, 200-mer, 300-mer, 400-mer, 500-mer, 1,000-mer, 1,500-mer, 2,000-mer, 2,500-mer, 3,000-mer, or at least a 3,500-mer of individual molecules of the protein. In some embodiments, the reagent is an oligomeric particle reagent that is described in Section II(A)(1) or (2), or is an oligomeric particle reagent that is manufactured by the methods described in section II(B)(3).

Oligomers can be generated using any methods known in the art, such as any described in published U.S. Patent Application No. US2004/0082012. In some embodiments, the oligomer or polymer contains two or more individual molecules that may be crosslinked, such as by a polysaccharide or a bifunctional linker.

In some embodiments, the oligomer or polymer is obtained by crosslinking individual molecules or a complex of subunits that make up an individual molecule in the presence of a polysaccharide. In some embodiments, oligomers or polymers can be prepared by the introduction of carboxyl residues into a polysaccharide, e.g. dextran. In some aspects, individual molecules of the reagent (e.g., monomers, tetramers) can be coupled via primary amino groups of internal lysine residues and/or the free N-terminus to the carboxyl groups in the dextran backbone using conventional carbodiimide chemistry. In some embodiments, the coupling reaction is performed at a molar ratio of about 60 moles of individual molecules of the reagent (e.g., monomers, tetramers) per mole of dextran.

In some embodiments the reagent is an oligomer or a polymer of one or more streptavidin or avidin or of any analog or mutein of streptavidin or an analog or mutein of avidin (e.g. neutravidin). In some embodiments, the binding site Z is a natural biotin binding site of avidin or streptavidin for which there can be up to four binding sites in an individual molecule (e.g. a tetramer contains four binding sites Z), whereby a homo-tetramer can contain up to 4 binding sites that are the same, i.e. Z1, whereas a hetero-tetramer can contain up to 4 binding sites that may be different, e.g. containing Z1 and Z2. In some embodiments, the oligomer is generated or produced from a plurality of individual molecules (e.g. a plurality of homo-tetramers) of the same streptavidin, streptavidin mutein, avidin or avidin mutein, in which case each binding site Z, e.g. Z1, of the oligomer is the same. For example, in some cases, an oligomer can contain a plurality of binding sites Z1, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more binding sites Z1. In some embodiments, the oligomer is generated or produced from a plurality of individual molecules that can be hetero-tetramers of a streptavidin, streptavidin mutein, avidin or avidin mutein and/or from a plurality of two or more different individual molecules (e.g. different homo-tetramers) of streptavidin, streptavidin mutein, avidin or avidin mutein that differ in their binding sites Z, e.g. Z1 and Z2, in which case a plurality of different binding sites Z, e.g. Z1 and Z2, may be present in the oligomer. For example, in some cases, an oligomer can contain a plurality of binding sites Z1 and a plurality of binding sites Z, which, in combination, can include at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 or more combined binding sites Z1 and Z2.

In some cases, the respective oligomer or polymer may be crosslinked by a polysaccharide. In one embodiment, oligomers or polymers of streptavidin or of avidin or of analogs of streptavidin or of avidin (e.g., neutravidin) can be prepared by the introduction of carboxyl residues into a polysaccharide, e. g. dextran, essentially as described in Noguchi, A, et al, Bioconjugate Chemistry (1992) 3,132-137 in a first step. In some such aspects, streptavidin or avidin or analogs thereof then may be linked via primary amino groups of internal lysine residue and/or the free N-terminus to the carboxyl groups in the dextran backbone using conventional carbodiimide chemistry in a second step. In some cases, cross-linked oligomers or polymers of streptavidin or avidin or of any analog of streptavidin or avidin may also be obtained by crosslinking via bifunctional molecules, serving as a linker, such as glutardialdehyde or by other methods described in the art.

In some embodiments, the oligomer or polymer is obtained by crosslinking individual molecules or a complex of subunits that make up an individual molecule using a bifunctional linker or other chemical linker, such as glutardialdehyde or by other methods known in the art. In some aspects, cross-linked oligomers or polymers of streptavidin or avidin or of any mutein or analog of streptavidin or avidin may be obtained by crosslinking individual streptavidin or avidin molecules via bifunctional molecules, serving as a linker, such as glutardialdehyde or by other methods described in the art. It is, for example, possible to generate oligomers of streptavidin muteins by introducing thiol groups into the streptavidin mutein (this can, for example, be done by reacting the streptavidin mutein with 2-iminothiolane (Trauts reagent) and by activating, for example in a separate reaction, amino groups available in the streptavidin mutein. In some embodiments, this activation of amino groups can be achieved by reaction of the streptavidin mutein with a commercially available heterobifunctional crosslinker such as sulfosuccinimidyl 4-(N-maleimidomethyl)cyclohexane-1-carboxylate (sulfo SMCC) or Succinimidyl-6-[(β-maleimidopropionamido)hexanoate (SMPH). In some such embodiments, the two reaction products so obtained are mixed together, typically leading to the reaction of the thiol groups contained in the one batch of modified streptavidin mutein with the activated (such as by maleimide functions) amino acids of the other batch of modified streptavidin mutein. In some cases, by this reaction, multimers/oligomers of the streptavidin mutein are formed. These oligomers can have any suitable number of individual molecules, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50, 100, 200, 300, 400, 500, 1,000, 1,500, 2,000, 2,500, 3,000, 3,500, 4,000 or more, and the oligomerization degree can be varied according to the reaction condition.

In some embodiments, the oligomeric or polymeric reagent can be isolated via size exclusion chromatography and any desired fraction can be used as the reagent. For example, in some embodiments, after reacting the modified streptavidin mutein, in the presence of 2-iminothiolan and a heterobifunctional crosslinker such as sulfo SMCC, the oligomeric or polymeric reagent can be isolated via size exclusion chromatography and any desired fraction can be used as the reagent. In some embodiments, the oligomers do not have (and do not need to have) a single molecular weight but they may observe a statistical weight distribution such as Gaussian distribution. In some cases, any oligomer with more than three streptavidin or mutein tetramers, e.g., homotetramers or heterotetramers, can be used as a reagent, such as generally 3 to 50 tetramers, e.g., homotetramers or heterotetramers, 10 to 40 tetramers, e.g., homotetramers or heterotetramers, or 25 to 35 tetramers, e.g., homotetramers or heterotetramers. The oligomers might have, for example, from 3 to 25 streptavidin mutein tetramers, e.g., homotetramers or heterotetramers. In some aspects, with a molecular weight of about 50 kDa for streptavidin muteins, the oligomers can have a molecular weight from about 150 kDa to about 2000 kDa, about 150 kDa to about 1500 kDa, about 150 kDa to about 1250 kDa, about 150 kDa to 1000 kDa, about 150 kDa to about 500 kDa or about 150 kDa to about 300 kDa, about 300 kDa to about 2000 kDa, about 300 kDa to about 1500 kDa, about 300 kDa to about 1250 kDa, about 300 kDa to 1000 kDa, about 300 kDa to about 500 kDa, about 500 kDa to about 2000 kDa, about 500 kDa to about 1500 kDa, about 500 kDa to about 1250 kDa, about 500 kDa to 1000 kDa, about 1000 kDa to about 2000 kDa, about 1000 kDa to about 1500 kDa, about 1000 kDa to about 1250 kDa, about 1250 kDa to about 2000 kDa or about 1500 kDa to about 2000 kDa. In some embodiments, the oligomers have a molecular weight of more than 2,000 kDa. Generally, because each streptavidin molecule/mutein has four biotin binding sites, such a reagent can provide 12 to 160 binding sites Z, such as 12 to 160 or more binding sites Z. In some embodiments, the oligomers are soluble reagents.

1. Oligomer Particle Reagents

Provided herein are oligomeric particle reagents that are composed of and/or contain a plurality of molecules, e.g., streptavidin or streptavidin mutein tetramers. In certain embodiments, the oligomeric particle reagents are soluble reagents. In certain embodiments, the oligomeric particle reagents provided herein contain at least one binding site that reversibly binds or is capable of reversibly binding to one or more agents, e.g., a stimulatory agent and/or a selection agent. In certain embodiments, the oligomeric particle reagents provided herein contain a plurality of binding sites that are capable of reversibly binding to the one or more agents, for example, at a site on a binding partner, e.g., a binding partner C, that is attached to the one or more agents. In some embodiments, oligomeric particle reagents are reversibly bound to one or more agents. In particular embodiments, the oligomer particle reagent is a an oligomeric particle that is manufactured, produced, or generated by any of the methods described in Section II(B).

In certain embodiments, the oligomeric particle reagents provided herein are composed of and/or contain oligomerized molecules that are proteins, polypeptides, peptides, and/or molecules that contain or include one or more amino acids. In some embodiments, the oligomeric particle reagents provided herein contain and/or are composed of oligomerized molecules that contain a plurality of binding sites that are capable of binding to one or more agents, e.g., receptor-binding agent. In some embodiments, the oligomeric particle reagent provided herein contains a plurality of binding sites that are capable of binding to an agent that is described in Section II(B)(4) and/or Section II(B)(5). In certain embodiments, the oligomeric particle reagents provided herein contain a plurality of binding sites that bind to or are capable of binding to a the one or more agents at a site within binding partner, e.g., a binding partner C, that is attached to the one or more agents. In particular embodiments, the molecule that is oligomerized contains a plurality of binding sites that are capable of binding to a binding partner C that is described in Section II(A). In some embodiments, the molecule that is oligomerized is or includes a streptavidin, a streptavidin mutein or analog, avidin, an avidin mutein or analog (such as neutravidin). In certain embodiments, streptavidin is a tetramer in the native state. Thus in certain embodiments, the molecule is a tetramer of a streptavidin, a streptavidin mutein or analog, avidin, an avidin mutein or analog (such as neutravidin). In particular embodiments, the oligomeric particle reagent contains a plurality of one or more of any of the reagents that are described in Section II(A).

In particular embodiments, the size of the oligomeric particle reagents are determined by any suitable means known in the art. In some embodiments, the mass and/or the molecular weight of the oligomeric particle reagents are determined by any suitable means in the art, including but not limited to electrophoresis, e.g., SDS-PAGE, chromatography, e.g., gel filtration chromatography or SEC, or mass spectrometry. In some embodiments, the size, e.g., the radius, of the oligomeric particle reagent is determined by dynamic light scattering techniques (DLS). In some embodiments, the size, e.g., the radius, is determined by flow field flow fractionation (F4) techniques. In certain embodiments, F4 may be used to separate and measure particles based on size independent of particle density. In certain embodiments, the particle size is measured by asymmetric flow field flow fractionation (AF4). In some embodiments, the size of the particle may be determined by measuring the diameter or radius of the particle. In certain embodiments, the size of the particle may be determined by measuring the hydrodynamic radius or the radius of gyration of the particle. In certain embodiments, the radius is determined with dynamic light scattering techniques. In certain embodiments, the radius, e.g., the hydrodynamic radius and/or the Stokes radius, may be determined from chromatography techniques, e.g., size exclusion chromatography SEC).

In particular embodiments, the oligomeric particle reagent provided herein has a radius, e.g., an average radius, of at least 5 nm, at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, at least 100 nm, at least 105 nm, at least 110 nm, at least 115 nm, at least 120 nm, at least 125 nm, at least 130 nm, at least 135 nm, at least or at least 140 nm. In certain embodiments, the oligomeric particle reagent has a radius of between 5 nm and 150 nm, between 25 nm and 150 nm, between 50 nm and 150 nm, between 75 nm and 125 nm, between 80 nm and 140 nm, between 85 nm and 135 nm, between 80 nm and 120 nm, between 80 nm and 115 nm, or between 90 nm and 110 nm, inclusive. In certain embodiments, the oligomeric particle reagent provided herein has a radius of about 85 nm, about 86 nm, about 87 nm, about 88 nm, about 89 nm, about 90 nm, about 91 nm, about 92 nm, about 93 nm, about 94 nm, about 95 nm, about 96 nm, about 97 nm, about 98 nm, about 99 nm, about 100 nm, about 101 nm, about 102 nm, about 103 nm, about 104 nm, about 105 nm, about 106 nm, about 107 nm, about 108 nm, about 109 nm, about 110 nm, about 111 nm, about 112 nm, about 113 nm, about 114 nm, or about 115 nm. In certain embodiments, the particles have a radius of between 80 nm and 115 nm, inclusive.

In some embodiments, the radius is the hydrodynamic radius, radius of gyration, Stokes radius, Stokes-Einstein radius, and/or the effective hydrated radius in solution. In certain embodiments, the radius is the hydrodynamic radius. In some embodiments, the radius is the Stokes radius. In particular embodiments, the hydrodynamic radius is the Stokes radius. In some embodiments, the radius is a mean, median, and/or average radius of a plurality of particles.

In certain embodiments, the oligomeric particle reagent provided herein has a molecular weight of at least $2\times10^6$ g/mol, $3\times10^6$ g/mol, $5\times10^6$ g/mol, $1\times10^7$ g/mol, at least $5\times10^7$ g/mol, at least $1\times10^8$ g/mol, at least $1.25\times10^8$ g/mol, at least $1.5\times10^8$ g/mol, at least $2\times10^8$ g/mol or at least $5\times10^8$ g/mol. In some embodiments, the oligomeric particle reagent provided herein has a molecular weight of between $1\times10^6$ g/mol and $1\times10^{10}$ g/mol, $2\times10^6$ g/mol and $1\times10^{10}$ g/mol, between $1\times10^7$ g/mol and $1\times10^9$ g/mol, between $5\times10^7$ g/mol and $5\times10^8$ g/mol, between $7.5\times10^7$ g/mol and $2.5\times10^8$ g/mol, between $2.5\times10^7$ g/mol and $2.75\times10^8$ g/mol, between $1\times10^8$ g/mol and $5\times10^8$ g/mol, between $7.5\times10^7$ g/mol and $5\times10^8$ g/mol, or between $1\times10^8$ g/mol and $2\times10^8$ g/mol, inclusive. In particular embodiments, the oligomeric particle reagent provided herein has a molecular weight of about $7.5\times10^7$ g/mol, about $8.0\times10^7$ g/mol, about $9.0\times10^7$ g/mol, about $1.0\times10^8$ g/mol, about $1.1\times10^8$ g/mol, about $1.2\times10^8$ g/mol, about $1.3\times10^8$ g/mol, about $1.4\times10^8$ g/mol, about $1.5\times10^8$ g/mol, about $1.6\times10^8$ g/mol, about $1.7\times10^8$ g/mol, about $1.8\times10^8$ g/mol, about $1.9\times10^8$ g/mol, about $2.0\times10^8$ g/mol, about $2.1\times10^8$ g/mol, about $2.2\times10^8$ g/mol, about $2.3\times10^8$ g/mol, about $2.4\times10^8$ g/mol, or about $2.5\times10^8$ g/mol. In certain embodiments, the oligomeric particle reagent provided herein has a molecular weight of between $5\times10^7$ g/mol and $2\times10^8$ g/mol, inclusive.

In some embodiments, the oligomeric particle reagent provided herein is composed of and/or contains a plurality of streptavidin or streptavidin mutein tetramers. In certain embodiments, the oligomeric particle reagent provided herein is composed of and/or contains at least 100, at least 200, at least 300, at least 400, at least 500, at least 600, at least 700, at least 800, at least 900, at least 1,000, at least 1,100, at least 1,200, at least 1,300, at least 1,400, at least 1,500, at least 1,600, at least 1,700, at least 1,800, at least 1,900, at least 2,200, at least 2,300, at least 2,400, at least 2,500, at least 2,600, at least 2,700, at least 2,800, at least 2,900, at least 3,000, at least 4,000, at least 5,000, at least 10,000, or at least 20,000 streptavidin or streptavidin mutein tetramers. In particular embodiments, the oligomeric particle reagents provided herein contain and/or are composed of between 100 and 50,000, between 500 and 10,000, between 1,000 and 20,000, between 500 and 5,000, between 300 and 7,500, between 1,500 and 7,500, between 500 and 3,500, between 1,000 and 5,000, between 1,500 and 2,500, between 1,500 and 2,500, between 2,000 and 3,000, between 2,500 and 3,500, between 2,000 and 4,000, or between 2,000 and 5,000 streptavidin or streptavidin mutein tetramers. In some embodiments, the oligomeric particle reagent provided herein is composed of and/or contains between about 2,000 and 3,500 streptavidin or streptavidin mutein tetramers.

In some embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius of between 25 nm and 150 nm, inclusive; a molecular weight of between $2\times10^6$ g/mol and $1\times10^{10}$ g/mol; and/or between 500 and 10,000 streptavidin or streptavidin mutein tetramers.

In particular embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average radius, of between 70 nm and 125 nm, inclusive; a molecular weight of between $1\times10^7$ g/mol and $1\times10^9$ g/mol, inclusive; and/or between 1,000 and 5,000 streptavidin or streptavidin mutein tetramers, inclusive. In some embodiments, the oligomeric particle reagent is bound, e.g., reversibly bound, to one or more agents such as an agent that binds to a molecule, e.g. receptor, on the surface of a cell. In certain embodiments, the one or more agents are agents described herein, e.g., in Section II-C-3. In some embodiments, the agent is an anti-CD3 and/or an anti-CD28 antibody or antigen binding fragment thereof, such as an antibody or antigen fragment thereof that contains a binding partner, e.g., a streptavidin binding peptide, e.g. Strep-tag® II. In particular embodiments, the one or more agents is an anti-CD3 and/or an anti CD28 Fab containing a binding partner, e.g., a streptavidin binding peptide, e.g. Strep-tag® II.

In some embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average radius, of between 80 nm and 120 nm, inclusive; a molecular weight, e.g., an average molecular weight of between $7.5\times10^6$ g/mol and $2\times10^8$ g/mol, inclusive; and/or an amount, e.g., an average amount, of between 500 and 10,000 streptavidin or streptavidin mutein tetramers, inclusive. In some embodiments, the oligomeric particle reagent is bound, e.g., reversibly bound, to one or more agents, such as an agent that binds to a molecule, e.g. receptor, on the surface of a cell. In certain embodiments, the one or more agents are agents described herein, e.g., in Section II-C-3. In some embodiments, the agent is an anti-CD3 and/or an anti-CD28 Fab, such as a Fab that contains a binding partner, e.g., a streptavidin binding peptide, e.g. Strep-tag® II. In particular embodiments, the one or more agents is an anti-CD3 and/or an anti CD28 Fab containing a binding partner, e.g., a streptavidin binding peptide, e.g. Strep-tag® II.

2 Compositions of Oligomer Particle Reagents

Provided herein are compositions containing oligomeric particle reagents, e.g., a plurality of oligomeric particle reagents, that are composed of and/or contain a plurality of molecules, e.g., streptavidin or streptavidin mutein tetramers. In some embodiments, the composition provided herein contains a plurality of any of the oligomeric particle reagents described herein. In particular embodiments, the composition contains a plurality of any of the oligomeric particle reagents described in Section II(A)(1). In some embodiments, the composition contains a plurality of oligomeric particle reagents that are manufactured, produced, and/or generated by any of the methods described in Section II(B).

In particular embodiments, the composition contains oligomeric particle reagents with an average, mean, and/or a median size. In certain embodiments, the composition contains oligomeric particle reagents with an average, mean, or median radius of at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, at least 100 nm, at least 105 nm, at least 110 nm, at least 115 nm, at least 120 nm, at least 125 nm, at least 130 nm, at least 135 nm, at least or at least 140 nm. In certain embodiments, the composition contains oligomeric particle reagents with an average, mean, or median radius of between 5 nm and 150 nm, between 25 nm and 150 nm, between 50 nm and 150 nm, between 75 nm and 125 nm, between 80 nm and 140 nm, between 85 nm and 135 nm, between 80 nm and 120 nm, between 80 nm and 115 nm, or between 90 nm and 110 nm, inclusive.

In some embodiments, the composition contains oligomeric particle reagents with an average, mean, or median radius of 90 nm±25 nm, 90 nm±20 nm, 90 nm±15 nm, 90 nm±10 nm, 90 nm±5 nm, 95 nm±25 nm, 95 nm±20 nm, 95 nm±15 nm, 95 nm±10 nm, 95 nm±5 nm, 97 nm±20 nm, 97 nm±15 nm, 97 nm±10 nm, 97 nm±5 nm.

In certain embodiments, the composition contains oligomeric particle reagents with an average, mean, or median radius of about 85 nm, about 86 nm, about 87 nm, about 88 nm, about 89 nm, about 90 nm, about 91 nm, about 92 nm, about 93 nm, about 94 nm, about 95 nm, about 96 nm, about 97 nm, about 98 nm, about 99 nm, about 100 nm, about 101 nm, about 102 nm, about 103 nm, about 104 nm, about 105 nm, about 106 nm, about 107 nm, about 108 nm, about 109 nm, about 110 nm, about 111 nm, about 112 nm, about 113 nm, about 114 nm, or about 115 nm. In certain embodiments, the composition contains oligomeric particle reagents with an average mean, or median radius of between 80 nm and 115 nm, inclusive.

In certain embodiments, the oligomeric particle reagents of the composition have an average, mean, or median molecular weight of at least $2 \times 10^6$ g/mol, $3 \times 10^6$ g/mol, $5 \times 10^6$ g/mol, $1 \times 10^7$ g/mol, at least $5 \times 10^7$ g/mol, at least $1 \times 10^8$ g/mol, at least $1.25 \times 10^8$ g/mol, at least $1.5 \times 10^8$ g/mol, at least $2 \times 10^8$ g/mol or at least $5 \times 10^8$ g/mol. In some embodiments, the oligomeric particle reagents of the composition have an average, mean, or median molecular weight of between $1 \times 10^6$ g/mol and $1 \times 10^{10}$ g/mol, $2 \times 10^6$ g/mol and $1 \times 10^{10}$ g/mol, between $1 \times 10^7$ g/mol and $1 \times 10^9$ g/mol, between $5 \times 10^7$ g/mol and $5 \times 10^8$ g/mol, between $7.5 \times 10^7$ g/mol and $2.5 \times 10^8$ g/mol, between $2.5 \times 10^7$ g/mol and $2.75 \times 10^8$ g/mol, between $1 \times 10^8$ g/mol and $5 \times 10^8$ g/mol, between $7.5 \times 10^7$ g/mol and $5 \times 10^8$ g/mol, or between $1 \times 10^8$ g/mol and $2 \times 10^8$ g/mol, inclusive. In particular embodiments, the oligomeric particle reagent of the composition have an average, mean, or median molecular weight of about $7.5 \times 10^7$ g/mol, about $8.0 \times 10^7$ g/mol, about $9.0 \times 10^7$ g/mol, about $1.0 \times 10^8$ g/mol, about $1.1 \times 10^8$ g/mol, about $1.2 \times 10^8$ g/mol, about $1.3 \times 10^8$ g/mol, about $1.4 \times 10^8$ g/mol, about $1.5 \times 10^8$ g/mol, about $1.6 \times 10^8$ g/mol, about $1.7 \times 10^8$ g/mol, about $1.8 \times 10^8$ g/mol, about $1.9 \times 10^8$ g/mol, about $2.0 \times 10^8$ g/mol, about $2.1 \times 10^8$ g/mol, about $2.2 \times 10^8$ g/mol, about $2.3 \times 10^8$ g/mol, about $2.4 \times 10^8$ g/mol, or about $2.5 \times 10^8$ g/mol. In certain embodiments, the oligomeric particle reagents of the composition have an average, mean, or median molecular weight of between $5 \times 10^7$ g/mol and $2 \times 10^8$ g/mol, inclusive.

In some embodiments, the oligomeric particle reagents of the composition are each composed of and/or contain a plurality of streptavidin or streptavidin mutein tetramers. In certain embodiments, the oligomeric particle reagents of the composition are composed of and/or contain an average, mean, or median amount of at least 100, at least 200, at least 300, at least 400, at least 500, at least 600, at least 700, at least 800, at least 900, at least 1,000, at least 1,100, at least 1,200, at least 1,300, at least 1,400, at least 1,500, at least 1,600, at least 1,700, at least 1,800, at least 1,900, at least 2,200, at least 2,300, at least 2,400, at least 2,500, at least 2,600, at least 2,700, at least 2,800, at least 2,900, at least 3,000, at least 4,000, at least 5,000, at least 10,000, or at least 20,000 streptavidin or streptavidin mutein tetramers. In particular embodiments, the oligomeric particle reagents of the composition contain and/or are composed an average, mean, or median amount of between 100 and 50,000, between 500 and 10,000, between 1,000 and 20,000, between 500 and 5,000, between 300 and 7,500, between 1,500 and 7,500, between 500 and 3,500, between 1,000 and 5,000, between 1,500 and 2,500, between 1,500 and 2,500, between 2,000 and 3,000, between 2,500 and 3,500, between 2,000 and 4,000, or between 2,000 and 5,000 streptavidin or streptavidin mutein tetramers. In some embodiments, the oligomeric particle reagents of the composition are composed of and/or contain an average, mean, or median amount of between about 2,000 and 3,500 streptavidin or streptavidin mutein tetramers.

In some embodiments, the composition contains oligomeric particle reagents with a size distribution. In some embodiments, the oligomeric particle reagents of the composition have a size distribution wherein at least 70%, 80%, 90%, or 95% of the oligomeric particle reagents of the composition have a size that is within ±100%, ±90%, ±80%, ±70%, ±60%, ±50%, ±40%, ±30%, ±25%, ±20%, ±15%, ±10%, ±5%, ±1%, ±0.5%, ±0.1%, ±0.01%, of±0.001% of the median or mean size of the oligomeric particle reagents of the composition. In certain embodiments, the size is measured by radius, molecular weight, or the number of molecules, e.g., streptavidin or streptavidin mutein tetramers, of the oligomeric particle reagent.

In some embodiments, at least 95% of the oligomeric particle reagents of the composition have a radius that is within ±100%, ±90%, ±80%, ±70%, ±60%, ±50%, ±40%, ±30%,±25%,±20%,±15%,±10%,±5%,±1%,±0.5%, ±0.1%, ±0.01%, of ±0.001% of the median or mean radius of the oligomeric particle reagents of the composition. In particular embodiments, at least 95% of the oligomeric particle reagents of the composition have a radius that is within between 10 nm and 250 nm, between 25 nm and 200 nm, between 50 and 150 nm, between 70 nm and 140 nm, between 70 and 130 nm, between 70 and 100 nm, between 80 nm and 110 nm, between 80 nm and 120 nm, between 80 nm and 115 nm, between 80 nm and 100 nm, between 90 and 120 nm, between 90 nm and 110 nm, between 100 nm and 120 nm, or between 85 and/or 115 nm, inclusive. In particular embodiments, at least 95% of the oligomeric particle reagents of the composition have a radius that is within ±25%, ±20%, ±15%, ±10%, ±5%, or±1% of the mean radius of the oligomeric particle reagents of the composition.

In particular embodiments, at least 95% of the oligomeric particle reagents of the composition have a molecular weight that is within ±100%, ±90%, ±80%, ±70%, ±60%, ±50%, ±40%, ±30%, ±25%, ±20%, ±15%, ±10%, ±5%, ±1%, ±0.5%, ±0.1%, ±0.01%, of±0.001% of the median or mean molecular weight of the oligomeric particle reagents of the composition. In some embodiments, at least 95% of the oligomeric particle reagents of the composition have a molecular weight between $2\times10^6$ g/mol and $1\times10^{10}$ g/mol, between $1\times10^6$ g/mol and $1\times10^8$ g/mol, between $1\times10^7$ g/mol and $1\times10^9$ g/mol, between $1\times10^8$ g/mol and $1\times10^{10}$ g/mol, between $1\times10^8$ g/mol and $1\times10^9$ g/mol, between $5\times10^7$ g/mol and $5\times10^8$ g/mol, between $1\times10^9$ g/mol and $1\times10^{10}$ g/mol, between $1\times10^7$ g/mol and x $10^8$ g/mol, between $7.5\times10^7$ g/mol and $2.5\times10^8$ g/mol, between $5\times10^7$ g/mol and $2.5\times10^8$ g/mol, between $1\times10^8$ g/mol and $3\times10^8$ g/mol, between $7.0\times10^7$ g/mol and $3.0\times10^8$ g/mol, or between $1\times10^8$ g/mol and $2\times10^8$ g/mol, inclusive. In some embodiments, at least 95% of the oligomeric particle reagents of the composition have a molecular weight that is within ±25%, ±20%, ±15%, ±10%, ±5%, or ±1% of the mean molecular weight of the oligomeric particle reagents of the composition.

In certain embodiments, the oligomeric particles of the composition are composed of a plurality of streptavidin or streptavidin mutein tetramers and at least 95% of the oligomeric particle reagents are composed of an amount of tetramers within ±100%, ±90%, ±80%, ±70%,±60%, 50%, ±40%,±30%,±25%,±20%,±15%,±10%,±5%,±1%,±0.5%, ±0.1%, ±0.01%, of±0.001% of the median or mean amount of tetramers per oligomeric particle reagent. In some embodiments, the oligomeric particles of the composition at least 95% of the oligomeric particle reagents are composed of between 100 and 50,000, between 500 and 10,000, between 1,000 and 20,000, between 1,000 and 5,000, between 5,000 and 10,000, between 10,000 and 15,000, between 1,500 and 4,000, between 2,000 and 4,500, between 2,500 and 5,000, between 3,000 and 5,000, between 3,500 and 5,500, between 4,000 and 6,000, or between 1,500 and 3,500 streptavidin or streptavidin mutein tetramers. In some embodiments, at least 95% of the oligomeric particle reagents of the composition are composed of an amount of tetramers within ±25%, ±20%, ±15%, ±10%, ±5%, or ±1% of the mean molecular weight of the oligomeric particle reagents of the composition.

In some embodiments, the composition of oligomeric particle reagents is stored for a period of time, for example after the oligomeric particle reagents have been manufactured produced and/or generated and prior to the addition of an agent, e.g., a receptor binding agent. In certain embodiments, the composition of oligomeric particle reagents is stored in a buffer with a neutral pH. In some embodiments, the composition is stored in separate aliquots. In some embodiments, the composition of oligomeric particle reagents is stored at or below room temperature, at or below 4° C., at or below −20° C., or at or below −80° C. In certain embodiments, the composition is stored for a period of time of, of about, or of at least 12 hours, 24 hours, 2 days, 3 days, 4 days, 5 days, 6 days, 7 days, 10 days, 14 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 18 weeks, 20 weeks, 22 weeks, 24 week, 26 weeks, 27 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 60 weeks, 70 weeks, 80 weeks, 90 weeks, 12 months, 16 months, 18 months, 24 months, 30 months, 36 months or more than 36 months. In particular embodiments, the composition of oligomeric particle reagents is stored at or below 4° C. for, for about, or for at least 1 week 9 weeks, 27 weeks, or 46 weeks. In certain embodiments, the composition of oligomeric particle reagents is stored at or below −80° C. for, for about, or for at least 1 week 9 weeks, 27 weeks, or 46 weeks. In particular embodiments, the size of the oligomeric particles are stable during storage, e.g., size does not change or increase by more than 25%, 20%, 15%, 10%, or 5%.

In particular embodiments, the oligomeric particle reagents of the composition do not undergo an increase in average, e.g., mean, particle size during storage. In certain embodiments, the composition is stored for a period of time and the oligomeric particle reagents do not experience an increase in average size, that is greater than 1%, greater than 5%, greater than 10%, greater than 20%, greater than 25%, greater than 30%, greater than 40%, or greater than a 50%. In particular embodiments, the composition is stored at about or below 4° C., at about or below −20° C., or at about or below −80° C. for at least 9, 27, or 46 weeks and do not experience an increase in average size that is greater than 1%, 5%, or 10%. In certain embodiments, the composition is stored at about −80° C.

In some embodiments, provided herein is a composition of oligomeric particle reagents that are composed of and/or contain a plurality of streptavidin or streptavidin mutein tetramers. In certain embodiments, the oligomeric particle reagents of the composition each contain a plurality of binding sites that reversibly bind or are capable of reversibly binding to one or more agents, e.g., a stimulatory agent and/or a selection agent. In some embodiments, the oligomeric particle reagents have an average, mean, or median radius of between 25 nm and 150 nm; an average, mean, or median molecular weight of between $2\times10^6$ g/mol and $1\times10^{10}$ g/mol; and/or an average, mean, or median amount of between 500 and 10,000 streptavidin or streptavidin mutein tetramers. In certain embodiments, at least 70%, 80%, 90%, or 95% of the oligomeric particle reagents of the composition have a radius, molecular weight, or an amount of tetramers that is within ±100%, ±90%, ±80%, ±70%, ±60%, ±50%, ±40%, ±30%, ±25%, ±20%, ±15%, ±10%, ±5%, ±1% of the average, mean, or median radius, molecular weight, or an amount of tetramers of the oligomeric particle reagents of the composition.

In particular embodiments, provided herein is a composition of oligomeric particle reagents that are composed of and/or contain a plurality of streptavidin or streptavidin mutein tetramers and that contain a plurality of binding sites that reversibly bind to one or more agagents, agents e.g., receptor binding agents such as anti-CD3 and/or anti-CD28 Fabs having a streptag. In some embodiments, the oligomeric particle reagents have an average, mean, or median radius of between 50 nm and 150 nm; an average, mean, or median molecular weight of between $1\times10^7$ g/mol and $1\times10^9$ g/mol; and/or an average, mean, or median amount of between 1,000 and 5,000 streptavidin or streptavidin mutein tetramers. In certain embodiments, at least 95% of the oligomeric particle reagents of the composition have a radius, molecular weight, or an amount of tetramers that is within ±50%, ±40%, ±30%, ±25%, ±20%, ±15%, ±10%, ±5%, ±1% of the average, mean, or median radius, molecular weight, or an amount of tetramers of the oligomeric particle reagents of the composition.

In some embodiments, provided herein is a composition of oligomeric particle reagents that are composed of and/or contain a plurality of streptavidin or streptavidin mutein tetramers and that contain a plurality of binding sites that reversibly bind to one or more agents. In some embodiments, the oligomeric particle reagents have an average, mean, or median radius of between 50 nm and 150 nm; an average, mean, or median molecular weight of between $5 \times 10^7$ g/mol and $5 \times 10^8$ g/mol; and/or an average, mean, or median amount of between 2,000 and 4,000 streptavidin or streptavidin mutein tetramers. In certain embodiments, at least 95% of the oligomeric particle reagents of the composition have a radius, molecular weight, or an amount of tetramers that is within ±25%, ±20%, ±15%, ±10%, ±5%, ±1% of the average, mean, or median radius, molecular weight, or an amount of tetramers of the oligomeric particle reagents of the composition. In particular embodiments, the oligomeric particle reagents do not undergo an increase in size of greater than 10% when stored at −80° C. for at least 9, 27 weeks, or 46 weeks.

In some embodiments, any of the provided oligomeric reagents are produced by the method for manufacturing or generating oligomeric reagents described in Section II.B below.

B. Manufacturing of Oligomeric Particle Reagents

Provided herein are methods for generating, producing, and/or manufacturing reagents that are composed of oligomerized reagents, i.e., oligomeric particle reagents. In particular embodiments, oligomeric particle reagents contain multiple binding sites that are capable of reversibly binding to an agent, e.g., a stimulatory agent. In some embodiments, oligomeric particle reagents contain multiple binding sites that are capable of reversibly binding to agents, e.g., stimulatory agents and/or selection agents, that recognize and/or bind to one or more molecules expressed on a cell. In certain embodiments, the methods provided herein are useful for generating, producing, and/or manufacturing oligomeric particle reagents of a desired or target size.

Provided herein are methods for manufacturing, generating, and/or producing regents that are oligomeric particle reagents. In some embodiments, the methods provided herein are useful for manufacturing, generating, and/or producing oligomeric particle reagents that contain and/or are composed of a plurality of molecules, e.g., streptavidin or streptavidin mutein tetramers. In some embodiments, the methods provided herein are for manufacturing, generating, and/or producing oligomeric particle reagents that are soluble reagents. In some embodiments, the methods provided herein for manufacturing, generating, and/or producing oligomeric particle reagents include or contain a step for incubating, treating, and/or contacting molecules, e.g., streptavidin or streptavidin mutein tetramers, under conditions suitable for oligomerizing the molecules. In certain embodiments, the methods provided herein for manufacturing, generating, and/or producing the oligomeric particle reagents contain a step for separating oligomeric particle reagents from molecules that did not oligomerize. In certain embodiments, the methods provided herein contain a step for stabilizing one or more properties of the oligomeric particle reagents, e.g., particle size.

In particular embodiments, the methods provided herein for manufacturing, generating, and/or producing oligomeric particle reagents contain a step for oligomerizing the molecules, a step for removing oligomerized molecules from molecules that did not oligomerize, and/or a step for stabilizing a property of the oligomeric particle reagents. In some embodiments, the methods provided herein for manufacturing, generating, and/or producing oligomeric particle reagents contain and/or include one or more steps for adding a functional group the molecule, e.g., a functional group that is suitable for a crosslinking or oligomerization reaction. In certain embodiments, the methods provided herein for manufacturing, generating, and/or producing oligomeric particle reagents contain and/or include one or more steps for adding a functional group the molecule and one or more steps for oligomerizing the molecule. In particular embodiments, the methods provided herein for manufacturing, generating, and/or producing oligomeric particle reagents contain and/or include steps for adding one or more functional groups the molecules, a step for oligomerizing the molecules, and a step for separating the oligomerized molecules, e.g., oligomeric particles, from molecules that did not oligomerize.

In certain embodiments, the molecules that are oligomerized are proteins, polypeptides, peptides, and/or molecules that contain or include one or more amino acids. In some embodiments, the molecule that is oligomerized contains a plurality of binding sites that are capable of binding to an agent, e.g., a receptor-binding agent. In some embodiments, the molecule that is oligomerized contains a plurality of binding sites that are capable of binding to an agent that is described in Section II(C)(3). In certain embodiments, the molecule that is oligomerized contains a plurality of binding sites that are capable of binding to a binding partner, e.g., a binding partner C. In particular embodiments, the molecule that is oligomerized contains a plurality of binding sites that are capable of binding to a binding partner C that is described in Section II(A). In some embodiments, the molecule that is oligomerized is or includes a streptavidin, a streptavidin mutein or analog, avidin, an avidin mutein or analog (such as neutravidin). In certain embodiments, streptavidin is a tetramer in the native state. Thus in certain embodiments, the molecule is a tetramer of a streptavidin, a streptavidin mutein or analog, avidin, an avidin mutein or analog (such as neutravidin). In particular embodiments, the molecule is any of the reagents described in Section II(A). In certain embodiments, the molecule is a tetramer of the reagents described in Section II(A).

Particular embodiments contemplate that the characteristics, e.g., size, of the oligomeric particle reagents that are manufactured, produced, and/or generated by the methods provided herein depend on the timing of the various steps, procedures, and incubations, as well as on conditions such as pH and temperature and the concentrations of regents at the different steps or stages of the procedure. Thus, in particular embodiments, one or more steps or stages of the methods provided herein are performed and/or recorded with precise timing and measurements, for example to insure that when the methods provided herein are repeated, the resulting manufactured oligomeric particle reagents will have the same or similar size and characteristics as other batches or lots produced by the methods provided herein. For example in some embodiments, buffers and reagents are measured to be within ±10%, ±5%, ±4%, ±3%, ±2%, ±1%, ±0.1%, ±0.01%, or ±0.001% of the target or desired amount or concentration. In certain embodiments, reactions, e.g., an incubation, treatment, or contacting is performed at a desired or target pH within a pH of ±1, ±0.5, ±0.1, ±0.05, ±0.04, ±0.03, ±0.02, ±0.01, ±0.001, or ±0.0001. In particular embodiments, an incubation, treatment, or contacting is performed for within 30 minutes, 15 minutes, 10 minutes, 5 minutes, 4 minutes, 3 minutes, 2 minutes, 90 seconds, 60 seconds, 45 seconds, 30 seconds, 15 seconds, 10 seconds, 5 seconds, or within 1 second of a target or desired amount of time. In particular embodiments, the time between steps, stages, and/or reactions, e.g., incubations or treatment, is within 30 minutes, 15 minutes, 10 minutes, 5 minutes, 4 minutes, 3 minutes, 2 minutes, 90 seconds, 60 seconds, 45 seconds, 30 seconds, 15 seconds, 10 seconds, 5 seconds, or within 1 second of a set target or desired time.

In some embodiments, particular features of the methods provided herein for the manufacture, production, or generation of oligomeric particle reagents are critical for the consistent production of oligomeric particle reagents. For example, in some embodiments, the methods provided herein include a step for thiolating the molecules, for example by incubating molecules with a thiolating agent, and the timing, the pH, and/or the concentrations and amounts of reagents of the incubation all fall within ±5%, ±2%, ±1%, ±0.1%, ±0.01%, or ±0.001% of the target or desired values to achieved consistent production of oligomeric particle reagents. In certain embodiments, the amount of time between the end of the step for thiolating the molecules and the step for oligomerizing the molecules, for example by incubating activated and thiolated molecules, falls within ±5%, ±2%, ±1%, ±0.1%, ±0.01%, or ±0.001% of a desired or target amount of time. In some embodiments, the methods provided herein include a step for activating the molecules, for example by incubating molecules with a activation agent that adds functional groups to the molecules, and the timing, the pH, and/or the concentrations and amounts of reagents of the incubation all fall within ±5%, ±2%, ±1%, ±0.1%, ±0.01%, or ±0.001% of the target or desired values to achieved consistent production of oligomeric particle reagents. In particular embodiments, the timing, the pH, and/or the concentrations and amounts of reagents for the step of oligomerizing the molecules all fall within ±5%, ±2%, ±1%, ±0.1%, ±0.01%, or ±0.001% of the target or desired values to achieved consistent production of oligomeric particle reagents. In particular embodiments, consistent production of oligomeric particle reagents results in or includes production of consistent batches or lots. Thus, in some embodiments, the methods provided herein result in consistent batches or lots of oligomeric particle reagents. For example, in some embodiments, the methods provided herein result in batches or lots of oligomeric particle reagents with average, e.g., mean, particle sizes that fall within ±50%, ±25%, ±20%, ±15%, ±10%, ±5%, ±4%, ±3%, ±2%, ±1%, ±0.5%, ±0.1%, ±0.01%, or ±0.001% of the average, e.g, mean, particle size of the lots or batches manufactured, produced, or generated by the methods herein.

In certain embodiments, the methods provided herein for manufacturing, generating, and/or producing oligomeric particle reagents include a step of activating molecules, e.g., streptavidin or streptavidin mutein tetramers, by incubating, treating, and/or contacting the molecules with an activation agent. In certain embodiments, the activation agent adds or is capable of adding to a molecule a functional group that reacts or is capable of reacting in a crosslinking reaction. In some embodiments, the activation agent adds or is capable of adding the functional group to one or more amines of the molecule. In some embodiments, the activation agent adds or is capable of adding to a molecule an amine-reactive group, a sulfhydryl-reactive or thiol-reactive group, an aldehyde-reactive group, a photoreactive group, and/or a hydroxyl-reactive group. In some embodiments, the activation agent adds to or is capable of adding to a molecule a sulfhydryl-reactive or thiol-reactive group. In certain embodiments, activation agent adds to or is capable of adding to a molecule a haloacetyl group, a maleimide group, an aziridine group, an acryloyl group, an arylating agent, a vinylsulfone group, a pyridyl disulfide, a TNB-thiol or a disulfide reducing agent. In certain embodiments, the activation agent adds to or is capable of adding to a maleimide group to the molecule. In certain embodiments, the activation agent is or contains sulfosuccinimidyl 4-(N-maleimidomethyl)cyclohexane-1-carboxylate (sulfo SMCC) and/or Succinimidyl-6-[(β-maleimidopropionamido)hexanoate (SMPH).

In particular embodiments, the molecules, e.g., streptavidin or streptavidin mutein tetramers, are incubated, treated, and/or contacted with an activation agent under conditions suitable to activate the molecules, i.e., add one or more functional groups to the molecules. In particular embodiments, the incubation, treatment, or contacting of the activation agent with the molecules is performed at a neutral pH. In some embodiments, incubation, treatment, or contacting of the activation agent with the molecules is performed at a pH of between 5.0 and 9.0, between 6.0 and 8.0, between 6.5 and 7.5, or between 7.0 and 7.5. In certain embodiments, incubation, treatment, or contacting of the activation agent with the molecules is performed at a pH of about 6.5, about 6.6, about 6.7, about 6.8, about 6.9, about 7.0, about 7.1, about 7.2, about 7.3, about 7.4, or about 7.5. In some embodiments, the pH is about 7.2. In particular embodiments, the pH is 7.2±0.1, ±0.05, ±0.02, ±0.01, ±0.005, or ±0.0001.

In some embodiments, the incubation, treatment, and/or contacting of the activation agent with the molecules, e.g., streptavidin or streptavidin mutein tetramers, is performed at a constant temperature. In some embodiments, the incubation, treatment, and/or contacting of the activation agent with the molecules is performed at a temperature of at least 4° C., at least 8° C., at least 12° C., at least 16° C., at least 20° C., at least 24° C., at least 28° C., at least 32° C., at least 37° C., at least 39° C., at least 50° C., at least 60° C., at least 70° C., at least 80° C., at least 90° C., or at least 100° C. In particular embodiments, the incubation, treatment, and/or contacting of the activation agent with the molecules is performed at a temperature of between 4° C. and 39° C., between 10° C. and 37° C., between 10° C. and 25° C., between 20° C. and 30° C., between 24° C. and 39° C., or between 40° C. and 100° C. In particular embodiments, the incubation, treatment, and/or contacting of the activation agent with the molecules is performed at room temperature. In some embodiments, the incubation and/or treatment to oligomerize the molecules is performed at or at about 24° C. In certain embodiments, the incubation and/or treatment to activate the molecules is performed at 24° C.±2° C., ±1° C., ±0.5° C., ±0.2° C., ±0.1° C., ±0.05° C., or ±0.01° C.

In certain embodiments, the incubation, treatment, and/or contacting of the activation agent with the molecules, e.g., streptavidin or streptavidin mutein tetramers, is performed for an amount of time. In some embodiments, the incubation, treatment, and/or contacting of the activation agent with the molecules is performed for between 5 minutes and 1 hour, between 15 minutes and 2 hours, between 30 minutes and 90 minutes, between 1 hour and 6 hours, between 6 hours and 24 hours, or more than 24 hours. In some embodiments, the incubation, treatment, and/or contacting of the activation agent with the molecules is performed for about 5 minutes, 15 minutes, about 30 minutes, about 45 minutes, about 1 hour, about 1.5 hours, about 2 hours, about 3 hours, about 6 hours, about 8 hours, about 12 hours, about 16 hours, about 18 hours, about 20 hours, or about 24 hours. In certain embodiments, the incubation, treatment, and/or contacting of the activation agent with the molecules is performed for or for about 1 hour. In particular embodiments, the incubation, treatment, or contacting of the activation agent with the molecules is performed for 1 hour±5 minutes, ±2 minutes, ±1 minute, ±30 seconds, ±15 seconds, ±10 seconds, ±5 seconds, or ±1 second.

In particular embodiments, the activation agent is incubated, treated, and/or contacted with the molecules, e.g., streptavidin or streptavidin mutein tetramers, at a molar ratio of the activation agent to the molecules. In certain embodiments, the molar ratio of the molecule to the activation agent is or is about 1:1, 1:2, 1:3, 1:4, 1:5, 1:6, 1:7, 1:8, 1:9, or 1:10. In particular embodiments, the molar ratio of the molecule to the activation agent is 1:1, 1:2, 1:3, 1:4, 1:5, 1:6, 1:7, 1:8, 1:9, or 1:10, ±10%, ±5%, ±2%, ±1%, ±0.5%, ±0.1%, ±0.05%, or ±0.001%. In certain embodiments, the molar ratio is 1:2, ±10%, ±5%, ±2%, ±1%, ±0.5%, ±0.1%, ±0.05%, or ±0.001%. In some embodiments, the molar ratio is 1:2±5%. In particular embodiments, the molar ratio 1:2±2%.

In certain embodiments, the incubation, treatment, and/or contact with the activation agent and the molecules, e.g., streptavidin or streptavidin mutein tetramers, are ended by removing the activation agent from the molecules. In some embodiments, the activation agent is removed from the molecules by chromatography. In certain embodiments, the activation agent is removed from the molecules by gel filtration chromatography, for example, with a desalting column.

In particular embodiments, the methods provided herein for manufacturing, generating, and/or producing oligomeric particle reagents include a step of thiolating molecules, e.g., streptavidin or streptavidin mutein tetramers, by incubating, treating, and/or contacting the molecules with a thiolating agent. In certain embodiments, the thiolating agent is an agent that adds or is capable of adding a thiol functional group to a molecule. In some embodiments, the thiolating agent is an agent that adds or is capable of adding the thiol functional group to one or more free amines. In some embodiments, the thiol functional group is added to the N-terminal amine group and/or to free amines present at the lysine residues of the molecule. In certain embodiments, the thiolating agent is or contains a cyclic thioimidate compound. In particular embodiments, the thiolating agent is or contains 2-iminothiolane (Traut's reagent). In some embodiments, the thiolating agent is or contains 2-iminothiolane and adds a thiol functional group to a free amine in a reaction as illustrated below:

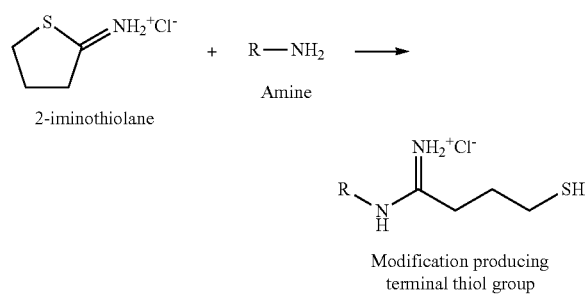

In particular embodiments, the thiolating agent, e.g., 2-iminothiolane, is purchased, stored, and/or obtained as a hydrochloride, e.g., a 2-iminothiolane-HCl salt. Thus, in some embodiments, the addition of the 2-iminothiolane to a solution induces a significant drop to the pH of the solution. In certain embodiments, the solution may be buffered to prevent or reduce the drop in pH. Particular embodiments contemplate that thiolation reactions performed at an acidic pH and/or a pH of below 7.0 limits the availability lysine residues, e.g., limits the availability of free amines on lysine residues, and thus limits the amount of thiol functional groups that are added to the molecule by the thiolation reagent. In certain embodiments, amine groups on lysine residues may become protonated to a degree that reduces or prevents the ability of thiolation and/or the addition of thiol functions to the amine groups at acidic pH values and/or at pH values that are below 7.0. Thus, in certain embodiments, the acidity of the solution containing the thiolating agent is adjusted and/or neutralized to increase the efficiency of the thiolation reaction.

In some embodiments, the incubation, treatment, and/or contacting of the thiolating agent with the molecules includes adding the thiolating agent to a buffer with a basic pH or a pH above 7.0 prior to or at the start of the incubation, treatment, of contact of the thiolating agent with the molecules. In particular embodiments, the thiolating agent is added to a buffer that has a pH of at least 7.0, at least 7.2, at least 7.4, at least 7.6, at least 7.8, at least 8.0, at least 8.1, at least 8.2, at least 8.3, at least 8.4, at least 8.5, at least 8.6, at least 8.7, at least 8.8, at least 8.9, at least 9.0, at least 9.5, or at least 10.0 prior to or at the start of the incubation, treatment, of contact of the thiolating agent with the molecules. In certain embodiments, the thiolating agent is added to a buffer has a pH of about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, or about 9.5 prior to or at the start of the incubation, treatment, of contact of the thiolating agent with the molecules.. In some embodiments, the pH of the buffer is about 8.5. In particular embodiments, the pH of the buffer is 8.5±0.1, ±0.05, ±0.02, ±0.01, ±0.005, or ±0.0001. In some embodiments, the buffer contains a buffering agent with a pK$_a$ at room temperature of greater than 7.0, greater than 7.5, greater than 8.0, greater than 8.5, or greater than 9.0. In particular embodiments, the buffering agent is or includes TES, HEPES, DIPSO, MOBS, TAPSO, Trizma, HEPPSO, POPSO, TEA, EPPS, tricine, Gly-gly, bicine, HEPBS, TAPS, AMPD, TABS, AMPSO, CHES, CAPSO, AMP, CAPS, CABS, and/or borate. In certain embodiments, the buffer is or contains a borate buffer. In particular embodiments, the borate buffer contains at least 25 mM borate, at least 50 mM borate, at least 75 mM borate, or about or at least 100 mM borate. In particular embodiments, the buffer is or includes 100 mM±10%, ±5%, ±2%, ±1%, ±0.5%, ±0.1%, ±0.05%, or ±0.001% borate.

In certain embodiments, the incubation, treatment, and/or contacting of the thiolating agent with the molecules is performed at a basic pH or a pH above 7.0. For example, in some embodiments, the pH of the solution when the thiolating agent and the molecules are added is a basic pH or a pH of above 7.0. In some embodiments, the pH during the incubation, treatment, or contacting of the thiolating agent with the molecules of between 7.0 and 11.0, between 7.0 and 9.0, between 7.5 and 8.5, or between 7.5 and 8.0. In certain embodiments, incubation, treatment, or contacting of the thiolating agent with the molecules is performed at a pH of about 7.0, about 7.1, about 7.2, about 7.3, about 7.4, about 7.5, about 7.6, about 7.7, about 7.8, about 7.9, or about 8.0. In some embodiments, the pH is or is about 7.7 during the incubation, treatment, or contacting of the thiolating agent with the molecules. In particular embodiments, the pH is 7.7±0.1, ±0.05, ±0.02, ±0.01, ±0.005, or ±0.0001 during the incubation, treatment, or contacting of the thiolating agent with the molecules.

In certain embodiments, the incubation, treatment, and/or contacting of the activation agent with the molecules, e.g., streptavidin or streptavidin mutein tetramers, is performed for an amount of time. In some embodiments, the incubation, treatment, and/or contacting of the activation agent with the molecules is performed for between 5 minutes and 1 hour, between 15 minutes and 2 hours, between 30 minutes and 90 minutes, between 1 hour and 6 hours, between 6 hours and 24 hours, or more than 24 hours. In some embodiments, the incubation, treatment, and/or contacting of the activation agent with the molecules is performed for about 5 minutes, 15 minutes, about 30 minutes, about 45 minutes, about 1 hour, about 1.5 hours, about 2 hours, about 3 hours, about 6 hours, about 8 hours, about 12 hours, about 16 hours, about 18 hours, about 20 hours, or about 24 hours. In certain embodiments, the incubation, treatment, and/or contacting of the activation agent with the molecules is performed for or for about 1 hour. In particular embodiments, the incubation, treatment, or contacting of the activation agent with the molecules is performed for 1 hour±5 minutes, ±2 minutes, ±1 minute, ±30 seconds, ±15 seconds, ±10 seconds, ±5 seconds, or ±1 second. In some embodiments, the incubation, treatment, and/or contacting of the activation agent with the molecules is performed for or for about 25 minutes. In particular embodiments, the incubation, treatment, or contacting of the activation agent with the molecules is performed for 25 minutes±5 minutes, ±2 minutes, ±1 minute, ±30 seconds, ±15 seconds, ±10 seconds, ±5 seconds, or ±1 second.

Particular embodiments contemplate that incubation, treatment, and/or contact of a molecule, e.g., a streptavidin or streptavidin mutein molecule, results in a first reaction that adds the desired thiol functional group. However, in some embodiments, the desired thiol functional group may re-isomerize into a more stable but inactive N-substituted form. Thus, in some embodiments, thiolation of a molecule by 2-iminothiolane adds a thiol functional group to the molecule that may re-isomerize to a more stable N-substituted form without the same reactivity as the thiol functional group (Singh et al. Anal Biochem 236(1): 114-1125 (1996)). An depiction of this reaction is shown below:

drop again after having reached a maximum. In certain embodiments, the half-life of a thiol functional group is 139 minutes.

In some embodiments, the maximum or peak level of thiol functional groups attached to the molecules that is achieved during a thiolation reaction is influenced by the pH of the solutions where the reaction takes place. In certain embodiments, the maximum or peak level of thiol functional groups is greater when the thiolating agent is added to a buffer with a more basic pH than when the thiolating agent is added to a buffer that is less basic. In some embodiments, the maximum or peak level of thiol functional groups is achieved in a shorter amount of time when the thiolating agent is added to a buffer with a more basic pH than when the thiolating agent is added to a buffer that is less basic. In certain embodiments, the maximum or peak level of thiol functional groups is greater when the thiolating agent is added to a buffer with a pH of or of about 8.5 than when the thiolating agent is added to a buffer that is less basic, e.g., a buffer with a pH of 8.3. In some embodiments, the maximum or peak level of thiol functional groups is achieved in a shorter amount of time when the thiolating agent is added to a buffer with a pH of or of about 8.5 than when the thiolating agent is added to a buffer that is less basic, e.g., a buffer with a pH of 8.3. In certain embodiments, the maximum or peak level of thiol functional groups is greater when the pH of the solution in which the incubation, treatment, and/or contacting with the thiolating agent and the molecule is at or at about a pH of 7.7 during the reaction than when the incubation, treatment and/or contacting takes place in a solution with a pH of less than 7.7 during the reaction, e.g., a pH of about 6.9. In some embodiments, the maximum or peak level of thiol functional groups is achieved in a shorter amount of time when the pH of the solution in which the incubation, treatment, and/or contacting with the thiolating agent and the molecule is at or at about a pH of 7.7 during the reaction than when the incubation, treatment and/or

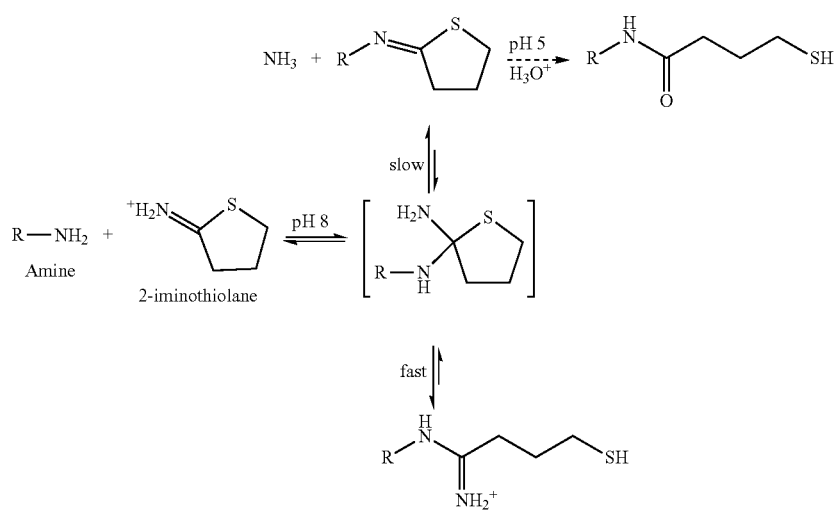

Therefore, in some embodiments, thiolation of a molecule with 2-iminothiolane should not result in a standard saturation curve and will instead result in a curve wherein the level or amount of thiol functional groups that are present on the molecules, e.g., a streptavidin or streptavidin mutein tetramers, will reach a peak or maximum level and then should contacting takes place in a solution with a pH of less than 7.7 during the reaction, e.g., a pH of about 6.9.

In some embodiments, the maximum or peak level of thiol functional groups that are added to the molecule is an average (e.g., mean) that is expressed as an amount of thiol functional groups that are added to the molecule. In some embodiments, the maximum or peak level of thiol functional groups is at least 4, at least 5, at least 6, at least 7, at least 8, at least 9, at least 10, at least 11, at least 12, at least 13, at least 14, at least 15, at least 16, at least 20, at least 25, at least 30, at least 40, or at least 50 thiol functional groups. In some embodiments, the maximum or peak level of thiol functional groups that are added to each molecule is the average (e.g., mean) percentage of lysine residues per molecule with an attached or added thiol functional group. In certain embodiments, the maximum or peak level is at least 60%, at least 65%, at least 70%, at least 75%, at least 80%, at least 85%, at least 90%, at least 95%, or at least 99% of the lysine residues with an attached or added thiol functional group. In particular embodiments, the molecule is a streptavidin or a streptavidin mutein tetramer, and the maximum or peak level of thiol functional groups is at least 6, at least 7, at least 8, at least 9, at least 10, at least 11, at least 12, at least 13, at least 14, at least 15, or at least 16 thiol functional groups per tetramer.

In some embodiments, the molecule is incubated, treated, and/or contacted with a thiolating agent for an amount of time that is sufficient to achieve a maximum or peak level of thiol functional groups that are added to the molecule. In particular embodiments, the maximum or peak level is reached within 1 minute, within 2 minutes, within 5 minutes, within 10 minutes, within 15 minutes, within 20 minutes, within 25 minutes, within 30 minutes, within 45 minutes, within 60 minutes, within 90 minutes, or within 120 minutes of the incubation, treatment, or contact of the thiolating agent with the molecule.

In particular embodiments, the thiolating agent is incubated, treated, and/or contacted with the molecule, and the amount of thiol functional groups that are added or attached to the molecules reaches a peak or maximum level and then begins to decline once the maximum or peak has been achieved. In some embodiments, the incubation, contacting, and/or treatment is ended after the peak or maximum level has been achieved. In some embodiments, the incubation, treatment, or contacting is ended at or before the amount of thiol functional groups attached to the molecules is 50% less, 40% less, 30% less, 25% less, 20% less, 15% less, 10% less, 5% less, or 1% less than the maximum or peak level. In certain embodiments, the incubation, treatment, and/or contacting is ended at a time point where the average (e.g., mean) amount of thiol functional groups is at least 3, at least 4, at least 5, at least 6, at least 7, at least 8, at least 9, at least 10, at least 11, at least 12, at least 13, at least 14, at least 15, at least 16, at least 20, at least 25, at least 30, at least 40, or at least 50 thiol functional groups. In some embodiments, the incubation, contacting, and/or treatment is ended at a time point when at least 50%, at least 55%, at least 60%, at 65%, at least 70%, at least 75%, at least 80%, at least 85%, at least 90%, at least 95%, or at least 99% of the lysine residues have an attached or added thiol functional group. In particular embodiments, the molecule is a streptavidin or a streptavidin mutein tetramer, and the incubation, contacting, and/or treatment is ended at a time point when the amount of thiol functional groups is at least 6, at least 7, at least 8, at least 9, at least 10, at least 11, at least 12, at least 13, at least 14, at least 15, or at least 16 thiol functional groups per tetramer. In particular embodiments, the incubation, treatment, and/or contacting of the thiolating agent and the molecule is ended after 1 hour. In some embodiments, the incubation, treatment, and/or contacting of the thiolating agent and the molecule is ended after 25 minutes.

In some embodiments, the incubation, treatment, and/or contacting of the thiolating agent with the molecules, e.g., streptavidin or streptavidin mutein tetramers, is performed at a constant temperature. In some embodiments, the incubation, treatment, and/or contacting of the thiolating agent with the molecules is performed at a temperature of at least 4° C., at least 8° C., at least 12° C., at least 16° C., at least 20° C., at least 24° C., at least 28° C., at least 32° C., at least 37° C., at least 39° C., at least 50° C., at least 60° C., at least 70° C., at least 80° C., at least 90° C., or at least 100° C. In particular embodiments, the incubation, treatment, and/or contacting of the thiolating agent with the molecules is performed at a temperature of between 4° C. and 39° C., between 10° C. and 37° C., between 10° C. and 25° C., between 20° C. and 30° C., between 24° C. and 39° C., or between 40° C. and 100° C. In particular embodiments, the incubation, treatment, and/or contacting of the thiolating agent with the molecules is performed at room temperature. In some embodiments, the incubation and/or treatment to oligomerize the molecules is performed at or at about 24° C. In certain embodiments, the incubation and/or treatment for the thiolation of the molecules is performed at 24° C.±2° C., ±1° C., ±0.5° C., ±0.2° C., ±0.1° C., ±0.05° C., or ±0.01° C.

In particular embodiments, the thiolating agent is incubated, treated, and/or contacted with the molecules, e.g., streptavidin or streptavidin mutein tetramers, at a molar ratio of the thiolating agent to the molecules. In some embodiments, the incubation, treatment, and/or contacting of the thiolating agent and the molecules is performed at a molar ratio of between 1:1 to 10:1 of the thiolating reagent to each primary amine per molecule. In particular embodiments, the incubation, treatment, and/or contacting of the thiolating agent and the molecules is performed at a molar ratio of 5:1 of the thiolating reagent to each primary amine per molecule. In certain embodiments, the molar ratio of the thiolating reagent to each primary amine per molecule is or is about 10:1, 9:1, 8:1, 7:1, 6:1, 5:1, 4:1, 3:1, 2:1, or 1:1. In particular embodiments, the molar ratio of the thiolating reagent to each primary amine per molecule is 10:1, 9:1, 8:1, 7:1, 6:1, 5:1, 4:1, 3:1, 2:1, or 1:1, ±10%, ±5%, ±2%, ±1%, ±0.5%, ±0.1%, ±0.05%, or ±0.001%. In certain embodiments, the molar ratio is 1:5, ±10%, ±5%, ±2%, ±1%, ±0.5%, ±0.1%, ±0.05%, or ±0.001%. In certain embodiments, the molar ratio of the thiolating agent to the molecule is 1:1 and 1,000:1, between 1:1 and 500:1, between 10:1 and 200:1, or between 100:1 and 1,000:1. In particular embodiments, the molar ratio of the activation agent to the molecule is about 100:1. In certain embodiments, the molar ratio is 100:1, ±10%, ±5%, ±2%, ±1%, ±0.5%, ±0.1%, ±0.05%, or ±0.001%.

In certain embodiments, the incubation, treatment, and/or contacting of the thiolating agent with the molecules, e.g., streptavidin or streptavidin mutein tetramers, is ended by removing or separating the thiolating agent from the molecules. Methods for removing or separating molecules, e.g., protein or polypeptide molecules such as streptavidin, are routine in the art, and include methods such as chromatography and/or gel filtration. In some embodiments, the thiolating agent is removed from the molecules by chromatography. In certain embodiments, the activation agent is removed from the molecules by gel filtration chromatography, for example, with a desalting column.

In certain embodiments, the methods provided herein for manufacturing, generating, and/or producing oligomeric particle reagents contain and/or include a step of oligomerizing molecules. In certain embodiments, the molecules are oligomerized by crosslinking individual molecules or a complex of subunits that make up an individual molecule. In some embodiments, the methods provided herein include one or more steps of treating, incubating, and/or contacting molecules with an agent that promotes oligomerization. For example, in some embodiments, molecules are oligomerized by incubating, treating, and/or contacting the molecules with an agent, e.g., an activation agent, that is a linker or crosslinker, e.g., a bifunctional linker or crosslinker or other chemical linker. In some embodiments, the linker or crosslinker is or includes a bifunctional linker. In some embodiments, the linker is a homobifunctional linker, e.g., a linker with at least two functional and/or reactive groups that are the same. In particular embodiments, the linker are a heterobifunctional linker, e.g., a linker with at least two functional and/or reactive groups that are different. In certain embodiments, the molecules are incubated with a linker to oligomerize or to become capable of oligomerizing. Suitable linkers for oligomerizing molecules are known in the art, and include, but are not limited to, glutaraldehyde, dimethyl adipimidate (DMA), dimethyl suberimidate (DMS), dimethyl pimelimidate (DMP), N-hydroxysuccinimide (NHS), dithiobis(succinimidylpropionate (DSP), dithiobis(sulfosuccinimidylpropionate) (DTSSP), ethylene glycol bis[succininimidylsuccinate], NHS ester, N-F-maleimidocaproic acid, N-[F-maleimidocaproic acid]hydrazide, N-succinimidyl S-acetylthioacetate, N-succinimidyl S-acetylthiopropionate, 2-Iminothiolane (Traut's reagent), 4-Succinimidyloxycarbonyl-Methyl-(2-Pyridyldithio)-Toluene Sulfosuccinimidyl, 4-[N-maleimidomethyl]-cyclohexane-1-carboxylate, N-[gamma-Maleimidobutyryloxy] sulfo-succinimide ester, N-(K-Maleimidoundecanoyloxy) Sulfosuccinimide Ester, Maleimidoacetic Acid N-Hydroxysuccinimide Ester, N-(Epsilon-Maleimidocaproic Acid) Hydrazide, N-(K-Maleimidoundecanoic Acid) Hydrazide, N-(Beta-Maleimidopropionic Acid) Hydrazide, and 3-(2-Pyridyldithio)Propionyl Hydrazide.

In some embodiments, the methods provided herein contain and/or include oligomerizing molecules that have been modified, e.g., chemically modified. In particular embodiments, one or more modified molecules are oligomerized. In particular embodiments, the one or more molecules are activated. In certain embodiments, the modified molecule is an activated molecule that has been activated by the addition and/or attachment of a functional group that reacts or is capable of reacting in a crosslinking and/or an oligomerization reaction. In some embodiments, the functional group is added or attached to an amine, e.g., a primary amine, of the molecule, e.g., an available and/or a free amine. In some embodiments, the amine, e.g., the primary amine is an N-terminal amine. In particular embodiments, the amine, e.g., the primary amineis on a lysine residue. In some embodiments, the activated molecule has been modified by the addition and/or attachment of a functional group that is or includes an amine-reactive group (e.g., an N-Hydroxysuccinimide Ester, imidoester, pentafluorophyl ester, or a hydroxymethyl phosphine), a sulfhydryl-reactive or thiol-reactive group (e.g., a maleimide, a haloacetyl, a pyridyldisulfide, a thiosulfonate, or a vinylsulfone), an aldehyde-reactive group (e.g., a hydrazide or an alkoxyamine), a photoreactive group (e.g., a diazirine or a aryl azide), and/or a hydroxyl-reactive group (e.g., isocyanate). In some embodiments, the activated molecule has been activated by the addition and/or attachment of a sulfhydryl-reactive or thiol-reactive group. In certain embodiments, the activated molecule has been activated by the addition and/or attachment of a haloacetyl group, a maleimide group, an aziridine group, an acryloyl group, an arylating agent, a vinylsulfone group, a pyridyl disulfide, a TNB-thiol or a disulfide reducing agent. In certain embodiments, the activated molecule has been activated by the addition and/or attachment of a maleimide group.

In certain embodiments, a molecule that has been modified is a thiolated molecule. In particular embodiments, the modified molecule has been modified by thiolation, e.g., the addition of a thiol (i.e., a thiol group, thiol function, or a thiol functional group). In particular embodiments, the thiolated molecule has been thiolated by the attachment and/or addition of a thiol functional group to one or more lysine residues.

In certain embodiments, methods provided herein for manufacturing, generating, and/or producing oligomeric particle reagents contain and/or include a step of incubating, treating, or contacting activated molecules with thiolated molecules. In some embodiments, the incubating, treating, and/or contacting oligomerizes and/or results in an oligomerization reaction between the thiolated molecules and the activated molecules. In particular embodiments, oligomers of the molecule are formed by incubating, treating, and/or contacting thiolated molecules with activated molecules. In certain embodiments, the activated molecule has one or more attached maleimide groups. In particular embodiments, the activated molecule is or includes an activated streptavidin or streptavidin mutein molecule. In certain embodiments, the activated streptavidin or streptavidin mutein molecule is or includes a streptavidin or streptavidin mutein molecule with one or more attached maleimide groups. In particular embodiments, the thiolated molecule is a thiolated streptavidin or streptavidin mutein molecule. In some embodiments, the thiolated streptavidin or streptavidin mutein molecule is a streptavidin or streptavidin mutein molecule with one or more thiol functional groups. In particular embodiments, the methods provided herein include a step of incubating, contacting, and/or treating thiolated streptavidin or streptavidin mutein tetramers with activated streptavidin or streptavidin mutein tetramers, for example to oligomerize the streptavidin or streptavidin mutein tetramers.

In particular embodiments, molecules are oligomerized by a crosslinking reaction. In some embodiments, a portion of the molecules have been thiolated by adding one or more thiol functional groups to the molecule. In certain embodiments, the thiol groups are added to free amine groups of the molecule, for example, on amine, e.g., primary amine, groups of lysine residues and/or an N-terminal amine, e. g., an N-terminal primary amine. In some embodiments, a portion of the molecules that are separate from the thiolated molecules are activated by the addition or attachment of maleimide groups. In some embodiments, the activated molecules do not contain cysteine residues and/or thiol functional groups. Therefore, in some embodiments, the activated molecules are not reactive with other activated molecules. In some embodiments, the activated and thiolated molecules are incubated, and a crosslinking reaction between maleimide functional groups of the activated molecules and the thiol functional group of the thiolated molecules occurs. For example, a cross linking reaction between a maleimide functional group on molecule R and a thiol (SH) function group on molecule P is illustrated below:

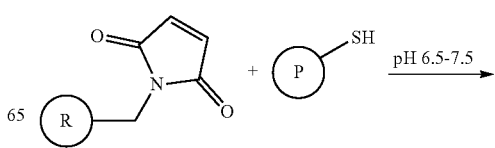

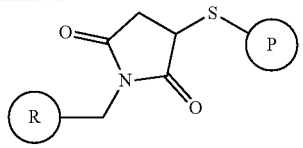

In some embodiments, the reaction between the thiol functional group and the maleimide functional group is suitable of crosslinking molecules to form oligomers. In certain embodiments, the molecules are streptavidin or streptavidin mutein tetramers.

In particular embodiments, the molecules, e.g., activated and thiolated streptavidin or streptavidin mutein tetramers are incubated and/or treated under conditions suitable to oligomerize the molecules. In particular embodiments, the incubation and/or treatment to oligomerize the molecules is performed at a neutral pH. In some embodiments, the incubation and/or treatment to oligomerize the molecules is performed at a pH of between 5.0 and 9.0, between 6.0 and 8.0, between 6.5 and 7.5, or between 7.0 and 7.5. In certain embodiments, the incubation and/or treatment to oligomerize the molecules is performed at a pH of about 6.5, about 6.6, about 6.7, about 6.8, about 6.9, about 7.0, about 7.1, about 7.2, about 7.3, about 7.4, or about 7.5. In some embodiments, the pH is about 7.2. In particular embodiments, the pH is 7.2±0.1, ±0.05, ±0.02, ±0.01, ±0.005, or ±0.0001.

In some embodiments, the molecules, e.g., activated and thiolated streptavidin or streptavidin mutein molecule, are incubated and/or treated under conditions that are suitable to oligomerize the molecules, and the suitable conditions include temperature. In some embodiments, the incubation and/or treatment to oligomerize the molecules is performed at a temperature of at least 4° C., at least 8° C., at least 12° C., at least 16° C., at least 20° C., at least 24° C., at least 28° C., at least 32° C., at least 37° C., at least 39° C., at least 50° C., at least 60° C., at least 70° C., at least 80° C., at least 90° C., or at least 100° C. In particular embodiments, the incubation and/or treatment to oligomerize the molecules is performed at a temperature of between 4° C. and 39° C., between 10° C. and 37° C., between 10° C. and 25° C., between 20° C. and 30° C., between 24° C. and 39° C., or between 40° C. and 100° C. In particular embodiments, the incubation and/or treatment to oligomerize the molecules is performed at room temperature. In some embodiments, the incubation and/or treatment to oligomerize the molecules is performed at or at about 24° C. In certain embodiments, the incubation and/or treatment to oligomerize the molecules is performed at 24° C.±2° C., ±1° C., ±0.5° C., ±0.2° C., ±0.1° C., ±0.05° C., or ±0.01° C.

In certain embodiments, the molecules, e.g., activated and thiolated streptavidin or streptavidin mutein tetramers, are incubated and/or treated under conditions that are suitable to oligomerize the molecules for an amount of time. In some embodiments, the molecules are incubated and/or treated under conditions that are suitable to oligomerize the molecules for between 5 minutes and 1 hour, between 15 minutes and 2 hours, between 30 minutes and 90 minutes, between 1 hour and 6 hours, between 6 hours and 24 hours, or more than 24 hours. In some embodiments, the incubation and/or treatment to oligomerize the molecules is performed for about 5 minutes, 15 minutes, about 30 minutes, about 45 minutes, about 1 hour, about 1.5 hours, about 2 hours, about 3 hours, about 6 hours, about 8 hours, about 12 hours, about 16 hours, about 18 hours, about 20 hours, or about 24 hours.

In certain embodiments, the incubation and/or treatment to oligomerize the molecules is performed for or for about 1 hour. In particular embodiments, the incubation and/or treatment to oligomerize the molecules is performed for 1 hour±5 minutes, ±2 minutes, ±1 minute, ±30 seconds, ±15 seconds, ±10 seconds, ±5 seconds, or ±1 second.

In particular embodiments, activated and thiolated molecules, e.g., activated and thiolated streptavidin or streptavidin mutein tetramers, are incubated and/or treated oligomerize the molecules at a molar ratio of activated molecules to thiolated molecules. In particular embodiments, the molar ratio of activated molecules to thiolated molecules 1:X. In some embodiments, X is the number, i.e., the sum, of lysines and N-terminal amines on the thiolated molecule. In some embodiments, X is the number of free or available amine groups on the molecule. In some embodiments, X is the number of lysines on the thiolated molecule prior to the addition of thiol functional groups. In particular embodiments, the molar ratio of activated molecules to thiolated molecules is or is about 1:1, 1:2, 1:3, 1:4, 1:5, 1:6, 1:7, 1:8, 1:9, or 1:10. In particular embodiments, the molar ratio of activated molecules to thiolated molecules is 1:1, 1:2, 1:3, 1:4, 1:5, 1:6, 1:7, 1:8, 1:9, or 1:10, ±10%, ±5%, ±2%, ±1%, ±0.5%, ±0.1%, ±0.05%, or ±0.001%. In certain embodiments, the molar ratio is 1:4, ±10%, ±5%, ±2%, ±1%, ±0.5%, ±0.1%, ±0.05%, or ±0.001%.

In certain embodiments, the incubation, treatment, and/or contacting under conditions to oligomerize the molecules, e.g., streptavidin or streptavidin mutein tetramers, is ended by adding one or more agents, e.g., a chemical agent, that ends and/or is capable of ending the oligomerization reaction. In some embodiments, the agent is an agent that modifies or otherwise prevents one or more functional groups, e.g., maleimide or thiol functional groups, from reacting in a crosslinking or oligomerization reaction. In some embodiments, the molecules are activated and thiolated molecules and the one or more agents is or includes an agent that saturates available maleimide groups, such as by adding and/or attaching a thiol group, or that cleaves and/or detaches maleimide groups from the molecues. In some embodiments, unreacted maleimide groups may be removed by an agent that elevates pH. In certain embodiments, the elevated pH would result in removal and/or detachment of unreacted maleimide groups, while crosslinked maleimide groups would be stable. In certain embodiments, the one or more agents include agent that catalyze a hydrolysis of the maleimide ring system, e.g., by a ring opening reaction. In some embodiments, the molecules are activated and thiolated molecules and the one or more agents is or includes an agent modifies and/or saturates thiol functional groups. In some embodiments, the saturation and/or modification of the thiol functional groups prevents oligomerization and/or crosslinking reactions with maleimide groups. In some embodiments, activated and thiolated molecules, e.g., activated and thiolated streptavidin or streptavidin mutein tetramers, are incubated, treated, and/or contacted with N-ethylmaleimide (NEM) to end oligomerization and/or crosslinking reactions.

In some embodiments, the molecules, e.g., activated and thiolated streptavidin or streptavidin mutein tetramers, are incubated, treated, and/or contacted with an agent that ends and/or is capable of ending oligomerization and/or the crosslinking reaction. In some embodiments, the agent that ends and/or is capable of ending oligomerization and/or crosslinking reactions is incubated, treated, and/or contacted with the molecules at a temperature of between 4° C. and 39° C., between 4° C. and 25° C., between 4° C. and 10° C., or between 20° C. and 30° C. In particular embodiments, the incubation, treatment, and/or contacting is initially performed at room temperature, and is then performed at about 4° C. In some embodiments, the incubation, treatment, and/or contacting is initially performed at or at about 24° C., and is then performed at about 4° C. In certain embodiments, the incubation, treatment, or contacting is initially performed for about 5 minutes, about 10 minutes, about 15 minutes, about 30 minutes, about 60 minutes, about 90 minutes, or about 120 minutes at room temperature and/or at about 24° C., and then is incubated, contacted, and/or treated for about 1 hour, about 2 hours, about 4 hours, about 6 hours, about 8 hours, about 12 hours, about 16 hours, about 24 hours, or more than 24 hours at about 4° C. In some embodiments, the incubation, treatment, or contacting is initially performed for about 15 minutes at room temperature and/or at about 24° C., and then performed for about 16 hours at about 4° C. In certain embodiments, the incubation, treatment, or contacting with NEM is initially performed for about 15 minutes at room temperature and/or at about 24° C., and then is incubated, contacted, and/or treated for about 16 hours at about 4° C.

In particular embodiments, the methods provided herein for manufacturing, generating, and/or producing oligomeric particle reagents include steps for thiolating molecules and for activating molecules. In certain embodiments, different populations or pluralities of the molecules are thiolated from the populations or pluralities of the molecules that are activated. In some embodiments, the activation and thiolation steps are performed at about the same time, for example, so that thiolated and activated molecules are both available for an incubation reaction without the need to store either the thiolated or activated molecules while the other process is taking place. In some embodiments, at least a portion of the incubation, treatment, and or contacting of the thiolating agent with the molecules and the incubation, treatment, and or contacting of the activation agent with the molecules are performed at the same time.

In certain embodiments, at least 1%, at least 5%, at least 10%, at least 20%, at least 30%, at least 40%, at least 50%, at least 60%, at least 70%, at least 80% at least 90%, or at least 95% of the incubation, treatment, and or contacting of the thiolating agent with the molecules is performed while the incubation, treatment, and or contacting of the activation agent with the molecules is performed. In certain embodiments, at least 1%, at least 5%, at least 10%, at least 20%, at least 30%, at least 40%, at least 50%, at least 60%, at least 70%, at least 80% at least 90%, or at least 95% of the incubation, treatment, and or contacting of the activation agent with the molecules is performed while the incubation, treatment, and or contacting of the thiolating agent with the molecules is performed.

In some embodiments, at least 1 minute, at least 5 minutes, at least 10 minutes, at least 15 minutes, at least 30 minutes, at least 45 minutes, at least 60 minutes, at least 90 minutes, at least 120 minutes, at least 4 hours, at least 6 hours, at least 8 hours, at least 12 hours, at least 16 hours, or at least 24 hours of the incubation, treatment, and or contacting of the activation agent with the molecules is performed while the incubation, treatment, and or contacting of the thiolating agent with the molecules is performed. In particular embodiments at least 1 minute, at least 5 minutes, at least 10 minutes, at least 15 minutes, at least 30 minutes, at least 45 minutes, at least 60 minutes, at least 90 minutes, at least 120 minutes, at least 4 hours, at least 6 hours, at least 8 hours, at least 12 hours, at least 16 hours, or at least 24 hours of the incubation, treatment, and or contacting of the thiolating agent with the molecules is performed while the incubation, treatment, and or contacting of the activating agent with the molecules is performed.

In some embodiments, the incubation, treatment, and/or contacting of the thiolating agent and the incubation, treatment, and/or contacting of the activation agent with the molecules are started at about the same time. In certain embodiments, the incubation, treatment, and/or contacting of the thiolating agent and the incubation, treatment, and/or contacting of the activation agent with the molecules are started within 30 minutes, within 15 minutes, within 10 minutes, within 5 minutes, within 1 minute, within 30 seconds, within 15 seconds, within 10 seconds, within 5 seconds, within 1 second of each other. In some embodiments, the incubation, treatment, and/or contacting of the thiolating agent and the incubation, treatment, and/or contacting of the activation agent with the molecules are ended at about the same time. In particular embodiments, the incubation, treatment, and/or contacting of the thiolating agent and the incubation, treatment, and/or contacting of the activation agent with the molecules are ended within 30 minutes, within 15 minutes, within 10 minutes, within 5 minutes, within 1 minute, within 30 seconds, within 15 seconds, within 10 seconds, within 5 seconds, within 1 second of each other.

Particular embodiments contemplate that when a thiol functional group is attached or added to a molecule, the thiol functional group may isomerize into a more stable but inactive N-substituted form. In some aspects, the thiol functional group is added or attached in the presence of 2-iminothiolane (Trauts reagent). Certain embodiments contemplate that when a thiol functional group is attached or added to a molecule in the presence of 2-iminothiolane (Trauts reagent), the thiol functional group may isomerize into a more stable but inactive N-substituted form. In certain embodiments, the thiol functional groups isomerize with a half-life of or about 139 minutes after removal of the thiolating agent. Thus, in some embodiments, the amount of the thiol functional groups on the molecules following the incubation, treatment, and/or contacting with the thiolating agent are reduced over time.

In particular embodiments, the methods provided herein for manufacturing, generating, and/or producing oligomeric particle reagents include steps of thiolating molecules, activating molecules, and oligomerizing the molecule, e.g., incubating the activated and thiolated molecules under conditions suitable for oligomerization. In particular embodiments, the step of oligomerizing the molecule is timed to begin within or at a precise amount of time after the thiolation step has ended or completed. In some embodiments, the step of oligomerizing the molecule is timed to begin within or at a precise amount of time after the thiolation step and the activation step has ended or completed.

In particular embodiments, the step of oligomerizing the molecule, e.g., incubating the activated and thiolated molecules under conditions suitable for oligomerization, is started within an amount of time after the end of thiolation step, e.g., the incubation of the molecule with the thiolating agent, has ended. In certain embodiments, the step of oligomerizing the molecule is begun or initiated before a loss, reduction, or decay of 50%, 40%, 30%, 25%, 20%, 15%, 10%, 5%, 1%, 0.5%, 0.1%, 0.01%, 0.001%, or 0.0001% of the thiol functional groups that are attached to the molecule at the end of the thiolation step. In particular embodiments, the step of oligomerizing the molecule is begun or initiated before a loss, reduction, or decay of 10% of the thiol functional groups that are attached to the molecule at the end of the thiolation step. In some embodiments, the step of oligomerizing the molecule is begun or initiated within 24 hours, within 16 hours, within 12 hours, within 8 hours, within 6 hours, within 4 hours, within 2 hours, within 90 minutes, within 60 minutes, within 45 minutes, within 30 minutes, within 15 minutes, within 10 minutes, within 5 minutes, or within 1 minute after the end of the thiolation step. In certain embodiments, the step of oligomerizing the molecule is begun or initiated 6 hours, 5 hours, 4 hours, 3 hours, 2 hours, 90 minutes, 60 minutes, 45 minutes, 30 minutes, 15 minutes, 10 minutes, 5 minutes, or 1 minute±5 minutes, ±2 minutes, ±1 minute, ±30 seconds, ±15 seconds, ±10 seconds, ±5 seconds, or ±1 second. In certain embodiments, the step of oligomerizing the molecule is begun or initiated within 15 minutes after the end of the thiolation step. In particular embodiments, the step of oligomerizing the molecule is begun or initiated 10 minutes±1 minute, ±30 seconds, ±15 seconds, ±10 seconds, ±5 seconds, or ±1 second after the end of the thiolation step.

In particular embodiments, the end of the thiolating step, e.g., the incubation of the molecule with the thiolating agent, is or occurs when the thiolating agent is removed from the molecules or when the process of removing the thiolating agent is begun or initiated. In some embodiments, the end of the thiolating step is or occurs when the process of removing the thiolating agent is begun or initiated. In particular embodiments, the process of removing the thiolating agent is or includes chromatography, for example gel filtration chromatography. In some embodiments, the end of the thiolation step is or occurs when or at the instant that the sample or solution containing the thiolating agent and the molecules are poured into a chromatography column, e.g., a gel filtration chromatography column, to remove or separate the thiolating agent from the molecules. In particular embodiments, the start of the step of oligomerizing the molecule begins and/or is initiated when activated molecules are contacted, added, and/or mixed with thiolated molecules.

In particular embodiments, the methods provided herein for manufacturing, generating, and/or producing oligomeric particle reagents include a step of removing and/or separating oligomer particle reagents and/or oligomerized molecules from molecules that have not oligomerized. In certain embodiments, the step of removing and/or separating oligomer particle reagents and/or oligomerized molecules from molecules that have not oligomerized occurs after the step of oligomerizing the molecules has been completed or ended.

In some embodiments, the oligomerized particle reagents and/or the oligomers of the molecules are removed and/or separated from the molecules that have not oligomerized and from oligomer particles that are less than or under a threshold size. In some embodiments, the threshold for size is or includes a radius of at least 5 nm, at least 10 nm, at least 15 nm, at least 20 nm, at least 25 nm, at least 30 nm, at least 40 nm, at least 50 nm, at least 60 nm, at least 70 nm, at least 75 nm, at least 80 nm, at least 85 nm, or at least 90 nm. In certain embodiments, the threshold for size is or includes a molecular weight of at least 100 kDa, at least 500 kDa, at least 1,000 kDa, at least 2,000 kDa, at least 5,000 kDa, at least 10,000 kDa, at least 50,000 kDa, or at least 100,000 kDa. In certain embodiments, the threshold size does not affect the average (e.g., mean) size and/or the size distribution of the oligomer particle reagents produced by the methods provided herein.

In some embodiments, the oligomer particle reagents, e.g., oligomers of streptavidin or streptavidin mutein tetramers, are removed from and/or separated from particles that have not oligomerized by size exclusion chromatography (SEC). In some embodiments, SEC is a technique that permits the separation of molecules by size without damaging or destroying the molecules, whereby molecules smaller than an exclusion limit are trapped in a column, and molecules larger than the exclusion limit pass through the column, e.g., without retardation. In certain embodiments, the exclusion limit is a size that falls between 1 kDa and 100,000 kDa, between 100 kDa and 10,000 kDa, between 500 kDa and 1,000 kDa, between 500 kDa and 5,000 kDa, between 5,000 kDa and 20,000 kDa, between 10,000 kDa and 50,000 kDa, or between 50,000 and 100,000 kDa. In certain embodiments, the exclusion limit is larger than the molecular weight of a monomer and/or a tetramer of the molecule. In some embodiments, the exclusion limit is larger than the molecular weight of a streptavidin or streptavidin mutein tetramer. In particular embodiments, all of the particles, e.g., oligomeric particles that pass through the SEC column, such as in the void volume, e.g., without retardation, are collected.

In particular embodiments, when SEC is performed the order at which the molecules exit the column is in relation to the size of the molecules, thus, in some embodiments, the eluate of the column can be collected in different fractions. In some embodiments, the fractions may be combined or discarded to remove particles of certain sizes. For example, in some embodiments, factions may be discarded to remove particles, e.g., oligomeric particle reagents, with a size of less than 100 kDa, less than 500 kDa, less than 1,000 kDa, less than 2,000 kDa, less than 5,000 kDa, less than 10,000 kDa, less than 50,000 kDa, or less than 100,000 kDa. In certain embodiments, SEC removes oligomeric particle reagents from molecules that have not oligomerized but not affect the average (e.g., mean) size and/or the size distribution of the oligomer particle reagents produced by the methods provided herein.

In certain embodiments, oligomeric particle reagents e.g., oligomerized streptavidin or streptavidin mutein tetramers, may continue to crosslink and/or oligomerize after the incubation, treatment, and/or contacting of the molecules for oligomerization has completed or ended. Thus, in some embodiments, the methods provided herein for manufacturing, generating, and/or producing oligomeric particle reagents include a step for stabilizing, e.g., stabilizing the size, of the oligomers. In some embodiments, the step for stabilizing the oligomers is or includes incubating, contacting, and/or treating oligomerized molecules, e.g., oligomeric particle reagents, with a stabilization agent.

In some embodiments, the stabilization agent is any agent that prevents or is capable of preventing a change in particle, e.g., oligomeric particle reagent, size. In some embodiments, the stabilization agent is any agent that modifies a functional group on the molecule or oligomeric particle that does or is capable of reacting in an oligomerization and/or crosslinking reaction. In certain embodiments, stabilization agent is any agent that prevents the formation, isomerization, and/or conversion to produce a functional group on the molecule or oligomeric particle that does or is capable of reacting in an oligomerization and/or crosslinking reaction. In some embodiments, the stabilization reagent is any agent that modifies or is capable of modifying a haloacetyl group, a maleimide group, an aziridine group, an acryloyl group, an arylating agent, a vinylsulfone group, a pyridyl disulfide, a TNB-thiol or a disulfide reducing agent that is attached to the molecule or oligomeric particle. In particular embodiments, the stabilization reagent is any agent that prevents the formation, isomerization, and/or conversion to produce a haloacetyl group, a maleimide group, an aziridine group, an acryloyl group, an arylating agent, a vinylsulfone group, a pyridyl disulfide, a TNB-thiol or a disulfide reducing agent that is attached to the molecule or oligomeric particle.

In some embodiments, the stabilization agent is incubated, treated, and/or contacted with an oligomeric particle. In some embodiments, the oligomeric particle is an oligomeric particle reagent that contains a plurality of thiolated molecules and activated molecules, e.g., activated and thiolated streptavidin or streptavidin mutein tetramers. In certain embodiments, the oligomeric particle contains more thiolated molecules that contain an attached N-substituted iminothiolane. In some embodiments, incubation and/or treatment with NEM saturates and/or modifies all available thiol functional groups thereby stopping the crosslinking and/or oligomerization reaction. However, in some embodiments, N-substituted iminothiolane is not reactive with NEM and these isomers remain on molecules and oligomeric particles after the incubation with NEM. In some embodiments, re-isomerization of the N-substituted iminothiolane to the thiol isomer may therefore lead to post-synthetic growth of the oligomeric particle reagent, for example by additional crosslinking and/or oligomerizing reactions, such as with remaining available maleimide groups on other oligomeric particles.

In some embodiments, the stabilization agent is an agent that is or is capable of modifying, removing, and/or preventing the N-substituted iminothiolane from re-isomerizing into a thiol functional group. In some embodiments, the stabilization agent is or includes hydroxylamine. In certain embodiments, an oligomeric particle and/or molecule that contains an attached N-substituted iminothiolane is incubated, treated, and/or contacted with a stabilization agent that is or is capable of modifying, removing, and/or preventing an N-substituted iminothiolane from re-isomerizing into a thiol functional group. In particular embodiments, an oligomeric particle and/or molecule that contains an attached N-substituted iminothiolane is incubated, treated, and/or contacted with hydroxylamine.

In some embodiments, the stabilization reagent, e.g., hydroxylamine, is contacted, treated, and/or incubated with the oligomerized molecules, e.g., oligomeric particle reagents, such as to perform a stabilization reaction. In some embodiments, the stabilization reagent, e.g., hydroxylamine, is added to the oligomerized molecules after the crosslinking reaction between thiol functional groups and maleimide functional groups is performed and/or completed. In particular embodiments, the stabilization reagent, e.g., hydroxylamine, is contacted, treated, and/or incubated with the oligomerized molecules, e.g., oligomeric particle reagents, after the crosslinking reaction is ended, completed, and/or terminated by the addition of NEM to the oligomerized molecules. In certain embodiments, the stabilization reagent, e.g., hydroxylamine, is contacted, treated, and/or incubated with the oligomerized molecules, e.g., oligomeric particle reagents, after the crosslinking reaction is ended, completed, and/or terminated by the addition of NEM to the oligomerized molecules. In certain embodiments, the stabilization reagent is contacted, treated, and/or incubated with the oligomerized molecules prior to long-term storage, e.g., storage at, at about, or below room temperature, 4° C., −20° C., or −80° C. for at least 1 day, 1 week, 3 weeks, 9 weeks, 27 weeks, 46 weeks, or 1 or more years. In some embodiments, the stabilization reagent, e.g., hydroxylamine, is contacted, treated, and/or incubated with the oligomerized molecules, e.g., oligomeric particle reagents, after the oligomerized molecules are loaded onto, passed through, and/or eluted from a column, such a chromatography column and/or an SEC column. In particular embodiments, the stabilization reagent is contacted, treated, and/or incubated with the oligomerized molecules after the oligomerized molecules are loaded onto, passed through, and/or eluted from an SEC column. In certain embodiments, the stabilization reagent is contacted, treated, and/or incubated with the oligomerized molecules prior to any step where the oligomerized molecules are loaded onto, passed through, and/or eluted from an SEC column.

In some embodiments, the stabilization reagent, e.g., hydroxylamine, is contacted, treated, and/or incubated with the oligomerized molecules, e.g., oligomeric particle reagents, for, for about, or for at least 1 minute, 5 minutes, 10 minutes, 15 minutes, 30 minutes, 45 minutes, 60 minutes, 90 minutes, 120 minutes, 4 hours, 6 hours, 8 hours, 12 hours, 16 hours, or 24 hours. In certain embodiments, the stabilization reagent is contacted, treated, and/or incubated with the oligomerized molecules for between 1 minute and 12 hours, between 1 minute and 1 hour, between 1 minute and 30 minutes, between 5 minute and 30 minutes, between 10 minutes and 60 minutes, between 10 minutes and 20 minutes, between 1 hour and 3 hours, between 1 hour and 2 hours, or between 6 hours and 12 hours. In particular embodiments, the stabilization reagent is contacted, treated, and/or incubated with the oligomerized molecules for between 5 minutes and 30 minutes, or for or for about 15 minutes. In certain embodiments, the treatment, contact, and/or incubation is performed with mixing, and/or rocking, e.g., gentle rocking and/or mixing.

In some embodiments, the stabilization reagent, e.g., hydroxylamine, is contacted, treated, and/or incubated with the oligomerized molecules, e.g., oligomeric particle reagents, at a temperature of, of about, or of 4° C., 8° C., 12° C., 16° C., 20° C., 24° C., 28° C., 32° C., 37° C., 39° C., 50° C., 60° C., 70° C., 80° C., 90° C., or 100° C. In some embodiments, the stabilization reagent is contacted, treated, and/or incubated with the oligomerized molecules at a temperature of between 4° C. and 39° C., between 10° C. and 37° C., between 10° C. and 25° C., between 20° C. and 30° C., between 24° C. and 39° C., or between 40° C. and 100° C. In particular embodiments, the stabilization reagent is contacted, treated, and/or incubated with the oligomerized molecules at room temperature. In certain embodiments, the stabilization reagent is contacted, treated, and/or incubated with the oligomerized molecules at or at about 23° C., 24° C., 25° C., or 26° C.±2° C., ±1° C., ±0.5° C., ±0.2° C., ±0.1° C., ±0.05° C., or ±0.01° C.

In some embodiments, the stabilization reagent, e.g., hydroxylamine, is removed and/or separated from the oligomerized molecules, e.g., oligomeric particle reagents. In particular embodiments, the stabilization reaction is ended and/or terminated by separating and/or removing the stabilization reagent from the oligomerized particles. In some embodiments, the stabilization reagent is removed and/or separated from the oligomerized particles with a chromatography step. In particular embodiments, the chromatography step is or includes SEC. In some embodiments, the stabilization reagent is removed from and/or separated from the oligomerized molecules with a column and/or a filter. In some embodiments, the column or filter is a desalting column. In certain embodiments, the desalting column contains a resin, e.g., a resin that is or contains sephadex, dextran, and/or epichlorohydrin.

In particular embodiments, the stabilization reagent, e.g., hydroxylamine, is contacted, treated, and/or incubated with the oligomerized molecules, e.g., oligomeric particle reagents, for between 1 minute and 1 hour at a temperature of between 4° C. and 39° C., between 10° C. and 25° C., or between 20° C. and 30° C. In some embodiments, the stabilization reagent, e.g., hydroxylamine, is contacted, treated, and/or incubated with the oligomerized molecules, e.g., oligomeric particle reagents, for between 5 minutes and 30 minutes at a temperature between 10° C. and 25° C.

In particular embodiments, oligomeric particle reagents, e.g., oligomeric particle reagents that contain a plurality of streptavidin or streptavidin mutein tetramers that are incubated, treated, or contacted with a stabilization agent are stable with respect to size. In some embodiments, oligomeric particle reagents that are incubated, treated, or contacted with a stabilization agent do not experience a change in size over time that is greater than 1%, greater than 5%, greater than 10%, greater than 20%, greater than 25%, greater than 30%, greater than 40%, or greater than a 50%, change in size, e.g., a change in radius or molecular weight, over an amount of time, e.g., 12 hours, 24 hours, 2 days, 3 days, 4 days, 5 days, 6 days, 7 days, 10 days, 14 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, or more than 16 weeks when the particles are stored at room temperature, at or at about 4° C. or under, at or at about −20° C. or under, or at or at about −80° C. In some embodiments, oligomeric particle reagents that are incubated, treated, or contacted with a stabilization agent oligomeric particle reagents that are incubated, treated, or contacted with a stabilization agent do not experience an increase in size over time that is greater than 1%, greater than 5%, greater than 10%, greater than 20%, greater than 25%, greater than 30%, greater than 40%, or greater than a 50% increase in size over 12 hours, 24 hours, 2 days, 3 days, 4 days, 5 days, 6 days, 7 days, 10 days, 14 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, or more than 16 weeks.

In some embodiments, the methods provided herein include one or more steps of filter sterilizing the molecules, e.g., streptavidin or streptavidin mutein tetramers, and/or the oligomeric particle reagents. In some embodiments, the oligomeric particle reagents are filter sterilized. In some embodiments, the molecules or oligomeric particle reagents are filter sterilized before or after incubation with an activation agent or a thiolating agent, before or after activated and thiolated molecules are crosslinked and/or oligomerized, before or after SEC is performed to remove oligomeric particle reagents from non oligomerized molecules, e.g., tetramers, and/or before or after oligomeric particle reagents are incubated with a stabilization agent. In some embodiments, the oligomeric particle reagents are or are capable of being filter sterilized. In certain embodiments, the oligomeric particle reagents do not aggregate, clog, or otherwise impede or prevent a process of filter sterilization. In some embodiments, the filter sterilization includes passing a solution containing the molecules or the oligomeric particle reagents through a porous filter or membrane. In some embodiments, the porous filter or membrane contains pores that are or are at least about 0.02 μm, about 0.05 μm, about 0.1 μm, about 0.15 μm, about 0.2 μm, about 0.22 μm, about 0.3 μm, about 0.4 μm, about 0.45 μm, or about 0.5 μm in diameter. In some embodiments, the pores are a size that is between 0.01 μm and 1.0 μm, between 0.1 μm and 0.05 μm, between 0.2 μm and 0.25 μm, 0.4 and 0.45 μm, or between 0.2 μm and 0.45 μm. In some embodiments, the oligomeric particles have a radius and/or an average radius that is at or below 150 nm. In particular embodiments, the oligomeric particles have a radius and/or an average radius that is about, at, or below 125 nm, 110 nm, or 100 nm.

In some embodiments, the oligomeric particle reagents are manufactured, generated, and/or produced by the methods provided herein and are then stored. In some embodiments, the oligomeric particle reagents are stored for an amount of time prior to any treatments or incubations to bind agents, e.g., receptor binding agents, to the oligomeric particle reagents. In particular embodiments, the oligomeric particle reagents are stored for an amount of time after one or more treatments or incubations to reversibly bind agents, e.g., receptor binding agents, to the oligomeric particle reagents. In some embodiments, the oligomeric particle reagents are stored in two or more aliquots. In certain embodiments, the oligomeric particle reagents are stored in a buffer. In some embodiments, the buffer has a neutral pH and/or a pH of between 6.5 and 7.5, between 6.8 and 7.4, or about 6.8, about 6.9, about 7.0, about 7.1, about 7.2, or about 7.3. In certain embodiments, the oligomeric particle reagents are stored in a buffer of a pH of about 7.2. In certain embodiments the buffer is a phosphate buffer, e.g., a sodium phosphate buffer. In certain embodiments, the oligomeric particle reagents are stored at room temperature, at or at about 4° C. or under, at or at about −20° C. or under, or at or at about −80° C. In particular embodiments, the oligomeric particle reagents are stored 12 hours, 24 hours, 2 days, 3 days, 4 days, 5 days, 6 days, 7 days, 10 days, 14 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, or more than 16 weeks. In some embodiments, the oligomeric particle reagents placed in a buffer with a neutral pH and are stored at a temperature of at or about −80° C.

In some embodiments, the methods provided herein for manufacturing, generating, and/or producing oligomeric particle reagents include or contain a step for incubating, treating, and/or contacting molecules, e.g., streptavidin or streptavidin mutein tetramers, under conditions suitable for oligomerizing the molecules, a step for separating oligomeric particle reagents from molecules that did not oligomerize by SEC, and a step of incubating the particles with a stabilization agent. In some embodiments, the step of incubating, treating, and/or contacting molecules under conditions suitable for oligomerizing the molecules is or includes incubating thiolated molecules with one or more attached thiol functional groups with activated molecules with one or more attached maleimide functional groups.

In some embodiments, the methods provided herein for manufacturing, generating, and/or producing oligomeric particle reagents include: a step for incubating a plurality of streptavidin or streptavidin mutein tetramers with a thiolating agent in a buffer with a basic pH for an amount of time between 15 to 90 minutes to thiolate the tetramers, a step for incubating a separate plurality of streptavidin or streptavidin mutein tetramers with an activating agent for an amount of time between 30 minutes and 90 minutes to add one or more maleimide functional groups to the tetramers, ending the 2-iminothiolane and SMPH incubations at or at about the same time, a step for incubating the thiolated and activated tetramers within an amount of time between five and fifteen minutes after the activating and thiolating incubations are ended, a step for separating oligomeric particle reagents from molecules that did not oligomerize by SEC, and a step of incubating the particles with a stabilization to stabilize the size of the oligomer particle reagents. In some embodiments, the methods include a step of storing the oligomeric particle reagents in buffer solution with a neutral pH at about or below −80° C., −20° C., or 4° C.

In some embodiments, the methods provided herein for manufacturing, generating, and/or producing oligomeric particle reagents include: a step for incubating a plurality of streptavidin or streptavidin mutein tetramers with 2-iminothiolane in a buffer with a basic pH of between 7.7 and 8.5 at a temperature of about 24° C. for 60 minutes to thiolate the tetramers, a step for incubating a separate plurality of streptavidin or streptavidin mutein tetramers with SMPH at a neutral pH of 7.2 at a temperature of about 24° C. for 1 hour to add one or more maleimide functional groups to the tetramers, a step of ending the 2-iminothiolane and SMPH incubations at the same time by separating 2-iminothiolane and SMPH incubations from the tetramers with chromatography, e.g., SEC, a step for incubating the thiolated and activated tetramers ten minutes after the 2-iminothiolane and SMPH incubations are ended, a step of ending the oligomization reaction between the thiolated and activated tetramers after 60 minutes by incubating the tetramers with NEM, a step for separating oligomeric particle reagents from molecules that did not oligomerize by SEC, and a step of incubating the particles with hydroxylamine to stabilize the size of the oligomer particle reagents. In some embodiments, the methods include a step of storing the oligomeric particle reagents in buffer solution with a neutral pH at −80° C. In some embodiments, the 2-iminothiolane is added to a buffer with a basic pH of 8.5. In certain embodiments, the buffer is or contains 100 mM borate buffer. In some embodiments, the particles are stable, e.g., do not undergo a change in size of greater than 10%, for at least 46 weeks.

In particular embodiments, the methods provided herein for manufacturing, generating, and/or producing oligomeric particle reagents include: a step for incubating a plurality of streptavidin or streptavidin mutein tetramers with 2-iminothiolane in a buffer with a basic pH of between 7.7 and 8.5 at a temperature of about 24° C. for 60 minutes to thiolate the tetramers; a step for incubating a separate plurality of streptavidin or streptavidin mutein tetramers with SMPH at a neutral pH of 7.2 at a temperature of about 24° C. for 1 hour to add one or more maleimide functional groups to the tetramers; a step of ending the 2-iminothiolane and SMPH incubations at the same time by separating 2-iminothiolane and SMPH incubations from the tetramers with chromatography, e.g., SEC; a step for incubating the thiolated and activated tetramers, optionally within 10 minutes, after the 2-iminothiolane and SMPH incubations are ended; a step of ending the oligomization reaction between the thiolated and activated tetramers after or after about 60 minutes by incubating the tetramers with NEM, a step of incubating the particles with hydroxylamine; an SEC step, and optionally a step of filtering the particles, e.g., through a membrane and/or filter with or with about a 0.45 μm and/or a 0.2 μm diameter pore size. In some embodiments, the methods include a step of storing the oligomeric particle reagents in buffer solution with a neutral pH at −80° C. In some embodiments, the particles are stable, e.g., do undergo a change in size of greater than 10%, for at least 46 weeks.

C. Format of Reagent
1. Support

In some embodiments, the reagent is comprised on a support, such as a solid support or surface, e.g., bead, or a solid phase or a stationary phase (chromatography matrix). In some such embodiments, the reagent is reversibly immobilized on the support. In some cases, the reagent is immobilized to the support via covalent bonds. In some aspects, the reagent is reversibly immobilized to the support non-covalently.

In some embodiments, the support is a solid support. Any solid support (surface) can be used for the reversible immobilization of the reagent. Illustrative examples of solid supports on which the reagent can be immobilized include a magnetic bead, a polymeric bead, a cell culture plate, a microtiter plate, a membrane, an agarose bead, a polystyrene bead or a hollow fiber. In some aspects, hollow fibers can be used as a bioreactor in the Quantum® Cell Expansion System, available from TerumoBCT Inc. (Lakewood, CO, USA). In some embodiments, the reagent is covalently attached to the solid support. In other embodiments, non-covalent interactions can also be used for immobilization, for example on plastic substrates. In some embodiments, the reagent can, for example, be a streptavidin or avidin mutein that reversibly binds a streptavidin binding peptide. Such streptavidin muteins can be covalently attached to any surface, for example, resin (beads) used for chromatography purification and are commercially available in such form from IBA GmbH, Göttingen, for example, as Strep-Tactin® Sepharose, Strep-Tactin® Superflow®, Strep-Tactin® Superflow® high capacity or Strep-Tactin® MacroPrep®. Other illustrative examples that are readily commercially available are immobilized metal affinity chromatography (IMAC) resins such as the TALON® resins (Westburg, Leusden, The Netherlands) that can be used for the reversible immobilization of oligo-histidine tagged (his-tagged) proteins, such as for the reversible binding of an agent (e.g., receptor-binding agent or selection agent) that contains as a binding partner C an oligohistidine tag such as an penta- or hexa-histidine tag. Other examples include calmodulin sepharose available from GE Life Sciences which can be used together with an agent (e.g., receptor-binding agent or selection agent) that contains a calmodulin binding peptide as a binding partner C or sepharose, to which glutathione is coupled. In some such cases, the binding partner C is glutathione-S-transferase.

In some embodiments, the support contains a solid phase or a stationary phase. Thus, in some embodiments, the reagent is comprised on a solid phase or a stationary phase (also called chromatography matrix). In some such embodiments, the reagent is reversibly immobilized on the solid phase or stationary phase. In some cases, the reagent is reversibly immobilized to the stationary phase via covalent bonds. In some aspects, the reagent is reversibly immobilized to the stationary phase non-covalently.

Any material may be employed as a chromatography matrix. In general, a suitable chromatography material is essentially innocuous, i.e. not detrimental to cell viability, such as when used in a packed chromatography column under desired conditions. In some embodiments, the stationary phase remains in a predefined location, such as a predefined position, whereas the location of the sample is being altered. Thus, in some embodiments the stationary phase is the part of a chromatographic system through which the mobile phase flows (either by flow through or in a batch mode) and where distribution of the components contained in the liquid phase (either dissolved or dispersed) between the phases occurs.

In some embodiments, the chromatography matrix has the form of a solid or semisolid phase, whereas the sample that contains the target cell to be isolated/separated is a fluid phase. The chromatography matrix can be a particulate material (of any suitable size and shape) or a monolithic chromatography material, including a paper substrate or membrane. Thus, in some aspects, the chromatography can be both column chromatography as well as planar chromatography. In some embodiments, in addition to standard chromatography columns, columns allowing a bidirectional flow such as PhyTip® columns available from PhyNexus, Inc. San Jose, CA, U.S.A. or pipette tips can be used for column based/flow through mode based methods. Thus, in some cases, pipette tips or columns allowing a bidirectional flow are also comprised by chromatography columns useful in the present methods. In some cases, such as where a particulate matrix material is used, the particulate matrix material may, for example, have a mean particle size of about 5 µm to about 200 µm, or from about 5 µm to about 400 µm, or from about 5 µm to about 600 µm. In some aspects, the chromatography matrix may, for example, be or include a polymeric resin or a metal oxide or a metalloid oxide. In some aspects, such as where planar chromatography is used, the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In one embodiment, the chromatography matrix/stationary phase is a non-magnetic material or non-magnetizable material.

In some embodiments, non-magnetic or non-magnetizable chromatography stationary or solid phases that are suitable in the present methods include derivatized silica or a crosslinked gel. In some aspects, a crosslinked gel may be based on a natural polymer, such as on a polymer class that occurs in nature. For example, a natural polymer on which a chromatography stationary phase may be based is a polysaccharide. In some embodiments, the solid phase or stationary phase is a polystyrene bead. In some cases, a respective polysaccharide is generally crosslinked. An example of a polysaccharide matrix includes, but is not limited to, an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® which is also available in different bead and pore sizes from GE Healthcare. Another illustrative example of such a chromatography material is CytoSorb polystyrene beads.

In some embodiments, a crosslinked gel may also be based on a synthetic polymer, such as on a polymer class that does not occur in nature. In some aspects, such a synthetic polymer on which a chromatography stationary or solid phase is based is a polymer that has polar monomer units, and which is therefore in itself polar. Thus, in some cases, such a polar polymer is hydrophilic. Hydrophilic molecules, also termed lipophobic, in some aspects contain moieties that can form dipole-dipole interactions with water molecules. In general, hydrophobic molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments, a chromatography stationary phase may also include natural and synthetic polymer components, such as a composite matrix or a composite or a copolymer of a polysaccharide and agarose, e.g. a polyacrylamide/agarose composite, or of a polysaccharide and N,N'-methylenebisacrylamide. An illustrative example of a copolymer of a dextran and N,N'-methylenebisacrylamide is the above-mentioned Sephacryl® series of material. In some embodiments, a derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

In some embodiments, the chromatography matrix is a gel filtration matrix, for example, when used in a removal cartridge as described herein. Generally, a gel filtration can be characterized by the property that it is designed to undergo. Hence, a gel filtration matrix in some aspects allows the separation of cells or other biological entities largely on the basis of their size. In some such aspects, the respective chromatography matrix is typically a particulate porous material as mentioned above. The chromatography matrix may have a certain exclusion limit, which is typically defined in terms of a molecular weight above which molecules are entirely excluded from entering the pores. In some embodiments, the respective molecular weight defining the size exclusion limit may be selected to be below the weight corresponding to the weight of a target cell. In such an embodiment, the target cell is prevented from entering the pores of the size exclusion chromatography matrix. Likewise, a stationary phase may have pores that are of a size that is smaller than the size of a chosen target cell. In illustrative embodiments chromatography matrix has a mean pore size of 0 to about 500 nm.

In some embodiments, components present in a sample such as agents (e.g., receptor-binding agents or selection agents) or a competition reagent may have a size that is below the exclusion limit of the pores and thus can enter the pores of the chromatography matrix. In some aspects, of such components that are able to partially or fully enter the pore volume, larger molecules, with less access to the pore volume can elute first, whereas the smallest molecules typically elute last. In some embodiments, the exclusion limit of the chromatography matrix is selected to be below the maximal width of the target cell. Hence, in some aspects, components that have access to the pore volume can remain longer in/on the chromatography matrix than target cell. Thus, in some cases, target cells can be collected in the eluate of a chromatography column separately from other matter/components of a sample. Therefore, in some aspects, components such as an agent (e.g., receptor-binding agent or selection agent), or where applicable a competition reagent, may elute at a later point of time from a gel filtration matrix than the target cell. In some embodiments, this effect can be further increased, such as if the gel permeation matrix contains a reagent (such as covalently bound thereon) that contains binding sites Z that are able to bind agents (e.g., receptor-binding agents or selection agents) and/or a competition reagent present in a sample. In some cases, the agent (e.g., receptor-binding agent or selection agent) and/or the competition reagent can be bound by the binding sites Z of the reagent and thereby immobilized on the matrix. In some aspects, this method is carried out in a removal cartridge.

In some embodiments, a chromatography matrix employed in the present methods may also include magnetically attractable matter such as one or more magnetically attractable particles or a ferrofluid. A respective magnetically attractable particle may comprise a reagent with a binding site that is capable of binding a target cell. In some cases, magnetically attractable particles may contain diamagnetic, ferromagnetic, paramagnetic or superparamagnetic material. In general, superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hutten, A. et al. (J. Biotech. (2004), 112, 47-63). In other embodiments, a chromatography matrix employed in the present methods is void of any magnetically attractable matter.

In some embodiments, provided is an apparatus that contains at least one arrangement of a first and a second stationary phase, such as chromatography column for selection of cells (a selection cartridge) and a second chromatography column (a removal cartridge) for removal of reagents. The apparatus may comprise a plurality of arrangements of first and second stationary phases (chromatography columns) being fluidly connected in series. The apparatus may comprise a sample inlet being fluidly connected to the first stationary phase of the first arrangement of the first and second stationary phases. In some embodiments, the apparatus may also comprise a sample outlet for cells, the sample outlet being fluidly connected to the second stationary phase of the last of the at least one arrangement of a first and second stationary phases for chromatography. In some aspects, the apparatus may also comprise a competition reagent container that is fluidly connected to at least one of the first stationary phases of the arrangements of the first and second stationary phases.

2 Soluble Reagents

In some embodiments, the reagent is not bound to a solid support, i.e. it is present in soluble form or is soluble. In principle, the same reagent can be used as in the case of a reagent that is immobilized on a support, such as a solid support or stationary phase. For example, any of the exemplary of reagents described above can be used without immobilizing or attaching such reagent to a support, e.g. not attaching solid support or stationary phase. In some embodiments, the reagent contains a plurality of binding sites, Z, for reversibly binding to a binding agent via interaction with a binding partner, C. In some cases, the reagent is an oligomer or polymer of individual molecules or an oligomer or polymer of a complex of subunits that make up the individual molecule (e.g. oligomers or polymers of a dimeric, trimeric or tetrameric protein). In some embodiments, the reagent can, for example, be a streptavidin mutein oligomer, a calmodulin oligomer, a compound (oligomer) that provides least two chelating groups K, wherein the at least two chelating groups are capable of binding to a transition metal ion, thereby rendering the reagent capable of binding to an oligohistidine affinity tag, multimeric glutathione-S-transferase, or a biotinylated carrier protein.

In some embodiments, the reagent is characterized by the absence of a solid support (surface) attached to the reagent. For example, in some embodiments, the reagent does not comprise or is not attached (directly or indirectly) to a particle, bead, nanoparticle, microsphere or other solid support. In some embodiments, the reagent is not rigid, inflexible or stiff or does not comprise or is not attached to a rigid, inflexible, or stiff surface. In some embodiments, the reagent is flexible or substantially flexible. In some cases, the reagent is able to adjust or adapt to the form of the surface of the cells. In some embodiments, the reagent does not or does not comprise a shape that is spherical or substantially spherical.

In some embodiments, substantially all, i.e. more than 80%, 85%, 90%, 91%, 92%, 93%, 94%, 95%, 96%, 97%, 98%, 99% or more of the reagent is, is composed of or contains organic material. For example, in some embodiments, more than 80%, 85%, 90%, 91%, 92%, 93%, 94%, 95%, 96%, 97%, 98%, 99% or more of the reagent is, is composed of or contains lipids, carbohydrates, proteins, peptides or mixtures thereof. In some embodiments, the reagent is, is composed of or contains an essential absence of inorganic material, an inorganic core, e.g. metal, e.g. iron, synthetic or inorganic polymers, such as styrene polymers, e.g. polystyrene, latex, silica or magnetic cores. For example, in some embodiments, the relative percentage of inorganic material of the reagent or that is comprised as part of the reagent is less than 20%, 15%, 10%, 5% or less.

In some embodiments, the majority (i.e. more than 50%), such as more than 60%, 70%, 80%, 90%, 95%, 99% or more of the total volume of the reagent in aqueous solution consists of the individual protein molecules that comprise the reagent, such as oligomers or polymers of individual molecules or a complex of subunits that make up an individual molecule (e.g. tetrameric molecule). In some embodiments, the total density of the soluble reagent is less than 1.2 g/cm$^3$, 1.1 g/cm$^3$, 1.0 g/cm$^3$ or less.

In some embodiments, the soluble reagent, e.g. not being attached to a support or solid support (e.g. is not attached to a bead), has a relatively small size, such as generally less than or about less than 20 nM in size, such as less than or about less than 15 nM, less than or about less than 10 nM, less than or about less than 5 nM or smaller.

In some embodiments, the soluble reagent, e.g. not being attached to a support or solid support (e.g. is not attached to a bead), is biologically inert, i.e. it is non-toxic to living cells. In some embodiments, the reagent may be biodegradable, for example, it can be degraded by enzymatic activity or cleared by phagocytic cells.

In some embodiments, it is possible to react the reagent (e.g. a streptavidin or mutein, such as tetrameric streptavidin muteins) to a carrier, such as an organic carrier. In some aspects, in addition to a reaction with a polysaccharide, it is also possible to use physiologically or pharmaceutically acceptable proteins such as serum albumin (for example human serum albumin (HSA) or bovine serum albumin (BSA)) as carrier protein. In such a case, the reagent, such as streptavidin or a streptavidin mutein (either as individual tetramer or also in the form of oligomers), can be coupled to the carrier protein via non-covalent interaction. In some such embodiments, biotinylated BSA (which is commercially available from various suppliers such as ThermoFisher Scientific, Sigma Aldrich or Vectorlabs, to name only a few) can be reacted with the reagent (e.g. streptavidin mutein). In some aspects, some of the reagent oligomers (e.g. streptavidin oligomers) can non-covalently bind via one or more binding sites Z to the biotinylated carrier protein, leaving the majority of the binding sites Z of the oligomer available for binding the agent (e.g., receptor-binding agent or selection agent) and any further agent as described herein. Thus, by such an approach a soluble reagent with a multitude of binding sites Z can be prepared.

In some embodiments, a reagent, such as a streptavidin mutein (either as an individual tetramer or also in the form of an oligomer), can be covalently coupled to a synthetic carrier such as a polyethylene glycol (PEG) molecule. Any suitable PEG molecule can be used for this purpose, for example, and the PEG molecule and the respective reagent can be soluble. Typically, PEG molecules up to a molecular weight of 1000 Da are soluble in water or culture media that may be used in the present methods. In some cases, such PEG based reagent can be prepared using commercially available activated PEG molecules (for example, PEG-NHS derivatives available from NOF North America Corporation, Irvine, California, USA, or activated PEG derivatives available from Creative PEGWorks, Chapel Hills, North Carolina, USA) with amino groups of the streptavidin mutein.

3. Agents

In some embodiments the agent (e.g., receptor-binding agent or selection agent) has one or binding sites, B, for binding to the molecule on the surface of the cell, e.g. cell surface molecule. Thus, in some instances, the agent (e.g., receptor-binding agent or selection agent) contains a binding site B or a plurality of binding sites B, wherein the specific binding between the agent (receptor-binding agent or selection agent) and the molecule on the surface of the target cells contains interaction between B and the molecule. In some embodiments, the agent contains only a single binding site, i.e. is monovalent. In some embodiments the agent (e.g., receptor-binding agent or selection agent) has at least two, such as a plurality of binding sites B including three, four or five binding sites B capable of binding to the cell surface molecule. In some such aspects, the at least two or plurality of binding sites B may be identical. In some embodiments, one or more of the at least two or plurality of binding sites B may be different (e.g. B1 and B2).

In some embodiments, one or more different agents (e.g. one or more different receptor-binding agent, selection agent or other agent that binds to a molecule on a cell) are reversibly bound to the reagent. In some embodiments, the reagent is an oligomeric particle reagent. In some embodiments, at least 2, 3, 4 or more different agents are reversibly bound to the same reagent. In some embodiments, at least two different agents are reversibly bound to the same reagent, whereby each reagent comprises a binding site B or a plurality of binding sites B for specific binding between the agent and the molecule. In some embodiments, the at least two or more agents contain the same binding site B, e.g. for the binding the same or substantially the same molecule. In some embodiments, the at least two or more agents contain different binding sites B, e.g. for the binding to different molecules. In some embodiments, a first agent (e.g. a first receptor-binding agent or a first selection agent) contains a binding site B1, B2, B3, B4, etc. and a second agent (e.g. a second receptor-binding agent or second selection agent) contains another of a binding site B1, B2, B3, B4, etc.. In some embodiments, a first agent (e.g. a first selection agent) contains a binding site B1 and a second agent (e.g. second selection agent) contains a binding site B3. In some embodiments, a first agent (e.g. a first receptor-binding agent) contains a binding site B2 and a second agent (e.g. a second receptor-binding agent) contains a binding site B4. In any of such embodiments, the first agent and second agent can contain a binding partner, C1 or C2. In some embodiments, C1 and C2 can be the same. In some embodiments, C1 and C2 are different. In some embodiments, the first agent and second agent contain the same binding partner, C1.

In some cases, the dissociation constant ($K_d$) of the binding between the agent (e.g., via the binding site B) and the binding site Z of the reagent may have a value in the range from about $10^{-2}$ M to about $10^{-13}$ M or from about $10^{-3}$ M to about $10^{-12}$ M or from about $10^{-4}$ M to about $10^{-11}$M, or from about $10^{-5}$M to about $10^{-10}$M. In some embodiments, the dissociation constant ($K_d$) for the binding between the binding agent and the molecule is of low affinity, for example, in the range of a $K_d$ of about $10^{-3}$ to about $10^{-7}$ M. In some embodiments, the dissociation constant ($K_d$) for the binding between the binding agent and the molecule is of high affinity, for example, in the range of a $K_d$ of about $10^{-7}$ to about $1\times10^{-10}$ M.

In some embodiments, the dissociation of the binding of the agent via the binding site B and the molecule occurs sufficiently fast, for example, to allow the target cell to be only transiently stained or associated with the agent after disruption of the reversible bond between the reagent and the agent. In some cases, when expressed in terms of the $k_{off}$ rate (also called dissociation rate constant for the binding between the agent (via the binding site B) and the molecule, the $k_{off}$ rate is about $0.5\times10^{-4}$ sec$^{-1}$ or greater, about $1\times10^{-4}$ sec$^{-1}$ or greater, about $2\times10^{-4}$ sec$^{-1}$ or greater, about $3\times10^{-4}$ sec$^{-1}$ or greater, about $4\times10^{-4}$ sec$^{-1}$ of greater, about $5\times10^{-4}$ sec$^{-1}$ or greater, about $1\times10^{-3}$ sec$^{-1}$ or greater, about $1.5\times10^{-3}$ sec$^{-1}$ or greater, about $2\times10^{-3}$ sec$^{-1}$ or greater, about $3\times10^{-3}$ sec$^{-1}$ or greater, about $4\times10^{-3}$ sec$^{-1}$, about $5\times10^{-3}$ sec$^{-1}$ or greater, about $1\times10^{-2}$ sec or greater, or about $5\times10^{-1}$ sec$^{-1}$ or greater. It is within the level of a skilled artisan to empirically determine the $k_{off}$ rate range suitable for a particular agent and cell molecule interaction (see e.g. U.S. published application No. US2014/0295458). For example, an agent with a rather high $k_{off}$ rate of, for example, greater than $4.0\times10^{-4}$ sec$^{-1}$ may be used so that, after the disruption of the binding complexes, most of the agent can be removed or dissociated within one hour. In other cases, an agent with a lower $k_{off}$ rate of, for example, $1.0\times10^{-4}$ sec$^{-1}$, may be used, so that after the disruption of the binding complexes, most of the agent may be removed or dissociated from the cell within about 3 and a half hours.

In some embodiments, the $K_d$ of this bond as well as the $K_d$, $k_{off}$ and $k_{on}$ rate of the bond formed between the binding site B of the agent (e.g., receptor-binding agent or selection agent) and the cell surface molecule can be determined by any suitable means, for example, by fluorescence titration, equilibrium dialysis or surface plasmon resonance.

In some aspects, the cell surface molecule is a molecule against which an agent (e.g., receptor-binding agent or selection agent) may be directed. In some embodiments, the cell surface molecule is a peptide or a protein, such as a receptor, e.g., a membrane receptor protein. In some embodiments, the receptor is a lipid, a polysaccharide or a nucleic acid. In some embodiments, a cell surface molecule that is a protein may be a peripheral membrane protein or an integral membrane protein. The cell surface molecule may in some embodiments have one or more domains that span the membrane. As a few illustrative examples, a membrane protein with a transmembrane domain may be a G-protein coupled receptor, such as an odorant receptors, a rhodopsin receptor, a rhodopsin pheromone receptor, a peptide hormone receptor, a taste receptor, a GABA receptor, an opiate receptor, a serotonin receptor, a Ca2+ receptor, melanopsin, a neurotransmitter receptor, such as a ligand gated, a voltage gated or a mechanically gated receptor, including the acetylcholine, the nicotinic, the adrenergic, the norepinephrine, the catecholamines, the L-DOPA-, a dopamine and serotonin (biogenic amine, endorphin/enkephalin) neuropeptide receptor, a receptor kinase such as serine/threonine kinase, a tyrosine kinase, a porin/channel such as a chloride channel, a potassium channel, a sodium channel, an OMP protein, an ABC transporter (ATP-Binding Cassette-Transporter) such as amino acid transporter, the Na-glucose transporter, the Na/iodide transporter, an ion transporter such as Light Harvesting Complex, cytochrome c oxidase, ATPase Na/K, H/K, Ca, a cell adhesion receptor such as metalloprotease, an integrin or a catherin.

In some embodiments, the cell surface molecule may be an antigen defining a desired cell population or subpopulation, for instance a population or subpopulation of blood cells, e.g., lymphocytes (e.g., T cells, T-helper cells, for example, CD4+T-helper cells, B cells or natural killer cells), monocytes, or stem cells, e.g. CD34-positive peripheral stem cells or Nanog or Oct-4 expressing stem cells. Examples of T-cells include cells such as CMV-specific CD8+T-lymphocytes, cytotoxic T-cells, memory T-cells and regulatory T-cells (Treg). An illustrative example of Treg is CD4 CD25 CD45RA Treg cells and an illustrative example of memory T-cells is CD62L CD8+ specific central memory T-cells. The cell surface molecule may also be a marker for a tumor cell.

As described above, in some embodiments, the agent (e.g., receptor-binding agent or selection agent) has, in addition to the binding site B that is able to bind the cell surface molecule, a binding partner C. In some aspects, this binding partner C is able to bind to a binding site Z of the reagent wherein the reagent has one or more binding sites for the binding partner C. In some embodiments, the non-covalent bond that may be formed between the binding partner C that is included in the agent (e.g., receptor-binding agent or selection agent) and the binding site(s) Z of the reagent may be of any desired strength and affinity, and may be disruptable or reversible under conditions under which the method is performed. The agent (e.g., receptor-binding agent or selection agent) may include at least one, including two, three or more, additional binding partners C and the reagent may include at least two, such as three, four, five, six, seven, eight or more binding sites Z for the binding partner C that is included in the agent (e.g., receptor-binding agent or selection agent). As described in U.S. Pat. Nos. 7,776,562, 8,298,782 or International Patent application WO 2002/054065, any combination of a binding partner C and a reagent with one or more corresponding binding sites Z can be chosen, for example, such that the binding partner C and the binding site Z are able to reversibly bind in a complex, such as to cause an avidity effect.

The binding partner C included in the agent (e.g., receptor-binding agent or selection agent) may for instance be hydrocarbon-based (including polymeric) and include nitrogen-, phosphorus-, sulphur-, carben-, halogen- or pseudohalogen groups. In some aspects, it may be an alcohol, an organic acid, an inorganic acid, an amine, a phosphine, a thiol, a disulfide, an alkane, an amino acid, a peptide, an oligopeptide, a polypeptide, a protein, a nucleic acid, a lipid, a saccharide, an oligosaccharide, or a polysaccharide. As further examples, it may also be a cation, an anion, a polycation, a polyanion, a polycation, an electrolyte, a polyelectrolyte, a carbon nanotube or carbon nanofoam. Generally, such a binding partner C has a higher affinity to the binding site of the reagent than to other matter. Examples of a respective binding partner C include, but are not limited to, a crown ether, an immunoglobulin, a fragment thereof and a proteinaceous binding molecule with antibody-like functions.

In some embodiments, the binding partner C that is included in the agent (e.g., receptor-binding agent or selection agent) includes biotin and the reagent includes a streptavidin analog or an avidin analog that reversibly binds to biotin. In some embodiments the binding partner C that is included in the agent (e.g., receptor-binding agent or selection agent) includes a biotin analog that reversibly binds to streptavidin or avidin, and the reagent includes streptavidin, avidin, a streptavidin analog or an avidin analog that reversibly binds to the respective biotin analog. In some embodiments, the binding partner C that is included in the agent (e.g., receptor-binding agent or selection agent) includes a streptavidin or avidin binding peptide and the reagent includes streptavidin, avidin, a streptavidin analog or an avidin analog that reversibly binds to the respective streptavidin or avidin binding peptide.

In some embodiments, the reagent is a streptavidin, such as a streptavidin mutein including any described above (e.g. set forth in SEQ ID NOS: 3-6 or 60-61), and the binding partner C that is included in the agent (e.g. receptor-binding agent or selection agent) may include a streptavidin-binding peptide. In some embodiments, the streptavidin-binding peptide may include a sequence with the general formula set forth in SEQ ID NO: 9, such as contains the sequence set forth in SEQ ID NO: 10. In some embodiments, the peptide sequence has the general formula set forth in SEQ ID NO: 11, such as set forth in SEQ ID NO: 12. In one example, the peptide sequence is Trp-Arg-His-Pro-Gln-Phe-Gly-Gly (also called Strep-tag®, set forth in SEQ ID NO: 7). In one example, the peptide sequence is Trp-Ser-His-Pro-Gln-Phe-Glu-Lys (also called Strep-tag® II, set forth in SEQ ID NO: 8). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa (SEQ ID NO: 9), where Xaa is glutamine, asparagine, or methionine, and wherein the other binding module has the same or different streptavidin peptide ligand, such as set forth in SEQ ID NO: 11 (see e.g. International Published PCT Appl. No. WO02/077018; U.S. Pat. No. 7,981,632). In some embodiments, the peptide ligand contains a sequence having the formula set forth in any of SEQ ID NO: 13 or 14. In some embodiments, the peptide ligand has the sequence of amino acids set forth in any of SEQ ID NOS: 15-19.

In some embodiment the binding partner C of the agent (e.g., receptor-binding agent or selection agent) includes a moiety known to the skilled artisan as an affinity tag. In such an embodiment, the reagent may include a corresponding binding partner, for example, an antibody or an antibody fragment, known to bind to the affinity tag. As a few illustrative examples of known affinity tags, the binding partner C that is included in the agent (e.g., receptor-binding agent or selection agent) may include dinitrophenol or digoxigenin, oligohistidine, polyhistidine, an immunoglobulin domain, maltose-binding protein, glutathione-S-transferase (GST), chitin binding protein (CBP) or thioredoxin, calmodulin binding peptide (CBP), FLAG'-peptide, the HA-tag (sequence: Tyr-Pro-Tyr-Asp-Val-Pro-Asp-Tyr-Ala) (SEQ ID NO: 20), the VSV-G-tag (sequence: Tyr-Thr-Asp-Ile-Glu-Met-Asn-Arg-Leu-Gly-Lys) (SEQ ID NO: 21), the HSV-tag (sequence: Gln-Pro-Glu-Leu-Ala-Pro-Glu-Asp-Pro-Glu-Asp) (SEQ ID NO: 22), the T7 epitope (Ala-Ser-Met-Thr-Gly-Gly-Gln-Gln-Met-Gly) (SEQ ID NO: 22), maltose binding protein (MBP), the HSV epitope of the sequence Gln-Pro-Glu-Leu-Ala-Pro-Glu-Asp-Pro-Glu-Asp (SEQ ID NO: 24) of herpes simplex virus glycoprotein D, the "myc" epitope of the transcription factor c-myc of the sequence Glu-Gln-Lys-Leu-Ile-Ser-Glu-Glu-Asp-Leu (SEQ ID NO: 25), the V5-tag (sequence: Gly-Lys-Pro-Ile-Pro-Asn-Pro-Leu-Leu-Gly-Leu-Asp-Ser-Thr) (SEQ ID NO: 26), or glutathione-S-transferase (GST). In such embodiments, the complex formed between the one or more binding sites Z of the reagent which may be an antibody or antibody fragment, and the antigen can be disrupted competitively by adding the free antigen, i.e. the free peptide (epitope tag) or the free protein (such as MBP or CBP). In some embodiments, the affinity tag might also be an oligonucleotide tag. In some cases, such an oligonucleotide tag may, for instance, be used to hybridize to an oligonucleotide with a complementary sequence, linked to or included in the reagent.

Further examples of a suitable binding partner C include, but are not limited to, a lectin, protein A, protein G, a metal, a metal ion, nitrilo triacetic acid derivatives (NTA), RGD-motifs, a dextrane, polyethyleneimine (PEI), a redox polymer, a glycoproteins, an aptamers, a dye, amylose, maltose, cellulose, chitin, glutathione, calmodulin, gelatine, polymyxin, heparin, NAD, NADP, lysine, arginine, benzamidine, poly U, or oligo-dT. Lectins such as Concavalin A are known to bind to polysaccharides and glycosylated proteins. An illustrative example of a dye is a triazine dye such as Cibacron blue F3G-A (CB) or Red HE-3B, which specifically bind NADH-dependent enzymes. Typically, Green A binds to Co A proteins, human serum albumin, and dehydrogenases. In some cases, the dyes 7-aminoactinomycin D and 4',6-diamidino-2-phenylindole bind to DNA. Generally, cations of metals such as Ni, Cd, Zn, Co, or Cu, are typically used to bind affinity tags such as an oligohistidine containing sequence, including the hexahistidine or the His-Asn-His-Arg-His-Lys-His-Gly-Gly-Gly-Cys tag (MAT tag) (SEQ ID NO: 35), and N-methacryloyl-(L)-cysteine methyl ester.

In some embodiments the binding between the binding partner C that is included in the agent (e.g., receptor-binding agent or selection agent) and the one or more binding sites Z of the reagent occurs in the presence of a divalent, a trivalent or a tetravalent cation. In this regard, in some embodiments the reagent includes a divalent, a trivalent or a tetravalent cation, typically held, e.g. complexed, by means of a suitable chelator. In some embodiments, the binding partner C that is included in the agent (e.g., receptor-binding agent or selection agent) may include a moiety that includes, e.g. complexes, a divalent, a trivalent or a tetravalent cation. Examples of a respective metal chelator, include, but are not limited to, ethylenediamine, ethylene-diaminetetraacetic acid (EDTA), ethylene glycol tetraacetic acid (EGTA), diethylenetri-aminepentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimer-capto-1-propanol (dimercaprol), porphine and heme. As an example, EDTA forms a complex with most monovalent, divalent, trivalent and tetravalent metal ions, such as e.g. silver ($Ag^*$), calcium ($Ca^{2+}$), manganese ($Mn^{2+}$), copper ($Cu^{2+}$), iron ($Fe^{2+}$), cobalt ($Co^+$) and zirconium ($Zr^{4+}$), while BAPTA is specific for $Ca^{2+}$. As an illustrative example, a standard method used in the art is the formation of a complex between an oligohistidine tag and copper ($Cu^{2+}$), nickel ($Ni^{2+}$), cobalt ($Co^{2+}$), or zinc ($Zn^{2+}$) ions, which are presented by means of the chelator nitrilotriacetic acid (NTA).

In some embodiments, the binding partner C that is included in the agent (e.g., receptor-binding agent or selection agent) includes a calmodulin binding peptide and the reagent includes multimeric calmodulin as described in U.S. Pat. No. 5,985,658, for example. In some embodiments, the binding partner C that is included in the agent (e.g., receptor-binding agent or selection agent) includes a FLAG peptide and the reagent includes an antibody that binds to the FLAG peptide, e.g. the FLAG peptide, which binds to the monoclonal antibody 4E11 as described in U.S. Pat. No. 4,851,341. In one embodiment, the binding partner C that is included in the agent (e.g., receptor-binding agent or selection agent) includes an oligohistidine tag and the reagent includes an antibody or a transition metal ion binding the oligohistidine tag. In some cases, the disruption of all these binding complexes may be accomplished by metal ion chelation, e.g. calcium chelation, for instance by adding EDTA or EGTA. In some embodiments, calmodulin, antibodies such as 4E11 or chelated metal ions or free chelators may be multimerized by conventional methods, e.g. by biotinylation and complexation with streptavidin or avidin or oligomers thereof or by the introduction of carboxyl residues into a polysaccharide, e.g. dextran, essentially as described in Noguchi, A, et al. Bioconjugate Chemistry (1992) 3, 132-137 in a first step and linking calmodulin or antibodies or chelated metal ions or free chelators via primary amino groups to the carboxyl groups in the polysaccharide, e.g. dextran, backbone using conventional carbodiimide chemistry in a second step. In some such embodiments, the binding between the binding partner C that is included in the agent (e.g., receptor-binding agent or selection agent) and the one or more binding sites Z of the reagent can be disrupted by metal ion chelation. The metal chelation may, for example, be accomplished by addition of EGTA or EDTA.

In some embodiments, the agent (e.g., receptor-binding agent or selection agent), which specifically bind to the cell surface molecule, may for instance be comprised by an antibody, a fragment thereof, or a proteinaceous binding molecule with antibody-like functions. In some embodiments, the binding site B of the agent is an antibody combining site, such as is or contains one or more complementarity determining regions (CDRs) of an antibody. Examples of (recombinant) antibody fragments include, but are not limited to, Fab fragments, Fv fragments, single-chain Fv fragments (scFv), a divalent antibody fragment such as an (Fab)2'-fragment, diabodies, triabodies (Iliades, P., et al, FEB S Lett (1997) 409, 437-441), decabodies (Stone, E., et al, Journal of Immunological Methods (2007) 318, 88-94) and other domain antibodies (Holt, L. J., et al, Trends Biotechnol. (2003), 21, 11, 484-490), single domain antibodies (nanobodies®). In some embodiments, the agent (e.g., receptor-binding agent or selection agent) may comprise a bivalent proteinaceous artificial binding molecule such as a dimeric lipocalin mutein that is also known as "duocalin".

In some embodiments, the agent (e.g., receptor-binding agent or selection agent) may have a single binding site B, i.e., it may be monovalent. Examples of monovalent agents (e.g., receptor-binding agents or selection agents) include, but are not limited to, a monovalent antibody fragment, a proteinaceous binding molecule with antibody-like binding properties or an MHC molecule. Examples of monovalent antibody fragments include, but are not limited to a Fab fragment, an Fv fragment, single domain antibodies, e.g., camelid derived nanobodies® and a single-chain Fv fragment (scFv), including a divalent single-chain Fv fragment.

In some embodiments, the agent is an antibody or an antigen-binding fragment thereof, such as a Fab fragments, Fv fragments, single-chain Fv fragments (scFv), single domain antibodies, e.g., camelid derived nanobodies®, a divalent antibody fragment such as an (Fab)2'-fragment. In some embodiments, the agent is or is derived from a parental antibody that is known to bind to a cell molecule of interest. Various antibody molecules or fragments thereof against cell surface molecules are well known in the art and any of a variety of such can be used as agents in the methods herein. In some embodiments, the agent is an antibody or fragment thereof that contains one or more amino acid replacements in the variable heavy chain of a parental or reference antibody, for example, to generate an antibody with an altered affinity or that exhibits a sufficiently fast off-rate as described above. For example, exemplary of such mutations are known the context of mutants of the anti-CD4 antibody 13B8.2 (see e.g., U.S. Pat. Nos. 7,482,000, U.S. Patent Appl. No. US2014/0295458 or International Patent Application No. WO2013/124474), and any of such mutations can be generated in another parental or reference antibody.

In some aspects, the agent (e.g., receptor-binding agent or selection agent) that can be monovalent, for example comprise a monovalent antibody fragment or a monovalent artificial binding molecule (proteinaceous or other) such as a mutein based on a polypeptide of the lipocalin family (also known as "Anticalin®), or a bivalent molecule such as an antibody or a fragment in which both binding sites are retained such as an F(ab')$_2$ fragment.

An example of a proteinaceous binding molecule with antibody-like functions includes a mutein based on a polypeptide of the lipocalin family (see for example, WO 03/029462, Beste et al, Proc. Natl. Acad. Sci. U.S.A. (1999) 96, 1898-1903). Generally, lipocalins, such as the bilin binding protein, the human neutrophil gelatinase-associated lipocalin, human Apo lipoprotein D or human tear lipocalin possess natural ligand-binding sites that can be modified so that they bind a given target. Further examples of a proteinaceous binding molecule with antibody-like binding properties that can be used as agent (e.g., receptor-binding agent or selection agent) that specifically binds to the cell surface molecule include, but are not limited to, the so-called glubodies (see e.g. international patent application WO 96/23879), proteins based on the ankyrin scaffold (Mosavi, L. K., et al, Protein Science (2004) 13, 6, 1435-1448) or crystalline scaffold (e.g. international patent application WO 01/04144) the proteins described in Skerra, J. Mol. Recognit. (2000) 13, 167-187, AdNectins, tetranectins and avimers. Generally, avimers, including multivalent avimer proteins evolved by exon shuffling of a family of human receptor domains, contain so called A-domains that occur as strings of multiple domains in several cell surface receptors (Silverman, J., et al, Nature Biotechnology (2005) 23, 1556-1561). Adnectins, generally derived from a domain of human fibronectin, typically contain three loops that can be engineered for immunoglobulin-like binding to targets (Gill, D. S. & Damle, N. K., Current Opinion in Biotechnology (2006) 17, 653-658). Tetranectins, generally derived from the respective human homotrimeric protein, likewise typically contain loop regions in a C-type lectin domain that can be engineered for desired binding. Peptoids, which can, in some cases, act as protein ligands, typically are oligo (N-alkyl) glycines that differ from peptides in that the side chain is connected to the amide nitrogen rather than the carbon atom. Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509).

Further examples of suitable proteinaceous binding molecules include, but are not limited to, an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill et al. Protein Eng (1997) 10, 949-57, a so called "minibody" (Martin et al, EMBO J (1994) 13, 5303-5309), a diabody (Holliger et al, PNAS USA (1993)90, 6444-6448), a so called "Janusis" (Traunecker et al, EMBO J (1991) 10, 3655-3659, or Traunecker et al, Int J Cancer (1992) Suppl 7, 51-52), a nanobody, a microbody, an affilin, an affibody, a knottin, ubiquitin, a zinc-finger protein, an autofluorescent protein, DARPins or a leucine-rich repeat protein. In some embodiments, a nucleic acid molecule with antibody-like functions can be an aptamer. Generally, an aptamer folds into a defined three-dimensional motif and shows high affinity for a given target structure.

In certain embodiments, one or more agents, e.g., agents containing a binding partner such as a binding partner C, are attached, connected, and/or bound to an oligomeric particle reagent. In particular embodiments, the one or more agents are reversibly attached, connected, and/or bound to the oligomeric particle reagent. In some embodiments, the one or more agents are attached, connected, and/or bound, e.g., reversibly bound, to the oligomeric particle reagents by contacting, treating, and/or incubating the one or more agents with the oligomeric particle reagents. In certain embodiments, the treatment, contact, and/or incubation is performed with mixing, and/or rocking, e.g., gentile rocking and/or mixing.

In certain embodiments, the one or more agents are incubated, treated, and/or contacted with the oligomeric particle reagents for, for about, or for at least 1 minute, 5 minutes, 10 minutes, 15 minutes, 30 minutes, 45 minutes, 60 minutes, 90 minutes, 120 minutes, 4 hours, 6 hours, 8 hours, 12 hours, 16 hours, or 24 hours. In some embodiments, the one or more agents are incubated, treated, and/or contacted with the oligomeric particle reagents for between 1 minute and 12 hours, between 1 minute and 1 hour, between 1 minute and 30 minutes, between 10 minutes and 60 minutes, between 10 minutes and 20 minutes, between 1 hour and 3 hours, between 1 hour and 2 hours, or between 6 hours and 12 hours. In certain embodiments, the one or more agents are incubated, treated, and/or contacted with the oligomeric particle reagents for between 5 minutes and 30 minutes, or for or for about 15 minutes.

In particular embodiments, the one or more agents are incubated, treated, and/or contacted with the oligomeric particle reagents at a temperature of, of about, or of at least 4° C., 8° C., 12° C., 16° C., 20° C., 24° C., 28° C., 32° C., 37° C., 39° C., 50° C., 60° C., 70° C., 80° C., 90° C., or 100° C. In some embodiments, the one or more agents are incubated, treated, and/or contacted with the oligomeric particle reagents at a temperature of between 4° C. and 39° C., between 10° C. and 37° C., between 10° C. and 25° C., between 20° C. and 30° C., between 24° C. and 39° C., or between 40° C. and 100° C. In particular embodiments, the one or more agents are incubated, treated, and/or contacted with the oligomeric particle reagents at room temperature. In certain embodiments, the one or more agents are incubated, treated, and/or contacted with the oligomeric particle reagents at or at about 23° C., 24° C., 25° C., or 26° C.±2° C., ±1° C., ±0.5° C., ±0.2° C., ±0.1° C., ±0.05° C., or ±0.01° C.

In certain embodiments, the one or more agents are incubated, treated, and/or contacted with the oligomeric particle reagents in an amount of, of about, or of at least 0.1 µg, 0.2 µg, 0.3 µg, 0.4 µg, 0.5 µg, 0.6 µg, 0.7 µg, 0.8 µg, 0.9 µg, 1.0 µg, 1.2 µg, 1.4 µg, 1.6 µg, 1.8 µg, 2.0 µg, 2.2 µg, 2.4 µg, 2.6 µg, 2.8 µg, or 3.0 µg agents per 0.5 µg, 1.0 µg, 1.5 µg, 2.0 µg, 2.5 µg, 3.0 µg, 4.0 µg, 5.0 µg, 6 µg, 7 µg, 8 µg, 9 µg or 10 µg of oligomeric particle reagent. In particular embodiments, the one or more agents are incubated, treated, and/or contacted with the oligomeric particle reagents in an amount of or of about 1.0 µg, agents per 2 µg, 3 µg, 4 µg, or 5 µg, of oligomeric particle reagent.

In some embodiments, one or more agents, e.g., agents containing a binding partner such as a binding partner C, are attached, connected, and/or bound to an oligomeric particle reagent by incubating, treating, and or contacting the oligomeric particle reagents with the one or more agents. In some embodiments, the one or more agents are incubated, treated, and/or contacted with the oligomeric particle reagents in an amount of or of about 1.0 µg agents per 2 µg, 3 µg, 4 µg, or 5 µg, of oligomeric particle reagent for between 1 minute and 1 hour at a temperature of between 4° C. and 39° C., between 10° C. and 25° C., or between 20° C. and 30° C. In particular embodiments, the one or more agents are incubated, treated, and/or contacted with the oligomeric particle reagents in an amount of or of about 1.0 µg agents per 3 µg of oligomeric particle reagent for between 5 minutes and 30 minutes at a temperature between 10° C. and 25° C. In certain embodiments, the one or more agents are agents described herein, e.g., in Section II-C-3. In some embodiments, the agent is an anti-CD3 and/or an anti-CD28 antibody or antigen binding fragment thereof, such as an antibody or antigen fragment thereof that contains a binding partner, e.g., a streptag. In particular embodiments, the one or more agents is an anti-CD3 and/or an anti CD28 Fab containing a binding partner, e.g., a streptavidin binding peptide, such as Strep-tagII.

a. Receptor-Binding Agents

In some embodiments, the agent is a receptor-binding agent. In some embodiments, the receptor-binding agent binds to a molecule (e.g. receptor) on the surface of a cell, which binding between the agent and the molecule is capable of inducing or modulating a signal in the cells. In some instances, the cell surface molecule (e.g. receptor) is a signaling molecule. In some such cases, the receptor-binding agent is capable of specifically binding to a signaling molecule expressed by one or more of the cells. In some instances, the receptor-binding agent is a stimulatory agent, which can be any agent that is capable of inducing a signal in a cell (e.g. a T cell) upon binding to a cell surface molecule, such as a receptor. In some embodiments, the signal can be immunostimulatory, in which case the receptor-binding agent or stimulatory agent is capable of inducing or modulating a signal that is involved in or that does stimulate an immune response by the cell (e.g. T cell), e.g. increase immune cell proliferation or expansion, immune cell activation, immune cell differentiation, cytokine secretion, cytotoxic activity or one or more other functional activities of an immune cell. In some embodiment, the signal can be inhibitory, in which case the receptor-binding agent or stimulatory agent is capable of inducing or modulating a signal in the cell (e.g. T cell) that is involved in or that does inhibit an immune response, e.g. inhibits or decreases immune cell proliferation or expansion, immune cell activation, immune cell differentiation, cytokine secretion, cytotoxic activity or one or more other functional activities of an immune cell.

In some embodiments, the receptor-binding agent, e.g., stimulatory agent is a first receptor-binding agent, e.g., first stimulatory agent. In some aspects, the first receptor-binding agent, e.g., first stimulatory agent, binds to a receptor molecule on the surface of the cells. Thus, in some cases, the first receptor-binding agent, e.g., first stimulatory agent, induces or modulates a signal. In some aspects, the inducing or modulating of a signal by the first receptor-binding agent, e.g., first stimulatory agent, effects the activation, stimulation, and/or expansion (proliferation) of the cells. Thus, in some cases, the first receptor-binding agent, e.g., first stimulatory agent, provides a primary activation signal to the cells, thereby activating the cells.

In some embodiments the cell population may be a population of lymphocytes including, but not limited a population of B cells, a population of T cells or a population of natural killer cells. Illustrative examples of cell populations are B cells carrying CD40 or CD137 (both cell population can be proliferated upon binding of only a first agent that provides an activation signal, for example 4-1BB ligand; or an αCD40 antibody molecule or an αCD137 antibody molecule (see for example Zhang et al., 2010, J Immunol, 184:787-795)). Other illustrative examples for agents (either first or second) that may be used for the expansion of B cells are agents that bind to IgG, CD19, CD28 or CD14, for example αCD19, αIgG, αCD28, or αCD14 antibody molecules. It is also envisioned that first or second agents for the expansion of B cell may comprise ligands for toll like receptors or interleukins, such as IL-21 (see for example Dienz O, et al. 2009. J. Exp. Med. 206:69). It is noted that lipopolysaccharide dependent activation of B cells is also encompassed in the present invention, as a lipopolysaccharide can also be used as first agent and can be equipped with a binding partner C1 as used herein.

Other illustrative examples of suitable cell populations include T cell population that expand after being activated by binding of a first agent to TCR/CD3 and binding of a second agent to an accessory molecule on the T cell such as CD28. In this case, the first agent stimulates a TCR/CD3 complex-associated signal in the T cells and the second agent provides a secondary stimulus by binding CD28 as accessory molecule. Agents that can be used for the expansion of T cells may also include interleukins, such as IL-2, IL-7, IL-15, or IL-21 (see for example Cornish et al. 2006, Blood. 108(2):600-8, Bazdar and Sieg, 2007, Journal of Virology, 2007, 81(22):12670-12674, Battalia et al, 2013, Immunology, 139(1):109-120). Other illustrative examples for agents that may be used for the expansion of T cells are agents that bind to CD8, CD45 or CD90, such as αCD8, αCD45 or αCD90 antibodies. Illustrative examples of T cell population including antigen-specific T cells, T helper cells, cytotoxic T cells, memory T cell (an illustrative example of memory T-cells are CD62L*CD8+ specific central memory T cells) or regulatory T cells (an illustrative example of Treg are CD4+CD25+CD45RA+ Treg cells).

Another illustrative example of a suitable cell population includes natural killer cells (NK cells), which may for example be expanded with agents that bind to CD16 or CD56, such as for example αCD16 or αCD56 antibodies. In illustrative example for such an αCD16 antibody is the antibody 3G8 with a VH sequence set forth in SEQ ID NO: 52 and a VL sequence set forth in SEQ ID NO: 53 (see for example Hoshino et al, Blood. 1991 Dec. 15; 78(12):3232-40.). Another agent that may be used for expansion of NK cells may be IL-15 (see for example Vitale et al. 2002. The Anatomical Record. 266:87-92). Yet another illustrative example of a suitable cell population includes monocytes, which may for instance be expanded using an agent that binds to CD14, such as an αCD14 antibody molecule.

In some aspects, the receptor-binding agent, e.g., stimulatory agent, specifically targets a molecule expressed on the surface of the target cells in which the molecule is a TCR or a chimeric antigen receptor. For example, the molecule expressed on the surface of the target cell is selected from a T cell or B cell antigen receptor complex, a CD3 chain, a CD3 zeta, an antigen-binding portion of a T cell receptor or a B cell receptor, or a chimeric antigen receptor. In some cases, the receptor binding agent targets peptide:MHC class I complexes. In some aspects, the receptor-binding agent, e.g., stimulatory agent, specifically binds to the antibody portion of the recombinant receptor, e.g., CAR. In some cases, the antibody portion of the recombinant receptor includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some cases, the reagent is loaded with αIgG that recognizes the IgG4 spacer.

In some embodiments, the first receptor-binding agent, e.g., first stimulatory agent, may stimulate a TCR/CD3 complex-associated signal in the cells, e.g., T cells. In some aspects, the first receptor-binding agent, e.g., first stimulatory agent, may be a binding agent that specifically binds CD3. In some cases, a first receptor-binding agent, e.g., first stimulatory agent, that specifically binds CD3 may be selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties. The divalent antibody fragment may be a (Fab)₂'-fragment, or a divalent single-chain Fv fragment while the monovalent antibody fragment may be selected from the group consisting of a Fab fragment, an Fv fragment, a nanobody (sdAntibody) and a single-chain Fv fragment (scFv). In some cases, a proteinaceous CD3 binding molecule with antibody-like binding properties may be an aptamer, a mutein based on a polypeptide of the lipocalin family, a glubody, a protein based on the ankyrin scaffold, a protein based on the crystalline scaffold, an adnectin, DARPin, or an avimer.

In some embodiments, an anti-CD3 Fab fragment can be derived from the CD3 binding monoclonal antibody produced by the hybridoma cell line OKT3 (ATCC® CRL-8001™; see also U.S. Pat. No. 4,361,549). The variable domain of the heavy chain and the variable domain of the light chain of the anti-CD3 antibody OKT3 are described in Arakawa et al J. Biochem. 120, 657-662 (1996) and comprise the amino acid sequences set forth in SEQ ID NO: 31 and 32, respectively.

In some aspects, the receptor-binding agent, e.g., stimulatory agent, is a second receptor-binding agent, e.g., second stimulatory agent. In some cases, the second receptor-binding agent, e.g., second stimulatory agent, binds to a molecule on the surface of the cells, such as a cell surface molecule, e.g., receptor molecule. In some embodiments, the second receptor-binding agent, e.g., second stimulatory agent, is capable of enhancing, dampening, or modifying a signal delivered through the first molecule. In some embodiments, the second receptor-binding agent, e.g., second stimulatory agent, induces or modulates a signal, e.g., a second or an additional signal. In some aspects, the second receptor-binding agent, e.g., second stimulatory agent, may enhance or potentiate a signal induced by the first receptor-binding agent, e.g., first stimulatory agent,. In some embodiments, the second receptor-binding agent, e.g., second stimulatory agent, binds to an accessory molecule and/or can stimulate or induce an accessory or secondary signal in the cell. In some aspects, the second receptor-binding agent, e.g., second stimulatory agent, binds to a co-stimulatory molecule and/or provides a costimulatory signal.

In some embodiments, the receptor-binding agent, e.g., stimulatory agent, which can be the second receptor-binding agent, e.g., second stimulatory agent, binds, e.g. specifically binds, to a second molecule that can be a costimulatory molecule, an accessory molecule, a cytokine receptor, a chemokine receptor, an immune checkpoint molecule, or a member of the TNF family or the TNF receptor family.

In some embodiments, the molecule on the cell, e.g., T cell, may be CD28 and the receptor-binding agent, e.g., stimulatory agent (e.g. which can be the second receptor-binding agent, e.g., second stimulatory agent,) specifically binds CD28. In some aspects, the receptor-binding agent, e.g., stimulatory agent (e.g. which can be the second receptor-binding agent, e.g., second stimulatory agent,) that specifically binds CD28 may be selected from the group consisting of an anti-CD28-antibody, a divalent antibody fragment of an anti-CD28 antibody, a monovalent antibody fragment of an anti-CD28-antibody, and a proteinaceous CD28 binding molecule with antibody-like binding properties. The divalent antibody fragment may be an (Fab)2'-fragment, or a divalent single-chain Fv fragment while the monovalent antibody fragment may be selected from the group consisting of a Fab fragment, an Fv fragment, and a single-chain Fv fragment (scFv). A proteinaceous CD28 binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer. In some cases, the receptor-binding agent, e.g., the first, second and/or additional receptor-binding agent, e.g., stimulatory agent that specifically binds receptor is an antibody or an antigen-binding fragment thereof, e.g., a Fab fragment.

In some embodiments, the receptor-binding agent, e.g., stimulatory agent, may be a ligand that binds, e.g., specifically binds, to the receptor, e.g., a cell surface molecule that stimulates or activates a T cell activation signal 2, e.g., co-stimulatory signal, upon binding of the agent. In some embodiments, the receptor-binding agent, e.g., the first, second and/or additional receptor-binding agent, is an endogenous ligand, a cognate ligand, a synthetic ligand and/or a portion, a variant or modified forms thereof. In some embodiments, the receptor-binding agent, e.g. stimulatory agent, can be an extracellular domain or a portion thereof, of an endogenous ligand and/or a cognate ligand.

In some embodiments, the receptor-binding agent, e.g., stimulatory agent is capable of binding to any one or more of CD28, CD5, CD4, CD8, MHCI, MHCII, CTLA-4, ICOS, PD-1, OX40, CD27L (CD70), 4-1BBL, CD30L and LIGHT. In some embodiments, the receptor-binding agent, e.g. stimulatory agent, can be an antibody, divalent antibody (e.g. a F(ab')₂-fragment or a divalent single-chain Fv fragment), monovalent antibody (e.g. a Fab fragment, an Fv fragment, or a single-chain Fv fragment (scFv)) or ligand to any one or more of CD28, CD5, CD4, CD8, MHCI, MHCII, CTLA-4, ICOS, PD-1, OX40, CD27L (CD70), 4-1BBL, CD30L and LIGHT, in which such agent is capable of inducing or modeling a signal in the cells upon binding of the receptor-binding agent, e.g., stimulatory agent to the molecule.

In some embodiments, the receptor-binding agent, e.g. stimulatory agent, can be a ligand to any one or more of CD28, CD5, CD4, CD8, MHCI, MHCII, CTLA-4, ICOS, PD-1, OX40, CD27L (CD70), 4-1BBL, CD30L and LIGHT, in which such agent is capable of inducing or modeling a signal in the cells upon binding of the receptor-binding agent, e.g., stimulatory agent to the molecule. In some embodiments, the receptor-binding agent, e.g. stimulatory agent, can be an extracellular domain or a portion thereof, of an endogenous ligand and/or a cognate ligand. For example, in some embodiments, the receptor-binding agent is or contains the extracellular domain or a portion thereof, of B7-1 (CD80), B7-2 (CD86), ICOS-L, PD-L1, OX40L, CD27, 4-1BB (CD137) and/or CD30.

In some embodiments, the receptor-binding agent, e.g., stimulatory agent, is capable of specifically binding to a molecule on the surface of the target cells other than CD28, CD3, CD137 or CD40. In some cases, the binding of the receptor-binding agent, e.g., stimulatory agent, to the molecule on the surface of the target cells other than CD28, CD3, CD137 or CD40 induces or modulates a signal in the target cells and/or alters a function of the target cells, thereby generating cultured target cells.

In some embodiments, the receptor-binding agent, e.g., stimulatory agent is capable of binding to any one or more of a member of the TNF family or the TNF receptor family, e.g., a member of the TNF receptor superfamily, and/or a Wnt receptor or co-receptor, e.g., the Frizzled (Fz) family of receptors.

In some embodiments, the molecule on the cell is a member of the TNF receptor superfamily, such as Tumor necrosis factor receptor 1 (CD120a), Tumor necrosis factor receptor 2 (CD120b), Lymphotoxin beta receptor (CD18), OX40 (CD134), CD40 (Bp50), Fas receptor (Apo-1, CD95), Decoy receptor 3 (TR6, M68), CD27 (S152, Tp55), CD30 (Ki-1), 4-1BB (CD137), Death receptor 4 (TRAILR1, Apo-2, CD261), Death receptor 5 (TRAILR2, CD262), Decoy receptor 1 (TRAILR3, LIT, TRID, CD263), Decoy receptor 2 (TRAILR4, TRUNDD, CD264), RANK (CD265), Osteoprotegerin (OCIF, TR1), TWEAK receptor (Fn14, CD266), TACI (IGAD2, CD267), BAFF receptor (CD268), Herpesvirus entry mediator (ATAR, TR2, CD270), Nerve growth factor receptor (p75NTR, CD271), B-cell maturation antigen (TNFRSF13A, CD269), Glucocorticoid-induced TNFR-related(AITR, CD357), TROY (TAJ, TRADE), Death receptor 6 (CD358), Death receptor 3 (Apo-3, TRAMP, LARD, WS-1) or Ectodysplasin A2 receptor (XEDAR).

In some cases, the receptor-binding agent that specifically binds the TNF receptor superfamily protein is an antibody or an antigen-binding fragment thereof, e.g., a Fab fragment. In some embodiments, the receptor-binding agent that specifically binds the TNF receptor superfamily protein may be a ligand that binds, e.g., specifically binds, to the receptor, and/or an extracellular domain or a portion thereof. In some embodiments, the ligand is or includes TNFα, Lymphotoxin beta (TNF-C), OX40L, CD154, FasL, FasL, LIGHT, TL1A, CD70, Siva, CD153, 4-1BB ligand, TRAIL, RANKL, TWEAK, APRIL, BAFF, CAMLG, BAFF, LIGHT, NGF, BDNF, NT-3, NT-4, BAFF, GITR ligand, TL1A or EDA-A2, or an extracellular domain or a portion thereof of any of the transmembrane proteins.

In some embodiments, the molecule on the cell is a Wnt receptor or co-receptor, receptors, such a Frizzled (Fz) family receptor, a lipoprotein receptor-related protein (LRP)-5/6, receptor tyrosine kinase (RTK), and receptor-related orphan receptor 2 (ROR2). In some embodiments, the molecule on the cell is, e.g., Frizzled-1 (FZD1), Frizzled-2 (FZD2), Frizzled-3 (FZD3), Frizzled-4 (FZD4), Frizzled-5 (FZD5), Frizzled-6 (FZD6), Frizzled-7 (FZD7), Frizzled-8 (FZD8), Frizzled-9 (FZD9) or Frizzled-10 (FZD10).

In some cases, the receptor-binding agent that specifically binds the Wnt receptor or co-receptor is an antibody or an antigen-binding fragment thereof, e.g., a Fab fragment. In some embodiments, the receptor-binding agent that specifically binds Wnt receptor or co-receptor may be a ligand that binds, e.g., specifically binds, to the receptor. In some embodiments, the ligand is or includes, e.g., WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11 or WNT16.

In some embodiments, the receptor-binding agent, e.g., stimulatory agent is capable of binding to any one or more of CD28, CD90 (Thy-1), CD95 (Apo-/Fas), CD137 (4-1BB), CD154 (CD40L), ICOS, LAT, CD27, OX40 and HVEM. In some embodiments, the receptor-binding agent, e.g. stimulatory agent, can be an antibody, divalent antibody (e.g. a F(ab')$_2$-fragment or a divalent single-chain Fv fragment), monovalent antibody (e.g. a Fab fragment, an Fv fragment, or a single-chain Fv fragment (scFv)) or ligand to any one or more of CD28, CD90 (Thy-1), CD95 (Apo-/Fas), CD137 (4-1BB), CD154 (CD40L), ICOS, LAT, CD27, OX40 and HVEM, in which such agent is capable of inducing or modeling a signal in the cells upon binding of the receptor-binding agent, e.g., stimulatory agent to the molecule.

In some embodiments, the receptor-binding agent, e.g. stimulatory agent, can be a ligand to any one or more of CD28, 4-1BB (CD137), CD40, CD40L, Linker for Activation of T cells (LAT), CD27, OX40 (CD134) and herpesvirus entry mediator (HVEM), in which such agent is capable of inducing or modeling a signal in the cells upon binding of the receptor-binding agent, e.g., stimulatory agent to the molecule. In some embodiments, the receptor-binding agent, e.g. stimulatory agent, can be an extracellular domain or a portion thereof, of an endogenous ligand and/or a cognate ligand. For example, in some embodiments, the receptor-binding agent is or contains the extracellular domain or a portion thereof, of B7-1 (CD80), B7-2 (CD86), 4-1BBL, CD40, CD40L, CD27L (CD70) and/or OX40L.

In some embodiments, the molecule on the cell, e.g., T cell, may be CD28 and the receptor-binding agent, e.g., stimulatory agent (e.g. which can be the second receptor-binding agent, e.g., second stimulatory agent) specifically binds CD28.

In some embodiments, the molecule on the cell, e.g., T cell, may be CD28 and the receptor-binding agent, e.g., stimulatory agent (e.g. which can be the second receptor-binding agent, e.g., second stimulatory agent) specifically binds CD28. In some aspects, the receptor-binding agent, e.g., stimulatory agent (e.g. which can be the second receptor-binding agent, e.g., second stimulatory agent) that specifically binds CD28 may be selected from the group consisting of an anti-CD28 antibody, a divalent antibody fragment of an anti-CD28 antibody, a monovalent antibody fragment of an anti-CD28 antibody, and a proteinaceous CD28 binding molecule with antibody-like binding properties. The divalent antibody fragment may be an F(ab')$_2$-fragment, or a divalent single-chain Fv fragment while the monovalent antibody fragment may be selected from the group consisting of a Fab fragment, a Fv fragment, a nanobody and a single-chain Fv fragment (scFv).

In some embodiments, an anti-CD28 Fab fragment can be derived from antibody CD28.3 (deposited as a synthetic single chain Fv construct under GenBank Accession No. AF451974.1; see also Vanhove et al, BLOOD, 15 Jul. 2003, Vol. 102, No. 2, pages 564-570) the heavy and light chain of which comprise SEQ ID NO: 33 and 34, respectively.

In some embodiments, the molecule on the cell, e.g., T cell, may be CD90 and the receptor-binding agent, e.g., stimulatory agent (e.g. which can be the second receptor-binding agent, e.g., second stimulatory agent,) specifically binds CD90. In some aspects, the receptor-binding agent, e.g., stimulatory agent (e.g. which can be the second receptor-binding agent, e.g., second stimulatory agent,) that specifically binds CD90 may be selected from the group consisting of an anti-CD90-antibody, a divalent antibody fragment of an anti-CD90 antibody, a monovalent antibody fragment of an anti-CD90-antibody, and a proteinaceous CD90 binding molecule with antibody-like binding properties. The antibody or antigen-binding fragment can be derived from any known in the art. See e.g. anti-CD90 antibody G7 (Biolegend, cat. no. 105201).

In some embodiments, the molecule on the cell, e.g., T cell, may be CD95 and the receptor-binding agent, e.g., stimulatory agent (e.g. which can be the second receptor-binding agent, e.g., second stimulatory agent,) specifically binds CD95. In some aspects, the receptor-binding agent, e.g., stimulatory agent (e.g. which can be the second receptor-binding agent, e.g., second stimulatory agent,) that specifically binds CD95 may be selected from the group consisting of an anti-CD95-antibody, a divalent antibody fragment of an anti-CD95 antibody, a monovalent antibody fragment of an anti-CD95-antibody, and a proteinaceous CD95 binding molecule with antibody-like binding properties. The antibody or antigen-binding fragment can be derived from any known in the art. For example, in some aspects, the anti-CD90 antibody can be monoclonal mouse anti-human CD95 CH11 (Upstate Biotechnology, Lake Placid, NY) or can be anti-CD95 mAb 7C11 or anti-APO-1, such as described in Paulsen et al. *Cell Death & Differentiation* 18.4 (2011): 619-631.

In some embodiments, the molecule on the cell, e.g., T cell or B cell, may be CD137 and the receptor-binding agent, e.g., stimulatory agent (e.g. which can be the second receptor-binding agent, e.g., second stimulatory agent,) specifically binds CD137. In some aspects, the receptor-binding agent, e.g., stimulatory agent, (e.g. which can be the second receptor-binding agent, e.g., second stimulatory agent) that specifically binds CD137 may be selected from the group consisting of an anti-CD137-antibody, a divalent antibody fragment of an anti-CD137 antibody, a monovalent antibody fragment of an anti-CD137-antibody, and a proteinaceous CD137 binding molecule with antibody-like binding properties. The antibody or antigen-binding fragment can be derived from any known in the art. For example, the anti-CD137 antibody can be LOB12, IgG2a or LOB12.3, IgG1 as described in Taraban et al. Eur J Immunol. 2002 Dec.; 32(12):3617-27. See also e.g. U.S. Pat. Nos. 6,569, 997, 6,303,121, Mittler et al. Immunol Res. 2004;29(1-3): 197-208.

In some embodiments, the molecule on the cell, e.g. B cell, may be CD40 and the receptor-binding agent, e.g., stimulatory agent, (e.g. which can be the second receptor-binding agent, e.g., second stimulatory agent) specifically binds CD40. In some aspects, the receptor-binding agent (which can be the second receptor-binding agent, e.g., second stimulatory agent) that specifically binds CD40 may be selected from the group consisting of an anti-CD40-antibody, a divalent antibody fragment of an anti-CD40 antibody, a monovalent antibody fragment of an anti-CD40-antibody, and a proteinaceous CD40 binding molecule with antibody-like binding properties. The antibody or antigen-binding fragment can be derived from any known in the art. For example, the anti-CD40 antibody can be chimeric monoclonal anti-human CD40 antibody Teneliximab and anti-human CD40 (Affymetrix cat. no. 14-0409-80), or any described in e.g., US 2002/0142358, US 2007/0077242, WO 2001/083755, Zhang et al., 2010, J Immunol, 184:787-795.

In some embodiments, the molecule on the cell, e.g., T cell, may be CD40L (CD154) and the receptor-binding agent, e.g., stimulatory agent, (e.g. which can be the second receptor-binding agent, e.g., second stimulatory agent) specifically binds CD40L. In some aspects, the receptor-binding agent, e.g., stimulatory agent, (e.g. which can be the second receptor-binding agent, e.g., second stimulatory agent) that specifically binds CD40L may be selected from the group consisting of an anti-CD40L-antibody, a divalent antibody fragment of an anti-CD40L antibody, a monovalent antibody fragment of an anti-CD40L-antibody, and a proteinaceous CD40L binding molecule with antibody-like binding properties. The antibody or antigen-binding fragment can be derived from any known in the art. For example, the anti-CD40L antibody can in some aspects be Hu5C8, as described in Blair et al. JEM vol. 191 no. 4 651-660. See also e.g. WO1999061065, US20010026932, U.S. Pat. No. 7,547, 438, WO2001056603.In some embodiments, the molecule on the cell, e.g., T cell, may be inducible T cell Costimulator (ICOS), Linker for Activation of T cells (LAT), CD27, OX40 (CD134), herpesvirus entry mediator (HVEM), CD90, and/or CD95, and the receptor-binding agent, e.g., stimulatory agent, (e.g. which can be the second receptor-binding agent, e.g., second stimulatory agent) specifically binds ICOS, LAT, CD27, CD134, HVEM, CD90, and/or CD95, respectively. In some aspects, the receptor-binding agent, e.g., stimulatory agent, (e.g. which can be the second receptor-binding agent, e.g., second stimulatory agent) that specifically binds ICOS, LAT, CD27, CD134, HVEM, CD90, and/or CD95 may be selected from the group consisting of an antibody, a divalent antibody fragment thereof, a monovalent antibody fragment thereof, and a proteinaceous binding molecule with antibody-like binding properties. The antibody or antigen-binding fragment can be derived from any known in the art.

In some embodiments, the molecule on the cell, e.g., T cell, to which the receptor-binding agent, which may be a second or an additional receptor-binding agent, binds to a cell surface molecule that stimulates or activates a cytokine signal, chemokine signal, cell adhesion signal, T cell activation signal or additional signals, e.g., environmental signals, upon binding of the agent. In some embodiments, the molecule on the cell, e.g., T cell, to which the receptor-binding agent, which may be a second or an additional receptor-binding agent, specifically binds, is a cytokine receptor or a chemokine receptor. In some cases, the receptor-binding agent, e.g., additional receptor-binding agent, is or contains an adhesion molecule, is a factor that induces cytokine production, chemokine production, expression of an adhesion molecule, and/or is involved in stimulating and/or modulating an accessory signal and/or an additional signal, e.g., an environmental signal.

In any of the embodiments provided herein, the receptor-binding agent, e.g., the first, second and/or additional receptor-binding agent, e.g., stimulatory agent, may be a binding agent that specifically binds a receptor, e.g., a receptor expressed on the surface of the cell.

In some embodiments, the receptor-binding agent, e.g., stimulatory agent, is an antibody or an antigen-binding fragment thereof, e.g., an antibody or antigen binding fragment thereof that binds to a cell surface molecule that stimulates or activates a cytokine signal, chemokine signal, cell adhesion signal, T cell activation signal or additional signals, e.g., environmental signals, upon binding of the agent. In some cases, the receptor-binding agent, e.g., the first, second and/or additional receptor-binding agent, e.g., stimulatory agent, that specifically binds receptor may be selected from the group consisting of an anti-receptor antibody, a divalent antibody fragment of an anti-receptor antibody, a monovalent antibody fragment of an anti-receptor antibody, and a proteinaceous receptor binding molecule with antibody-like binding properties. The divalent antibody fragment may be a F(ab')$_2$-fragment, or a divalent single-chain Fv fragment while the monovalent antibody fragment may be selected from the group consisting of an Fab fragment, an Fv fragment, and a single-chain Fv fragment (scFv). In some cases, a proteinaceous receptor binding molecule with antibody-like binding properties may be an aptamer, a mutein based on a polypeptide of the lipocalin family, a glubody, a protein based on the ankyrin scaffold, a protein based on the crystalline scaffold, an adnectin, a DARPin or an avimer. In some cases, the receptor-binding agent, e.g., the first, second and/or additional receptor-binding agent, e.g., stimulatory agent that specifically binds receptor is an antibody or an antigen-binding fragment thereof, e.g., a Fab fragment.

In some embodiments, the receptor-binding agent, e.g., stimulatory agent, may be a ligand that binds, e.g., specifically binds, to the receptor, e.g., a cell surface molecule that stimulates or activates a cytokine signal, chemokine signal, cell adhesion signal, T cell activation signal or additional signals, e.g., environmental signals, upon binding of the agent. In some embodiments, the receptor-binding agent, e.g., the first, second and/or additional receptor-binding agent, is an endogenous ligand, a cognate ligand, a synthetic ligand and/or a portion, a variant or modified forms thereof. In some embodiments, the receptor-binding agent, e.g. stimulatory agent, can be an extracellular domain or a portion thereof, of an endogenous ligand and/or a cognate ligand.

In some embodiments, the receptor-binding agent, e.g., a second or an additional receptor-binding agent, is or contains a ligand that specifically binds to a cytokine receptor. In some embodiments, the receptor-binding agent, e.g., a second or an additional receptor-binding agent, is or comprises a ligand of the cytokine receptor, e.g., a cytokine or a portion thereof. Exemplary cytokine receptors include, but are not limited to, IL-2R, IL-7R, IL-21R, CD132 (IL receptor common gamma chain), IL-1R, IL-15R, IFN-gammaR, TNF-alphaR, IL-4R, IL-10R, Type I IFNR, IL-12R, IL-17R, TNFR1 and TNFR2. Exemplary ligands, e.g., cytokines, include, but are not limited to, IL-2, IL-7, IL-21, IL-1, IL-15, IFN-gamma, TNF-alpha, IL-4, IL-10, Type I interferons (e.g., IFNα and/or IFNβ), IL-12, IL-17, IL-9 and TNF, and biologically active fragments thereof.

In some embodiments, the receptor-binding agent, e.g., a second or an additional receptor-binding agent, is an antibody or antigen-binding fragment thereof that specifically binds to a cytokine receptor. In some cases, the receptor-binding agent, e.g., a second or an additional receptor-binding agent, that specifically binds cytokine receptor may be selected from the group consisting of an anti-(cytokine receptor) antibody, a divalent antibody fragment of an anti-(cytokine receptor) antibody, a monovalent antibody fragment of an anti-(cytokine receptor) antibody, and a proteinaceous cytokine receptor binding molecule with antibody-like binding properties. The divalent antibody fragment may be a F(ab')$_2$-fragment, or a divalent single-chain Fv fragment while the monovalent antibody fragment may be selected from the group consisting of a Fab fragment, an Fv fragment, and a single-chain Fv fragment (scFv).

In some embodiments, the receptor-binding agent, e.g., additional receptor-binding agent, is or contains a ligand that specifically binds to a chemokine receptor. In some embodiments, the receptor-binding agent, e.g., a second or an additional receptor-binding agent, is or comprises a ligand of the chemokine receptor, e.g., a chemokine or a portion thereof. Exemplary chemokine receptors include, but are not limited to, CCR1, CCR2, CCR3, CCR4, CCR5, CCR7, CCR9, CXCR1, CXCR3 and CXCR4. Exemplary ligands, e.g., chemokines, include but are not limited to, CXCL9, CXCL10, CCL19, CCL21 and CCL25 or biologically active fragments thereof.

In some embodiments, the receptor-binding agent, e.g., a second or an additional receptor-binding agent, is an antibody or antigen-binding fragment thereof that specifically binds to a chemokine receptor. In some cases, the receptor-binding agent, e.g., a second or an additional receptor-binding agent, that specifically binds chemokine receptor may be selected from the group consisting of an anti-(chemokine receptor) antibody, a divalent antibody fragment of an anti-(chemokine receptor) antibody, a monovalent antibody fragment of an anti-(chemokine receptor) antibody, and a proteinaceous chemokine receptor binding molecule with antibody-like binding properties. The divalent antibody fragment may be a F(ab')$_2$-fragment, or a divalent single-chain Fv fragment while the monovalent antibody fragment may be selected from the group consisting of a Fab fragment, an Fv fragment, and a single-chain Fv fragment (scFv).

In some cases, the receptor-binding agent that specifically binds the adhesion molecule or factors that induce cytokine is an antibody or an antigen-binding fragment thereof, e.g., a Fab fragment. In some embodiments, the receptor-binding agent that specifically binds the adhesion molecule or factors that induce cytokine may be a ligand that binds, e.g., specifically binds, to the receptor. In some embodiments, the receptor-binding agent is an endogenous ligand, a cognate ligand, a synthetic ligand and/or a portion, a variant or modified forms thereof, of the adhesion molecule and/or the receptor. In some embodiments, the receptor-binding agent, e.g. stimulatory agent, can be an extracellular domain or a portion thereof, of an endogenous ligand and/or a cognate ligand that is itself a cell-surface or transmembrane protein.

In some instances, the molecule on the cell, e.g., adhesion molecule, is CD44, CD31, CD18/CD11a (LFA-1; full length alpha and beta chain sequence set forth in SEQ ID NOS: 36 and 37 respectively), CD29, CD54 (ICAM-1), CD62L (L-selectin; full length sequence set forth in SEQ ID NO:38), CD29/CD49d (VLA-4; full length sequence set forth in SEQ ID NO:40), CD106 (VCAM-1; full length sequence set forth in SEQ ID NO:39) or is a biologically active fragment thereof. In some embodiments, the receptor-binding agent is an antibody or an antigen-binding fragment thereof that binds, e.g., specifically binds to an adhesion molecule, e.g., CD44, CD31, CD18/CD11a (LFA-1), CD29, CD54 (ICAM-1), CD62L (L-selectin), CD29/CD49d (VLA-4), CD106 (VCAM-1) or is a biologically active fragment thereof. In some embodiments, the receptor-binding agent is a ligand or a portion thereof, that binds, e.g., specifically binds to an adhesion molecule, e.g., CD44, CD31, CD18/CD11a (LFA-1), CD29, CD54 (ICAM-1), CD62L (L-selectin), CD29/CD49d (VLA-4), CD106 (VCAM-1). Such receptor-binding agents include an agent that is or comprises an extracellular domain (ECD) or a portion thereof, of an endogenous ligand and/or a cognate ligand of an adhesion molecule. In some embodiments, the receptor-binding agent is an extracellular domain or a portion thereof, of an adhesion molecule, and can bind one or more adhesion molecules on the surface of a cell. Exemplary of such receptor-binding agents include the extracellular domain of LFA-1α (ECD set forth in SEQ ID NO: 54); LFA-1β (ECD set forth in SEQ ID NO: 55); L-selectin (ECD set forth in SEQ ID NO: 57); VCAM-1 (ECD set forth in SEQ ID NO: 56); and VLA-4 (ECD set forth in SEQ ID NO: 58), or any portion thereof.

In some embodiments, the factor that induces cytokine production, chemokine production and/or expression of an adhesion molecule is or contains a nuclear factor, such as a retinoic acid receptor-related orphan receptor gamma (ROR-gamma) or RORalpha.

In some embodiments, the receptor-binding agent, e.g., a second or an additional receptor-binding agent, is or contains a ligand that specifically binds to a cytokine receptor.

In some embodiments, the molecule on the cell, e.g., T cell, may be IL-2R, IL-7R (CD127), IL-21R (CD360), IL receptor common gamma chain (γc; or CD132), IL-1R (CD121) such as IL-1R1 or IL-1R2, IL-15R (CD215), interferon gamma receptor (IFNγR; CD119), tumor necrosis factor alpha receptor (TNFαR) including TNFR1 (CD120a) and TNFR2 (CD120b), IL-4R, IL-10R, Interferon type I receptor, e.g., IFNα receptor (IFNAR), including IFNAR1 and IFNAR2, IL-17R (CD217), and/or IL-12R, and the receptor-binding agent, e.g., stimulatory agent specifically binds to the molecule. In some aspects, the receptor-binding agent, e.g., stimulatory agent, (e.g. which can be an additional receptor-binding agent, e.g., additional stimulatory agent) that specifically binds the molecule on the cell may be selected from the group consisting of an antibody, a divalent antibody fragment, a monovalent antibody fragment, and a proteinaceous binding molecule with antibody-like binding properties.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as an IL-2 ligand, an IL-7 ligand, an IL-21 ligand, an IL-1 ligand, an IL-15 ligand, an IL-9 ligand, an IFNγ ligand, a TNFα ligand, an IL-4 ligand, an IL-10 ligand, an IL-12 ligand, an IL-17 ligand, or a biologically active portion or variant thereof. In some embodiments, the biologically active portion or variant retains activity to bind to the receptor and/or a functional activity to modulate one or more signals to the receptor.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a Type I interferon, e.g., IFNα, IFNβ, IFNκ, IFNδ, IFNε, IFNτ, IFNω, and IFNζ (also known as limitin) or a biologically active portion thereof.

In some embodiments, the molecule on the cell, e.g., T cell, may be CXCR3, CCR7, CXCR1, or CXCR4, and the receptor-binding agent, e.g., stimulatory agent, (e.g. which can be an additional receptor-binding agent, e.g., additional stimulatory agent) specifically binds CXCR3, CCR7, CXCR1, or CXCR4. In some aspects, the receptor-binding agent, e.g., stimulatory agent, (e.g. which can be an additional receptor-binding agent, e.g., additional stimulatory agent) that specifically binds CXCR3, CCR7, CXCR1, or CXCR4, may be selected from the group consisting of an antibody, a divalent antibody fragment, a monovalent antibody fragment, and a proteinaceous binding molecule with antibody-like binding properties.

In some embodiments, the receptor-binding agent, e.g., stimulatory agent, (e.g. which can be an additional receptor-binding agent, e.g., additional stimulatory agent) can include a ligand of a stimulatory receptor or other receptor capable of inducing a signal in the cell, such as a CXCL9 ligand, CXCL10 ligand, CCL19 ligand, CCL21 ligand, CCL25 ligand, or a biologically active portion thereof that retains activity to bind to the receptor and/or a functional activity to modulate one or more signals to the receptor.

In some cases, the receptor-binding agent, e.g., additional receptor-binding agent, is or contains an adhesion molecule or is a factor that induces cytokine production, chemokine production, expression of an adhesion molecule, and/or is involved in stimulating and/or modulating an accessory signal and/or an additional signal. In some embodiments, the molecule on the cell, e.g., T cell, may be CD62L and the receptor-binding agent, e.g., stimulatory agent, (e.g. which can be an additional receptor-binding agent, e.g., additional stimulatory agent) specifically binds CD62L. In some embodiments, the molecule on the cell, e.g., T cell, may be RORγt and the receptor-binding agent, e.g., stimulatory agent, (e.g. which can be an additional receptor-binding agent, e.g., additional stimulatory agent) specifically binds RORγt. In some embodiments, the molecule on the cell, e.g., T cell, may be RORα and the receptor-binding agent, e.g., stimulatory agent, (e.g. which can be an additional receptor-binding agent, e.g., additional stimulatory agent) specifically binds RORα.

In some embodiments, the receptor-binding agent, e.g., stimulatory agent is capable of binding to any one or more of CD28, CD5, CD4, CD8, MHCI, MHCII, CTLA-4, ICOS, PD-1, OX40, CD27L (CD70), 4-1BBL, CD30L and LIGHT, and the receptor-binding agent, e.g. stimulatory agent, can be an antibody, divalent antibody (e.g. a (Fab)2'-fragment or a divalent single-chain Fv fragment), monovalent antibody (e.g. a Fab fragment, an Fv fragment, or a single-chain Fv fragment (scFv)) or ligand to any one or more of CD28, CD5, CD4, CD8, MHCI, MHCII, CTLA-4, ICOS, PD-1, OX40, CD27L (CD70), 4-1BBL, CD30L and LIGHT, in which such agent is capable of inducing or modeling a signal in the cells upon binding of the receptor-binding agent, e.g., stimulatory agent to the molecule.

In some embodiments, the receptor-binding agent, e.g., stimulatory agent, is capable of specifically binding to a molecule on the surface of the target cells other than CD28, CD3, CD137 or CD40. In some cases, the binding of the receptor-binding agent, e.g., stimulatory agent, to the molecule on the surface of the target cells other than CD28, CD3, CD137 or CD40 induces or modulates a signal in the target cells and/or alters a function of the target cells, thereby generating cultured target cells.

In any of the above examples, the divalent antibody fragment may be an (Fab)$_2$'-fragment, or a divalent single-chain Fv fragment while the monovalent antibody fragment may be selected from the group consisting of a Fab fragment, an Fv fragment, and a single-chain Fv fragment (scFv). In any of the above examples, the proteinaceous binding molecule with antibody-like binding properties may be an aptamer, a mutein based on a polypeptide of the lipocalin family, a glubody, a protein based on the ankyrin scaffold, a protein based on the crystalline scaffold, an adnectin, a nanobody, a DARPin and an avimer.

b. Selection Agents

In some embodiments, the agent is a selection agent. In some embodiments, the selection agent binds to a molecule on the surface of a cell, such as a cell surface molecule. In some instances, the cell surface molecule is a selection marker. In some such cases, the selection agent is capable of specifically binding to a selection marker expressed by one or more of the cells. In some embodiments, a selection agent or agents that are reversibly bound to a reagent can be used to facilitate selection or isolation of cells.

In any of the embodiments provided herein, the receptor-binding agent, e.g., the first, second and/or additional receptor-binding agent, e.g., stimulatory agent, may be a binding agent that specifically binds a receptor, e.g., a receptor expressed on the surface of the cell. In some cases, the receptor-binding agent, e.g., the first, second and/or additional receptor-binding agent, e.g., stimulatory agent, that specifically binds receptor may be selected from the group consisting of an anti-receptor antibody, a divalent antibody fragment of an anti-receptor antibody, a monovalent antibody fragment of an anti-receptor antibody, and a proteinaceous receptor binding molecule with antibody-like binding properties. The divalent antibody fragment may be a F(ab')$_2$-fragment, or a divalent single-chain Fv fragment while the monovalent antibody fragment may be selected from the group consisting of an Fab fragment, an Fv fragment, and a single-chain Fv fragment (scFv). In some cases, a proteinaceous receptor binding molecule with antibody-like binding properties may be an aptamer, a mutein based on a polypeptide of the lipocalin family, a glubody, a protein based on the ankyrin scaffold, a protein based on the crystalline scaffold, an adnectin, a nanobody, a DARPin or an avimer. In some cases, the receptor-binding agent, e.g., the first, second and/or additional receptor-binding agent, e.g., stimulatory agent that specifically binds receptor is an antibody or an antigen-binding fragment thereof, e.g., a Fab fragment.

In some aspects, the cell surface molecule, e.g., selection marker, may be an antigen defining a desired cell population or subpopulation, for instance a population or subpopulation of blood cells, e. g. lymphocytes (e.g. T cells, T-helper cells, for example, CD4+T-helper cells, B cells or natural killer cells), monocytes, or stem cells, e.g. CD34-positive peripheral stem cells or Nanog or Oct-4 expressing stem cells. In some embodiments, the selection marker can be a marker expressed on the surface of T cells or a subset of T cells, such as CD25, CD28, CD62L, CCR7, CD27, CD127, CD3, CD4, CD8, CD45RA, and/or CD45RO Examples of T-cells include cells such as CMV-specific CD8+T-lymphocytes, cytotoxic T-cells, memory T-cells and regulatory T-cells (Treg). An illustrative example of Treg includes CD4 CD25 CD45RA Treg cells and an illustrative example of memory T-cells includes CD62L CD8+ specific central memory T-cells. The cell surface molecule, e.g., selection marker, may also be a marker for a tumor cell.

In some embodiments, the selection marker may be CD4 and the selection agent specifically binds CD4. In some aspects, the selection agent that specifically binds CD4 may be selected from the group consisting of an anti-CD4-antibody, a divalent antibody fragment of an anti-CD4 antibody, a monovalent antibody fragment of an anti-CD4-antibody, and a proteinaceous CD4 binding molecule with antibody-like binding properties (e.g. an anticalin or a nanobody). In some embodiments, an anti-CD4-antibody, such as a divalent antibody fragment or a monovalent antibody fragment (e.g. CD4 Fab fragment) can be derived from antibody 13B8.2 or a functionally active mutant of 13B8.2 that retains specific binding for CD4. For example, exemplary mutants of antibody 13B8.2 or m13B8.2 are described in U.S. Pat. Nos. 7,482,000, U.S. Patent Appl. No. US2014/0295458 or International Patent Application No. WO2013/124474; and Bes, C, et al. J Biol Chem 278, 14265-14273 (2003). The mutant Fab fragment termed "m133B8.2" carries the variable domain of the CD4 binding murine antibody 13B8.2 and a constant domain containing constant human CH1 domain of type gamma for the heavy chain and the constant human light chain domain of type kappa, as described in U.S. Pat. No. 7,482,000. In some embodiments, the anti-CD4 antibody, e.g. a mutant of anti-body 13B8.2, contains the amino acid replacement H91A in the variable light chain, the amino acid replacement Y92A in the variable light chain, the amino acid replacement H35A in the variable heavy chain and/or the amino acid replacement R53A in the variable heavy chain, each by Kabat numbering. In some aspects, compared to variable domains of the 13B8.2 Fab fragment in m13B8.2 the His residue at position 91 of the light chain (position 93 in SEQ ID NO: 30) is mutated to Ala and the Arg residue at position 53 of the heavy chain (position 55 in SEQ ID NO: 29) is mutated to Ala. In some embodiments, the reagent that is reversibly bound to anti-CD4 or a fragment thereof is commercially available or derived from a reagent that is commercially available (e.g. catalog No. 6-8000-206 or 6-8000-205 or 6-8002-100; IBA GmbH, Gottingen, Germany).

In some embodiments, the selection marker may be CD8 and the selection agent specifically binds CD8. In some aspects, the selection agent that specifically binds CD8 may be selected from the group consisting of an anti-CD8-antibody, a divalent antibody fragment of an anti-CD8 antibody, a monovalent antibody fragment of an anti-CD8-antibody, and a proteinaceous CD8 binding molecule with antibody-like binding properties. In some embodiments, an anti-CD8-antibody, such as a divalent antibody fragment or a monovalent antibody fragment (e.g. CD8 Fab fragment) can be derived from antibody OKT8 (e.g. ATCC CRL-8014) or a functionally active mutant thereof that retains specific binding for CD8. In some embodiments, the reagent that is reversibly bound to anti-CD8 or a fragment thereof is commercially available or derived from a reagent that is commercially available (e.g. catalog No. 6-8003 or 6-8000-201; IBA GmbH, Gottingen, Germany).

In some embodiments, the selection marker may be CD3 and the selection agent specifically binds CD3. In some aspects, the selection agent that specifically binds CD3 may be selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties. In some embodiments, an anti-CD3-antibody, such as a divalent antibody fragment or a monovalent antibody fragment (e.g. CD3 Fab fragment) can be derived from antibody OKT3 (e.g. ATCC CRL-8001; see e.g., Stemberger et al. PLoS One. 2012; 7(4): e35798) or a functionally active mutant thereof that retains specific binding for CD3. In some embodiments, the reagent that is reversibly bound to anti-CD3 or a fragment thereof is commercially available or derived from a reagent that is commercially available (e.g. catalog No. 6-8000-201, 6-8001-100; IBA GmbH, Gottingen, Germany).

In some embodiments, the selection marker may be CD25 and the selection agent specifically binds CD25. In some aspects, the selection agent that specifically binds CD25 may be selected from the group consisting of an anti-CD25-antibody, a divalent antibody fragment of an anti-CD25 antibody, a monovalent antibody fragment of an anti-CD25-antibody, and a proteinaceous CD25 binding molecule with antibody-like binding properties. In some embodiments, an anti-CD25-antibody, such as a divalent antibody fragment or a monovalent antibody fragment (e.g. CD25 Fab fragment) can be derived from antibody FRT5 (See e.g., Stemberger et al. 2012) or a functionally active mutant thereof that retains specific binding for CD25. In some embodiments, the reagent that is reversibly bound to anti-CD4 or a fragment thereof is commercially available or derived from a reagent that is commercially available (e.g. catalog No. 6-8000-205 or 6-8000-207 or 6-8004-050; IBA GmbH, Gottingen, Germany).

In some embodiments, the selection marker may be CD62L and the selection agent specifically binds CD62L. In some aspects, the selection agent that specifically binds CD62L may be selected from the group consisting of an anti-CD62L-antibody, a divalent antibody fragment of an anti-CD62L antibody, a monovalent antibody fragment of an anti-CD62L-antibody, and a proteinaceous CD62L binding molecule with antibody-like binding properties. In some embodiments, an anti-CD62L-antibody, such as a divalent antibody fragment or a monovalent antibody fragment (e.g. CD62L Fab fragment) can be derived from antibody DREG56 (e.g. ATCC HB300; see e.g. Stemberger et al. 2012) or a functionally active mutant thereof that retains specific binding for CD62L. In some embodiments, the reagent that is reversibly bound to anti-CD62L or a fragment thereof is commercially available or derived from a reagent that is commercially available (e.g. catalog No. 6-8000-204 or 6-8005-050; IBA GmbH, Gottingen, Germany).

In some embodiments, the selection marker may be CD45RA and the selection agent specifically binds CD45RA. In some aspects, the selection agent that specifically binds CD45RA may be selected from the group consisting of an anti-CD45RA-antibody, a divalent antibody fragment of an anti-CD45RA antibody, a monovalent antibody fragment of an anti-CD45RA-antibody, and a proteinaceous CD45RA binding molecule with antibody-like binding properties. In some embodiments, an anti-CD45RA-antibody, such as a divalent antibody fragment or a monovalent antibody fragment (e.g. CD45RA Fab fragment) can be derived from antibody MEM56 (e.g. Millipore 05-1413; see e.g. Stemberger et al. 2012) or a functionally active mutant thereof that retains specific binding for CD45RA. In some embodiments, the reagent that is reversibly bound to anti-CD45RA or a fragment thereof is commercially available or derived from a reagent that is commercially available (e.g. catalog No. 6-8000-208 or 6-8007-050; IBA GmbH, Gottingen, Germany).

In some embodiments, the selection marker may be CD45RO and the selection agent specifically binds CD45RO. In some aspects, the selection agent that specifically binds CD45RO may be selected from the group consisting of an anti-CD45RO-antibody, a divalent antibody fragment of an anti-CD45RO antibody, a monovalent antibody fragment of an anti-CD45RO-antibody, and a proteinaceous CD45RO binding molecule with antibody-like binding properties. In some embodiments, the reagent that is reversibly bound to anti-CD45RO or a fragment thereof is commercially available or derived from a reagent that is commercially available (e.g. catalog No. 6-8000-209 or 6-8012-020; IBA GmbH, Gottingen, Germany).

In some embodiments, the selection marker may be CD154 and the selection agent specifically binds CD154. In some aspects, the selection agent that specifically binds CD154 may be selected from the group consisting of an anti-CD154-antibody, a divalent antibody fragment of an anti-CD154 antibody, a monovalent antibody fragment of an anti-CD154-antibody, and a proteinaceous CD154 binding molecule with antibody-like binding properties. In some embodiments, the reagent that is reversibly bound to anti-CD154 or a fragment thereof is commercially available or derived from a reagent that is commercially available (e.g. catalog No. 6-8000-202 or 6-5510-050; IBA GmbH, Gottingen, Germany).

In some embodiments, the selection marker may be CD16 and the selection agent specifically binds CD16. In some aspects, the selection agent that specifically binds CD16 may be selected from the group consisting of an anti-CD16-antibody, a divalent antibody fragment of an anti-CD16 antibody, a monovalent antibody fragment of an anti-CD16-antibody, and a proteinaceous CD16 binding molecule with antibody-like binding properties. In some embodiments, the reagent that is reversibly bound to anti-CD16 or a fragment thereof is commercially available or derived from a reagent that is commercially available. In some aspects, the CD16 binding molecule comprises the heavy chain and/or light chain sequences set forth in SEQ ID NO: 52 and 53, respectively.

In any of the above examples, the divalent antibody fragment may be an $(Fab)_2$'-fragment, or a divalent single-chain Fv fragment while the monovalent antibody fragment may be selected from the group consisting of a Fab fragment, an Fv fragment, and a single-chain Fv fragment (scFv). In any of the above examples, the proteinaceous binding molecule with antibody-like binding properties may be an aptamer, a mutein based on a polypeptide of the lipocalin family, a glubody, a protein based on the ankyrin scaffold, a protein based on the crystalline scaffold, an adnectin, a nanobody, DARPin and an avimer.

III. Methods of Culturing Cells

Provided herein are methods of culturing cells which include incubating a composition containing target cells (e.g. T cells) in the presence of an agent (e.g. first or second, receptor-binding agents, e.g. stimulatory agents, or selection agents) that is capable of binding to a molecule on the surface of targets cells (e.g. T cells) in the composition and that is reversibly bound to a reagent containing a plurality of binding sites capable of reversibly binding to the agent. In certain embodiments, the reagent is an oligomeric particle reagent, such as any as described. In some embodiments, the incubation is performed under conditions in which the agent binds, such as specifically binds, to the molecule on the cell. In some cases, for certain receptor-binding agents (e.g. stimulatory agents), such binding can induce or modulate a signal in target cells (e.g. T cells) in the compositions, such as a primary signal or accessory signal as described. In some embodiments, binding of the agent to the molecule results in one or more of the stimulation, activation, expansion (proliferation) and/or differentiation of target cells in the composition.

In some embodiments, the provided method can be used for selectively inducing ex vivo expansion of a population of cells such as B cells, T cells or natural killer cells. In some cases, the stimulation can be in the absence of exogenous growth factors, such as lymphokines, and accessory cells. In some embodiments, the proliferation of these cells such as B cells or T cells can be induced without the need for antigen, thus providing an expanded cell population such as a T cell population which is polyclonal with respect to antigen reactivity. The methods disclosed herein may provide for sustained proliferation of a selected population of T cells such as CD4+ or CD8+ T cells over an extended period of time to yield a multi-fold increase in the number of these cells relative to the original T cell population. In general, in case of a (clonal) expansion of a lymphocyte population as described herein, all progeny may share the same antigen specificity as the cell population that was selected for expansion.

In some embodiments, the methods relate to expanding a population of antigen specific T cells. In some embodiments, to produce a population of antigen specific T cells, T cells are contacted with an antigen in a form suitable to trigger a primary activation signal in the T cell, i.e., the antigen is presented to the T cell such that a signal is triggered in the T cell through the TCR/CD3 complex. For example, the antigen can be presented to the T cell by an antigen presenting cell in conjunction with an MHC molecule. An antigen presenting cell, such as a B cell, macrophage, monocyte, dendritic cell, Langerhans cell, or other cell which can present antigen to a T cell, can be incubated with the T cell in the presence of the antigen (e.g., a soluble antigen) such that the antigen presenting cell presents the antigen to the T cell. Alternatively, a cell expressing an antigen of interest can be incubated with the T cell. For example, a tumor cell expressing tumor-associated antigens can be incubated with a T cell together to induce a tumor-specific response. Similarly, a cell infected with a pathogen, e.g., a virus, which presents antigens of the pathogen can be incubated with a T cell. Following antigen specific activation of a population of T cells, the cells can be expanded in accordance with the provided methods. For example, after antigen specificity has been established, T cells can be expanded by culture with an anti-CD3 antibody (used as first agent) and an anti-CD28 antibody (used as second agent) according to the methods described herein. In another embodiment, the first agent can be an MHC I: peptide complex, which binds to an antigen specific T cell population. In such an embodiment, any antigen specific peptide that is known and that can be complexed with the respective MHC I molecule can be used. Alternatively, it is also possible to use as first agent the natural ligand of a receptor that triggers of cell expansion. For example, the extracellular domain of CD19 can be used to cause the activation of intracellular signaling cascades of cells transduced to express chimeric CD19 binding antigen receptor (CAR). Exemplary aspects of the above are shown in Examples.

In some embodiments, provided is an in vitro-method of culturing a population of cells, comprising contacting a sample comprising a composition comprising a plurality of cells with a multimerization reagent and/or an oligomeric particle regent bound to one or more agents. In some embodiments, the mulimerization reagent is an oligomeric particle reagent. The multimerization reagent and/or an oligomeric particle regent bound to one or more agents has reversibly immobilized thereon (bound thereto) an agent (first or second, receptor-binding, e.g. stimulatory agent, or selection agent), which can be used for the selection, stimulation, expansion and/or differentiation of cells. In some embodiments, a first agent that provides a primary activation signal to the cells, wherein the multimerization reagent and/or an oligomeric particle regent bound to one or more agents comprising at least one binding site Z1 for the reversible binding of the first agent. The first agent comprises at least one binding partner C1, wherein the binding partner C1 is able of reversibly binding to the binding site Z1 of the multimerization reagent and/or an oligomeric particle regent bound to one or more agents, wherein the first agent is bound to the multimerization reagent via the reversible bond formed between the binding partner C1 and the binding site Z1. The first agent binds to a receptor molecule on the surface of the cells, thereby providing a primary activation signal to the cells and thereby activating the cells.

In some embodiments, the multimerization reagent and/or an oligomeric particle regent bound to one or more agents is immobilized on a support, such as a solid surface. In some embodiments, the multimerization reagent and/or an oligomeric particle regent bound to one or more agents is not bound to a support, such as not bound to a solid surface or stationary phase.

For example, in some embodiments, provided is an in vitro-method of expanding a population of cells, comprising contacting a sample comprising a population of cells with a multimerization reagent and/or an oligomeric particle regent bound to one or more agents, wherein the multimerization reagent and/or an oligomeric particle regent bound to one or more agents is not immobilized on a solid support, i.e. is in a soluble form, and has bound thereto an agent (first or second, receptor-binding, e.g. stimulatory agent, or selection agent), which can be used for the selection, stimulation, expansion and/or differentiation of cells. In some embodiments, a first agent that provides a primary activation signal to the cells is reversibly bound to the multimerization reagent and/or an oligomeric particle regent bound to one or more agents. The multimerization reagent and/or an oligomeric particle regent bound to one or more agents comprises at least one binding site, e.g. Z1 for the binding of the first agent, wherein the first agent comprises at least one binding partner, e.g. C1, wherein the binding partner C1 is able of binding to the binding site Z1 of the multimerization reagent and/or an oligomeric particle regent bound to one or more agents. In some embodiments, the first agent is bound to the multimerization reagent and/or an oligomeric particle regent bound to one or more agents via the bond formed between the binding partner C1 and the binding site Z1, and the first agent binds to a receptor molecule on the surface of the cells, thereby providing a primary activation signal to the cells and thereby activating the cells. In some embodiments, when a soluble multimerization agent is used, the bond between the binding part C, e.g. C1 and the binding site Z, e.g. Z1 does not need to be reversible.

For example, in some embodiments, the provided methods also include the use of a multimerization reagent and/or an oligomeric particle regent bound to one or more agents having bound thereto a second agent, such as an accessory or co-stimulatory molecules that stimulates an accessory molecule on the surface of the cells. In some cases, the multimerization agent is immobilized on a support, e.g. a solid support, solid phase, or stationary phase. In some embodiments, the multimerization agent is not immobilized on a support, i.e. is in soluble form. In some embodiments, the second agent comprises a binding partner, e.g. C2, wherein the binding partner, e.g. C2 is able of being reversibly bound to a binding site, e.g. Z2 of the multimerization reagent and/or an oligomeric particle regent, wherein the second agent is bound to the multimerization reagent and/or an oligomeric particle regent via the reversible bond formed between the binding partner C2 and the binding site Z2. In some embodiments, the bond formed between the binding partner C1 and the binding site Z1 may be reversible and the bond formed between the binding partner C2 and the binding site Z2 may be reversible. In this case, the dissociation constant ($K_d$) for the reversible binding between said binding site Z1 and said binding partner C1 and/or for the reversible binding between said binding site Z2 and said binding partner C2 may be in the range of $10^{-2}$ M to $10^{-13}$ M. In some aspects, such as when the multimerization reagent and/or an oligomeric particle regent bound to one or more agents is not bound to a support (e.g. not bound to a solid support or stationary phase), the bond formed between the binding partner C1 and the binding site Z1 may be irreversible and/or also the bond formed between the binding partner C2 and the binding site Z2 may be irreversible.

In some cases, the second agent binds to the accessory molecule on the surface on the surface of the cells, thereby stimulating the activated cells. In this embodiment, the first agent may stimulate a TCR/CD3 complex-associated signal in the T cells and may be a binding agent that specifically binds CD3. In this embodiment the accessory molecule on the T cell may be CD28 and the second agent that binds the accessory molecule is a binding reagent that specifically binds CD28. Alternatively, in some embodiments, it is found that targeting other accessory molecules also can be employed, which can, in some cases, alter, such as improve, one or more features, properties or characteristics of the cultured cells. In some embodiments, the accessory molecule can be one or more of IL-12R, IFNγR, IL-4R, IL-17R, RORγt, RORα, CXCR3, CCR7, CD62L, CXCR1 or CXCR4 (e.g. an anti-IL-12R antibody, an anti-IFNγR antibody, an anti-IL-4R antibody, and an anti-IL-17R antibody, anti-RORγt antibody, anti-RORα antibody, anti-CXCR3 antibody, anti-CCR7 antibody, anti-CD62L antibody, anti-CXCR1 antibody or anti-CXCR4 antibody, respectively. Exemplary agents, such as receptor-binding agents (e.g. stimulatory agents), are described below.

In some embodiments, the provided method may be carried out at any temperature at which the viability of the cell population is at least essentially uncompromised. In some embodiments, the condition at which incubation or culture is carried out include any conditions that are at least essentially not harmful, not detrimental or at least essentially not compromising viability, for example, under which the percentage of the population of cells that are to be expanded with full viability, is at least 70%, including at least 75%, at least 80%, at least 85%, at least 90%, at least 92%, at least 95%, at least 97%, at least 98%, at least 99% or at least 99.5%. In some embodiments, the provided method is carried out at a temperature of about 20° C. or higher. Depending on the cell population to be expanded a suitable temperature range may for instance be from about 20° C. to about 45° C., including from about 25° C. to about 40° C., or from about 32° C. to 37° C. In some embodiments a method according to the invention is carried out at a constant temperature value, or at a selected temperature value±about 5° C., ±about 4° C., ±about 3° C., ±about 2° C., ±about 1° C. or ±about 0.5° C. The person skilled in the art is able to empirically determine a suitable temperature, taking into account the nature of the cells and the expansion conditions. Typically human cells are expanded at a temperature such as 37° C.

In accordance with the disclosure herein, also provided are multimerized agents, or composition comprising multimerization reagents and/or an oligomeric particle regents bound to one or more agents that care capable of expanding a population of cells. Such a multimerized agent and/or an oligomeric particle regent bound to one or more agents that is capable of expanding a population of cells is a multimerization reagent and/or an oligomeric particle regent bound to one or more agents that is not bound to a support (e.g. in soluble form) and comprises at least one binding site Z, e.g. Z1, for the reversible binding of a first agent that provides a primary activation signal to the cells, wherein the multimerization reagent and/or an oligomeric particle regent bound to one or more agents has reversibly bound thereto said first agent that provides a primary activation signal to the cells; wherein the first agent comprises at least one binding partner C, e.g. C1, wherein the binding partner C1 is able of reversibly binding to the at least one binding site Z1 of the multimerization reagent and/or an oligomeric particle regent bound to one or more agents, wherein the first agent is bound to the multimerization reagent and/or an oligomeric particle regent bound to one or more agents via the reversible bond formed between the binding partner C1 and the binding site Z1. It should be noted here that such a multimerization agent can have immobilized thereon any of the first agent that are described herein.

In some embodiments, a multimerized reagent provided herein may further comprise at least one binding site, e.g. Z2 for the reversible binding of a second agent that stimulates an accessory molecule on the surface of the cells, wherein the multimerization reagent and/or an oligomeric particle regent bound to one or more agents has reversibly bound thereto the second agent that stimulates an accessory molecule on the surface of the cells, wherein the second agent comprises a binding partner, e.g. C2, wherein the binding partner C2 is able of binding to the at least one binding site Z2 of the multimerization reagent and/or an oligomeric particle regent. In this embodiment the second agent is bound to the multimerization reagent and/or an oligomeric particle regent via the bond formed between the binding partner C2 and the binding site Z2. In some embodiments, the second agent is any that can bind to IL-12R, IFNγR, IL-4R, IL-17R, RORγt, RORα, CXCR3, CCR7, CD62L, CXCR1 or CXCR4 (e.g. an anti-IL-12R antibody, an anti-IFNγR antibody, an anti-IL-4R antibody, and an anti-IL-17R antibody, anti-RORγt antibody, anti-RORα antibody, anti-CXCR3 antibody, anti-CCR7 antibody, anti-CD62L antibody, anti-CXCR1 antibody or anti-CXCR4 antibody, respectively).

In some embodiments, the culturing of the composition containing target cells (e.g. T cells) with the multimerized agent (e.g. anti-CD3/anti-CD28 mutein streptavidin or oligomer thereof) can be carried out in a bioreactor such as a hollow-fiber bioreactor (e.g. hollow fiber bioreactor of the Quantum® cell expansion system) or a plastic bag bioreactor (e.g. Cellbag® used in Xuri Cell Expansion System W25 from GE Healthcare).

In some embodiments, the method further includes contacting the cultured target cells (e.g. T cells) in the reaction mixture (e.g. containing the target cells, e.g. T cells, bound to the multimerization reagent and/or an oligomeric particle regent via, for example, the first agent and the second agent) with (i) a competition reagent (e.g. free first binding partner C, e.g. C1) or an analog thereof capable of disrupting the bond between the first binding partner, e.g. C1 and the binding site, e.g. Z1 and/or (such as if necessary) (ii) a second competition reagent, e.g. free second binding partner, e.g. C2, or an analog thereof, capable of disrupting the bond between the second binding partner C2 and the binding site Z2. By so doing the reversible bond between said binding partner C1 of the first agent and said binding sites Z1 as well as the reversible bond between said binding partner C2 of the second agent and said binding site Z2 of said multimerization reagent and/or an oligomeric particle regent is disrupted, thereby releasing in an eluate the T cells bound to the multimerization reagent and/or an oligomeric particle regent via the first agent and the second agent and disrupting the stimulation and/or expansion of the T cells.

In some embodiments, the competition reagent (e.g. the first and/or second competition reagent) is added within 14, days, 10 days, 7 days, or 5 days after initiation of the incubation, such as within 10 days, 9 days, 8 days, 7 days, 6 days, 5 days, 4 days, 3 days, 2 days or 1 day after initiation of the incubation. In particular embodiments, the competition reagent is added within 5 days after initiation of the incubation, such as within 4 days, 3 days, 2 days, or 1 day after the initiation of the incubation. In certain embodiments, the competition reagent is added within 1 day after the initiation of the incubation, such as within 18 hours, 16 hours, 12 hours, 8 hours, 6 hours, 4 hours, 3 hours, 2 hours, 90 minutes, 60 minutes, or 30 minutes after initiation of the incubation. Hence, by controlling the time at which the stimulation is disrupted, one or more particular features of the cultured T cells eluted from the multimerized agent can be altered as described herein. For example, in some embodiments, adding the competition reagent within 5 days, 4 days, 3 days, 2 days, or 1 day after the incubation is initiated will increase a stimulation, activation, enrichment, expansion, selection, and/or proliferation of one or more cultured cells.

In some embodiments, the method further includes separating or removing one or more of the components remaining after the reversible dissociation of components. In some embodiments, any unbound or residual biotin in the cultured target cells (e.g. T cells) can be separated or removed. In some embodiments, the multimerization reagent and/or an oligomeric particle regent is removed or separated from the cells in the cultured target cell composition. For example, in some embodiments, the separation/removal might be carried out using a second stationary phase. For this purpose, a mixture comprising the target cells (e.g. T cells) and the soluble multimerization reagent and/or an oligomeric particle regent bound to one or more agents are exposed, before or after being applied onto the first stationary phase described above, to chromatography on a suitable second stationary phase. This secondary stationary phase may be a gel filtration matrix and/or affinity chromatography matrix, wherein the gel filtration and/or affinity chromatography matrix comprises an affinity reagent. The affinity reagent comprised on the chromatography resin include a binding partner D that (specifically) binds to the binding site Z1 and/or binding site Z2, if present, of the multimerization reagent and/or an oligomeric particle regent bound to one or more agents, thereby immobilizing the multimerization reagent and/or an oligomeric particle regent bound to one or more agents on the stationary phase. If a streptavidin based multimerization reagent and/or an oligomeric particle regent bound to one or more agents is used and both first and second agents have a streptavidin binding peptide as binding partner C1 or C2, the binding partner D that is comprised in the affinity reagent of this second stationary phase can be biotin. The soluble oligomer of streptavidin or of a streptavidin mutein that is used as multimerization reagent and/or an oligomeric particle regent then binds to the biotin that is usually covalently coupled to a chromatography matrix such as biotin-Sepharose™ that is commercially available. In some such embodiments, the cultured cells (e.g. cultured T cells) can be recovered away from the multimerization reagent and/or an oligomeric particle regent.

A. Cells

Cells contained in the composition containing target cells generally are eukaryotic cells, such as mammalian cells, and typically are human cells. In some embodiments, the cells are derived from the blood, bone marrow, lymph, or lymphoid organs, or are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen.

In some embodiments, the reversibly-bound agents, such as multimerized agents, provided herein are capable of expanding a lymphocyte population or a subpopulation contained in the lymphocyte population. The lymphocyte population to be expanded may any suitable population, for example, a B cell population, a T cell population, or a natural killer cell population. The T-cell population may be an antigen-specific T cell population, a T helper cell population, a cytotoxic T cell, a memory T cell, a regulatory T cell, or a natural killer T cell population. Accordingly, in such embodiments of the multimerized reagent the first agent is able to stimulate a TCR/CD3 complex-associated signal in the T cells. The first agent present in the multimerized agent may thus be binding reagent that specifically binds CD3, while the second agent that binds the accessory molecule, such as may be a binding agent that specifically binds CD28, CD137, IL-12R, IFNγR, IL-4R, IL-17R, RORγt, RORα, CXCR3, CCR7, CD62L, CXCR1 or CXCR4.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

1. Preparation of Cells

In some embodiments, preparation of the cells includes one or more culture and/or preparation steps. The cells may be isolated from a sample, such as a biological sample, e.g., one obtained from or derived from a subject. In some embodiments, the subject from which the cells are isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. Separation methods may include any of those disclosed herein, including methods using reversible reagent systems, e.g., agents (such as receptor binding agents or selection agents) and reagents as described herein.

In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. (2012) Blood.1:72-82; Wang et al. (2012) J Immunother. 35(9):689-701. In some embodiments, combining $T_{CM}$-enriched CD8+ T cells and CD4+ T cells further enhances efficacy.

In embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps.

CD4+ T helper cells are sorted into naïve, central memory, and effector cells by identifying cell populations that have cell surface antigens. CD4+ lymphocytes can be obtained by standard methods. In some embodiments, naive CD4+T lymphocytes are CD45RO-, CD45RA+, CD62L+, CD4+ T cells. In some embodiments, central memory CD4+ cells are CD62L+ and CD45RO+. In some embodiments, effector CD4+ cells are CD62L− and CD45RO−

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead contains a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakuraet al. (2012) Blood.1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,1 77 to Riddell et al., Klebanoff et al.(2012) J Immunother. 35(9): 651-660, Terakuraet al. (2012) Blood.1:72-82, and/or Wang et al. (2012) J Immunother. 35(9):689-701.

In some embodiments, the T cells are expanded by adding to the composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

B. Apparatus and Articles of Manufactures

In some embodiments, also provided is an apparatus or article of manufacture. In some embodiments, provided is an arrangement of a bioreactor and a first stationary phase for chromatography. The bioreactor is suitable for the expansion of cells, and the stationary phase is suitable for cell separation and removal of reagents. The first stationary phase is a gel filtration matrix and/or affinity chromatography matrix, wherein the gel filtration and/or affinity chromatography matrix comprises an affinity reagent, wherein the affinity reagent comprises a binding site Z1 specifically binding to a binding partner C1 comprised in a first agent and/or the affinity reagent comprises a binding site Z2 specifically binding to a binding partner C2 comprised in a second agent. The first stationary phase is thereby being suitable of immobilizing thereon the first agent and/or the second agent, the first binding partner C1 and/or the free second binding partner C2. In addition the bioreactor and the stationary phase are fluidly connected. This arrangement can be used in the serial expansion as explained above and can be integrated into known cell expansion systems such as the Quantum® cell expansion system) or the Xuri Cell Expansion System W25.

In this arrangement the first stationary phase is either comprised in a chromatography column or is a planar stationary phase. The arrangement may further comprise a second stationary phase which is fluidly connected to the first stationary phase. The secondary stationary phase may be a gel filtration matrix and/or affinity chromatography matrix, wherein the gel filtration and/or affinity chromatography matrix comprises an affinity reagent. This affinity reagent may comprise a binding partner D that (specifically) binds to the binding site Z1 of the multimerization reagent and/or an oligomeric particle regent, thereby being suitable of immobilizing the multimerization reagent and/or an oligomeric particle regent on the stationary phase.

The invention is further directed to an apparatus for purification (e.g. selection) and culture, such as stimulation or expansion, of a composition of cells, the apparatus comprising at least one arrangement of a bioreactor and a first stationary phase and/or a second stationary phase for chromatography as defined above.

The apparatus may further comprise a plurality of arrangements of a bioreactor and a stationary phase being fluidly connected in series.

The apparatus may comprise a sample inlet being fluidly connected to the bioreactor of the arrangement of a bioreactor and the stationary phase for chromatography. The apparatus may also comprise a sample outlet for purified and expanded target cells, the sample outlet being fluidly connected to the stationary phase of the last of the at least one arrangement of a bioreactor and the stationary phase for chromatography.

In certain embodiments, the apparatus may be designed as a functionally closed system.

C. Exemplary Features of Cultured Cells

In some embodiments, the cultured target cells, (e.g. cultured T cells), which can include cultured cells generated or produced in accord with the methods provided herein, exhibit one or more specified phenotypic and/or functional features, based on or related to their proliferation capacity, surface marker expression, differentiation state, activation state and/or metabolic profile. In some embodiments, the culturing of the target cells (e.g. culturing of T cells) in accord with any of the provided methods results in a change in a parameter associated with the function (e.g. increase or decrease of a functional activity) or phenotype (e.g. higher or lower expression of a marker or markers) of cells compared to the corresponding or respective function or phenotype of cells in the composition prior to incubation in accord with methods provided herein. In some embodiments, the cultured T cells exhibit the change with respect to a parameter from among expansion and/or proliferation capacity, CD4+/CD8+ T cell distribution or ratio, surface marker expression, functional activity, or metabolic profile.

In some embodiments, the change in the parameter as measured in the cultured T cells is compared or with reference to the same or similar parameter as measured in a reference T cell composition or preparation. Typically, T cells in the reference T cell composition or preparation include or are derived from the same or substantially the same composition of T cells prior to incubation with the reversibly-bound agent (e.g. multimerized agent, such as incubation with a stimulatory agent reversibly bound to an oligomeric mutein streptavidin), except such cells were not subject to the incubation or were subject to a different incubation. In some embodiments, the reference T cell preparation is subject to the incubation using substantially the same protocol or conditions (e.g. type of stimulatory agents or agent, format of stimulatory agent or agents, substantially the same starting cell numbers, washes, presence or absence of additional reagents, timing of incubation, temperature of incubation), except at least one aspect, and in some cases only one aspect, of such incubation in a reference T cell preparation is different than in the incubation producing the cultured T cells.

In some embodiments, the reference T cell composition or preparation is the composition containing T cells prior to incubation with a reversibly-bound agent (e.g. multimerized agent, such as incubation with a stimulatory agent reversibly bound to an oligomeric mutein streptavidin).

In some embodiments, the cultured T cells are generated by incubation with a reversibly-bound agent (e.g. multimerized agent, such as incubation with a stimulatory agent reversibly bound to an oligomeric mutein streptavidin) for less than 28 days, 21 days, 14 day, 10 days, 9 days, 8 days, 7 days, 6 days, 5 days, 4 days, 3 days, 2 days, or 1 day and/or where the association of such agent with one or more molecules on the cell is disrupted (e.g. in the presence of a competition reagent, e.g. biotin or a biotin analog), such as disrupted with 28 days, 21 days, 14 day, 10 days, 9 days, 8 days, 7 days, 6 days, 5 days, 4 days, 3 days, 2 days, or 1 day of initiation of incubation with such agent. For example, in some aspects, cultured T cells are generated or produced following incubation with a reversibly-bound agent (e.g. multimerized agent, such as incubation with a stimulatory agent reversibly bound to an oligomeric mutein streptavidin) as described herein, wherein the incubation is terminated and/or disrupted within 28 days, 21 days, 14 day, 10 days, 9 days, 8 days, 7 days, 6 days, 5 days after initiation of such incubation (such as within or about 4, 3, 2, or 1 day, or less), and/or where a competing agent (e.g. biotin) that dissociates the reversibly-bound agent from the cells is added to the incubated cells within 28 days, 21 days, 14 day, 10 days, 9 days, 8 days, 7 days, 6 days, 5 days after initiation of such incubation (such as within or about 4, 3, 2, or 1 day, or less).

In some embodiments, the reference T cell preparation is generated or produced following incubation with the same or substantially the same reversibly-bound agent (e.g. multimerized agent, such as incubation with a stimulatory agent reversibly bound to an oligomeric mutein streptavidin), but where the incubation is performed for greater than 5 days, is not terminated and/or disrupted to lessen or terminate the signal induced or modulated in the cell, and/or where the T cell preparation is produced without the addition of a competing agent (e.g. biotin or biotin analog) that dissociates the reagent from the cells.

In some embodiments, the cultured T cells are generated by incubation with a reversibly-bound agent (e.g. multimerized agent, such as incubation with a stimulatory agent reversibly bound to an oligomeric mutein streptavidin) in which the receptor-binding agent (e.g. stimulatory agent) is one that does not bind to CD28 and/or induce signaling, i.e. is not an anti-CD28 antibody or fragment thereof. For example, in some embodiments, the cultured T cells are produced or generated following incubation with a reversibly-bound reagent in which one or more stimulatory agents are reversibly bound to a mutein streptavidin in which at least one stimulatory agent is specific for CD3 (e.g. anti-CD3 antibody or fragment thereof) and a second stimulatory agent can be specific for one or more of CD90, CD95, CD137, CD154, ICOS, LAT, CD27, OX40 or HVEM (e.g. an anti-CD90 antibody, an anti-CD95 antibody, an anti-CD137 antibody, and an anti-CD154 antibody, anti-ICOS antibody, anti-LAT antibody, anti-CD27 antibody, anti-OX40 antibody or anti-HVEM antibody, respectively, or antigen-binding fragments thereof). In some embodiments, the reference T cell preparation is a T cell culture generated or produced following incubation with a reversibly-bound agent (e.g. multimerized agent, such as incubation with a stimulatory agent reversibly bound to an oligomeric mutein streptavidin), but where the reagent comprises an agent that specifically binds CD28 and/or induces or modulates CD28 signaling. For example, in some embodiments, the reference T cell preparation is generated or produced following incubation of a T cell composition with anti-CD3/anti-CD28 Dynabeads®, anti-CD3/anti-CD28 ExPact® beads or other anti-CD3/anti-CD28 stimulatory agent. In some embodiments, such other anti-CD3/anti-CD28 stimulatory agent is one in which the antibody reagents are bound to a support (e.g. solid support), e.g. a bead, particle, magnetic particle or bead, nanoparticle or microsphere. In some embodiments, the cultured T cells are prepared by incubation with a reversibly-bound agent (e.g. multimerized agent, such as incubation with a stimulatory agent reversibly bound to an oligomeric mutein streptavidin) that is soluble, i.e. not bound to a support (e.g. solid support).

For example, in some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an enhanced expansion and/or proliferation capacity compared to a reference T cell composition or preparation. In some embodiments, the enhanced expansion and/or proliferation capacity comprises an increase in the number or percentage of CD3+ T cells, CD4+ T cells, and/or CD8+ T cells in the cultured T cells by at least about 2-fold (such as by at least about any of 3-fold, 4-fold, 5-fold, 6-fold, 7-fold, 8-fold, 9-fold, 10-fold, or more) compared to the number or percentage of CD3+ T cells, CD4+ T cells, and/or CD8+ T cells, respectively, in the reference T cell composition or preparation.

In some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an enhanced expansion and/or proliferation capacity of CD3+ T cells compared to a reference T cell culture. In some embodiments, the enhanced expansion and/or proliferation capacity comprises an increase in the number or percentage of CD3+ T cells in the cultured T cells by at least about 2-fold (such as by at least about any of 3-fold, 4-fold, 5-fold, 6-fold, 7-fold, 8-fold, 9-fold, 10-fold, or more) compared to the number or percentage of CD3+ T cells in the reference T cell composition or preparation.

In some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an enhanced expansion and/or proliferation capacity of CD4+ T cells compared to a reference T cell composition or preparation. In some embodiments, the enhanced expansion and/or proliferation capacity comprises an increase in the number or percentage of CD4+ T cells in the cultured T cells by at least about 2-fold (such as by at least about any of 3-fold, 4-fold, 5-fold, 6-fold, 7-fold, 8-fold, 9-fold, 10-fold, or more) compared to the number or percentage of CD4+ T cells in the reference T cell composition or preparation.

In some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an enhanced expansion and/or proliferation capacity of CD8+ T cells compared to a reference T cell composition or preparation. In some embodiments, the enhanced expansion and/or proliferation capacity comprises an increase in the number or percentage of CD8+ T cells in the cultured T cells by at least about 2-fold (such as by at least about any of 3-fold, 4-fold, 5-fold, 6-fold, 7-fold, 8-fold, 9-fold, 10-fold, or more) compared to the number or percentage of CD8+ T cells in the reference T cell composition or preparation.

In some embodiments, there are provided cultured T cells, such as prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), in which the cultured T cells are characterized by an altered CD8+/CD4+ T cell distribution or normalized T cell distribution, such as an altered CD8+/CD4+ ratio or normalized CD8+/CD4+ T cell ratio, compared to a reference T cell composition or preparation. The CD8+/CD4+ ratio or normalized ratio can be increased or decreased. In some embodiments, the altered CD8+/CD4+ T cell ratio results from an increase in the number or percentage or normalized number or percentage of CD8+ T cells in the cultured T cells relative or compared to the number or percentage or normalized number or percentage in a reference composition or preparation. In some embodiments, number of CD8+ T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of CD8+ T cells or the normalized number or percentage of CD8+ T cells in the reference T cell composition or preparation. In some embodiments, the ratio of CD8+/CD4+ T cells or the normalized ratio of CD8+/CD4+ is increased by at least about 2-fold (such as by at least about any of 3-fold, 4-fold, 5-fold, 6-fold, 7-fold, 8-fold, 9-fold, 10-fold, or more) compared to the ratio of CD8+/CD4+ T cells or the normalized ratio of CD8+/CD4+ in the reference T cell composition or preparation. In some embodiments, the number, percentage or ratio in the cultured T cells or in a composition or preparation is normalized to the number, percentage or ratio in the starting composition containing the T cells prior to the incubation.

In some embodiments, there are provided cultured T cells prepared according to any of the methods provided herein, wherein the cultured T cells are generated or produced following incubation with a reversibly-bound agent as described herein (e.g. multimerized agent, such as incubation with a stimulatory agent reversibly bound to an oligomeric mutein streptavidin), and wherein the cultured T cells are characterized by an altered surface marker expression profile compared to a reference T cell composition or preparation. In some embodiments, the altered surface marker expression profile is due to a change in the number or percentage of one or more subsets of T cells that are positive, negative or low for one or more surface markers selected from CD45RA, CD45RO, CD62L, CD69, CCR7, CD27, CD28, CD122, t-bet, IL-7Rα, CD95, IL-2Rβ, CXCR3, LFA-1, KLRG1. In some embodiments, the number or percentage of the T cell subset in the cultured T cells is increased at least about 2-fold (such as by at least about any of 3-fold, 4-fold, 5-fold, 6-fold, 7-fold, 8-fold, 9-fold, 10-fold, or more) compared to the number or percentage of the subset of T cells in the reference composition or preparation.

In some embodiments, the T cell subset in the cultured T cells (e.g. a T cell subset that is increased in the cultured T cells compared to the reference composition or preparation) exhibits a decreased or reduced differentiation or activation state compared to the reference T cell composition or preparation. In some embodiments, the T cell subset is not or does not include an effector T cell ($T_E$) or effector memory T cell ($T_{EM}$) phenotype. In some embodiments, the subset of T cells contains a surface phenotype that is one or more of $CD62L^+$, $CCR7^+$, $CD27^+$, $CD28^+$, or $KLRG1^{low/}$. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the T cell subset in the cultured T cells (e.g. a T cell subset that is increased in the cultured T cells compared to the reference composition or preparation) is positive for CD62L and/or IL-7Ru (CD127) and/or negative or low for t-bet. In some embodiments, the subset of T cells is positive for CD45RA and/or negative or low for CD45RO. In some embodiments, the subset of T cells is positive for one or more of CCR7, CD45RA, CD62L, CD27, CD28, IL-7Rα (CD127), CD95, IL-2Rβ, CXCR3, and LFA-1, and/or negative for CD45RO. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the T cell subset in the cultured T cells (e.g. a T cell subset that is increased in the cultured T cells compared to the reference composition or preparation) is or includes cells that are positive for CD62L (CD62L+). In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the T cell subset in the cultured T cells (e.g. a T cell subset that is increased in the cultured T cells compared to the reference composition or preparation) is or includes cells that are CD62L+ and a) any one or more of CD45RA$^{low/+}$, CD45RO$^{low/+}$, CCR7+ and CD27+ and b) any one or more of t-bet$^{low}$, IL-7Rα+(CD127+), CD95+, IL-2Rβ+, CXCR3+ and LFA-1+. In some embodiments, the T cell subset also can be CD3+, CD4+, or CD8+. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the T cell subset, such as a CD62L+ T cell subset, in the cultured T cells are or include or share phenotypic characteristics with memory T cells or particular subsets thereof, such as long-lived memory T cells. In some embodiments, such memory T cells are central memory T cells (Tcm) or T memory stem cells (Tscm) cells. In some embodiments, the memory T cells are Tscm cells. Tscm cells may be described as having one or more phenotypic differences or functional features compared to other memory T cell subsets or compared to naïve T cells, such as being less differentiated or more naïve (see e.g., Ahlers and Belyakov (2010) Blood, 115:1678); Cieri et al. (2015) Blood, 125:2865; Flynn et al. (2014) Clinical & Translational Immunology, 3, e20; Gattinoni et al. (2012) Nat. Med., 17:1290-1297; Gattinoni et al. (2012) Nat. Reviews, 12:671; Li et al. (2013) PLOS ONE, 8:e67401; and published PCT Appl. No. WO2014/039044). In some cases, Tscm cells are thought to be the only memory T cells able to generate effector T cells and all three subsets of memory T cells (Tscm, Tcm, and Tem). In some aspects, Tscm cells have the highest survival and proliferation response to antigenic or homeostatic stimuli of all the memory T cell subsets, and the least attrition absent cognate antigen. In some embodiments, the less-differentiated Tscm cells may exhibit greater expansion, long-term viability, and target cell destruction following adoptive transfer than other memory T cells, and thus may be able to mediate more effective treatment with fewer transferred cells than would be possible for either Tcm or Tem cells.

In some aspects, examples of phenotypic or functional features that have been reported or are known for Tscm cells include, for example, that such cells a) are CD45RO$^-$, CCR7$^+$, CD45RA$^+$, CD62L$^+$, CD27$^+$, CD28$^+$, IL-7Rα$^+$, CD95$^+$, IL-2Rβ$^+$+, CXCR3$^+$, and LFA-1$^+$; b) are CD45RA$^+$, CCR7$^+$, CD62L$^+$, and CD95$^+$; c) are CD45RA$^+$, CD45RO$^+$, CCR7$^+$, CD62L$^+$, CD27$^+$, CD28$^+$, CD95$^+$, and IL-2RD$^+$; d) are CD45RO$^-$, CD45RA$^+$, CCR7$^+$, CD62L$^+$, CD27$^+$, CD28$^+$, CD127$^+$, and CD95$^+$; e) are CD45RA$^+$, CD44$^{+/-}$, CD62L$^+$, CD127$^+$, IL-2R(3, CD28$^+$, CD43$^-$, KLRG1$^-$, Peforin$^-$, and GranzymeB$^-$; f) express high levels of CCR7, CD62L, CD27, and CD28, intermediate levels of CD95 and IL-2RD, low levels of CD45RA, and do not express CD45RO or KLRG-1; or g) express high levels of CD62L, low levels of CD44 and t-bet, and are Sca-1$^+$; and/or have intermediate IL-2-producing capacity, low IFNγ-producing capacity, low cytotoxicity, and high self-renewal capacity.

In some embodiments, the T cell subset in the cultured T cells (e.g. a T cell subset that is increased in the cultured T cells compared to the reference composition or preparation) is or includes memory T cells, such as long-lived memory T cells. In some embodiments, the memory T cells are central memory (Tcm) T cells. In some embodiments, the T cell subset has a phenotypic characteristic CD45RA–, CD45RO$^{low/+}$, CCR7+, CD62L+, CD27+, CD28+, CD95+ CD122+ and/or KLGR$^{low}$. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the memory T cells are stem central memory (Tscm) T cells. In some embodiments, the T cell subset has a phenotypic characteristic CD45RA$^{low/+}$, CD45RO$^{low/+}$, CCR7+, CD62L+, CD27+, CD28+, CD95+, CD122+ and/or KLGR1–. In some embodiments, the T cell subset has a phenotypic characteristic CD45RA$^{low/+}$, CD45RO$^-$, CCR7+, CD62L+, CD27+, CD28+, CD95+, CD122+ and/or KLGR1–. In some embodiments, the T cell subset has a phenotypic characteristic CD45RO$^-$, CCR7$^+$, CD45RA$^+$, CD62L$^+$, CD27$^+$, CD28$^+$, IL-7Rα$^+$, CD95+, IL-2Rβ$^+$, CXCRβ$^+$, and/or LFA-1$^+$. In some embodiments, the T cell subset has a phenotypic characteristic CD45RA$^+$, CCR7$^+$, CD62L$^+$, and/or CD95$^+$. In some embodiments, the T cell subset has a phenotypic characteristic CD45RA$^+$, CD45RO$^+$, CCR7$^+$, CD62L$^+$, CD27$^+$, CD28$^+$, CD95$^+$, and/or IL-2Rβ$^+$. In some embodiments, the T cell subset has a phenotypic characteristic CD45RO$^-$, CD45RA$^+$, CCR7$^+$, CD62L$^+$, CD27$^+$, CD28$^+$, CD127$^+$, and/or CD95$^+$. In some embodiments, the T cell subset has a phenotypic characteristic CD45RA$^+$, CD44$^{+/-}$, CD62L$^+$, CD127$^+$, IL-2Rβ$^+$, CD28$^+$, CD43$^-$, KLRG1$^-$, Peforin$^-$, and/or GranzymeB$^-$. In some embodiments, the T cell subset expresses high levels of CCR7, CD62L, CD27, and/or CD28, intermediate levels of CD95 and/or IL-2RD, low levels of CD45RA, and/or does not express CD45RO and/or KLRG-1. In some embodiments, the T cell subset expresses high levels of CD62L, low levels of CD44 and t-bet, and/or is Sca-1$^+$. In some embodiments, the T cell subset has a phenotypic characteristic intermediate IL-2-producing capacity, low IFNγ-producing capacity, low cytotoxicity, and/or high self-renewal capacity. In some embodiments, such a subset of T cells in the cultured T cells is increased by at least about 2-fold (such as by at least about any of 3-fold, 4-fold, 5-fold, 6-fold, 7-fold, 8-fold, 9-fold, 10-fold, or more) compared to the number or percentage of the subset of T cells in the reference T cell composition or culture.

In some embodiments, the subset of T cells, such as any subset of T cells described above, is present at a greater percentage of the total T cells in the cultured T cells or a greater number of total T cells in the cultured T cells compared to a reference T cell composition or preparation. In some embodiments, the percentage of the T cell subset in the cultured T cells as a percentage of the total T cells or total cells in the culture is at least 35%, 40%, 45%, 50%, 55%, 60%, 65%, 70%, 75%, 80%, 85%, 90%, 95% or more. n some embodiments, the percentage of the T cell subset in the cultured cells, such as any T cell subset described above, is greater, e.g. at least 1.5-fold greater, at least 2-fold, at least 3-fold, at least 4-fold, at least 5-fold or more greater, than the corresponding percentage of the subset of cells in a T cell in a T cell composition isolated or enriched directly from a human subject based on surface expression of one or markers comprising the phenotype, but without the incubation or culture. In some embodiments, the total number, relative number or normalized number of the T cells subset in the cultured cells, such as any T cell subset described above, is greater, e.g. at least 1.5-fold greater, at least 2-fold, at least 3-fold, at least 4-fold, at least 5-fold or more greater, than the number, relative number or normalized number of the T cell subset in a reference T cell composition or preparation, such as any reference T cell composition or preparation described above, e.g. the T cell composition prior to the incubation with the reversibly-bound agent (e.g. multimerized agent, such as incubation with a stimulatory agent reversibly bound to an oligomeric mutein streptavidin) in accord with any of the methods provided herein. In some embodiments, the number of T cells corresponding to the T cell subset present in the T cell culture is at least or at least about 1×10$^6$ cells, 2×10$^6$ cells, 3×10$^6$ cells, 4×10$^6$ cells, 5×10$^6$ cells or more.

In some embodiments, the T cell subset is CD62L+ and/or IL-7Rα+(CD127+) and the percentage of the CD62L+ and/or IL-7Rα+(CD127+) subset in the cultured T cells as a percentage of the total T cells or total cells in the culture is at least 35%, 40%, 45%, 50%, 55%, 60%, 65%, 70%, 75%, 80%, 85%, 90%, 95% or more. In some embodiments, the T cell subset is CD45RA−, CD45RO$^{low/+}$, and/or KLRG1$^{low}$ and the percentage of the CD45RA−, CD45RO$^{low/+}$, and/or KLRG1$^{low}$ subset in the cultured T cells as a percentage of the total T cells or total cells in the culture is at least 35%, 40%, 45%, 50%, 55%, 60%, 65%, 70%, 75%, 80%, 85%, 90%, 95% or more. In some embodiments, the T cell subset is CD45RA$^{low/+}$, CD45RO$^{low/+}$, and/or KLRG1− and the percentage of the CD45RA$^{low/+}$, CD45RO$^{low/+}$, and/or KLRG1− subset in the cultured T cells as a percentage of the total T cells or total cells in the culture is at least 35%, 40%, 45%, 50%, 55%, 60%, 65%, 70%, 75%, 80%, 85%, 90%, 95% or more.

In some embodiments, the T cell subset is or includes Tcm cells. In some embodiments, the percentage of the Tcm subset in the cultured T cells as a percentage of the total T cells or total cells in the culture is at least 35%, 40%, 45%, 50%, 55%, 60%, 65%, 70%, 75%, 80%, 85%, 90%, 95% or more.

In some embodiments, the T cell subset is or includes Tscm cells. In some embodiments, the percentage of the Tscm subset in the cultured T cells as a percentage of the total T cells or total cells in the culture is at least 35%, 40%, 45%, 50%, 55%, 60%, 65%, 70%, 75%, 80%, 85%, 90%, 95% or more.

In some embodiments, the subset of T cells, such as CD62L+ T cells, have or exhibit a) a low level of TCR rearrangement excisions circles (TREC); and/or b) express a proliferation marker (e.g., Ki-67); and/or c) exhibit the capacity to proliferate in the presence of a stimulatory agent; and/or d) exhibit a capacity to produce a cytokine selected from among IFN-gamma, TNF and IL-2 in the presence of a stimulatory agent; and/or e) are refractory to attrition in the absence of a stimulatory agent; and/or f) are able to generate Tscm, Tcm, Tem, and Teff cells; and/or g) have low cytotoxicity; and/or h) can produce the same or greater response following adoptive transfer of fewer cells than with Tcm or Tem cells. In some embodiments, the stimulatory agent is an antigen, a homeostatic cytokine (e.g., IL-15 or IL-17), or is an agent that is capable of initiating a TCR/CD3 complex-associated signal in the T cells. In some embodiments, the capacity to produce a cytokine comprises a low capacity to produce IFNγ and/or an intermediate capacity to produce IL-2.

In some embodiments, there are provided cultured T cells, such as prepared according to any of the methods provided herein, wherein the cultured T cells are generated or produced following incubation as described herein, and wherein the cultured T cells are characterized by a modified functional activity profile compared to a reference T cell composition or preparation. In some embodiments, the cultured T cells or a specific subset of T cells present in the culture exhibits an altered functional activity profile compared to a reference composition or preparation or compared to the subset of T cells in the reference composition or preparation, such as a functional activity that is altered (e.g. increased or decreased) at least 1.5-fold, 2-fold, 3-fold, 4-fold, 5-fold, 6-fold, 7-fold, 8-fold, 9-fold, 10-fold. In some embodiments, the functional activity is selected from one or more of a) a low level of TCR rearrangement excisions circles (TREC); and/or b) expression of a proliferation marker (e.g., Ki-67); and/or c) the capacity to proliferate in the presence of a stimulatory agent; and/or d) the capacity to produce a cytokine selected from among IFN-gamma, TNF and IL-2 in the presence of a stimulatory agent; and/or e) are refractory to attrition in the absence of a stimulatory agent; and/or f) are able to generate Tscm, Tcm, Tem, and Teff cells; and/or g) have low cytotoxicity. In some embodiments, the stimulatory agent is an antigen, a homeostatic cytokine (e.g., IL-15 or IL-17), or is an agent that is capable of initiating a TCR/CD3 complex-associated signal in the T cells. In some embodiments, the capacity to produce a cytokine comprises a low capacity to produce IFNγ and/or an intermediate capacity to produce IL-2. In some embodiments, the subset of T cells comprises memory T cells, such as long-lived memory T cells, in the cultured T cells. In some embodiments, the memory T cells are Tscm cells.

In some embodiments, the cultured T cells or a specific subset of T cells present in the culture can produce the same or greater response following adoptive transfer of fewer cells than can be achieved by a reference composition or preparation or by the subset of T cells in the reference composition or preparation. In some embodiments, such response is achieved with at least about 2-fold (such as by at least about any of 3-fold, 4-fold, 5-fold, 6-fold, 7-fold, 8-fold, 9-fold, 10-fold, or more) fewer cells. In some embodiments, the response is increased or is greater by at least about 2-fold (such as by at least about any of 3-fold, 4-fold, 5-fold, 6-fold, 7-fold, 8-fold, 9-fold, 10-fold, or more).

In some embodiments, the percentage of the T cell subset in the cultured cells, such as any T cell subset described above, is greater, e.g. at least 1.5-fold greater, at least 2-fold, at least 3-fold, at least 4-fold, at least 5-fold or more greater, than the corresponding subset of cells in a preparation of T cells that were incubated in the presence of a GSK-P inhibitor. In some embodiments, the composition of cultured T cells does not contain a GSK-P inhibitor.

In some embodiments, the percentage of the T cell subset in the cultured cells, such as any T cell subset described above, is greater, e.g. at least 1.5-fold greater, at least 2-fold, at least 3-fold, at least 4-fold, at least 5-fold or more greater, than the corresponding subset of cells that were incubated in the presence of a recombinant homeostatic cytokine, optionally IL-7 or IL-15. In some embodiments, the composition of cultured T cells does not contain a recombinant (e.g. exogenous) IL-7 cytokine or a recombinant (e.g. exogenous) IL-15 cytokine.

In some embodiments, the composition of cultured T cells was produced or generated in accord with any of the methods provided herein in which a substance, such as a competition agent, was added to T cells to disrupt, such as to lessen and/or terminate, the signaling of the stimulatory agent or agents. In some embodiments, the composition of cultured T cells contains the presence of a substance, such as a competition agent, e.g. biotin or a biotin analog, e.g. D-Biotin. In some embodiments, the substance, such as a competition agent, e.g. biotin or a biotin analog, e.g. D-Biotin, is present in an amount that is at least 1.5-fold greater, at least 2-fold, at least 3-fold, at least 4-fold, at least 5-fold, at least 10-fold, at least 100-fold, at least 1000-fold or more greater than the amount of the substance in a reference composition or preparation of cultured T cells in which the substance was not added exogenously during the incubation. In some embodiments, the amount of the substance, such as a competition agent, e.g. biotin or a biotin analog, e.g. D-Biotin, in the composition of cultured T cells is from or from about 10 µM to 100 µM, 100 µM to 1 mM, 100 µM to 500 µM or 10 µM to 100 PM.

IV. Methods of Genetically Engineering Cultured Cells, Antigen Receptors and Genetically Engineered Cells In some embodiments, the cultured cells contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8+ or CD4+ cells are enriched or selected. Among the compositions are pharmaceutical compositions and formulations for administration, such as for adoptive cell therapy. Also provided are therapeutic methods for administering the cells and compositions to subjects, e.g., patients.

Thus, in some embodiments, the cultured cells include one or more nucleic acids introduced via genetic engineering, and thereby express recombinant or genetically engineered products of such nucleic acids. In some embodiments, gene transfer is accomplished by first stimulating the cultured cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example, in some aspects, the cultured cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)). In some aspects, the cultured cells further are engineered to promote expression of cytokines or other factors.

A. Nucleic Acids Encoding Antigen Receptors, e.g. Chimeric Antigen Receptors

Provided are methods, nucleic acids, compositions, and kits for producing the genetically engineered cells. The genetic engineering generally involves introduction of a nucleic acid encoding the recombinant or engineered component into a composition containing the cultured cells, such as by retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

1. Chimeric Antigen Receptors (CARs)

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592,, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens targeted by the receptors in some embodiments include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, OEPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In certain embodiments of any of the methods provided herein, the target cells express a CAR that binds to an antigen associated with a disease and/or a cancer. In particular embodiments of any of the methods provided herein, the antigen is avP6 integrin (avb6 integrin), B cell maturation antigen (BCMA), B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, 0-acetylated GD2 (OGD2), ganglioside GD3, glycoprotein 100 (gp100), G Protein Coupled Receptor 5D (GPCR5D), Her2/neu (receptor tyrosine kinase erbB2), Her3 (erb-B3), Her4 (erb-B4), erbB dimers, human high molecular weight-melanoma-associated antigen (HMW-MAA), hepatitis B surface antigen, Human leukocyte antigen A1 (HLA-AI), human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, preferentially expressed antigen of melanoma (PRAME), progesterone receptor, a prostate specific antigen, prostate stem cell antigen (PSCA), prostate specific membrane antigen (PSMA), receptor tyrosine kinase like orphan receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms tumor 1 (WT-1), a pathogen-specific antigen or an antigen associated with a universal tag, and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR).

In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO2014031687.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3( ) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. In some aspects, the T cell costimulatory molecule is CD28 or 41BB.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

In some embodiments, the receptor, e.g., the CAR, expressed by the cells in the consecutive dose contains at least one immunoreactive epitope as the receptor, e.g., the CAR, expressed by the cells of the first dose. In some aspects, the receptor, e.g., the CAR, expressed by the cells administered in the consecutive dose is identical to the receptor, e.g., the CAR, expressed by the first dose or is substantially identical to the receptor, e.g., the CAR, expressed by the cells of administered in the first dose.

The recombinant receptors, such as CARs, expressed by the cells administered to the subject in the various doses generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells in the first dose express a CAR that specifically binds to an antigen expressed by a cell or tissue of the disease or condition or associated with the disease or condition.

2. TCRs

In some embodiments, the genetically engineered antigen receptors include recombinant T cell receptors (TCRs) and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; an Hackett et al. (2010) Molecular Therapy: The Journal of the American Society of Gene Therapy. 18:674-683.

3. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptors include intracellular signaling domains of costimulatory receptors that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

B. Vectors and Methods for Genetic Engineering

Various methods for the introduction of genetically engineered components, e.g., antigen receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cultured cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some cases, a vector may be used that does not require that the cells, e.g., T cells, are activated. In some such instances, the cells may be selected and/or transduced prior to activation. Thus, the cells may be engineered prior to, or subsequent to the culturing of the cells as described herein, and in some cases at the same time as or during at least a portion of the culturing. In some embodiments, the cells that to be engineered are the cultured cells, or in some cases, cells may be transduced prior to performing the culturing as described herein.

C. Methods of Transducing Cells

In some embodiments, the methods of transferring viral viral into cell is carried out using any of the provided oligomeric protein (e.g. streptavidin or streptavidin mutein) reagent. In some embodiments, the oligomeric protein reagent used in accord with the provided transduction methods is a multimerization reagent and/or an oligomeric particle regent bound to one or more agents. In some embodiments, the cells are for use in cell therapy, such as primary cells prepared for autologous or allogeneic transfer, e.g., in adoptive cell therapy. In some embodiments, the reagent also can be exploited in the methods to facilitate one or more other processing step associated with preparing an engineered cell composition, such as one or more of selection or modulation, activation and/or stimulation of cells. The methods may include additional cell processing steps, such as cell washing, isolation, separation, formulation or other steps related to producing a cell composition.

In some embodiments, the provided methods are used to introduce viral vector particles, such as retroviral vector particles, into cells, such immune cells, including T cells. In some embodiments, the viral vector particles have a genome that contains a nucleic acid encoding an antigen receptor, such as a chimeric antigen receptor (CAR) or transgenic T cell receptor (TCR). Hence, in some embodiments, the provided methods can be used for expressing in immune cells, such as T cells, a genetically engineered antigen receptor, such as a transgenic TCR or a CAR. Also provided are cells transduced by such particles and methods and compositions containing such cells, and methods for using the same.

In some embodiments, the retroviral vector particles and methods include features that result in an increased transduction of immune cells and/or certain populations and/or subpopulations thereof, desirable for use in adoptive immunotherapy. In some embodiments of the provided transduction methods and viral vector particles, cells, e.g., T cells, in the populations being transduced are not or need not be stimulated and/or activated prior to and/or in conjunction with contacting or incubating the cells with the provided retroviral vector particle.

a. Incubating Cells with Viral Vector Particles

In some embodiments, the provided methods involve methods of transducing cells by contacting, e.g. incubating, a cell composition comprising a plurality of cells (hereinafter also called an "input composition") with a (1) an oligomeric protein (e.g. streptavidin mutein) reagent, such as a multimerization reagent and/or an oligomeric particle regent bound to one or more agents and (2) a viral particle. In some embodiments, the method involves admixing the cells with the reagent and with the viral particles simultaneously or sequentially. In some embodiments, the method involves premixing the viral particles and the reagent together and then contacting the cell composition with the mixture of viral particles associated with the reagent. In some embodiments, the contacting is for 30 minutes to 72 hours, such as 30 minute to 48 hours, 30 minutes to 24 hours or 1 hour to 24 hours, such as at least or about at least 30 minutes, 1 hour, 2 hours, 6 hours, 12 hours, 24 hours, 36 hours or more.

In some embodiments of any of the methods provided herein, (i) the incubating includes admixing the target cells with the reagent, and/or admixing the target cells with the viral particle, sequentially, in either order, optionally wherein the admixing in (a) and the admixing in (b) are carried out within a period of no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, or 72 hours and/or the admixing in (a) is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours apart from the admixing in (b); (ii) the incubating includes admixing the target cells, the reagent, and the viral particle, said admixing carrired out simultaneously or substantially simultaneously; (iii) the incubating includes admixing a composition that contains the target cells and the viral particles, and not including the reagent,, optionally wherein: no more than 5%, 10%, 20%, 30%, or 40% of the target cells in the composition including the target cells and the reagent are activated cells, express a surface marker selected from the group consisting of HLA-DR, CD25, CD69, CD71, CD40L and 4-1BB; includes intracellular expression of a cytokine selected from the group consisting of IL-2, IFNgamma, TNF-alpha, and/or are capable of proliferating; and/or the admixing is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours following an admixing of the target cells and the viral particles in the composition; (iv) the incubation includes admixing a composition that contains the target cells and the reagent, and not including the viral particle, with the viral particle, optionally wherein: no more than 5%, 10%, 20%, 30%, or 40% of the target cells in the composition including the target cells and the reagent activated cells, express a surface marker selected from the group consisting of HLA-DR, CD25, CD69, CD71, CD40L and 4-1BB; including intracellular expression of a cytokine selected from the group consisting of IL-2, IFNgamma, TNF-alpha, and/or are capable of proliferating; and/or the admixing is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours following an admixing of the target cells and the viral particles in the composition; and/or (v) the incubation includes admixing a composition including the viral particles and the reagent with a composition that contains the target cells and not the viral particle and/or not the reagent, optionally wherein: no more than 5%, 10%, 20%, 30%, or 40% of the target cells in the composition including the target cells and the reagent are activated cells express a surface marker selected from the group consisting of HLA-DR, CD25, CD69, CD71, CD40L and 4-1BB; includes intracellular expression of a cytokine selected from the group consisting of IL-2, IFNgamma, TNF-alpha, and/or are capable of proliferating.

In some embodiments, the incubating includes admixing the cell with the reagent and with the viral particle, simultaneously or sequentially, in either order. In some embodiments, during at least a portion of the incubating, the reagent and viral particle are in the presence of or contacted with the cell simultaneously.

In some embodiments, the provided methods involve (a) contacting a viral particle with an oligomeric protein reagent, thereby generating a composition including viral particles and the reagent, wherein the viral particles are optionally associated with the reagent; and (b) incubating the composition in (a) with a plurality of cells including target cells, wherein the method produces an output composition including one or more cells transduced with the viral particle.

In some embodiments, the provided methods involve admixing a composition containing viral particles and an oligomeric protein reagent with a plurality of cells including target cells, wherein the method produces an output composition including one or more cells transduced with the viral particle.

In some embodiments, the provided methods involve (a) contacting a viral particle with an oligomeric protein reagent including a streptavidin or mutein or a biologically active fragment of any of the foregoing, and/or multiple subunits of any of the foregoing, thereby generating a composition including viral particles and the reagent, wherein the viral particles are optionally associated with the reagent; and (b) incubating the composition in (a) with a plurality of cells, wherein the method produces an output composition including one or more cells transduced with the viral particle.

In some embodiments, the provided methods involve admixing a composition containing viral particles and a protein reagent with a plurality of cells including target cells, wherein: the protein reagent includes a streptavidin, an avidin, a streptavidin analog or mutein, an avidin analog, a mutein or a biologically active fragment of any of the foregoing, and/or multiple subunits of any of the foregoing; and the method produces an output composition including one or more cells transduced with the viral particle. In some embodiments, the reagent and/or each of the monomeric units and/or each of the multimeric units, has a net positive charge or an overall positive charge.

In some embodiments, the provided methods involve incubating a plurality of cells including target cells with: 1) an oligomeric protein reagent including a plurality of binding sites capable of reversibly binding to a binding agent, wherein one or more binding sites are reversibly bound to the binding agent; and 2) a viral particle, wherein at least a portion of the incubation in (1) occurs simultaneously with (2) and wherein the method produces an output composition including one or more cells transduced with the viral particle.

In some embodiments, the provided methods involve (1) contacting (a) a composition including one or more viral particles and (b) a binding agent that is a viral-binding agent that (i) is capable of specifically binding to a molecule on the surface of the viral particle and ii) is reversibly bound to a reagent including a plurality of binding sites capable of reversibly binding to the viral-binding agent; and (2) incubating at least a plurality of cells including target cells in the presence of the one or more viral particles, wherein the contacting in (1) and the incubating in (2) are carried out simultaneously or sequentially, in either order, wherein the method generates an output composition including a plurality of cells transduced with the viral particle.

In some embodiments of any of the methods provided herein, the contacting in (1) and the incubating in (2) are carried out within a period of no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, or 72 hours and/or the admixing in (a) is carried out no more than 1 hour, 2 hours, 3 hours, 4 hours, 5 hours, 6 hours, 7 hours, 8 hours, 9 hours, 10 hours, 11 hours, 12 hours, 18 hours, 24 hours, 36 hours, or 48 hours apart from the incubating in (b). In some embodiments, the viral vector particle comprises a genome encoding a recombinant antigen receptor, optionally a chimeric antigen receptor.

The composition that contains the viral vector particles and cells during the transduction step may further include one or more additional agents, such as those to promote transduction efficiency, such as polycations including protamine (e.g. protamine sulfate), hexadimethrine bromide (POLYBRENE®, Abbott Laboratories Corp), and CH-296 (RETRONECTIN®, Clontech). In some embodiments, the polycation can be present in the input composition at a final concentration of 1 µg/mL to 100 µg/mL, such as 5 µg/mL to 50 µg/mL. The composition may also include media, including cell culture medium including medium designed for culture of the cell type to be processed, such as hematopoietic stem cell medium, e.g., serum free medium.

In some embodiments, the concentration of cells of the input composition is from or from about $1.0 \times 10^5$ cells/mL to $1.0 \times 10^8$ cells/mL, such as at least or about at least or about $1.0 \times 10^5$ cells/mL, $5 \times 10^5$ cells/mL, $1 \times 10^6$ cells/mL, $5 \times 10^6$ cells/mL, $1 \times 10^7$ cells/mL, $5 \times 10^7$ cells/mL or $1 \times 10^8$ cells/mL.

In some embodiments, the viral particles are provided at a certain ratio of copies of the viral vector particles or infectious units (IU) thereof, per total number of cells (IU/cell) in the input composition or total number of cells to be transduced. For example, in some embodiments, the viral particles are present during the contacting at or about or at least at or about 0.5, 1, 2, 3, 4, 5, 10, 15, 20, 30, 40, 50, or 60 IU of the viral vector particles per one of the cells.

In some embodiments, the titer of viral vector particles is between or between about $1 \times 10^6$ IU/mL and $1 \times 10^8$ IU/mL, such as between or between about $5 \times 10^6$ IU/mL and $5 \times 10^7$ IU/mL, such as at least $6 \times 10^6$ IU/mL, $7 \times 10^6$ IU/mL, $8 \times 10^6$ IU/mL, $9 \times 10^6$ IU/mL, $1 \times 10^7$ IU/mL, $2 \times 10^7$ IU/mL, $3 \times 10^7$ IU/mL, $4 \times 10^7$ IU/mL, or $5 \times 10^7$ IU/mL.

In some embodiments, transduction can be achieved at a multiplicity of infection (MOI) of less than 100, such as generally less than 60, 50, 40, 30, 20, 10, 5 or less.

In some embodiments, contacting is performed in solution, such as using a souble oligomeric protein (e.g. streptavidin mutein) reagent or multimerization reagent and/or an oligomeric particle regent bound to one or more agents. In some embodiments, the cells, oligomeric reagent and viral particles are contacted in a volume of from or from about 0.5 mL to 500 mL, such as from or from about 0.5 mL to 200 mL, 0.5 mL to 100 mL, 0.5 mL to 50 mL, 0.5 mL to 10 mL, 0.5 mL to 5 mL, 5 mL to 500 mL, 5 mL to 200 mL, 5 mL to 100 mL, 5 mL to 50 mL, 5 mL to 10 mL, 10 mL to 500 mL, 10 mL to 200 mL, 10 mL to 100 mL, 10 mL to 50 mL, 50 mL to 500 mL, 50 mL to 200 mL, 50 mL to 100 mL, 100 mL to 500 mL, 100 mL to 200 mL or 200 mL to 500 mL.

In some embodiments, when the contacting is carried out in solution, e.g. using a soluble oligomeric protein (e.g. streptavidin mutein) reagent, the contacting can be carried out in which at least a portion of the contacting is with centrifugation, such as spinoculation (e.g. centrifugal inoculation). In some embodiments, the composition containing cells, viral particles and reagent can be rotated, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm). In some embodiments, the rotation is carried at a force, e.g., a relative centrifugal force, of from or from about 100 g to 3200 g (e.g. at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In some embodiments, the oligomeric reagent, such as multimerization reagent and/or an oligomeric particle regent bound to one or more agents, is not bound to a support, such as not bound to a solid surface or stationary phase.

In some embodiments, the oligomeric reagent, such as multimerization reagent and/or an oligomeric particle regent bound to one or more agents, is immobilized on a support, such as a solid surface or stationary phase. In some embodiments, the contacting is performed in a stationary phase, such as using a chromatography matrix in which is immobilized thereon the protein (streptavidin mutein), such as an oligomeric protein (e.g. streptavidin mutein) reagent. Exemplary of such formats for use in connection with the provided methods are described herein. Thus, in some embodiments, an on-column transduction can be performed in accord with the provided methods.

In some embodiments, the input composition that is contacted with the cells comprises activated cells. In some embodiments, at least 40%, 50%, 60%, 70%, 80%, 90% or more of the cells, e.g. T cells, in the input composition are activated, such as, in some cases, are surface positive for one or more of HLA-DR, CD25, CD69, CD71, CD40L and/or 4-1BB. In some embodiments, cells are activated with an activating agent, such as in the presence of anti-CD3/anti-CD28, prior to initiation of the contacting, e.g. prior to initiation of transduction. Methods of expanding T cell populations in vitro in the absence of exogenous growth factors or low amounts of exogenous growth factors are known in the art (see e.g. U.S. Pat. No. 6,352,694 B1 and European Patent EP 0 700 430 B1). In general, such methods employ a solid phase surfaces of greater than 1 µM to which various bind agents (e.g. anti-CD3 antibody and/or anti-CD28 antibody) are immobilized. For example, Dynabeads® CD3/CD28 (Invitrogen) are commercially available reagents for T cell expansion, which are uniform, 4.5 µm superparamagnetic, sterile, non-pyrogenic polystyrene beads coated with a mixture of affinity purified monoclonal antibodies against the CD3 and CD28 cell surface molecules on human T cells. In some embodiments, the activating agent, e.g. anti-CD3 and/or anti-CD28, can be immobilized on beads, such as magnetic beads.

In some embodiments, the cell activation is also performed in the presence IL-2 (e.g. from or from about 50 IU/mL to 200 IU/mL, such as or about 100 IU/mL). In some embodiments, the activation is carried out between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some embodiments, the activation is carried out at a temperature greater than or greater than about 25° C., such as generally greater than or greater than about 32° C., 35° C. or 37° C., for example at or about 37° C.±2° C., such as at a temperature of at or about 37° C.

In some embodiments, cells are not activated with an activating agent, such as in the presence of anti-CD3/anti-CD28, prior to initiation of the contacting, e.g. prior to initiation of transduction. In some embodiments, the input composition that is contacted with the cells comprises a plurality of resting cells. In some embodiments, at least 40%, 50%, 60%, 70%, 80%, 90% or more of the T cells in the population are resting T cells, such as T cells that lack a T cell activation marker, such as a surface marker or intracellular cytokine or other marker, and/or T cells that are in the $G_0$ or $G_0G_{1a}$ stage of the cell cycle.

In particular aspects, the provided methods allow transduction to happen in T cells without the need for activation prior to the contacting and/or incubation with the oligomeric protein reagent, such as multimerization reagent and/or an oligomeric particle regent bound to one or more agents. In some embodiments, the methods include transducing a population of T cells that contain resting or naïve T cells with a viral vector in the presence of an oligomeric protein (e.g. streptavidin) reagent in accord with the provided methods, without first, i.e. prior to the transduction, activating and/or stimulating the T cells. In some such embodiments, the provided methods can be used to prepare immune cells, such as T cells, for adoptive therapy, that do not include a step of activating and/or stimulating T cells.

In some embodiments, the oligomeric protein (e.g streptavidin mutein) is naked.

In some embodiments, the oligomeric protein (e.g. streptavidin mutein) is a multimerization reagent and/or an oligomeric particle regent bound to one or more agents that has bound thereto one or more binding agent that is capable of binding to a molecule on the surface of targets cells (e.g. T cells) or, in some cases, on the surface of viral particles in the composition. In some embodiments, the binding agent is reversibly bound to a reagent containing a plurality of binding sites capable of reversibly binding to the agent. In some embodiments, the incubation is performed under conditions in which the agent binds, such as specifically binds, to the molecule on the cell or viral particle. In some embodiments as described, the oligomeric reagent has reversibly immobilized thereon (bound thereto) an agent or agents (e.g. first or second or third, etc.), which can include receptor-binding, e.g. stimulatory agent or accessory agents, selection agent or viral-binding agents, which can be used for the selection, stimulation, expansion and/or differentiation of cells or modulation of transduction of cells.

In some cases, for certain receptor-binding agents (e.g. stimulatory agents or accessory agents), such binding can induce or modulate a signal in target cells (e.g. T cells) in the compositions, such as a primary signal or accessory signal as described. In some embodiments, binding of the agent to the molecule results in one or more of the stimulation, activation, expansion (proliferation) and/or differentiation of target cells in the composition. In some embodiments, the reagent comprises a stimulatory agent that provides a primary activation signal to the cells, wherein the stimulatory agent comprises at least one binding partner C (e.g. C1, C2 or C3, etc), wherein the binding partner C is able of reversibly binding to the binding site Z1 of the oligomeric reagent reagent for reversible binding of the agent. In some embodiments, the reagent comprises an accessory agent that provides an accessory signal to the cells, wherein the accessory agent comprises at least one binding partner C (e.g. C1, C2 or C3, etc), wherein the binding partner C is able of reversibly binding to the binding site Z1 of the oligomeric reagent reagent for reversible binding of the agent. In some embodiments, the reagent comprises a selection agent that specifically targets binding to a particular cell surface molecule or marker, wherein the selection agent comprises at least one binding partner C (e.g. C1, C2 or C3, etc), wherein the binding partner C is able of reversibly binding to the binding site Z1 of the oligomeric reagent reagent, for reversible binding of the agent.

In some embodiments, activation of the cells in the input composition is initiated during the contacting of cells of the input composition with the oligomeric protein reagent and/or viral particle. In such instances, the oligomeric protein reagent can have immobilized thereon a receptor binding agent, e.g. stimulatory agent and/or accessory agent, capable of inducing or modulating a signal in the cells, such as T cells. In some embodiments, the stimulatory agent comprises an MHC I:peptide complex or functional portion thereof, an MHCII:peptide complex or functional portion thereof, and/or is capable of delivering a stimulatory signal through a TCR/CD3 complex in a T cell, a CD3-containing complex in a T cell, and/or an ITAM-containing molecule in a T cell. In some embodiments, the oligomeric reagent can have immobilized thereon an accessory agent capable of provided an accessory signal to the cells, such as T cells. In some embodiments, the receptor binding agent, e.g. stimulatory agent and/or accessory agent, is any agent as described herein, such as anti-CD3 and/or anti-CD28 antibody (e.g. Fabs). Alternatively, it is also possible to use as the stimulatory agent a ligand, such as a natural ligand, of a receptor that triggers of cell expansion. For example, the extracellular domain of CD19 can be used to cause the activation of intracellular signaling cascades of cells transduced to express chimeric CD19 binding antigen receptor (CAR). In some embodiments, the oligomeric protein (e.g. streptavidin) reagent is able to both modulate cell transduction and activate, such as stimulate cells, during the contacting and, optionally the further incubation. In some embodiments, binding of the oligomeric reagent comprising the stimulating agent is reversible, such as in the presence of a competing agent, e.g. biotin.

In some embodiments, the provided method can be used for selectively inducing transduction and/or ex vivo expansion of a specific population of cells such as B cells, T cells or natural killer cells. In some embodiments, the oligomeric protein (e.g. streptavidin mutein) reagent is a multimerization reagent and/or an oligomeric particle regent bound to one or more agents that can include at least one selection agent reversibly bound to the same reagent used for modulating transduction. In some embodiments, the oligomeric (e.g. streptavidin mutein) reagent is a multimerization reagent and/or an oligomeric particle regent bound to one or more agents that can contain the selection agent and one or both of the first or second receptor binding agents (e.g. stimulatory agent or accessory agent) on the same reagent. In some embodiments, the oligomeric protein (e.g. streptavidin) reagent, such as multimerization reagent and/or an oligomeric particle regent bound to one or more agents, is able to both modulate cell transduction and preferentially target the transduction to a particular subpopulation of selected or targeted cells. In some embodiments, the oligomeric protein (e.g. streptavidin) reagent, such as multimerization reagent and/or an oligomeric particle regent bound to one or more agents, is able to modulate cell transduction, such as preferentially target the transduction to a particular subpopulation of selected or targeted cells, and activate, such as stimulate cells, during the contacting and, optionally the further incubation.

In some embodiments, binding of the oligomeric reagent comprising the binding agents, e.g. selection agent and/or stimulatory agent, is reversible, such as in the presence of a competing agent, e.g. biotin. As described below, in some aspects, the method includes adding or incubating the composition containing cells, viral particles and oligomeric reagent (e.g. multimerization reagent and/or an oligomeric particle regent bound to one or more binding agent) with a competition substance to reverse, dissociate or disrupt binding of the one or more binding agent to the cell or viral particles. In some embodiments, following the reversal, dissociation or disruption, one or more components of the composition can be removed, such as the dissociated oligomeric reagent, one or more binding agent and/or the competition substance..

In some embodiments, cells produced from the provided method (hereinafter also called "output composition" or "incubated composition") include those transduced with the viral vector, such as a viral vector containing nucleotides encoding a heterologous protein, such as a recombinant receptor, e.g. a CAR. By heterologous in this context refers to a protein that is not normally expressed from a virus and/or not encoded by a viral genome. In some embodiments, integration of a viral vector into a host genome can be assessed by measuring the level of expression of a recombinant protein, such as a heterologous protein, encoded by a nucleic acid contained in the genome of the viral vector particle following incubation. A number of well-known methods for assessing expression level of recombinant molecules may be used, such as detection by affinity-based methods, e.g., immunoaffinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof.

V. Compositions, Formulations and Methods of Administration

Also provided are compositions containing the engineered receptor (e.g., engineered antigen receptor), such as CAR or TCR, and compositions containing the engineered cells, including pharmaceutical compositions and formulations. Also provided are methods of using and uses of the compositions, such as in the treatment of diseases, conditions, and disorders in which the antigen is expressed, or in detection, diagnostic, and prognostic methods.

A. Compositions/Formulations

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being treated with the cells, preferably those with activities complementary to the cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

B. Methods of Administration

Provided are methods of administering the cells, populations, and compositions, and uses of such cells, populations, and compositions to treat or prevent diseases, conditions, and disorders, including cancers. In some embodiments, the cells, populations, and compositions are administered to a subject or patient having the particular disease or condition to be treated, e.g., via adoptive cell therapy, such as adoptive T cell therapy. In some embodiments, cells and compositions prepared by the provided methods, such as engineered compositions and end-of-production compositions following incubation and/or other processing steps, are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) PLoS ONE 8(4): e61338.

As used herein, a "subject" is a mammal, such as a human or other animal, and typically is human. In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments. In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

VI. Definitions

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X". In particular embodiments, "about" is ±25%, ±20%, ±15%, ±10%, ±5%, ±1%, ±0.5%, ±0.1%, ±0.01%, or ±0.001%.

As used herein, a composition refers to any mixture of two or more products, substances, or compounds, including cells. It may be a solution, a suspension, liquid, powder, a paste, aqueous, non-aqueous or any combination thereof.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

As used herein, a subject includes any living organism, such as humans and other mammals. Mammals include, but are not limited to, humans, and non-human animals, including farm animals, sport animals, rodents and pets.

As used herein, a control refers to a sample that is substantially identical to the test sample, except that it is not treated with a test parameter, or, if it is a plasma sample, it can be from a normal volunteer not affected with the condition of interest. A control also can be an internal control.

VII. Exemplary Embodiments

Among the provided embodiments are:

1. An oligomeric particle reagent comprising a plurality of streptavidin or streptavidin mutein molecules, wherein the size of the oligomeric particle reagent comprises i) a radius of greater than 25 nm, ii) a molecular weight of at least $5\times10^6$ g/mol; and/or (iii) at least 100 streptavidin or streptavidin mutein tetramers per oligomeric particle reagent.

2. The oligomeric particle reagent of embodiment 1, wherein the streptavidin or streptavidin mutein molecules bind to or are capable of binding to biotin, avidin, a biotin analog or mutein, an avidin analog or mutein, and/or a biologically active fragment thereof, or a streptavidin-binding peptide.

3. The oligomeric particle reagent of embodiment 2, wherein the streptavidin or streptavidin mutein molecules reversibly bind to or are capable of reversibly binding to biotin, avidin, a biotin analog or mutein, an avidin analog or mutein, and/or a biologically active fragment thereof, or a streptavidin-binding peptide.

4. The oligomeric particle reagent of any of embodiments 1-3, wherein the oligomeric particle reagent comprises a plurality of streptavidin mutein molecules, wherein the streptavidin mutein molecules comprising the amino acid sequence $Val^{44}$-$Thr^{45}$-$Ala^{46}$-$Arg^{47}$ (SEQ ID NO: 62) or $Ile^{44}$-$Gly^{45}$-$Ala^{46}$-$Arg^{47}$ (SEQ ID NO: 63) at sequence positions corresponding to positions 44 to 47 with reference to positions in streptavidin in the sequence of amino acids set forth in SEQ ID NO: 1.

5. The oligomeric particle reagent of any of embodiments 1-4, wherein the oligomeric particle reagent comprises a plurality of streptavidin mutein molecules that comprise:
  a) the sequence of amino acids set forth in any of SEQ ID NOS: 3-6, 27, 28, 60, or 61;
  b) a sequence of amino acids that exhibit at least 85%, 86%, 87%, 88%, 89%, 89%, 90%, 91%, 92%, 93%, 94%, 95%, 96%, 97%, 98%, 99% or more sequence identity to any of SEQ ID NOS: 3-6, 27, 28, 60, or 61 and contain the amino acid sequence corresponding to $Val^{44}$-$Thr^{45}$-$Ala^{46}$-$Arg^{47}$ (SEQ ID NO: 62) or $Ile^{44}$-$Gly^{45}$-$Ala^{46}$-$Arg^{47}$ (SEQ ID NO: 63) and/or reversibly bind to biotin or a biologically active form thereof, a biotin analog or mutein or a biologically active fragment thereof or a streptavidin-binding peptide; or
  c) a functional fragment of a) or b) that reversibly binds to biotin or a biologically active form thereof, a biotin analog or mutein or a biologically active fragment thereof or a streptavidin-binding peptide.

6. The oligomeric particle reagent of any of embodiments 1-5, wherein the oligomeric particle reagent comprises a plurality of streptavidin mutein molecules that comprise the sequence of amino acids set forth in SEQ ID NO: 6 or 61.

7. The oligomeric particle reagent of any of embodiments 4-6, wherein the streptavidin mutein molecule further comprises an amino acid replacement or replacements at a position corresponding to 117, 120 and/or 121 with reference to positions in streptavidin in the sequence of amino acids set forth in SEQ ID NO:1.

8. The oligomeric particle reagent of embodiment 7, wherein:
  the amino acid replacement or replacements are selected from among Glu117, Asp117, Arg117, Ser120, Ala120, Gly120, Trp121, Tyr121 or Phe121; or
  the amino acid replacement or replacements are selected from one or more of Glu117, Gly120 or Tyr121; or
  the amino acid replacements are selected from Glu117, Gly120 or Tyr121.

9. The oligomeric particle reagent of any of embodiments 1-8, wherein the oligomeric particle reagent comprises a plurality of streptavidin mutein molecules that comprise:
  a) the sequence of amino acids set forth in SEQ ID NO: 27 or 28;
  b) a sequence of amino acids that exhibits at least 85%, 86%, 87%, 88%, 89%, 89%, 90%, 91%, 92%, 93%, 94%, 95%, 96%, 97%, 98%, 99% or more sequence identity to SEQ ID NO: 28 and contains the amino acid sequence corresponding to $Val^{44}$, $Thr^{45}$, $Ala^{46}$, $Arg^{47}$, $Glu^{117}$, $Gly^{120}$ and $Tyr^{121}$ and/or reversibly binds to biotin or a biologically active fragment, a biotin analog or mutein or a biologically active fragment thereof or a streptavidin-binding peptide; or
  c) a functional fragment of a) or b) that reversibly binds to biotin or a biologically active fragment, a biotin analog or mutein or a biologically active fragment thereof or a streptavidin-binding peptide.

10. The oligomeric particle reagent of any of embodiments 1-9, wherein the oligomeric particle reagent is bound to or is capable of binding to one or more agents.

11. The oligomeric particle reagent of embodiment 10, wherein the one or more agents comprise a binding partner, wherein the binding partner is capable of binding, optionally reversibly binding, to one or more binding site on the oligomeric particle reagent.

12. The oligomeric particle reagent of embodiment 11, wherein the binding partner comprises a streptavidin-binding peptide.

13. The oligomeric particle reagent of embodiment 11 or 12, wherein the binding partner comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

14. The oligomeric particle reagent of any of embodiments 10-13, wherein the one or more agents binds or is capable of binding to a molecule expressed on the surface of a target cell.

15. The oligomeric particle reagent of any of embodiments 10-14, wherein the one or more agents is or comprises an antibody or an antigen-binding fragment thereof.

16. The oligomeric particle reagent of embodiment 15, wherein the one or more reagents is or comprises a monovalent antibody fragment.

17. The oligomeric particle reagent of embodiment 15 or embodiment 16, wherein the one or more agents is or comprises a Fab.

18. The oligomeric particle reagent of any of embodiments 10-17, wherein the one or more agents is a receptor-binding agent that binds to or is capable of binding to a receptor expressed on the surface of a target cell.

19. The oligomeric particle reagent of any of embodiments 10-18, wherein the receptor-binding agent is or comprises a stimulatory agent capable of binding to a molecule on the surface of a target cell, wherein binding induces or modulates a signal in the target cell.

20. The oligomeric particle reagent of embodiment 18 or claim 19, wherein the target cell is an immune cell.

21. The oligomeric particle reagent of any of embodiments 18-20, wherein the target cell is a T cell.

22. The oligomeric particle reagent of any of embodiments 18-21, wherein the receptor-binding agent is capable of initiating a TCR/CD3 complex-associated signal in T cells, binds to a member of a TCR/CD3 complex; and/or specifically binds to CD3.

23. The oligomeric particle reagent of embodiment 22, wherein the stimulatory agent is a first receptor-binding agent and the oligomeric particle reagent comprises a second receptor-binding agent, wherein the second receptor-binding agent is capable of specifically binding to a second molecule on the surface of the target cell, which binding to the second molecule is optionally capable of inducing or modulating a signal in the target cells.

24. The oligomeric particle reagent of embodiment 23, wherein the second receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

25. The oligomeric particle reagent of embodiment 22 or embodiment 23, wherein the second receptor-binding agent specifically binds to a costimulatory molecule and the costimulatory molecule is CD28.

26. The oligomeric particle reagent of any of embodiments 10-25, wherein the one or more agents is an anti-CD3 antibody and an anti-CD28 antibody, optionally an anti-CD3 Fab and an anti-CD28 Fab.

27. The oligomeric particle reagent of any of embodiments 18-21, wherein the receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

28. The oligomeric particle reagent of any of embodiments 18-21, 23, or 24, wherein the receptor-binding agent (second receptor-binding agent) binds to a costimulatory or accessory molecule and the costimulatory or accessory molecule is selected from CD28, CD90 (Thy-1), CD95 (Apo-/Fas), CD137 (4-1BB), CD154 (CD40L), ICOS, LAT, CD27, OX40 or HVEM.

29. The oligomeric particle reagent of any of embodiments 18-21, 23, or 24,, wherein the receptor-binding agent (second receptor-binding agent) specifically binds to a cytokine receptor and the cytokine receptor is selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2.

30. The oligomeric particle reagent of any of embodiments 18-21, 23, or 24, wherein the receptor-binding agent (second receptor-binding agent) specifically binds to a chemokine receptor and the chemokine receptor is selected from among CCR1, CCR2, CCR3, CCR4, CCR5, CCR7, CCR9, CXCR1, CXCR3 and CXCR4.

31. The oligomeric particle reagent of any of embodiments 18-21, 23, or 24, wherein the receptor-binding agent (second receptor-binding agent) is a factor that induces cytokine or chemokine production and the factor is a ligand that specifically binds to a cytokine or chemokine receptor.

32. The oligomeric particle reagent of embodiment 31, wherein the receptor-binding agent (second receptor-binding agent) is a ligand that specifically binds to a cytokine receptor, wherein the ligand specifically binds IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the ligand is selected from among IL-2, IL-1, IL-15, IFN-gamma, TNF-alpha, IL-4, IL-10, IL-12, IL-15, IL-17 and TNF, or is a biologically active fragment thereof.

33. The oligomeric particle reagent of embodiment 30, wherein the receptor-binding agent (second receptor-binding agent) is a ligand that specifically binds to a chemokine receptor, wherein
the ligand specifically binds to a chemokine receptor selected from among CCR1, CCR2, CCR3, CCR4, CCR5, CCR7, CCR9, CXCR1, CXCR3 and CXCR4; or
the ligand is selected from among CXCL9, CXCL10, CCL19, CCL21 and CCL25 or is a biologically active fragment thereof.

34. The oligomeric particle reagent of any of embodiments 18-21, 23, or 24, wherein the receptor-binding agent (second receptor-binding agent) is an adhesion molecule and the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof.

35. The oligomeric particle reagent of any of embodiments 10-34, wherein the one or more agents comprises a selection agent, wherein the selection agent binds to or is capable of binding to a selection marker that is expressed on the surface of a target cell.

36. The oligomeric particle reagent of embodiment 35, wherein the target cell is an immune cell.

37. The oligomeric particle reagent of embodiment 35 or embodiment 36, wherein the target cell is a lymphocyte or an antigen-presenting cell.

38. The oligomeric particle reagent of any of embodiments 35-37, wherein the target cell is a T cell, B cell, NK cell, macrophage or dendritic cell.

39. The oligomeric particle reagent of any of embodiments 35-38, wherein the target cell is a T cell.

40. The oligomeric particle reagent of any of embodiments 35-39, wherein the selection marker is CD25, CD28, CD62L, CCR7, CD27, CD127, CD3, CD4, CD8, CD45RA, and/or CD45RO.

41. The oligomeric particle reagent of any of embodiments 1-40, wherein the oligomeric particle reagent comprises a radius of greater than 25 nm, greater than 50 nm, greater than 60 nm, greater than 70 nm, greater than 80 nm, or greater than 90 nm.

42. The oligomeric particle reagent of any of embodiments 1-41, wherein the oligomeric particle reagent comprises a radius of between 25 nm and 150 nm, between 50 nm and 150 nm, between 75 nm and 125 nm, between 80 nm and 115 nm, or between 90 nm and 110 nm, inclusive, or 90 nm±15 nm, or 95 nm±20-25 nm.

43. The oligomeric particle reagent of any of embodiments 1-42, wherein the oligomeric particle reagent has a radius of less than 150 nm.

44. The oligomeric particle reagent of any of embodiments 41-43, wherein the radius is a hydrodynamic radius.

45. The oligomeric particle reagent of any of embodiments 1-44, wherein the oligomeric particle reagent comprises a molecular weight of at least at least $1 \times 10^7$ g/mol, at least $5 \times 10^7$ g/mol, or at least $1 \times 10^8$ g/mol.

46. The oligomeric particle reagent of any of embodiments 1-45, wherein the oligomeric particle reagent comprises a molecular weight of between $1 \times 10^6$ g/mol and $1 \times 10^{10}$ g/mol, between $1 \times 10^7$ g/mol and $1 \times 10^9$ g/mol, between $5 \times 10^7$ g/mol and $5 \times 10^8$ g/mol, between $1 \times 10^8$ g/mol and $5 \times 10^8$ g/mol, or between $1 \times 10^8$ g/mol and $2 \times 10^8$ g/mol.

47. The oligomeric particle reagent of any of embodiments 1-46, wherein the oligomeric particle reagent comprises at least 100 streptavidin or streptavidin mutein tetramers, at least 500 streptavidin or streptavidin mutein tetramers, at least 1,000 streptavidin or streptavidin mutein tetramers, at least 1,500 streptavidin or streptavidin mutein tetramers, or at least 2,000 streptavidin or streptavidin mutein tetramers.

48. The oligomeric particle reagent of any of embodiments 1-47, wherein the oligomeric particle reagent comprises between 100 and 50,000 streptavidin or streptavidin mutein tetramers, between 1,000 and 20,000 streptavidin or streptavidin mutein tetramers, between 1,000 and 10,000 streptavidin or streptavidin mutein tetramers, or between 2,000 and 5,000 streptavidin or streptavidin mutein tetramers.

49. The oligomeric particle reagent of any of embodiments 1-48, wherein the plurality of streptavidin or streptavidin mutein comprise lysine residues, wherein less than 20%, 10%, 5%, 1%, of the lysine residues comprise N-substituted iminothiolane.

50. A composition comprising one or more oligomeric particle reagent of any of embodiments 1-49.

51. The composition of embodiment 50, wherein the one or more oligomeric particle reagents is a plurality of oligomeric particle reagents.

52. The composition of embodiment 51, wherein the plurality of oligomeric particle reagents comprises i) an average radius of greater than 70 nm; ii) an average molecular weight of at least $1 \times 10^8$ g/mol; and/or iii) an average number of streptavidin or streptavidin tetramers per oligomeric particle reagent of at least 2,000 and/or iv) a radius size distribution wherein at least 95% of the plurality of oligomeric particle reagents comprise a radius of between 10 nm to 150 nm.

53. The composition of embodiment 51 or 52, wherein the plurality of oligomeric particle reagents comprises an average radius of greater than 25 nm, greater than 50 nm, greater than 60 nm, greater than 70 nm, greater than 80 nm, greater than 90 nm, or greater than 100 nm.

54. The composition of any of embodiments 51-53, wherein:
the plurality of oligomeric particle reagents comprise an average radius of between 25 nm and 150 nm, between 50 nm and 150 nm, between 75 nm and 125 nm, between 80 nm and 110 nm, or between 90 nm and 110 nm, inclusive; or
the plurality of oligomeric particle reagents comprise an average radius average radious 90 nm±15 nm, 95 nm±20-25 nm or 97±10 nm.

55. The composition of any of embodiments 51-54, wherein at least 95% of the plurality of oligomeric particle reagents comprise a radius of between 50 and 150 nm, between 70 nm and 140 nm, between 80 nm and 120 nm, between 80 nm and 115 nm, between 80 nm and 100 nm, between 90 nm and 110 nm, and/or between 100 nm and 120 nm.

56. The composition of any of embodiments 51-55, wherein at least 95% of the oligomeric particle reagents comprise a radius between ±50%, ±25%, ±20%, ±15%, ±10%, and/or ±5% of the average and/or the median radius of the plurality of oligomeric particle reagents.

57. The composition of any of embodiments 51-56, wherein the plurality of oligomeric particle reagents comprising an average radius of between 80 nm and 115 nm and wherein at least 95% of the oligomeric particle reagents comprise a radius between ±25% of the average radius.

58. The composition of any of embodiments 51-57, wherein the plurality of particles comprise an average molecular weight of between $1 \times 10^8$ g/mol and $5 \times 10^8$ g/mol, or between $1 \times 10^8$ g/mol and $2 \times 10^8$ g/mol, inclusive.

59. The composition of any of embodiments 51-58, wherein the plurality of oligomeric particle reagents comprises an average number of streptavidin or streptavidin tetramers per oligomeric particle reagent of at least 100, at least 500, at least 1,000, at least 1,500, or at least 2,000.

60. The composition of any of embodiments 51-59, wherein the plurality of oligomeric particle reagents comprises an average number of streptavidin or streptavidin tetramers per oligomeric particle reagent of between 100 and 50,000, between 1,000 and 20,000, between 1,000 and 10,000, or between 2,000 and 5,000,each inclusive.

61. The composition of any of embodiments 51-60, wherein the average radius of the plurality the oligomer particles does not increase by more than 25% or 10% when stored at about or below −80° C., at about or below −20° C., and/or at about or below 4° C. for at least 1, 3, 9, 27, or 46 weeks.

62. The composition of any of embodiments 51-61, wherein the average radius of the plurality the oligomer particles does not increase by more than 10% when stored at about or below 4° C. for at least one week.

63. The composition of any of embodiments 61-62, wherein the average radius of the plurality of the oligomer particles does not increase by more than 10% when stored at about or below 4° C. for at least 3 weeks.

64. The composition of any of clams 51-63, wherein the average radius of the plurality of the oligomer particles does not increase by more than 10% when stored at about or below 4° C. for at least 9 weeks.

65. A method for producing an oligomeric particle reagent comprising streptavidin or a streptavidin mutein, the method comprising:
incubating a plurality of activated streptavidin or streptavidin mutein molecules comprising a thiol-reactive functional group capable of reacting with a thiol functional group and a plurality of thiolated streptavidin or streptavidin mutein molecules comprising one or more thiol functional group, thereby generating a particle composition comprising the oligomeric streptavidin or streptavidin mutein particles;

separating the oligomeric particles from monomer and/or smaller oligomeric molecules; and contacting the oligomeric particle with a stabilizing agent, thereby producing the oligomeric particle reagent.

66. The method of embodiment 65, wherein the plurality of activated streptavidin or streptavidin mutein molecules is generated by incubating a first plurality of streptavidin or streptavidin mutein molecules with an activation agent that is capable of converting one or more amines to a thiol-reactive functional group.

67. The method of embodiment 65 or embodiment 66, wherein the plurality of thiolated streptavidin or streptavidin mutein molecules is generated by incubation of a second plurality of streptavidin or streptavidin mutein molecules with a thiolating agent that adds or is capable of adding a thiol functional group to one or more lysine residue.

68. A method for producing oligomeric particle reagents, the method comprising:

(a) incubating a first plurality of streptavidin or streptavidin mutein molecules with an activation agent under conditions to convert one or more amines to a thiol-reactive group capable of reacting with a thiol functional group, thereby generating a plurality of activated streptavidin or streptavidin mutein molecules;

(b) incubating a second plurality of streptavidin or streptavidin mutein molecules with a thiolating agent that adds or is capable of adding a thiol functional group to one or more lysine residue, thereby generating a plurality of thiolated streptavidin or streptavidin mutein molecules; and (c) incubating the plurality of activated streptavidin or streptavidin mutein molecules with the plurality of thiolated streptavidin or streptavidin mutein molecules, thereby generating particle composition comprising the oligomeric particle reagents;

wherein the method is carried out under conditions in which, at the time of initiation of the incubation in (c), the plurality of thiolated streptavidin or streptavidin mutein molecules are such that at least 60% of the lysines, on average, comprise a thiol functional group, and/or at least 10 lysines, on average, per thiolated streptavidin or streptavidin mutein tetramer comprise a thiol functional group.

69. The method of embodiment 68, further comprising separating the oligomeric particle reagents from monomer and/or smaller oligomeric streptavidin or streptavidin mutein molecules.

70. The method of any of embodiments 65-69, wherein the incubation of the first plurality of streptavidin or streptavidin mutein molecules with the activation agent is performed at a molar ratio of between 1:1 and 1:10 of streptavidin or streptavidin mutein to the activation reagent.

71. The method of any of embodiments 66-70, wherein the incubation of the first plurality of streptavidin or streptavidin mutein molecules with the activation agent is performed at a molar ratio of 1:2±2% of streptavidin or streptavidin mutein to the activation reagent.

72. The method of any of embodiments 66-71, wherein the activation agent comprises a heterobifunctional crosslinker.

73. The method of any of embodiments 66-72, wherein the activation agent comprises sulfosuccinimidyl 4-(N-maleimidomethyl)cyclohexane-1-carboxylate (sulfo SMCC) and/or Succinimidyl-6-[(β-maleimidopropionamido) hexanoate (SMPH).

74. The method of any of embodiments 65-73, wherein the thiol-reactive functional group is a haloacetyl group, a maleimide group, an aziridine group, an acryloyl group, an arylating agent, a vinylsulfone group, a pyridyl disulfide, a TNB-thiol or a disulfide reducing agent.

75. The method of any of embodiments 65-74, wherein the thiol-reactive functional group is a maleimide group.

76. The method of any of embodiments 65-75, wherein the first plurality of streptavidin or streptavidin mutein molecules and the activation agent are incubated at a neutral pH.

77. The method of any of embodiments 65-76, wherein the first plurality of streptavidin or streptavidin mutein molecules and the activation agent are incubated at a pH of between 6.8 and 7.5.

78. The method of any of embodiments 65-77, wherein the first plurality of streptavidin or streptavidin mutein molecules and the activation agent are incubated at a pH of between 7.0 and 7.4, optionally of or about 7.2.

79. The method of any of embodiments 65-78, wherein the first plurality of streptavidin or streptavidin mutein molecules and the activation agent are incubated at a temperature between 4° C. and 39° C.

80. The method of any of embodiments 65-79, wherein the first plurality of streptavidin or streptavidin mutein molecules and the activation agent are incubated at room temperature, optionally between 20° C. and 25° C., optionally about 23° C. or about 24° C.

81. The method of any of embodiments 65-80, wherein the first plurality of streptavidin or streptavidin mutein molecules and the activation agent are incubated for between 15 minutes and 6 hours or 30 minutes and 2 hours, each inclusive.

82. The method of any of embodiments 65-81, wherein the first plurality of streptavidin or streptavidin mutein molecules and the activation agent are incubated for between 45 minutes and 1.5 hours, inclusive, optionally for or for about 1 hour.

83. The method of any of embodiments 66-82, wherein the incubation of the second plurality of streptavidin or streptavidin mutein molecules with the thiolating agent is performed at a molar ratio of between 10:1 and 1:1, inclusive, of the thiolating reagent to each primary amine per streptavidin or streptavidin mutein molecule.

84. The method of any of embodiments 66-83, wherein the incubation of the second plurality of streptavidin or streptavidin mutein molecules with the thiolating agent is performed at a molar ratio of between 1:50 and 1:500, inclusive, of streptavidin or streptavidin mutein tetramer to the thiolating agent.

85. The method of any of embodiments 66-84, wherein the incubation of the second plurality of streptavidin or streptavidin mutein molecules with the thiolating agent is performed at a molar ratio of or about 1:100 of streptavidin or streptavidin mutein tetramer to the activation reagent.

86. The method of any of embodiments 66-85, wherein the thiolating agent is or comprises 2-iminothiolane.

87. The method of any of embodiments 66-86, wherein the second plurality of streptavidin or streptavidin mutein molecules and the thiolating agent are incubated at a pH of 7.0 or greater, optionally between 7.0 and 8.0, inclusive.

88. The method of any of embodiments 66-87, wherein the second plurality of streptavidin or streptavidin mutein molecules and the thiolating agent are incubated at a pH of about 7.7.

89. The method of any of embodiments 66-88, wherein the incubation of the second plurality of streptavidin or streptavidin mutein molecules and the thiolating agent is initiated in the presence of a buffer with a pH of 8.0 or greater, optionally between 8.0 and 9.0, inclusive.

90. The method of any of embodiments 66-89, wherein the incubation of the second plurality of streptavidin or streptavidin mutein molecules and the thiolating agent is initiated in the presence of a buffer with a pH of or about 8.5.

91. The method of embodiment 89 or 90, wherein the buffer comprises borate.

92. The method of any of embodiments 89-91, wherein the buffer comprises 10 mM to 200 mM borate or 50 mM to 100 mM borate, each inclusive, optionally about 100 mM borate.

93. The method of any of embodiments 65-92, wherein the second plurality of streptavidin or streptavidin mutein molecules and the thiolating agent are incubated at a temperature between 4° C. and 39° C.

94. The method of any of embodiments 65-93, wherein the second plurality of streptavidin or streptavidin mutein molecules and the thiolating agent are incubated at room temperature, optionally between 20° C. and 25° C., optionally at or about 23° C. or at or about 24° C.

95. The method of any of embodiments 66-94, wherein the second plurality of streptavidin or streptavidin mutein molecules and the thiolating agent are incubated for between 15 minutes and 2 hours or 15 minutes and 1.5 hours.

96. The method of any of embodiments 66-95, wherein the second plurality of streptavidin or streptavidin mutein molecules and the thiolating agent are incubated for between 15 minutes and 2 hours or 25 minutes and 1 hour, each inclusive.

97. The method of any of embodiments 66-96, wherein the second plurality of streptavidin molecules and the thiolating agent are incubated for or for about 1 hour.

98. The method of any of embodiments 66-97, wherein the second plurality of streptavidin or streptavidin mutein molecules and the thiolating agent are incubated for or for about 25 minutes.

99. The method of any of embodiments 65-98, wherein the plurality of activated streptavidin or streptavidin mutein molecules to the plurality of thiolated streptavidin or streptavidin mutein molecules during the incubation is, at a molar ratio of 1:X, wherein X is the number of lysine residues available to be thiolated per molecule of streptavidin or streptavidin mutein.

100. The method of any of embodiments 65-99, wherein the molar ratio is from 1:1 to 1:8 or 1:2 to 1:6, optionally of or about 1:4.

101. The method of any of embodiments 65-100, wherein the plurality of activated streptavidin or streptavidin mutein molecules and the plurality of thiolated streptavidin or streptavidin mutein molecules, are incubated at a pH of between 6.8 and 7.5, inclusive.

102. The method of any of embodiments 65-101, wherein the plurality of activated streptavidin or streptavidin mutein molecules and the plurality of thiolated streptavidin or streptavidin mutein molecules, are incubated at a pH of between 7.0 and 7.4, inclusive.

103. The method of any of embodiments 65-102, wherein the plurality of activated streptavidin or streptavidin mutein molecules and the plurality of thiolated streptavidin or streptavidin mutein molecules, are incubated at a pH of or about 7.2.

104. The method of any of embodiments 65-103, wherein the plurality of activated streptavidin or streptavidin mutein molecules and the plurality of thiolated streptavidin or streptavidin mutein molecules, are incubated at a temperature between 4° C. and 39° C., inclusive.

105. The method of any of embodiments 65-104, wherein the plurality of activated streptavidin or streptavidin mutein molecules and the plurality of thiolated streptavidin or streptavidin mutein molecules, are incubated at at room temperature, optionally between 20° C. and 25° C., inclusive, optionally at or about 23° C. or at or about 24° C.

106. The method of any of embodiments 65-105, wherein the plurality of activated streptavidin molecules and the plurality of thiolated streptavidin molecules, are incubated for between 15 minutes and 6 hours or 30 minutes and 2 hours, each inclusive.

107. The method of any of embodiments 65-106, wherein the plurality of activated streptavidin molecules and the plurality of thiolated streptavidin molecules, are incubated for between 45 minutes and 1.5 hours, inclusive, optionally for or for about 1 hour.

108. The method of any of embodiments 65-107, wherein the incubation of activated streptavidin or streptavidin mutein molecules and the thiolated streptavidin or streptavidin mutein molecules is ended by contacting the molecules with N-ethylmaleimide (NEM).

109. The method of any of embodiments 68-108, wherein at least a portion of the incubating of the first plurality of streptavidin or streptavidin mutein molecules with the activation agent and at least a portion of the incubating of the second plurality of streptavidin or streptavidin mutein molecules with the thiolating agent are carried out separately at the same time.

110. The method of embodiment 109, wherein the incubating of the first plurality of streptavidin or streptavidin mutein molecules with the activation agent and the incubating of the second plurality of streptavidin or streptavidin mutein molecules with the thiolating agent are carried out for substantially the same amount of time and/or are completed at substantially the same time.

111. The method of any of embodiments 68-110, wherein, prior to incubating the thiolated streptavidin or streptavidin mutein molecules and the activated streptavidin or streptavidin mutein molecules, the method comprises:

(i) removing the activation agent from the composition comprising the activated streptavidin or streptavidin mutein molecules; and/or (ii) removing the thiolating agent from the composition comprising the thiolated streptavidin or streptavidin mutein molecules.

112. The method of any of embodiments 68-111, wherein the incubation of the plurality of activated streptavidin or streptavidin mutein molecules and the plurality of thiolated streptavidin or streptavidin mutein molecules is initiated within 15 minutes after the incubating of the second plurality of streptavidin molecules with the thiolating agent is ended and/or after the removing of the thiolating agent from composition comprising the thiolated streptavidin or streptavidin mutein molecules..

113. A method for producing oligomeric particle reagents, comprising:

incubating a first plurality of streptavidin or streptavidin mutein molecules with Succinimidyl-6-[(β-maleimidopropionamido)hexanoate (SMPH) for or for about 1 hour at a pH of or of about 7.2, thereby generating a plurality of activated streptavidin or streptavidin mutein molecules comprising a maleimide thiol-reacting functional group;

incubating a second plurality of streptavidin or streptavidin mutein molecules with 2-iminothiolane for or for about 1 hour at a pH of between 7.5 and 8.5, inclusive, thereby generating a plurality of thiolated streptavidin molecules comprising one or more thiol functional groups; and incubating the plurality of activated streptavidin or streptavidin mutein molecules with the plurality of thiolated streptavidin molecules for or for about 1 hour at a pH of or of about 7.2, thereby generating a particle composition comprising the oligomeric particle reagents;

wherein the incubating of the plurality of activated streptavidin molecules with the plurality of thiolated streptavidin molecules is initiated within 10 minutes after the incubation of the second plurality of streptavidin molecules with 2-iminothiolane ends.

114. The method of any of embodiments 68-113, wherein the method further comprises contacting the oligomeric particle reagents with a stabilizing agent.

115. The method of any of embodiments 65-67 or 114, wherein the stabilization agent reduces an amount of N-substituted iminothiolane present on lysine residues of the oligomeric particle reagents.

116. The method of any of embodiments 65-67 or 114-115, wherein the stabilization agent reduces an amount of N-substituted iminothiolane present on lysine residues of the oligomeric particle reagents by at least 25%, at least 50%, at least 60%, at least 70%, at least 80%, at least 90%, or at least 95%.

117. The method of any of embodiments 65-67 and 114-116, wherein the stabilization agent comprises hydroxylamine.

118. The method of any of embodiments 65-67 and 114-117, wherein the stabilization agent is removed from the oligomeric particle reagents by a chromatography, optionally by size exclusion chromatography (SEC).

119. The method of any of embodiments 65-118, wherein the oligomeric particle reagents have a radius of less than 150 nm.

120. The method of any of embodiments 65-119, further comprising filter sterilizing the oligomeric particle reagents.

121. The method of any of embodiments 65-67 and 69-120, wherein the oligomeric particle reagents are separated from the monomer or smaller oligomeric streptavidin or streptavidin mutein molecules by size exclusion chromatography.

122. The method of embodiment 113, wherein the size exclusion limit is greater than or greater than about 100 kDa, 500 kDa, 750 kDa, 1000 kDa or 2000 kDa.

123. The method of embodiment 121 or embodiment 122, wherein the size exclusion limit is from or from about 500 kDa to 1000 kDa.

124. The method of any of embodiments 121-123, wherein the size exclusion limit is or is about 75 kDa.

125. The method of any of embodiments 65-67 and 69-124, comprising collecting one or more fractions comprising the void volume, thereby separating oligomeric particle reagents from the monomer or smaller oliomeric streptavidin or streptavidin mutein molecules.

126. The method of any of embodiments 65-125, further comprising storing the oligomeric particle reagents at a temperature at about or below 4° C., at about or below −20° C., or about or below −80° C.

127. The method of any of embodiments 65-126, further comprising mixing the oligomeric particle reagents with one or more agents under conditions to reversibly bind the one or more agents to the oligomeric particle reagents.

128. An oligomeric particle reagent produced by the method of any of embodiments 65-127.

129. A method of multimerizing one or more agent to an oligomeric particle reagent, the method comprising mixing an oligomeric particle reagent of any of claims 1-49, a composition comprising an oligomeric particle reagent of any of claims 50-64, or an oligomeric particle reagent produced by the method of any of embodiments 65-128 with one or more agents under conditions to reversibly bind the one or more agents to the oligomeric particle reagents.

130. The method of embodiment 127 or embodiment 129 wherein the one or more agents comprise a binding partner, wherein the binding partner is capable of binding to one or more binding site on the oligomeric particle reagent.

131. The method of embodiment 130, wherein the binding partner comprises a streptavidin-binding peptide.

132. The method of embodiment 130 or embodiment 131, wherein the binding partner comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

133. The method of any of embodiments 130-132, wherein the one or more agents binds or is capable of binding to a molecule expressed on the surface of a target cell.

134. The method of any of embodiments 130-133, wherein the one or more agents comprises an antibody or an antigen-binding fragment thereof.

135. The method of embodiment 134, wherein the one or more agents is or comprises a monovalent antibody fragment.

136. The method of embodiment 134 or embodiment 135, wherein the one or more agents is or comprises a Fab.

137. The method of any of embodiments 130-136, wherein the one or more agents is a receptor binding-agent that binds to or is capable of binding to a receptor expressed on the surface of a target cell.

138. The method of embodiment 137, wherein the receptor binding agent is or comprises a stimulatory agent capable of binding to a molecule on the surface of a target cell, wherein binding induces or modulates a signal in the target cell.

139. The method of embodiment 137 or embodiment 138, wherein the target cell is an immune cell.

140. The method of any of embodiments 137-139, wherein the target cell is a T cell.

141. The method of any of embodiments 137-140, wherein the receptor-binding agent is capable of initiating a TCR/CD3 complex-associated signal in T cells, binds to a member of a TCR/CD3 complex; and/or specifically binds to CD3.

142. The method of embodiment 141, wherein the stimulatory agent is a first receptor-binding agent and the method further comprises reversibly binding to the oligomeric particle reagent a second receptor-binding agent, wherein the second receptor-binding agent is capable of specifically binding to a second molecule on the surface of the target cell, which binding to the second molecule is optionally capable of inducing or modulating a signal in the target cells.

143. The method of embodiment 142, wherein the second receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

144. The method of embodiment 142 or embodiment 143, wherein the second receptor-binding agent specifically binds to a costimulatory molecule and the costimulatory molecule is CD28.

145. The method of any of embodiments 127and 129-144, wherein the one or more agents is an anti-CD3 antibody and an anti-CD28 antibody, optionally an anti-CD3 Fab and an anti-CD28 Fab.

146. The oligomeric particle reagent of embodiment 137 or embodiment 138, wherein the receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

147. The method of any of embodiments 137, 138, 143, or 144, wherein the receptor-binding agent (second receptor-binding agent) binds to a costimulatory or accessory molecule and the costimulatory or accessory molecule is selected fromCD28, CD90 (Thy-1), CD95 (Apo-/Fas), CD137 (4-1BB), CD154 (CD40L), ICOS, LAT, CD27, OX40 or HVEM.

148. The method of any of embodiments 137, 138, 143, or 144, wherein the receptor-binding agent (second receptor-binding agent) specifically binds to a cytokine receptor and the cytokine receptor is selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2.

149. The method of any of embodiments 137, 138, 143, or 144, wherein the receptor-binding agent (second receptor-binding agent) specifically binds to a chemokine receptor and the chemokine receptor is selected from among CCR1, CCR2, CCR3, CCR4, CCR5, CCR7, CCR9, CXCR1, CXCR3 and CXCR4.

150. The method of any of embodiments 137, 138, 143, or 144, wherein the receptor-binding agent (second receptor-binding agent) is a factor that induces cytokine or chemokine production and the factor is a ligand that specifically binds to a cytokine or chemokine receptor.

151. The method of embodiment 150, wherein the receptor-binding agent (second receptor-binding agent) is a ligand that specifically binds to a cytokine receptor, wherein the ligand specifically binds IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the ligand is selected from among IL-2, IL-1, IL-15, IFN-gamma, TNF-alpha, IL-4, IL-10, IL-12, IL-15, IL-17 and TNF, or is a biologically active fragment thereof.

152. The oligomeric particle reagent of embodiment 151, wherein the receptor-binding agent (second receptor-binding agent) is a ligand that specifically binds to a chemokine receptor, wherein the ligand specifically binds to a chemokine receptor selected from among CCR1, CCR2, CCR3, CCR4, CCR5, CCR7, CCR9, CXCR1, CXCR3 and CXCR4; or the ligand is selected from among CXCL9, CXCL10, CCL19, CCL21 and CCL25 or is a biologically active fragment thereof.

153. The method of any of embodiments 137, 138, 143, or 144, wherein the receptor-binding agent (second receptor-binding agent) is an adhesion molecule and the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof.

154. The method of any of embodiments 127-153, wherein the one or more agents comprises a selection agent, wherein the selection agent binds to or is capable of binding to a selection marker that is expressed on the surface of a target cell.

155. The method of embodiment 154 wherein the target cell is an immune cell.

157. The method of embodiment 154 or embodiment 155, wherein the target cell is a lymphocyte or an antigen-presenting cell.

158. The method of any of embodiments 154-156, wherein the target cell is a T cell, B cell, NK cell, macrophage or dendritic cell.

159. The method of any of embodiments 154-158, wherein the target cell is a T cell.

160. The method of any of embodiments 154-159, wherein the selection marker is CD25, CD28, CD62L, CCR7, CD27, CD127, CD3, CD4, CD8, CD45RA, and/or CD45RO.

161. A composition comprising oligomeric particle reagents produced by the method of any of embodiment 65-160.

162. A composition comprising a plurality of the oligomeric particle reagents produced by the method of any of embodiment 65-161.

163. An article of manufacture, comprising the oligomeric particle reagent of any of embodiments 1-49 or the composition of any of embodiments 50-64 or 161-162.

164. A method for modulating cells, the method comprising incubating a cell composition comprising target cells in the presence of the oligomeric particle reagent of any of embodiments 1-49 or in the presence of the composition of any of embodiments 50-64 or 161-163, thereby modulating the target cells.

165. The method of embodiment 164, wherein modulating the target cells comprises activating, enriching, and/or expanding the target cells.

166. A method for culturing cells, the method comprising incubating a cell composition comprising target cells in the presence of the oligomeric particle reagent of any of embodiments 1-49 or in the presence of the composition of any of embodiments 50-64 or 161-163.

167. The method of any of embodiments 164-166, wherein the oligomeric particle reagent comprises are reversibly bound to one or more agents.

168. The method of embodiment 167, wherein the one or more agents comprise a binding partner, wherein the binding partner is capable of binding to one or more binding site on the oligomeric particle reagent, thereby reversibly binding the one or more agents to the oligomeric particle reagent.

169. The method of embodiment 168, wherein the binding partner comprises a streptavidin-binding peptide.

170. The method of embodiment 168 or 169, wherein the binding partner comprises a streptavidin-binding peptide selected from the group consisting of Trp-Ser-His-Pro-Gln-Phe-Glu-Lys (SEQ ID NO: 8), Trp-Ser-His-Pro-Gln-Phe-Glu-Lys-(GlyGlyGlySer)$_3$-Trp-Ser-His-Pro-Gln-Phe-Glu-Lys ((SEQ ID NO: 17), Trp-Ser-His-Pro-Gln-Phe-Glu-Lys-(GlyGlyGlySer)$_2$-Trp-Ser-His-Pro-Gln-Phe-Glu-Lys (SEQ ID NO: 18) and Trp-Ser-His-Pro-Gln-Phe-Glu-Lys-(GlyGlyGlySer)$_2$Gly-Gly-Ser-Ala-Trp-Ser-His-Pro-Gln-Phe-Glu-Lys (SEQ ID NO: 19).

171. The method of any of embodiments 167-170, wherein the one or more agents binds or is capable of binding to a molecule expressed on the surface of a target cell.

172. The method of any of embodiments 167-171, wherein the one or more agents comprises an antibody, optionally a Fab.

173. The method of any of embodiments 167-172, wherein the one or more agents is a receptor binding-agent that binds to or is capable of binding to a receptor expressed on the surface of a target cell.

174. The method of embodiment 173, wherein the receptor binding agent is or comprises a stimulatory agent capable of binding to a molecule on the surface of a target cell, thereby inducing or modulating a signal in the target cell.

175. The method of embodiment 173 or embodiment 174, wherein the receptor-binding agent is capable of initiating a TCR/CD3 complex-associated signal in T cells, binds to a member of a TCR/CD3 complex; and/or specifically binds to CD3.

176. The method of embodiment 175, wherein the stimulatory agent is a first receptor-binding agent and the method further comprises reversibly binding to the oligomeric particle reagent a second receptor-binding agent, wherein the second receptor-binding agent is capable of specifically binding to a second molecule on the surface of the target cell, which binding to the second molecule is optionally capable of inducing or modulating a signal in the target cells.

177. The method of embodiment 176, wherein the second receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

178. The method of embodiment 176 or 177, wherein the receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

179. The method of any of embodiments 174, 175, 177, or 178, wherein the receptor-binding agent (second receptor-binding agent) binds to a costimulatory or accessory molecule and the costimulatory or accessory molecule is selected fromCD28, CD90 (Thy-1), CD95 (Apo-/Fas), CD137 (4-1BB), CD154 (CD40L), ICOS, LAT, CD27, OX40 or HVEM.

180. The method of any of embodiments 174, 175, 177, or 178, wherein the receptor-binding agent (second receptor-binding agent) specifically binds to a cytokine receptor and the cytokine receptor is selected from among IL-2R, IL-1R, IL-15R, IFN-gammaR, TNF-alphaR, IL-4R, IL-10R, Type I IFNR, IL-12R, IL-15R, IL-17R, TNFR1 and TNFR2.

181. The method of any of embodiments 174, 175, 177, or 178 wherein the receptor-binding agent (second receptor-binding agent) specifically binds to a chemokine receptor and the chemokine receptor is selected from among CCR1, CCR2, CCR3, CCR4, CCR5, CCR7, CCR9, CXCR1, CXCR3 and CXCR4.

182. The method of any of embodiments 174, 175, 177, or 178 wherein the receptor-binding agent (second receptor-binding agent) is a factor that induces cytokine or chemokine production and the factor is a ligand that specifically binds to a cytokine or chemokine receptor.

183. The method of embodiment 182, wherein the receptor-binding agent (second receptor-binding agent) is a ligand that specifically binds to a cytokine receptor, wherein the ligand specifically binds IL-2R, IL-1R, IL-15R, IFN-gammaR, TNF-alphaR, IL-4R, IL-10R, Type I IFNR, IL-12R, IL-15R, IL-17R, TNFR1 and TNFR2; and/or the ligand is selected from among IL-2, IL-1, IL-15, IFN-gamma, TNF-alpha, IL-4, IL-10, IL-12, IL-15, IL-17 and TNF, or is a biologically active fragment thereof.

184. The method of embodiment 183, wherein the receptor-binding agent (second receptor-binding agent) is a ligand that specifically binds to a chemokine receptor, wherein
the ligand specifically binds to a chemokine receptor selected from among CCR1, CCR2, CCR3, CCR4, CCR5, CCR7, CCR9, CXCR1, CXCR3 and CXCR4; or
the ligand is selected from among CXCL9, CXCL10, CCL19, CCL21 and CCL25 or is a biologically active fragment thereof.

185. The method of any of embodiments 174, 175, 177, or 178, wherein the receptor-binding agent (second receptor-binding agent) is an adhesion molecule and the adhesion molecule is selected from among CD44, CD31, CD18/CD11a (LFA-1), CD29, CD54 (ICAM-1), CD62L (L-selectin), and CD29/CD49d (VLA-4), CD106 (VCAM-1) or is a biologically active fragment thereof.

186. The method of any of embodiments 164-185, wherein the one or more agents comprises a selection agent, wherein the selection agent binds to or is capable of binding to a selection marker that is expressed on the surface of a target cell.

187. The method of embodiment 186, wherein the target cell is an immune cell.

188. The method of embodiment 186 or embodiment 187, wherein the target cell is a lymphocyte or an antigen-presenting cell.

189. The method of any of embodiments 186-188, wherein the target cell is a T cell, B cell, NK cell, macrophage or dendritic cell.

190. The method of any of embodiments 186-189, wherein the target cell is a T cell.

191. The method of any of embodiments 186-190, wherein the selection marker is CD25, CD28, CD62L, CCR7, CD27, CD127, CD3, CD4, CD8, CD45RA, and/or CD45RO.

192. The method of any of embodiments 186-191, wherein the target cells comprise blood cells, leukocytes, lymphocytes, B cells, a population of B cells, T cells, a population of T cells, NK cells, dendritic cells and/or macrophages.

193. The method of any of embodiments186-192, wherein the target cells express a recombinant receptor.

194. The method of any of embodiments186-193, wherein the target cells express a recombinant T cell receptor and/or a chimeric antigen receptor (CAR).

195. The method of any of embodiments186-194, wherein the target cells express a CAR that binds to an antigen associated with a disease and/or a cancer.

196. The method of embodiment 195, wherein the antigen is avP6 integrin (avb6 integrin), B cell maturation antigen (BCMA), B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), Her2/neu (receptor tyrosine kinase erbB2), Her3 (erb-B3), Her4 (erb-B4), erbB dimers, human high molecular weight-melanoma-associated antigen (HMW-MAA), hepatitis B surface antigen, Human leukocyte antigen A1 (HLA-AI), human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, preferentially expressed antigen of melanoma (PRAME), progesterone receptor, a prostate specific antigen, prostate stem cell antigen (PSCA), prostate specific membrane antigen (PSMA), receptor tyrosine kinase like orphan receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms tumor 1 (WT-1), or a pathogen-specific antigen.

197. The method of any of embodiments 186-196, further comprising disrupting the reversible binding between the one or more agent and the oligomeric particle reagent.

198. The method of embodiment 197, wherein said disruption comprises introducing to the target cells a composition comprising a substance capable of reversing the bond between the one or more agent and the oligomeric particle reagent.

199. The method of embodiment 198, wherein the substance is a free binding partner and/or is a competition agent.

200. The method of any of embodiments 197-199, wherein said disruption terminates or lessens the signal induced or modulated by the one or more agent in the target cells, optionally T cells.

201. The method of any of embodiments 197-200, wherein the substance comprises a streptavidin-binding peptide, biotin or a biologically active fragment, optionally a D-biotin, or a biotin analog or biologically active fragment.

202. The method of embodiment 201, wherein the substance is a streptavidin-binding peptide is selected from the group consisting of Trp-Ser-His-Pro-Gln-Phe-Glu-Lys (SEQ ID NO: 8), Trp-Ser-His-Pro-Gln-Phe-Glu-Lys-(GlyGlyGly-Ser)₃-Trp-Ser-His-Pro-Gln-Phe-Glu-Lys ((SEQ ID NO: 17), Trp-Ser-His-Pro-Gln-Phe-Glu-Lys-(GlyGlyGlySer)₂-Trp-Ser-His-Pro-Gln-Phe-Glu-Lys (SEQ ID NO: 18) and Trp-Ser-His-Pro-Gln-Phe-Glu-Lys-(GlyGlyGlySer)₂Gly-Gly-Ser-Ala-Trp-Ser-His-Pro-Gln-Phe-Glu-Lys (SEQ ID NO: 19).

203. The method of any of embodiments 197-202 wherein the disruption is carried out within 5 days after initiation of said incubation.

204. The method of any of embodiments 164-203, wherein the one or more receptor-binding agents is comprises an antibody or an antigen-binding fragment thereof.

205. The method of embodiment 204, wherein the one or more receptor-binding agents is or comprises a monovalent antibody fragment.

206. The method of embodiment 204 or embodiment 205, wherein the one or more agents is or comprises a Fab.

207. The method of any of embodiments 164-206, wherein the target cell is an immune cell.

208. The method of any of embodiments 164-207, wherein the target cell is a T cell.

209. The method of any of embodiments 176-208, wherein the receptor-binding agent is or comprises a stimulatory agent capable of binding to a molecule on the surface of the target cell, wherein binding induces or modulates a signal in the target cell.

210. The method of any of claims 176-209, wherein the receptor-binding agent is capable of initiating a TCR/CD3 complex-associated signal in T cells, binds to a member of a TCR/CD3 complex; and/or specifically binds to CD3.

211. The method of claim 209 or claim 210, wherein the stimulatory agent is a first receptor-binding agent and the oligomeric particle reagent comprises a second receptor-binding agent, wherein the second receptor-binding agent is capable of specifically binding to a second molecule on the surface of the target cell, wherein binding to the second molecule is optionally capable of inducing or modulating a signal in the target cells.

212. The method of claim 211, wherein the second receptor-binding agent specifically binds to a costimulatory molecule, accessory molecule, immune checkpoint molecule, is a member of the TNF family or the TNF family receptor, cytokine receptor, chemokine receptor, or is or comprises an adhesion molecule or a factor that induces cytokine production, chemokine production and/or expression of an adhesion molecule.

213. The method of claim 211 or claim 212, wherein the second receptor-binding agent specifically binds to a costimulatory molecule and the costimulatory molecule is CD28.

214. The method of any of claims 176-213, wherein the one or more agents is an anti-CD3 antibody and an anti-CD28 antibody, optionally an anti-CD3 Fab and an anti-CD28 Fab.

VIII. EXAMPLES

The following examples are included for illustrative purposes only and are not intended to limit the scope of the invention.

Example 1: Methods for Preparing an Oligomeric Reagent Comprising a Streptavidin Mutein An oligomeric reagent was prepared by polymerizing an exemplary streptavidin mutein designated STREP-TAC-TIN® M2 (a streptavidin homo-tetramer containing the mutein sequence of amino acids set forth in SEQ ID NO:61, see e.g. U.S. Pat. No. 6,103,493 and Voss and Skerra (1997) Protein Eng., 1:975-982). To prepare streptavidin muteins for oligomerization, streptavidin muteins containing one or more reactive thiol groups were incubated with maleimide activated streptavidin muteins. To prepare the thiolated streptavidin mutein, about 100 mg of streptavidin mutein tetramer was thiolated by incubation with 2-iminothiolane hydrochloride at a molar ratio of 1:100 at a pH of about 8.5 at 24° C. for 1 hour in 100 mM Borate buffer in a total volume of 2.6 mL. For the activation reaction introducing maleimides, about 400 mg of streptavidin mutein tetramer was incubated with succinimidyl-6-[(β-maleimidopropionamido) hexanoate (SMPH) at a molar ratio of 1:2 at a pH of about 7.2 at 24° C. for 1 hour in a total volume of about 10.4 mL in a sodium phosphate buffer. The thiolation and maleimide activation reactions were coordinated to start at about the same time, and the duration of the reactions was controlled.

After the reactions, the 2-Iminothiolane hydrochloride and SMPH that had not reacted with STREP-TACTIN® M2, along with low molecular weight reaction by-products (predominantly NHS), were removed from the samples by individually carrying out gel filtration of the samples with PD-10 desalting columns (GE Healthcare). For each 2.5 mL volume of sample, a PD-10 column (8.3 ml bed volume) was equilibrated and loaded with either thiolated mutein streptavidin or maleimide mutein streptavidin and elution was carried out by adding 3.5 mL of coupling buffer (100 mM $NaH_2P_4$, 150 mM NaCl, 5 mM EDTA, pH 7.2). Gel filtration of the maleimide mutein streptavidin was carried out on 4 columns to account for the >10 mL volume and eluates were pooled. The timing of the activation and thiolation reactions and the timing between the end of the activation and thiolation reactions and the start of the oligomerization reactions were carefully controlled. Generally, at or approximately ten minutes was allowed to pass from the start of gel filtrations, i.e. the end of the activation and thiolation reactions, to when oligomerization reaction was initiated.

For oligomerization, the maleimide streptavidin mutein and thiolated streptavidin mutein samples were then combined into an overall volume of about 17.5 mL and incubated for 1 hour at a pH of 7.2 at 24° C. under stirring conditions at about 600 rpm. Because four times more streptavidin mutein was incubated with SMPH than with 2-iminothiolane hydrochloride, the molar ratio of thiolated streptavidin mutein and maleimide streptavidin mutein was 1:4 during the oligomerization reaction. After the reaction, remaining SH groups of the oligomerized streptavidin mutein reagent were saturated by incubation with N-Ethylmaleimide (NEM)for 15 min at 24° C. with stirring (about 600 rpm) followed by incubation for a further 16-20 hours at 4° C.

After incubation with NEM, the sample containing oligomerized Strep-Tactin mutein was centrifuged and the supernatant was filtered through a 0.45 μm membrane (Millex-HP 0.45 μm from Merck Millipore). The filtered solution was then loaded onto a column (Sephacryl S-300 HR HiPrep 26/60, GE Healthcare) for size exclusion chromatography (SEC) with an AKTA Explorer chromatography system (GE Healthcare). Fractions having at the end of collection milli absorbance units (mAU) greater than or equal to 1500 mAU were pooled.

The pooled sample containing oligomeric streptavidin mutein was treated with 100 mM hydroxylamine by the addition of 890 mM pH 6.35 for 15 minutes at room temperature. To remove the hydroxylamine after treatment, sample was loaded onto a PD10 column (2.5 mL per column) equilibrated with 100 mM $NaH_2PO_4$, 140 mM NaCl, 1 mM EDTA, pH 7.2 and eluted with 3.5 mL of the same buffer (100 mM $NaH_2PO_4$, 140 mM NaCl, 1 mM EDTA, pH 7.2.) The PD10 eluates were pooled and sterile filtered with a 0.45 μm filter followed by a 0.22 μm filter and then samples were frozen and stored at −80° C. Prior to freezing, the final concentration of the oligomeric streptavidin mutein reagent was measured and the size of the oligomeric streptavidin mutein reagent was determined by dynamic light scattering (DLS).

To evaluate the consistency of the oligomerization process, 10 oligomeric streptavidin mutein reagents were prepared using the methods described above from five different lots of streptavidin mutein (SAM). The average size, percent yield (determined by measuring absorbance at 280 nm without baseline correction), and activity (biotin binding) of the oligomers were assessed and the results are shown in Table E1. The results indicated that the resulting oligomeric streptavidin mutein reagents were consistent in these parameters with an average radius of 97 nm±10 nm and biotin binding of 40 nmol/mg±3 nmol/mg.

TABLE E1

Comparison of oligomerized STREP-TACTIN from different batches.

| | SAM lot | Radius (nm) | Yield (%) | Biotin Binding (nmol/mg) |
|---|---|---|---|---|
| Batch 1 | 1 | 92 | 74 | 41 |
| Batch 2 | 2 | 100 | 68 | 40 |
| Batch 3 | 2 | 106 | 82 | 37 |
| Batch 4 | 2 | 94 | 73 | 39 |
| Batch 5 | 3 | 87 | 79 | 41 |
| Batch 6 | 3 | 90 | 81 | 39 |
| Batch 7 | 4 | 97 | 84 | 43 |
| Batch 8 | 4 | 97 | 76 | 43 |
| Batch 9 | 5 | 102 | 85 | 42 |
| Batch 10 | 5 | 87 | 63 | 42 |

The average molecular weight (MW) of three oligomeric streptavidin mutein reagents generated as described above was measured by asymmetrical flow field-flow fractionation (AF4) performed with an HPLC system (AGILENT 1100 and Wyatt ECLIPSE DUALTEC) with UV detection (Agilent UV detector coupled with MALLS DAWN HELEOS (Wyatt)). The measurements by AF4 allowed for the calculation of the average number of streptavidin mutein tetramers in each oligomeric reagent assuming the average molecular weight of a streptavidin mutein tetramer of 52,500 g/mol (52.5 kDa) (Table E2).

TABLE E2

Size and Molecular Weight of oligomeric streptavidin mutein reagents

| Radius (nm) | MW (g/mol) | Number of Tetramers |
|---|---|---|
| 102 | $1.65 \times 10^8$ | 3150 |
| 82 | $1.08 \times 10^8$ | 2050 |
| 92 | $1.26 \times 10^8$ | 2280 |

Example 2: Assessment of Parameters Impacting Oligomerization of a Streptavidin Mutein Reagent Various parameters in the method described in Example 1 were evaluated to assess impacts on different aspects of the procedure for generating an oligomeric streptavidin mutein reagent.

A. pH Level

The effect of performing the thiolation reaction at different pHs on oligomer size and product yield was assessed. Iminothiolane was purchased as hydrochloride, and its dissolution in 100 mM borate buffer at pH 8.5 to a concentration of 100 mg/mL induced a drop in pH of±0.7 units to pH 7.8. When the borate buffer was used at lower strength, i.e., 25 mM, the addition of the iminothiolane hydrochloride to a concentration of 100 mg/mL induced a greater pH drop of 1.6 units to pH 6.9. Thiolation reactions were performed at different pH by incubation of 100 mg of streptavidin mutein with 2-iminothiolane hydrochloride at a molar ratio of 1:100 in 25 mM borate buffer at pH 7.5, pH 8.5, and pH 9.5. The thiolated streptavidin mutein was combined with maleimide activated streptavidin mutein and the oligomerization process was carried out essentially as described in Example 1.

As shown in Table E3, reducing the pH of the borate buffer used with the thiolation reaction led to a reduction of oligomer size and yield while increasing pH led to increase of size and yield. An inadvertent loss of material occurred during the experiment with the pH 9.5 condition, which resulted in a reduced yield. The value in parentheses in Table E3 reflects the calculated yield had the loss not occurred.

TABLE E3

STREP-TACTIN oligomer size and yield following thiolization at different pHs

| Thiolization Reaction pH | Radius (nm) | Yield (%) |
|---|---|---|
| pH 7.5 | 14 | 6 |
| pH 8.5 | 40 | 48 |
| pH 9.5 | 52 | 14(62) |

To assess if a stronger buffer (i.e. 100 mM borate buffer compared to 25 mM with concomitant pH increase in the final reaction mixture) alters reaction kinetics, an iminothiolane activation reaction was performed as described in Example 1. Net thiol function content was determined by Ellman's reagent at multiple time points during the reaction. The reaction velocity in 100 mM borate buffer is depicted in FIG. 1, and was observed to be faster and to introduce more SH groups than when the reaction was performed in 25 mM borate buffer. The iminothiolane activation reaction achieved a peak concentration of thiol functions beginning as early as 25 min after the start of the reaction in 100 mM borate buffer, as compared to between 50 and 150 minutes when the reaction was performed in 25 mM borate buffer which is a result of the higher final pH under which the reaction occurs when using the 100 mM buffer instead of the 25 mM buffer.

The effects of pH on other steps of the oligomerization process also was assessed. Oligomerization reactions were performed with reaction buffers (25 mM borate) at different pH, pH 8.3 and 8.5, and with coupling buffers (100 mM phosphate) at different pH, pH 7.0 and 7.2. Performing the thiolation reaction at a lower pH (8.3 instead of 8.5) had a greater influence on oligomer size than performing the activation or coupling reactions at a lower pH (7.0 instead of 7.3). However, performing the activation reaction or the coupling reaction at pH 7.0 did reduce oligomer size as compared to performing the reactions at pH 7.2.

B. Effect of Timing and pH on Thiolation Reaction

Analysis of iminothiolane-activated (thiolated) streptavidin mutein was carried out to determine if decay of thiol functions was due to disulfide formation (which cannot react with maleimide) or isomerization towards N-substituted iminothiolane.

Figure 2:
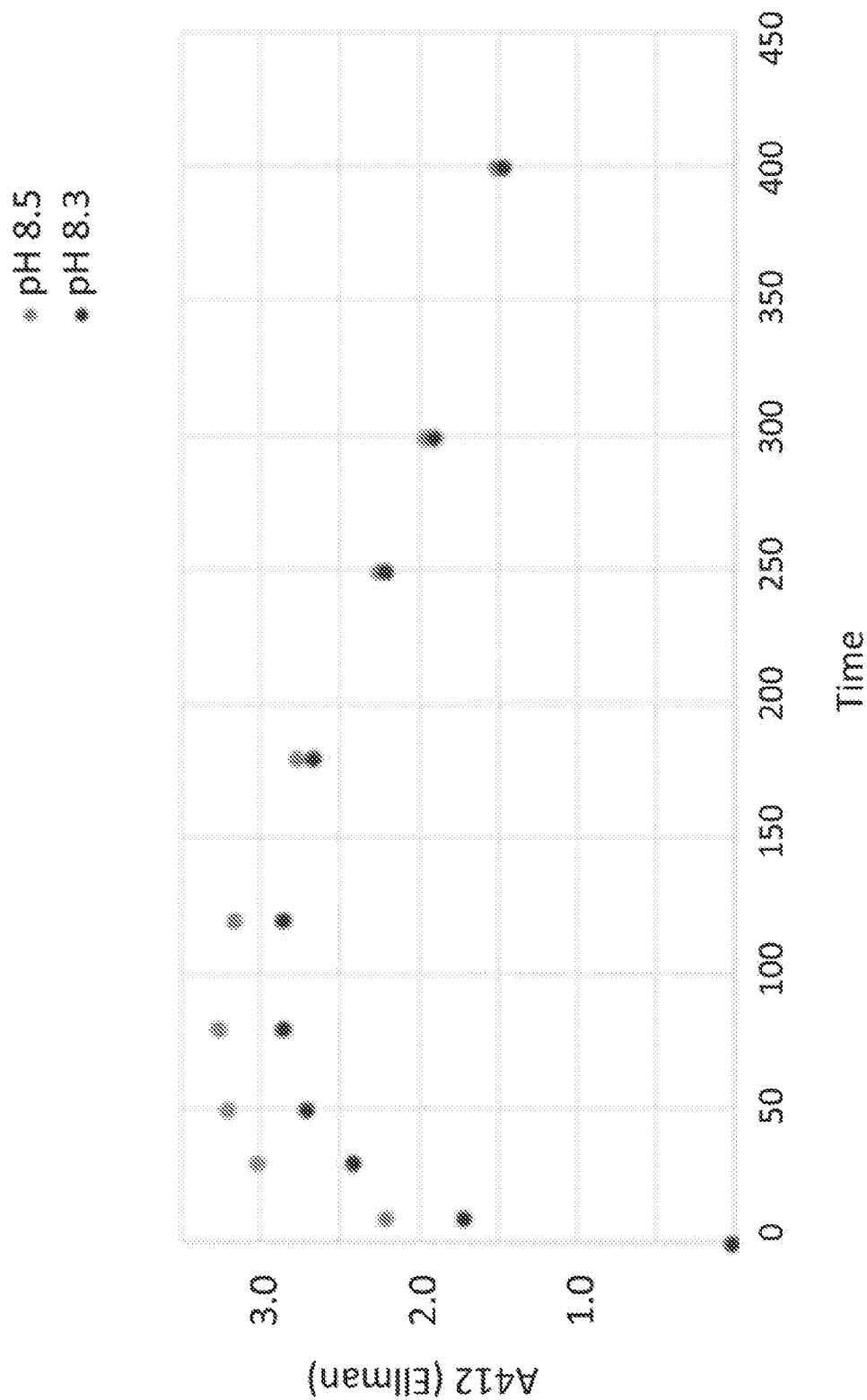
FIG. 2 shows a graph displaying levels of thiol functional groups attached to streptavidin mutein tetramers during an incubation of the exemplary streptavidin mutein STREP-TACTIN® M2 with 2-iminothiolane in 25 mM borate buffer at a pH of 8.3 or 8.5.

In one experiment, net thiol function content was detected at different time points with Ellman's reagent by measuring absorbance at 412 nm after a thiolation reaction with iminothiolane. The reaction was performed with 25 mM borate buffer that had starting pHs of 8.3 or 8.5, although the actual pH during the reaction was slightly below 7. As shown in FIG. 2, the thiol function content reached a maximum between 50 and 150 minutes (earlier using pH 8.5 and later using pH 8.3) and the height was pH dependent (higher using pH 8.5 as compared to using pH 8.3). Thiol function content of the streptavidin mutein during the reaction at both pHs converged after 3h, demonstrating that, after 3 hours, the streptavidin mutein generated using higher pH 8.5 included more N-substituted iminothiolane. Additional experiments indicated that the decrease of SH function was not influenced by the addition of the reducing agent tris(2-carboxyethyl)phosphine (TCEP) which would have been reversed if disulfide formation would have been the cause for decrease in SH function.

Figure 3:
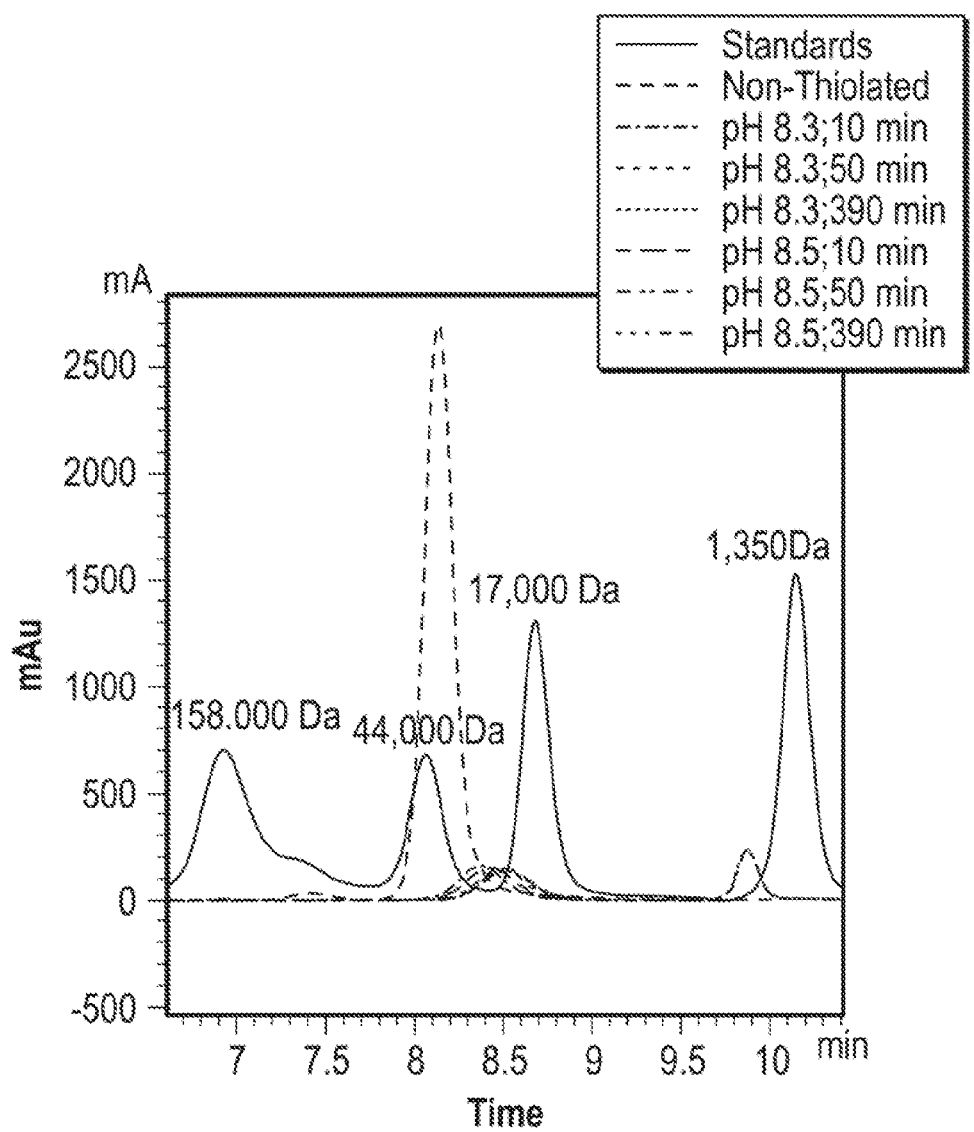
FIG. 3 shows SEC elution profiles of streptavidin mutein incubated with 2-iminothiolane. Elution peaks for molecular weight standards are shown as a solid line for molecular weights of 158,000 Da, 44,000 Da, 17,000 Da or 1350 Da are shown. The elution profile of non-thiolated exemplary streptavidin mutein STREP-TACTIN® M2 is shown as a dotted line. The remaining elution profiles depict elution profiles of various thiolated STREP-TACTIN® M2 streptavidin muteins that were incubated in the presence of 25 mM borate buffer at pH of 8.3 or pH 8.5 for either 10 minutes, 50 minutes or 390 minutes. Specifically shown are elution profiles following incubation of the exemplary streptavidin mutein STREP-TACTIN® M2 with 2-iminothiolane in the presence of 25 mM borate buffer at a pH of 8.3 for 10 minutes, 25 mM borate buffer at a pH of 8.3 for 50 minutes, 25 mM borate buffer at a pH of 8.3 for 390 minutes, or 25 mM borate buffer at pH of 8.5 for 10 minutes, 25 mM borate buffer at pH of 8.5 for 50 minutes, or 25 mM borate buffer at pH of 8.5 for 390 minutes.

Further, streptavidin muteins were thiolated by incubation with iminothiolane for 10 minutes, 50 minutes or 390 minutes using 25 mM borate buffer at pH 8.3 and 8.5, and the reaction products were analyzed via size exclusion chromatography (SEC) using a flow rate of 0.4 mL/min with 100 mM $NaH_2PO_4$, 140 mM NaCl, 1 mM EDTA, pH 7.0 and using an Agilent Bio SEC-3 3 µm 300A column. For determination of size, molecular weight standards were employed (indicated by peaks at 158,000 Da, 44,000 Da, 17,000 da or 1,350 Da in FIG. 3). An analysis of the SEC is shown in FIG. 3, in which non-activated streptavidin mutein tetramer is shown by the dotted line. Non-activated mutein tetramer was observed to have the lowest retention time, while the thiolated samples migrate slower (consistent with a smaller molecular weight) the longer they have been reacted with iminothiolane. Observed peaks of samples that had been reacted with iminothiolane were essentially identical is size and no peaks with lower retention times were observed. Thus, from the analysis, it could be concluded that no dimers or higher order oligomers were generated during prolonged reaction with iminothiolane which should have been the case in case of disulfide formation.

Figure 4:
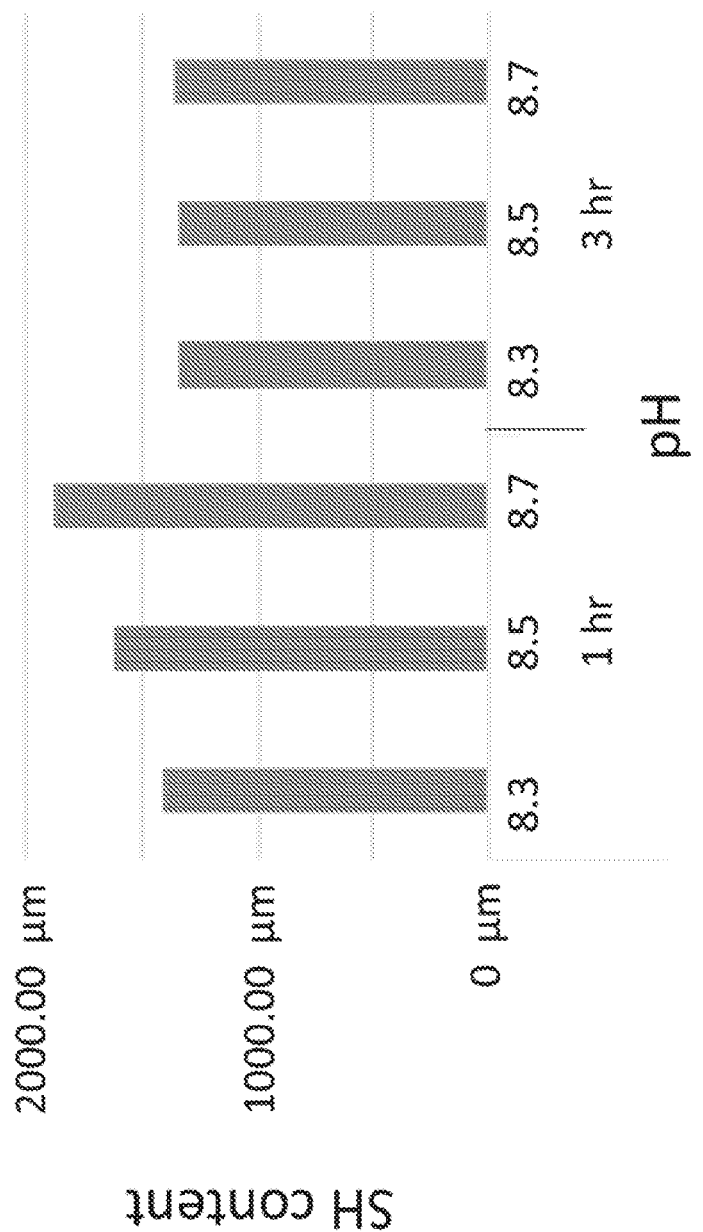
FIG. 4 depicts the concentration of thiol functional groups (SH content) following incubation of the exemplary streptavidin mutein STREP-TACTIN® M2 with 2-iminothiolane for 1 hour or 3 hours with 25 mM borate buffer at a pH of 8.3, 8.5, and 8.7.

To assess the effect of timing on SH content decay, the net thiol function content at the end of a 1h or 3h iminothiolane activation of streptavidin mutein at different pHs (pH 8.3, 8.5, or 8.7) in 25 mM borate buffer was assessed. After the reaction and PD10 gel filtration, SH content was determined by measuring absorbance at 412 nM after adding Ellman's reagent 5,5'-dithiobis-(2-nitrobenzoate) (DTNB). The reaction releases the 5-thio-2-nitrobenzoate ion TNB2-, which has an absorption maximum at 412 nm. By measuring the increase in absorbance at 412 nm and dividing by the molar extinction coefficient of the TNB2-ion at 412 nm, the free sulfhydryl content of the molecule can be calculated. As shown in FIG. 4, while thiol function content after a 1 hour reaction was pH dependent, very little effect of pH on thiol function content was evident after a 3h reaction. It is hypothesized that longer activation reaction can reduce the influence of pH on thiol function content and, thereby, make the reaction more robust in terms of pH dependent size variations, but may also increase N-substituted iminothiolane which could be a source of long-term size instability due to re-isomerization.

Figure 5:
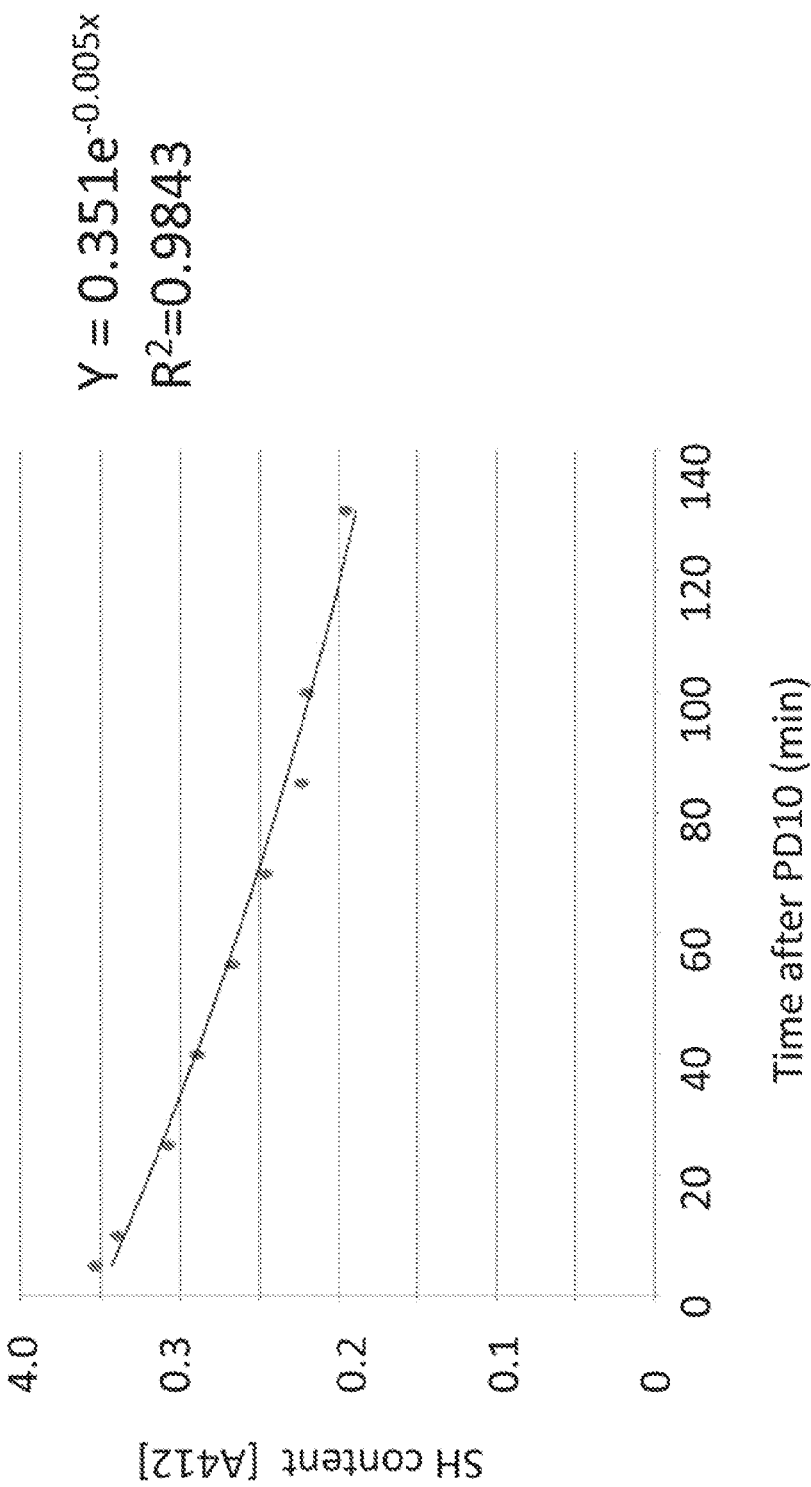
FIG. 5 depicts the loss of thiol functional groups (SH content) of the exemplary streptavidin mutein STREP-TACTIN® M2 at different time points following incubation of with 2-iminothiolane and gel filtration with PD10 columns.

To measure thiol function decay in the absence of thiol formation, thiol function content was measured at several time points after the thiolation reaction ended, i.e., after the removal of the iminothiolane reagent. The SH content of thiolated streptavidin was measured with Ellman's reagent at various times after removing the 2-Iminothiolane by PD10 gel filtration. As shown in FIG. 5 a 5% decay of thiol functions was detected 10 minutes after the reaction ended, a 26% decay was detected 60 minutes after the reaction, and a 45% decay of thiol functions was detected at 120 minutes after the reaction. The half-life of SH loss was calculated as 139 min. This indicates the effect of using different timeframes between end of iminothiolane and SMPH activation and start of the multimerization reaction.

C. Molar Ratios of Streptavidin Mutein and SMPH

To assess the impact of SMPH and streptavidin mutein concentration in the SMPH activation reaction on oligomerization of streptavidin mutein, oligomerization procedures were performed with different concentrations (ranging±10%) of SMPH and streptavidin mutein. A ten percent increase or decrease in the concentrations of SMPH or streptavidin resulted in detectable differences of streptavidin mutein oligomer size. In some aspects, it is recommended that accuracy of these parameters (concentration of Strep-Tactin and of SMPH) should be better than ±2%.

D. Stabilization of Oligomers

Non-reacted N-substituted iminothiolane from thiolation may remain on lysine residues and at the free N-terminus of streptavidin mutein and contribute to postsynthetic increases in oligomer size. To assess effects of hydroxylamine treatment on postsynthetic oligomer growth, oligomerization procedures were performed as described in Example 1, with the exception that procedures either involved a 1 hour activation reaction with iminothiolane (samples 1 and 2) or a 3.5 hour activation reaction with iminothiolane (samples 3 and 4). Further, in these studies, after SEC was performed, the samples containing the oligomeric streptavidin mutein reagents either received treatment with 100 mM hydroxylamine (HA) at a pH of 6.35 for 15 minutes at room temperature (samples 1 and 3) or received no hydroxylamine treatment (samples 2 and 4). Samples were split into fractions that were stored at either −80° C., 4° C., or 37° C. Oligomer size was measured by DLS immediately after synthesis (day 0) and at 1 week, 3 weeks, and 9 weeks post synthesis. The results are shown in Table E4.

TABLE E4

Effects of Storage Temperature and Hydroxylamine treatment Postsynthetic Growth

| Sample | Storage conditions | Radius at d 0 | Radius after w 1 | Radius after w 3 | Radius after w 9 | Radius after w 27 |
| --- | --- | --- | --- | --- | --- | --- |
| Sample 1 | −80° C. | 89 nm | 94 nm | 93 nm | 91 nm | 91 nm |
| +HA | 4° C. | 89 nm | 95 nm | 95 nm | 96 nm | 100 nm |
| 1 hr Act | 37° C. | 89 nm | 99 nm | 108 nm | 107 nm | 114 nm |
| Sample 2 | −80° C. | 88 nm | 93 nm | 96 nm | 94 nm | 94 nm |
| −HA | 4° C. | 88 nm | 97 nm | 106 nm | 106 nm | 112 nm |
| 1 hr Act | 37° C. | 88 nm | 115 nm | 137 nm | 178 nm | 329 nm |
| Sample 3 | −80° C. | 94 nm | 100 nm | 98 nm | 94 nm | 92 nm |
| +HA | 4° C. | 94 nm | 96 nm | 98 nm | 100 nm | 102 nm |
| 3.5 hr Act | 37° C. | 94 nm | 108 nm | 121 nm | 142 nm | 249 nm |
| Sample 4 | −80° C. | 91 nm | 98 nm | 98 nm | 96 nm | 100 nm |
| −HA | 4° C. | 91 nm | 111 nm | 138 nm | 157 nm | 99 nm |
| 3.5 hr Act | 37° C. | 91 nm | 148 nm | 177 nm | 265 nm | 409 nm |

As shown in Table E4, hydroxylamine treatment reduced the growth of oligomers during storage at temperatures of 4° C. and 37° C. Size was observed to be stable during storage at −80° C., regardless of hydroxylamine treatment. Samples 3 and 4 were activated for 3.5 hours and displayed a more pronounced post-synthetic growth of the oligomers. Without wishing to be bound by theory, in some aspects, the 3.5 hour activation time is not as sensitive to pH variations as the 1 hour activation time (see Example 2B), but may result in a higher content of N-substituted iminothiolane. Together, the results showed that hydroxylamine treatment reduces post-synthetic growth of streptavidin mutein oligomers. The data also demonstrated that storage at −80° C. enhances stability of the oligomers. Thus, in some aspects, combining both hydroxylamine treatment followed by storage at a temperature of −80° C. may provide enhanced stability for maintaining consistent size, including during prolonged storage.

Example 3: Generation of a Soluble Stimulatory Reagent, Containing Oligomerized Anti-CD3 and Anti-CD28 Fab Fragments Reversibly Bound to Streptavidin Mutein Oligomers Stimulatory agents (anti-CD3 and anti-CD28 Fab fragments) were multimerized by reversible binding to an oligomeric streptavidin mutein reagent generated as described in Example 1. Anti-CD3 and anti-CD28 Fab fragments were reversibly bound to the streptavidin mutein oligomer via a streptavidin peptide-binding partner fused to each Fab fragment. The anti-CD3 Fab fragment was derived from the CD3 binding monoclonal antibody produced by the hybridoma cell line OKT3 (ATCC® CRL-8001™; see also U.S. Pat. No. 4,361,549), and contained the heavy chain variable domain and light chain variable domain of the anti-CD3 antibody OKT3 described in Arakawa et al J. Biochem. 120, 657-662 (1996). These sequences are set forth in SEQ ID NOS: 31 and 32, respectively. The anti-CD28 Fab fragment was derived from antibody CD28.3 (deposited as a synthetic single chain Fv construct under GenBank Accession No. AF451974.1; see also Vanhove et al., BLOOD, 15 Jul. 2003, Vol. 102, No. 2, pages 564-570) and contained the heavy and light chain variable domains of the anti-CD28 antibody CD28.3 set forth in SEQ ID NOS: 33 and 34, respectively. The Fab fragments were individually fused at the carboxy-terminus of their heavy chain to a streptavidin peptide-binding sequence containing a sequential arrangement of two streptavidin binding modules having the sequence of amino acids SAWSHPQFEK(GGGS)2GG-SAWSHPQFEK (SEQ ID NO: 16). The peptide-tagged Fab fragments were recombinantly produced (see International Patent App. Pub. Nos. WO 2013/011011 and WO 2013/124474).

To carry out reversible binding, peptide-tagged anti-CD3 and anti-CD28 Fab fragments were mixed with the oligomeric streptavidin mutein reagent at approximately room temperature, thereby reversibly binding them to the reagent via interaction between twin-strep-tags on the Fab fragments, which were binding partners capable of reversibly binding to binding sites on the reagent. In some cases, the peptide-tagged Fab fragments were pre-mixed prior to immobilization onto the oligomeric streptavidin mutein reagent, which, in some instances, can result in a more uniform distribution of the different Fab molecules.

Example 4: Activity Assessment of Oligomerized Anti-CD3 and Anti-CD28 Fab Fragments Reversibly Bound to Streptavidin Mutein Oligtomers Anti-CD3 and anti-CD28 Fab fragments, reversibly bound to various oligomeric streptavidin reagents from each of the batches described in Table E1 by the process described in Example 1, were assessed for the ability to stimulate T cells. These oligomeric streptavidin reagents had an average radius of about 95 nm. Metabolic activity of cells as an indicator of cell proliferation was assessed by colorimetric monitoring of cleavage of the stable tetrazolium salt WST-1 to a soluble formazan dye complex.

T cells, from three different donors, were incubated with the anti-CD3/anti-CD28 multimerized Fab fragments reversibly bound on an oligomeric streptavidin reagent. Cells were also incubated with control oligomeric reagents that had either an average radius of 101 (internal reference) or 36 nm, which also were reversibly bound to anti-CD3/anti-CD28 Fab fragments. After the incubation, WST-1 reagent was applied to the cells and the levels of metabolic activity were assessed by measuring the absorbance at 450 nm as a readout. The results were normalized to the number of cells in the culture being assayed and depicted as the ratio of WST-1 per cell number.

Figures 6A, 6B:
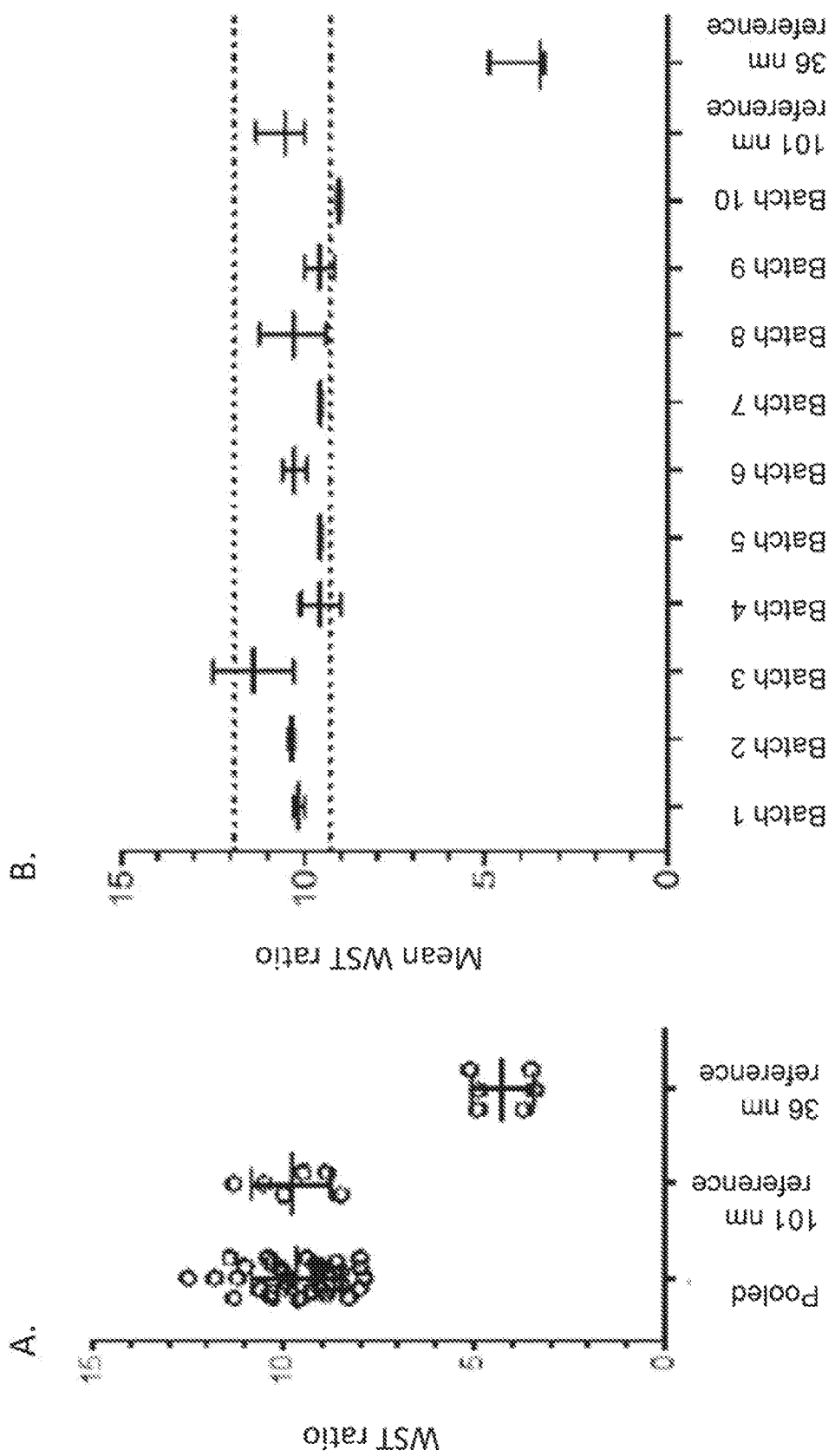
FIGS. 6A and 6B show results of a WST metabolic assay of T cells from three different donors incubated with anti-CD3/anti-CD28 multimerized on different batches of oligomeric reagents composed of the exemplary streptavidin mutein STREP-TACTIN® M2.

As shown in FIG. 6B, mean WST-1 activity of T cells stimulated with each of the tested reagents were comparable. Moreover, the degree of stimulation was similar for all tested reagents and was comparable to a similarly sized internal reference reagent (varying generally within ±2 standard deviations). FIG. 6A shows the WST-1 activity depicted as a separate data point for each reagent. FIG. 6A and FIG. 6B indicate that stimulation of T cells, as observed by WST-1 activity, was lower using anti-CD3/anti-CD28 Fabs multimerized on a smaller 36 nm oligomeric streptavidin mutein reagent backbone.

Example 5: Exemplary Method for Preparing an Oligomeric Streptavidin Mutein

Oligomeric streptavidin mutein reagents were generated by an exemplary method similar to the method described in Example 1 with some modifications. Specifically, after incubation with NEM, the sample containing oligomerized streptavidin mutein was centrifuged and the supernatant was filtered through a 0.45 μm membrane. The filtered solution was then treated with 100 mM hydroxylamine at a pH of 6.35 for 15 minutes at room temperature. The sample was then loaded onto a column for size exclusion chromatography (SEC) with an AKTA Explorer chromatography system (GE Healthcare). Fractions with a milli absorbance unit (mAU) greater than or equal to 1500 mAU were pooled and then sterile filtered with a 0.45 μm filter followed by a 0.22 μm filter. The oligomerized streptavidin was stored at −80° C. Thus, unlike the method described in Example 1, no further PD-10 based gel filtration was carried out.

Figure 11:
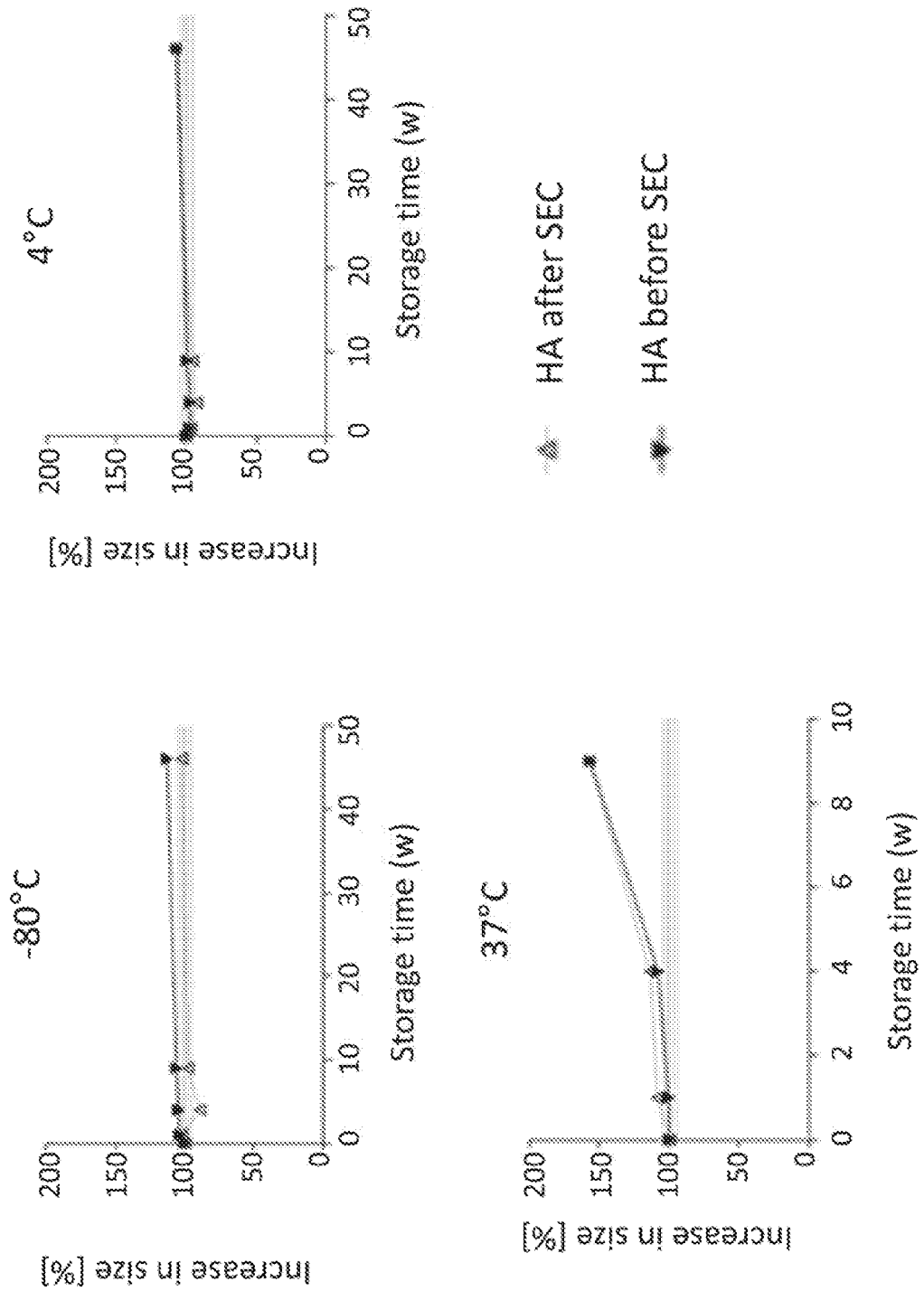
FIG. 11 shows graphs of changes in size as measured by dynamic light scattering of oligomeric streptavidin mutein reagents at various time points following storage at −80° C., 4° C., or 37° C.

The size and stability of the oligomeric streptavidin mutein reagents produced by the exemplary method were compared to the oligomers produced by the method described in Example 1. The oligomers were split into fractions that were stored at either −80° C., 4° C., or 37° C. Oligomer size was measured by DLS immediately after synthesis (day 0) and at various time points post synthesis. Both methods, whether hydroxylamine was removed after SEC or before SEC, produced oligomers of comparable size and stability. As shown in FIG. 11, oligomers stored at −80° C. or 4° C. displayed an average change in size of less than 10% for as long as 46 weeks post synthesis. Oligomers stored at 37° C. displayed an increase in size of approximately 50% by 9 weeks post synthesis.

Example 6:Evaluation of Different Manufactured Lots of Oligomeric Streptavidin Mutein Reagents Different lots of oligomeric streptavidin mutein reagents composed from different raw material batches were evaluated as part of a process for engineering T cells with a chimeric antigen receptor (CAR). Three discrete oligomeric streptavidin mutein reagent lots were generated from individual lots of STREP-TACTIN® M2 substantially as described above. Anti-CD3 and anti-CD28 Fabs containing fused streptavidin peptide-binding partner from the same manufacturing lot were reversibly bound to the individual streptavidin mutein oligomers from each lot substantially as described above. The three discrete oligomeric streptavidin mutein reagent lots had average diameters between 100 nm and 109 nm.

The three individual lots of anti-CD3/anti-CD28 Fab conjugated streptavidin mutein oligomeric reagents were used to stimulate primary CD4+ and CD8+ T cells. The CD4+ and CD8+ T cells were individually selected from an apheresis sample from three individual donors prior to combining the selected cells at a specified ratio of CD4+ to CD8+ T cells. The combined CD4+ and CD8+ T cells were then engineered with a chimeric antigen receptor (CAR) by an exemplary engineering process that included incubating the cells with a lot of the anti-CD3/anti-CD28 Fab conjugated streptavidin mutein oligomeric reagents, transducing with a lentivirus, and then cultivating for expansion. Prior to completion of expansion, the cells were treated with biotin to dissociate the anti-CD3/anti-CD28 Fabs from the streptavidin oligomeric reagents. The conditions for incubation, transduction and cultivation were the same for all tested lots of the anti-CD3/anti-CD28 Fab conjugated streptavidin mutein reagents, and each lot was tested with up to four replicates for each of the three donor samples. To monitor transduction efficiency of engineered T cells, the lentivirus delivered a polynucleotide encoding the CAR separated from a truncated receptor by a ribosomal skipping sequence for use as a surrogate marker for detecting the CAR expression.

Figure 12B:
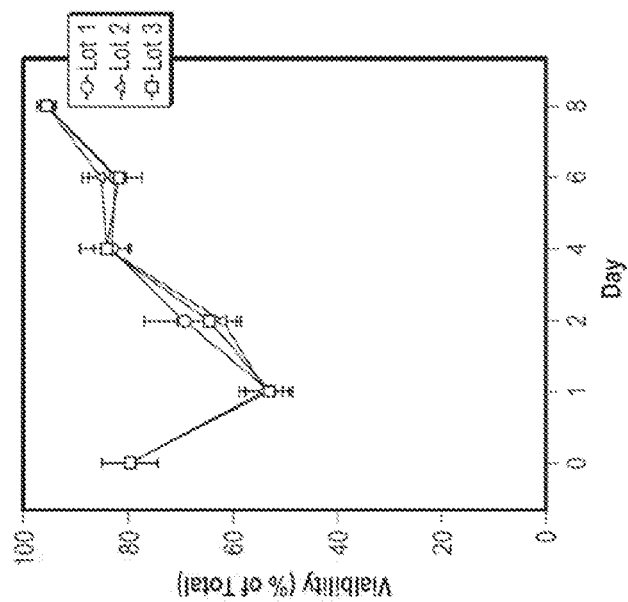
FIGS. 12A and B shows graphs of the total cells (FIG. 12A) and the percentage of viable cells (FIG. 12B) over time during incubation with different individual lots of anti-CD3/anti-CD28 Fab conjugated oligomeric streptavidin mutein reagents during an exemplary engineering process for generating T cell compositions containing chimeric antigen receptor (CAR) expressing T cells.
Figure 12A:
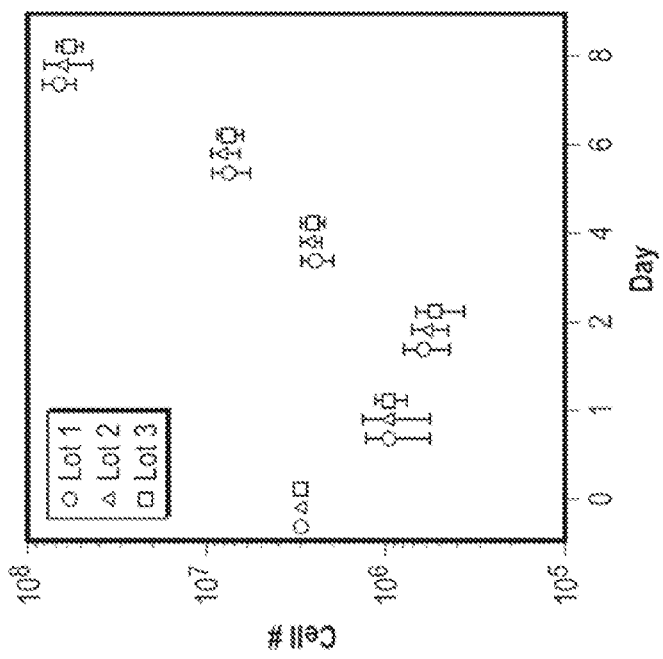

The total number of viable cells at various stages of the exemplary engineering process was quantified. Cells were labeled with a viability stain prior to the addition of the Fab conjugated streptavidin mutein oligomeric reagent (day 0), and at various days of the process. As shown in FIGS. 12A and 12B, the total amounts of viable cells and the percentage of viable cells measured at the different stages of the engineering process were consistent between cells obtained from different donors and using different lots of the Fab-conjugated streptavidin mutein oligomeric reagents.

Figure 13:
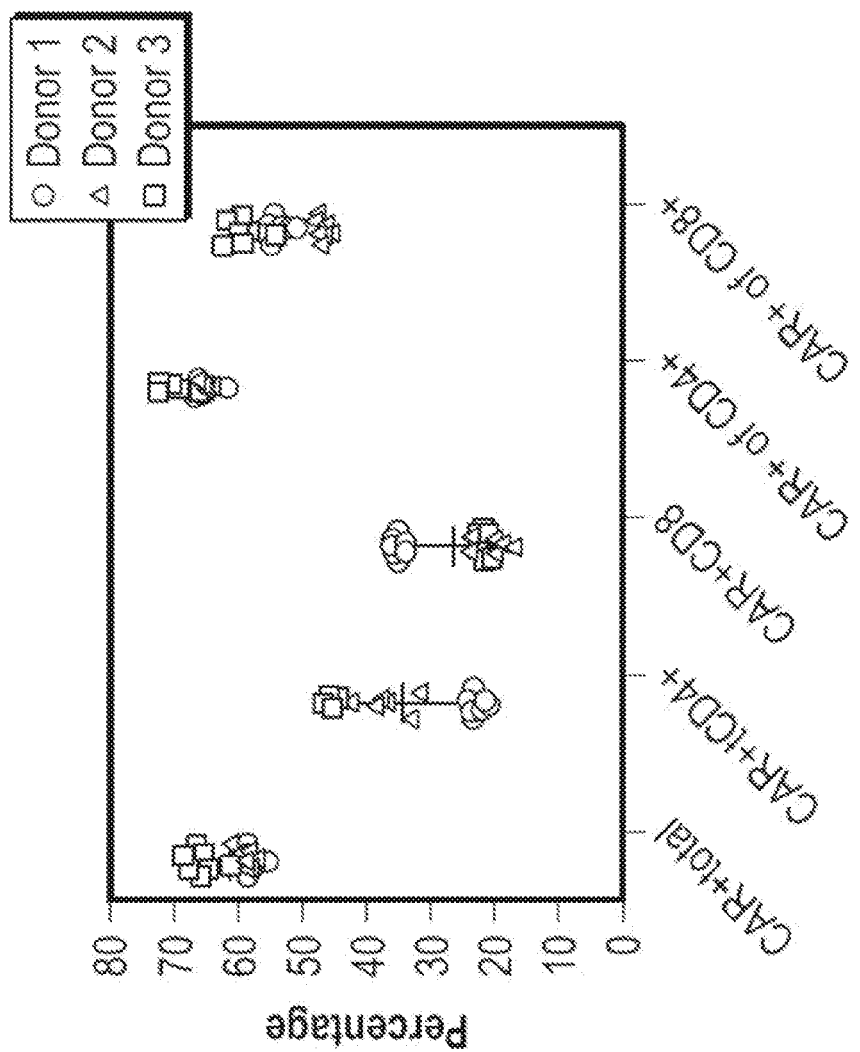
FIG. 13 shows a graph displaying the percentages of total CAR+, CD4+CAR+, and CD8+CAR+ cells as well as the percentage of CAR+CD4+ T cells among CD4+ T cells and the percentage of CAR+CD8+ T cells among CD8+ T cells of T cell compositions incubated with different individual lots of anti-CD3/anti-CD28 Fab conjugated oligomeric streptavidin mutein reagents during an exemplary engineering process for generating CAR T cell compositions.

Transduction efficiency was measured in cells collected from exemplary engineering process. Cells were labeled with antibodies specific to CD4, CD8, and the surrogate marker and analyzed by flow cytometry. The percentage CAR+, CAR+CD4+, CAR+CD8+ cells among the total viable T cells are shown in FIG. 13. The transduction efficiency was consistent among different Fab-conjugated oligomeric streptavidin mutein reagent lots, and the observed variability was mainly dependent on the donor source.

Engineered CAR+ T cells were also examined for different markers associated with memory or exhaustion phenotypes. T Cells were labeled with antibodies specific to CD3, CD4, CD8, and the surrogate markers as well as for the memory-associated markers CCR7, CD27, CD28, CD45RA, CD45RO, and CD62L or with the exhaustion-associated markers CCR7, LAG3, PD-1, and TIM3 and then analyzed by flow cytometry. No significant variations in staining for memory-associated or exhaustion associated markers were observed. A principle component analysis according to the memory-associated and exhaustion-associated phenotypic markers was performed. Clusters derived from the cumulative data comparison, separated according to donors rather than the individual lots of Fab-conjugated oligomeric streptavidin mutein reagents, was in agreement with a consistency of the reagents on memory and exhaustion related phenotypes of T cells that may occur during the engineering process.

Figure 14:
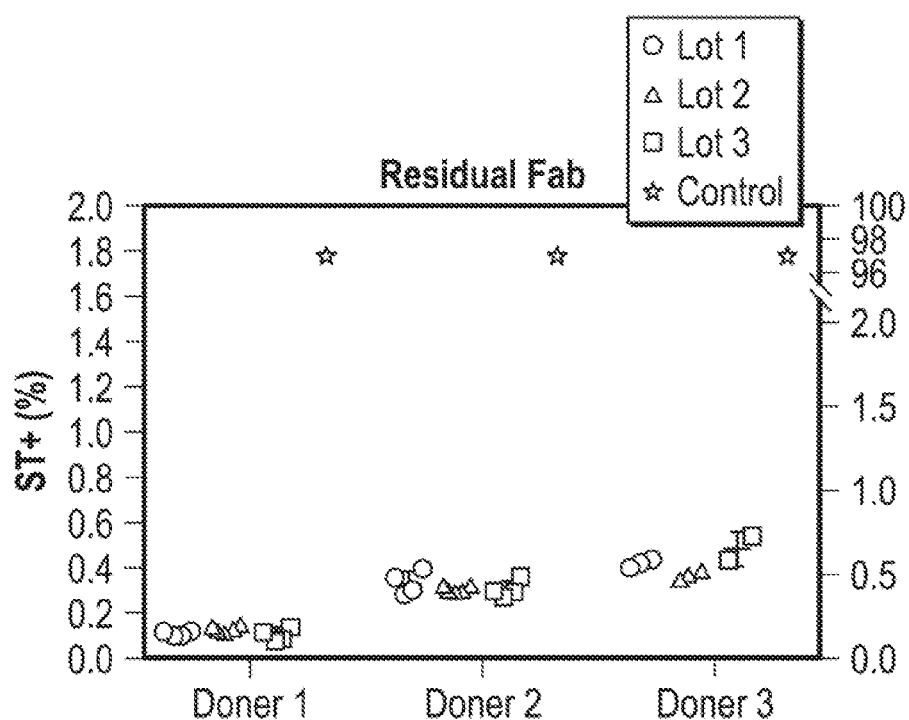
FIG. 14 shows graphs displaying the percentage of cells positive for residual Fab staining (top panel) or residual streptavidin mutein (bottom panel) among compositions of cells that were incubated with different individual lots of Fab conjugated oligomeric streptavidin mutein reagents.
Figure 14:
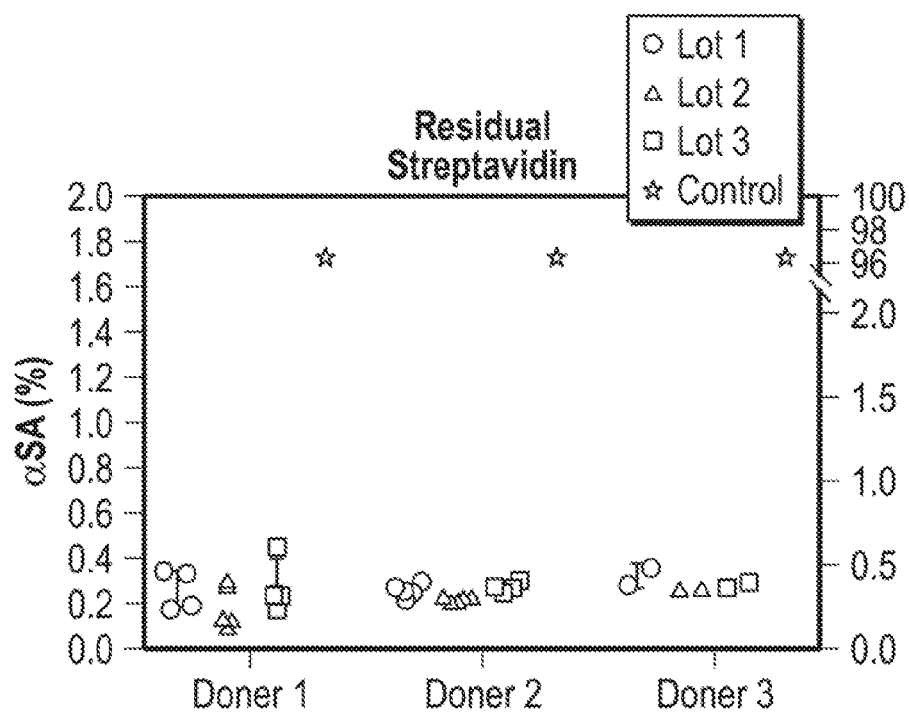

Engineered CAR+ T cells were analyzed for the presence of residual Fab or mutein streptavidin on cellular surfaces by detection of residual anti-CD3 and anti-CD28 Fabs by StrepTactin-PE staining or by detection of residual mutein streptavidin with an antibody specific to StrepTactin. As shown in FIG. 14, less than 1% of the viable T cells were positive for Fab or mutein streptavidin.

CAR-dependent antigen activity was assessed by co-culturing engineered CAR+ T cells with irradiated cells expressing the target antigen of the CAR. T cells cultured in the absence of the irradiated antigen expressing cells served as a negative control. After four hours of co-culture, the T cells were assessed for intracellular IL-2, IFN-gamma, and TNF-alpha by intracellular cytokine staining (ICS), stained for the surrogate marker indicating CAR expression and CD3, and evaluated by flow cytometry. Similar percentages of cells positive for IL-2, IFN-gamma, and TNF-alpha, as well as percentages of cells expressing two or three of the cytokines were observed among CAR+CD3+ T cells originating from different donors and among cells produced in the presence of different lots of Fab-conjugated oligomeric streptavidin mutein reagents.

Figure 15:
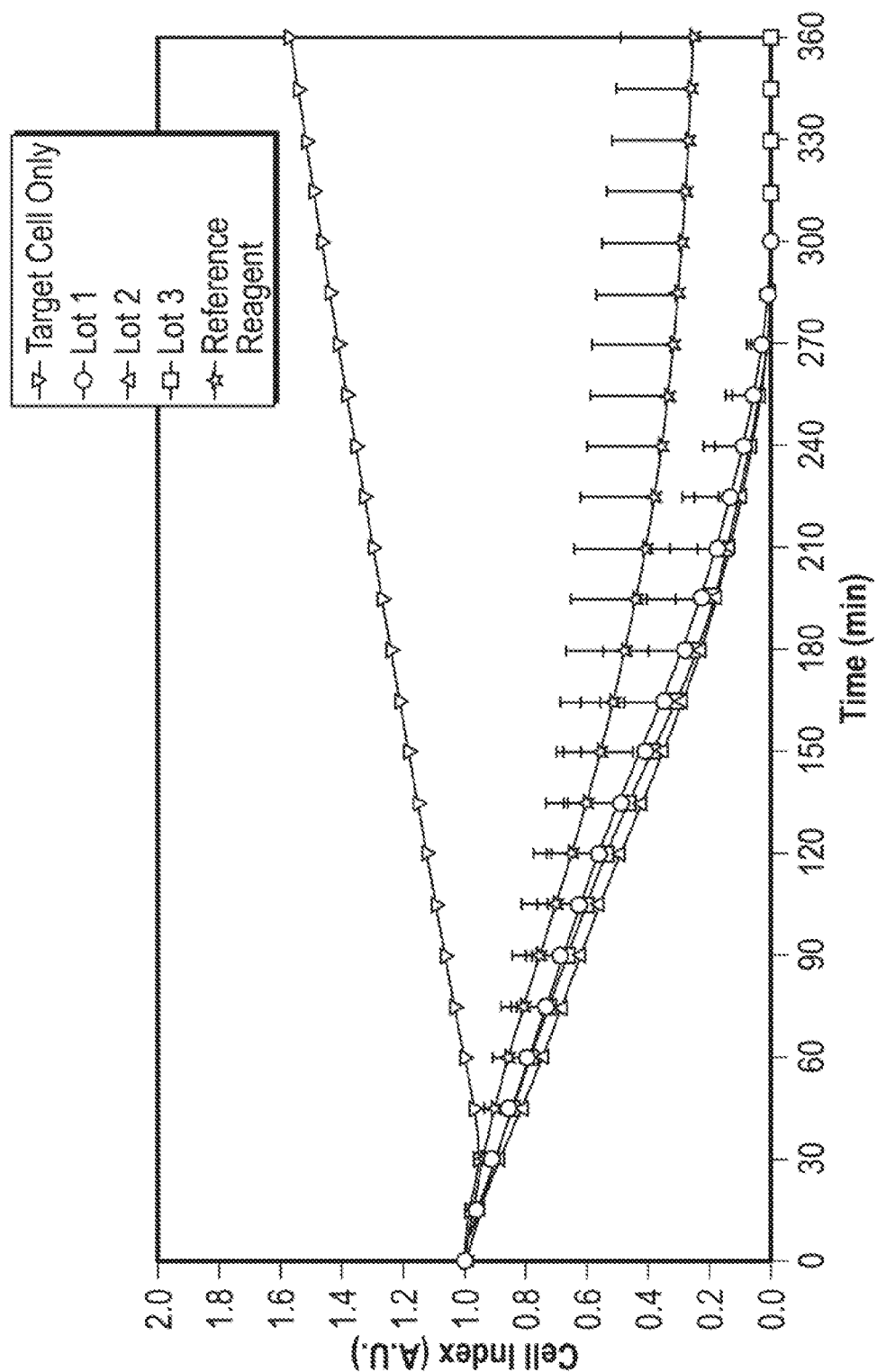
FIG. 15 shows a graph displaying the cytolytic activity of T cell compositions containing CAR T cells that were generated by an exemplary engineering process that involved incubation with different individual lots of anti-CD3/anti-CD28 Fab conjugated oligomeric streptavidin mutein reagents.

Cytolytic activity was assessed in engineered CAR+ T cells following co-culture of the cells with target cells expressing the target antigen of the CAR at a ratio of effector cells to target cells of 5:1. The adherent target cells were seeded in the wells of an electronic microtiter plate and target cell number was quantified by measuring impedance of electrical current between attached electrodes. For controls, target cells were cultured alone or with T cells that had incubated during the exemplary engineering process with a reference anti-CD3/anti-CD28 antibody conjugated paramagnetic bead reagent. As shown in FIG. 15, CAR+ T cells demonstrated effective killing in the assay. The observed cytolytic activity was comparable among T cells obtained from different individual donors and among different manufactured lots of Fab-conjugated oligomeric streptavidin mutein reagents.

Taken together, these data are in agreement with a high degree of consistency of Fab-conjugated oligomeric streptavidin mutein reagents generated by the provided methods.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| No. | Sequence | Description |
|---|---|---|
| 1 | DPSKDSKAQVSAAEAGITGTWYNQLGSTFIVTAGADGALT GTYESAVGNAESRYVLTGRYDSAPATDGSGTALGWTVAW KNNYRNAHSATTWSGQYVGGAEARINTQWLLTSGTTEAN AWKSTLVGHDTFTKVKPSAASIDAAKKAGVNNGNPLDAV QQ | Streptavidin Species: *Streptomyces avidinii* UniProt No. P22629 |
| 2 | EAGITGTWYNQLGSTFIVTAGADGALTGTYESAVGNAESRY VLTGRYDSAPATDGSGTALGWTVAWKNNYRNAHSATTWS GQYVGGAEARINTQWLLTSGTTEANAWKSTLVGHDTFTKV KPSAAS | Minimal streptavidin Species: *Streptomyces avidinii* |
| 3 | DPSKDSKAQVSAAEAGITGTWYNQLGSTFIVTAGADGALT GTYVTARGNAESRYVLTGRYDSAPATDGSGTALGWTVAW KNNYRNAHSATTWSGQYVGGAEARINTQWLLTSGTTEAN AWKSTLVGHDTFTKVKPSAASIDAAKKAGVNNGNPLDAV QQ | Mutein Streptavidin Val44-Thr45-Ala46-Arg47 Species: *Streptomyces avidinii* |
| 4 | EAGITGTWYNQLGSTFIVTAGADGALTGTYVTARGNAESR YVLTGRYDSAPATDGSGTALGWTVAWKNNYRNAHSATT WSGQYVGGAEARINTQWLLTSGTTEANAWKSTLVGHDTFT KVKPSAAS | Mutein Streptavidin Val44-Thr45-Ala46-Arg47 Species: *Streptomyces avidinii* |
| 5 | DPSKDSKAQVSAAEAGITGTWYNQLGSTFIVTAGADGALT GTYIGARGNAESRYVLTGRYDSAPATDGSGTALGWTVAW KNNYRNAHSATTWSGQYVGGAEARINTQWLLTSGTTEAN AWKSTLVGHDTFTKVKPSAASIDAAKKAGVNNGNPLDAV QQ | Mutein Streptavidin Ile44-Gly45-Ala-46-Arg47 Species: *Streptomyces avidinii* |
| 6 | EAGITGTWYNQLGSTFIVTAGADGALTGTYIGARGNAESRY VLTGRYDSAPATDGSGTALGWTVAWKNNYRNAHSATTWS GQYVGGAEARINTQWLLTSGTTEANAWKSTLVGHDTFTKV KPSAAS | Mutein Streptavidin Ile44-Gly45-Ala-46-Arg47 Species: *Streptomyces avidinii* |

-continued

| No. | Sequence | Description |
|---|---|---|
| 7 | Trp-Arg-His-Pro-Gln-Phe-Gly-Gly | Streptavidin binding peptide, Strep-tag ® |
| 8 | WSHPQFEK | Strep-tag ® II |
| 9 | His-Pro-Baa | Streptavidin Binding peptide Baa is selected from glutamine, asparagine and methionine |
| 10 | His-Pro-Gln-Phe | Streptavidin-binding peptide |
| 11 | Oaa-Xaa-His-Pro-Gln-Phe-Yaa-Zaa | Streptavidin-binding peptide Oaa is Trp, Lys or Arg; Xaa is any amino acid: Yaa is Gly or Glu Zaa is Gly, Lys or Arg |
| 12 | -Trp-Xaa-His-Pro-Gln-Phe-Yaa-Zaa- | Streptavidin-binding peptide Xaa is any amino acid; Yaa is Gly or Gla Zaa is Gly, Lys or Arg |
| 13 | Trp-Ser-His-Pro-Gln-Phe-Glu-Lys-(Xaa)n-Trp-Ser-His-Pro-Gln-Phe-Glu-Lys- | Sequential modules of streptavidin-binding peptide Xaa is any amino acid; n is either 8 or 12 |
| 14 | Trp-Ser-His-Pro-Gln-Phe-Glu-Lys-(GlyGlyGlySer)n-Trp-Ser-His-Pro-Gln-Phe-Glu-Lys | Sequential modules of streptavidin-binding peptide n is 2 or 3 |
| 15 | SAWSHPQFEKGGGSGGGSGGGSWSHPQFEK | Twin-Strep-tag |
| 16 | SAWSHPQFEKGGGSGGGSGGSAWSHPQFEK | Twin-Strep-tag |
| 17 | WSHPQFEKGGGSGGGSGGGSWSHPQFEK | Twin-Strep-tag |
| 18 | WSHPQFEKGGGSGGGSWSHPQFEK | Twin-Strep-tag |
| 19 | WSHPQFEKGGGSGGGSGGSAWSHPQFEK | Twin-Strep-tag |
| 20 | Tyr-Pro-Tyr-Asp-Val-Pro-Asp-Tyr-Ala | HA-tag |
| 21 | Tyr-Thr-Asp-Ile-Glu-Met-Asn-Arg-Leu-Gly-Lys | VSV-G-tag |
| 22 | Gln-Pro-Glu-Leu-Ala-Pro-Glu-Asp-Pro-Glu-Asp | HSV-tag |
| 23 | Ala-Ser-Met-Thr-Gly-Gly-Gln-Gln-Met-Gly | T7 epitope |
| 24 | Glu-Gln-Lys-Leu-Ile-Ser-Glu-Glu-Asp-Leu | HSV epitope |
| 25 | Glu-Gln-Lys-Leu-Ile-Ser-Glu-Glu-Asp-Leu | Myc epitope |
| 26 | Gly-Lys-Pro-Ile-Pro-Asn-Pro-Leu-Leu-Gly-Leu-Asp-Ser-Thr | V5-tag |
| 27 | EAGITGTWYNQLGSTFIVTAGADGALTGTYVTARGNAESRYVLTGRYDS APATDGSGTALGWTVAWKNNYRNAHSATTWSGQYVGGAEARINTQWLLT SGTTEENAGYSTLVGHDTFTKVKPSAAS | Mutein Streptavidin Ile44-Gly45-Ala-46-Arg47 and Glu117, Gly120, Try121 (mutein m1-9) Species: *Streptomyces avidinii* |
| 28 | DPSKDSKAQVSAAEAGITGTWYNQLGSTFIVTAGADGALT GTYVTARGNAESRYVLTGRYDSAPATDGSGTALGWTVAW KNNYRNAHSATTWSGQYVGGAEARINTQWLLTSGTTEENA GYSTLVGHDTFTKVKPSAAS | Mutein Streptavidin Ile44-Gly45-Ala-46-Arg47 and Glu117, Gly120, Try121 (mutein m1-9) Species: *Streptomyces avidinii* |
| 29 | AMQVQLKQSGPGLVQPSQSLSITCTVSGFSLTTFGVHWVRQSPGK GLEWLGVIWASGITD YNVPFMSRLSITKDNSKSQVFFKLNSLQPD DTAIYYCAKNDPGTGFAYWGQGTLVTVSAGSTKGPSVFPLAPSSK STSGGTAALGCLVKDYFPEPVTVSWNSGALTSGVHTFPAVLQSSG | Variable Heavy chain of Fab fragment m13B8.2 |

| No. | Sequence | Description |
|---|---|---|
| | LYSLSSVVTVPSSSLGTQTYICNVNHKPSNTKVDKKVEPKSCGSA<br>WSHPQ FEKGGGSGGG SGGSAWSHPQFEK | |
| 30 | AMDIQMTQSPASLSASVGETVTFTCRASEMIYSYLAWYQQKQGK<br>SPQLLVHDAKTLAEGVPSRFSGGGSGTQFSLKINTLQPEDFGTYYC<br>QAHYGNPPTFGGGTKLEIKRGIAAPSVFIFPPSDEQLKSGTASVVCL<br>LNNFYPREAKVQWKVDNALQSGNSQESVTEQDSKDSTYSLSSTLT<br>LSKADYEK HKVYACEVTHQGLSSPVTKSFNRGECGS | Variable Light chain of Fab Fragment m13B8.2 |
| 31 | Gln Val Gln Leu Gln Gln Ser Gly Ala Glu Leu Ala Arg Pro Gly Ala Ser<br>Val Lys Met Ser Cys Lys Ala Ser Gly Tyr Thr Phe Thr Arg Tyr Thr Met<br>His Trp Val Lys Gln Arg Pro Gly Gln Gly Leu Glu Trp Ile Gly Tyr Ile<br>Asn Pro Ser Arg Gly Tyr Thr Asn Tyr Asn Gln Lys Phe Lys Asp Lys Ala<br>Thr Leu Thr Thr Asp Lys Ser Ser Ser Thr Ala Tyr Met Gln Leu Ser Ser<br>Leu Thr Ser Glu Asp Ser Ala Val Tyr Tyr Cys Ala Arg Tyr Tyr Asp Asp<br>His Tyr Cys Leu Asp Tyr Trp Gly Gln Gly Thr Thr Leu Thr Val Ser Ser | Variable Heavy chain of anti-CD3 antibody OKT3 |
| 32 | Gln Ile Val Leu Thr Gln Ser Pro Ala Ile Met Ser Ala Ser Pro Gly Glu<br>Lys Val Thr Met Thr Cys Ser Ala Ser Ser Ser Val Ser Tyr Met Asn Trp<br>Tyr Gln Gln Lys Ser Gly Thr Ser Pro Lys Arg Trp Ile Tyr Asp Thr Ser<br>Lys Leu Ala Ser Gly Val Pro Ala His Phe Arg Gly Ser Gly Ser Gly Thr<br>Ser Tyr Ser Leu Thr Ile Ser Gly Met Glu Ala Glu Asp Ala Ala Thr Tyr<br>Tyr Cys Gln Gln Trp Ser Ser Asn Pro Phe Thr Phe Gly Ser Gly Thr Lys<br>Leu Glu Ile Asn | Variable Light chain of anti-CD3 antibody OKT3 |
| 33 | Leu Gln Gln Ser Gly Ala Glu Leu Val Lys Pro Gly Ala Ser Val Arg Leu<br>Ser Cys Lys Ala Ser Gly Tyr Thr Phe Thr Glu Tyr Ile Ile His Trp Ile<br>Lys Leu Arg Ser Gly Gln Gly Leu Glu Trp Ile Gly Trp Phe Tyr Pro Gly<br>Ser Asn Asp Ile Gln Tyr Asn Ala Lys Phe Lys Gly Lys Ala Thr Leu Thr<br>Ala Asp Lys Ser Ser Ser Thr Val Tyr Met Glu Leu Thr Gly Leu Thr Ser<br>Glu Asp Ser Ala Val Tyr Phe Cys Ala Arg Arg Asp Asp Phe Ser Gly Tyr<br>Asp Ala Leu Pro Tyr Trp Gly Gln Gly Thr Met Val Thr Val | Variable Heavy chain of anti-CD28 antibody CD28.3 |
| 34 | Asp Ile Gln Met Thr Gln Ser Pro Ala Ser Leu Ser Val Ser Val Gly Glu<br>Thr Val Thr Ile Thr Cys Arg Thr Asn Glu Asn Ile Tyr Ser Asn Leu Ala<br>Trp Tyr Gln Gln Lys Gln Gly Lys Ser Pro Gln Leu Leu Ile Tyr Ala Ala<br>Thr His Leu Val Glu Gly Val Pro Ser Arg Phe Ser Gly Ser Gly Ser Gly<br>Thr Gln Tyr Ser Leu Lys Ile Thr Ser Leu Gln Ser Glu Asp Phe Gly Asn<br>Tyr Tyr Cys Gln His Phe Trp Gly Thr Pro Cys Thr Phe Gly Gly Gly Thr<br>Lys Leu Glu Ile Lys Arg | Variable Light chain of anti-CD28 antibody CD28.3 |
| 35 | His-Asn-His-Arg-His-Lys-His-Gly-Gly-Gly-Cys | MAT tag |
| 36 | YNLDVRGARSFSPPRAGRHFGYRVLQVGNGVIVGAPGEGNSTGSL<br>YQCQSGTGHCLPVTLRGSNYTSKYLGMTLATDPTDGSILACDPGL<br>SRTCDQNTYLSGLCYLFRQNLQGPMLQGRPGFQECIKGNVDLVFL<br>FDGSMSLQPDEFQKILDFMKDVMKKLSNTSYQFAAVQFSTSYKTE<br>FDFSDYVKRKDPDALLKHVKHMLLLTNTFGAINYVATEVFREELG<br>ARPDATKVLIIITDGEATDSGNIDAAKDIIRYIIGIGKHFQTKESQET<br>LHKFASKPASEFVKILDTFEKLKDLFTELQKKIYVIEGTSKQDLTSF<br>NMELSSSGISADLSRGHAVVGAVGAKDWAGGFLDLKADLQDDTF<br>IGNEPLTPEVRAGYLGYTVTWLPSRQKTSLLASGAPRYQHMGRVL<br>LFQEPQGGGHWSQVQTIHGTQIGSYFGGELCGVDVDQDGETELLL<br>IGAPLFYGEQRGGRVFIYQRRQLGFEEVSELQGDPGYPLGRFGEAI<br>TALTDINGDGLVDVAVGAPLEEQGAVYIFNGRHGGLSPQPSQRIE<br>GTQVLSGIQWFGRSIHGVKDLEGDGLADVAVGAESQMIVLSSRPV<br>VDMVTLMSFSPAEIPVHEVECSYSTSNKMKEGVNITICFQIKSLIPQ<br>FQGRLVANLTYTLQLDGHRTRRRGLFPGGRHELRRNIAVTTSMSC<br>TDFSFHFPVCVQDLISPINVSLNFSLWEEEGTPRDQRAQGKDIPPIL<br>RPSLHSETWEIPFEKNCGEDKKCEANLRVSFSPARSRALRLTAFAS<br>LSVELSLSNLEEDAYWVQLDLHFPPGLSFRKVEMLKPHSQIPVSCE<br>ELPEESRLLSRALSCNVSSPIFKAGHSVALQMMFNTLVNSSWGDS<br>VELHANVTCNNEDSDLLEDNSATTIIPILYPINILIQDQEDSTLYVSF<br>TPKGPKITHQVKHMYQVRIQPSIHDHNIPTLEAVVGVPQPPSEGPITH<br>QWSVQMEPPVPCHYEDLERLPDAAEPCLPGALFRCPVVFRQEILV<br>QVIGTLELVGEIEASSMFSLCSSLSISFNSSKHFHLYGSNASLAQVV<br>MKVDVVYEKQMLYLVLSGIGGLLLLLLIFIVLYKVGFFKRNLKE<br>KMEAGRGVPNGIPAEDSEQLASGQEAGDPGCLKPLHEKDSESGGG<br>KD | LFA-1α (homo sapiens) |
| 37 | QECTKFKVSSCRECIESGPGCTWCQKLNFTGPGDPDSIRCDTRPQL<br>LMRGCAADDIMDPTSLAETQEDHNGGQKQLSPQKVTYLRPGQA<br>AAFNVTFRRAKGYPIDLYYLMDLSYSMLDDLRNVKKLGGDLLRA<br>LNEITESGRIGFGSFVDKTVLPFVNTHPDKLRNPCPNKEKECQPPFA<br>FRHVLKLTNNSNQFQTEVGKQLISGNLDAPEGGLDAMMQVAACP | LFA-1β (homo sapiens) |

| No. | Sequence | Description |
|---|---|---|
| | EEIGWRNVTRLLVFATDDGFHFAGDGKLGAILTPNDGRCHLEDNL<br>YKRSNEFDYPSVGQLAHKLAENNIQPIFAVTSRMVKTYEKLTEIIP<br>KSAVGELSEDSSNVVQLIKNAYNKLSSRVFLDHNALPDTLKVTYD<br>SFCSNGVTHRNQPRGDCDGVQINVPITFQVKVTATECIQEQSFVIR<br>ALGFTDIVTVQVLPQCECRCRDQSRDRSLCHGKGFLECGICRCDT<br>GYIGKNCECQTQGRSSQELEGSCRKDNNSIICSGLGDCVCGQCLC<br>HTSDVPGKLIYGQYCECDTINCERYNGQVCGGPGRGLCFCGKCRC<br>HPGFEGSACQCERTTEGCLNPRRVECSGRGRCRCNVCECHSGYQL<br>PLCQECPGCPSPCGKYISCAECLKFEKGPFGKNCSAACPGLQLSNN<br>PVKGRTCKERDSEGCWVAYTLEQQDGMDRYLIYVDESRECVAGP<br>NIAAIVGGTVAGIVLIGILLLVIWKALIHLSDLREYRRFEKEKLKSQ<br>WNNDNPLFKSATTTVMNPKFAES | |
| 38 | DFLAHHGTDCWTYHYSEKPMNWQRARRFCRDNYTDLVAIQNKA<br>EIEYLEKTLPFSRSYYWIGIRKIGGIWTWVGTNKSLTEEAENWGDG<br>EPNNKKNKEDCVEIYIKRNKDAGKWNDDACHKLKAALCYTASC<br>QPWSCSGHGECVEIINNYTCNCDVGYYGPQCQFVIQCEPLEAPEL<br>GTMDCTHPLGNFSFSSQCAFSCSEGTNLTGIEETTCGPFGNWSSPE<br>PTCQVIQCEPLSAPDLGIMNCSHPLASFSFTSACTFICSEGTELIGKK<br>KTICESSGIWSNPSPICQKLDKSFSMIKEGDYNPLFIPVAVMVTAFS<br>GLAFIIWLARRLKKGKKSKRSMNDPY | L-selectin<br>(homo sapiens) |
| 39 | FKIETTPESRYLAQIGDSVSLTCSTTGCESPFFSWRTQIDSPLNGKV<br>TNEGTTSTLTMNPVSFGNEHSYLCTATCESRKLEKGIQVEIYSFPK<br>DPEIHLSGPLEAGKPITVKCSVADVYPFDRLEIDLLKGDHLMKSQE<br>FLEDADRKSLETKSLEVTFTPVIEDIGKVLVCRAKLHIDEMDSVPT<br>VRQAVKELQVYISPKNTVISVNPSTKLQEGGSVTMTCSSEGLPAPE<br>IFWSKKLDNGNLQHLSGNATLTLIAMRMEDSGIYVCEGVNLIGKN<br>RKEVELIVQEKPFTVEISPGPRIAAQIGDSVMLTCSVMGCESPSFSW<br>RTQIDSPLSGKVRSEGTNSTLTLSPVSFENEHSYLCTVTCGHKKLE<br>KGIQVELYSFPRDPEIEMSGGLVNGSSVTVSCKVPSVYPLDRLEIEL<br>LKGETILENIEFLEDTDMKSLENKSLEMTFIPTIEDTGKALVCQAKL<br>HIDDMEFEPKQRQSTQTLYVNVAPRDTTVLVSPSSILEEGSSVNMT<br>CLSQGFPAPKILWSRQLPNGELQPLSENATLTLISTKMEDSGVYLC<br>EGINQAGRSRKEVELIIQVTPKDIKLTAFPSESVKEGDTVIISCTCGN<br>VPETWIILKKKAETGDTVLKSIDGAYTIRKAQLKDAGVYECESKN<br>KVGSQLRSLTLDVQGRENNKDYFSPELLVLYFASSLIIPAIGMIIYF<br>ARKANMKGSYSLVEAQKSKV | VCAM-1<br>(homo sapiens) |
| 40 | YNVDTESALLYQGPHNTLFGYSVVLHSHGANRWLLVGAPTANW<br>LANASVINPGAIYRCRIGKNPGQTCEQLQLGSPNGEPCGKTCLEER<br>DNQWLGVTLSRQPGENGSIVTCGHRWKNIFYIKNENKLPTGGCYG<br>VPPDLRTELSKRIAPCYQDYVKKFGENFASCQAGISSSFYTKDLIVM<br>GAPGSSYWTGSLFVYNITTNKYKAFLDKQNQVKFGSYLGYSVGA<br>GHFRSQHTTEVVGGAPQHEQIGKAYIFSIDEKELNILHEMKGKKLG<br>SYFGASVCAVDLNADGFSDLLVGAPMQSTIREEGRVFVYINSGSG<br>AVMNAMETNLVGSDKYAARFGESIVNLGDIDNDGEEDVAIGAPQ<br>EDDLQGAIYIYNGRADGISSTFSQRIEGLQISKSLSMFGQSISGQIDA<br>DNNGYVDVAVGAFRSDSAVLLRTRPVVIVDASLSHPESVNRTKFD<br>CVENGWPSVCIDLTLCFSYKGKEVPGYIVLFYNMSLDVNRKAESP<br>PRFYFSSNGTSDVITGSIQVSSREANCRTHQAFMRKDVRDILTPIQI<br>EAAYHLGPHVISKRSTEEFPPLQPILQQKKEKDIMKKTINFARFCA<br>HENCSADLQVSAKIGFLKPHENKTYLAVGSMKTLMLNVSLFNAG<br>DDAYETTLHVKLPVGLYFIKILELEEKQINCEVTDNSGVVQLDCSI<br>GYIYVDHLSRIDISFLLDVSSLSRAEEDLSITVHATCENEEEMDNLK<br>HSRVTVAIPLKYEVKLTVHGFVNPTSFVYGSNDENEPETCMVEKM<br>NLTFHVINTGNSMAPNVSVEIMVPNSFSPQTDKLFNILDVQTTTGE<br>CHFENYQRVCALEQQKSAMQTLKGIVRFLSKTDKRLLYCIKADPH<br>CLNFLCNFGKMESGKEASVHIQLEGRPSILEMDETSALKEEIRATG<br>FPEPNPRVIELNKDENVAHVLLEGLHHQRPKRYFTIVIISSSLLLGLI<br>VLLLISYVMWKAGFFKRQYKSILQEENRRDSWSYINSKSNDD | VLA-4<br>(homo sapiens) |
| 41 | APTSSSIKKTQLQLEHLLLDLQMILNGINNYKNPKLTRMLTFKFY<br>MPKKATELKHLQCLEEELKPLEEVLNLAQSKNFHLRPRDLISNINV<br>IVLELKGSETTFMCEYADETATIVEFLNRWITFCQSIISTLT | IL-2 |
| 42 | HKCDITLQEIIKTLNSLTEQKTLCTELTVTDIFAASKNTTEKETFCR<br>AATVLRQFYSHHEKDTRCLGATAQQFHRHKQLIRFLKRLDRNLW<br>GLAGLNSCPVKEANQSTLENFLERLKTIMREKYSKCSS | IL-4 |
| 43 | DCDIEGKDGKQYESVLMVSIDQLLDSMKEIGSNCLNNEFNFFKRHI<br>CDANKEGMFLFRAARKLRQFLKMNSTGDFDLHLLKVSEGTTILLN<br>CTGQVKGRKPAALGEAQPTKSLEENKSLKEQKKLNDLCFLKRLL<br>QEIKTCWNKILMGTKEH | IL-7 |

-continued

| No. | Sequence | Description |
|---|---|---|
| 44 | SPGQGTQSENSCTHFPGNLPNMLRDLRDAFSRVKTFFQMKDQLD<br>NLLLKESLLEDFKGYLGCQALSEMIQFYLEEVMPQAENQDPDIKA<br>HVNSLGENLKTLRLRLRRCHRFLPCENKSKAVEQVKNAFNKLQE<br>KGIYKAMSEFDIFINYIEAYMTMKIRN | IL-10 |
| 45 | GIHVILGCFSAGLPKTEANWVNVISDLKKIEDLIQSMHIDATLYTE<br>SDVHPSCKVTAMKCFLLELQVISLESGDASIHDTVENLIILANNSLS<br>SNGNVTESGCKECEELEEKNIKEFLQSFVHIVQMFINTS | IL-1 5 |
| 46 | GITIPRNPGCPNSEDKNFPRTVMVNLNIHNRNTNTNPKRSSDYYNR<br>STSPWNLHRNEDPERYPSVIWEAKCRHLGCINADGNVDYHMNSV<br>PIQQEILVLRREPPHCPNSFRLEKILVSVGCTCVTPIVHHVA | IL-17 |
| 47 | TPVVRKGRCSCISTNQGTIHLQSLKDLKQFAPSPSCEKIEIIATLKNG<br>VQTCLNPDSADVKELIKKWEKQVSQKKKQKNGKKHQKKKVLKV<br>RKSQRSRQKKTT | CXCL9 |
| 48 | VPLSRTVRCTCISISNQPVNPRSLEKLEIIPASQFCPRVEIIATMKKK<br>GEKRCLNPESKAIKNLLKAVSKERSKRSP | CXCL10 |
| 49 | GTNDAEDCCLSVTQKPIPGYIVRNFHYLLIKDGCRVPAVVFTTLRG<br>RQLCAPPDQPWVERIIQRLQRTSAKMKRRSS | CCL19 |
| 50 | SDGGAQDCCLKYSQRKIPAKVVRSYRKQEPSLGCSIPAILFLPRKR<br>SQAELCADPKELWVQQLMQHLDKTPSPQKPAQGCRKDRGASKT<br>GKKGKGSKGCKRTERSQTPKGP | CCL21 |
| 51 | QGVFEDCCLAYHYPIGWAVLRRAWTYRIQEVSGSCNLPAAIFYLP<br>KRHRKVCGNPKSREVQRAMKLLDARNKVFAKLHHNTQTFQAGP<br>HAVKKLSSGNSKLSSSKFSNPISSSKRNVSLLISANSGL | CCL25 |
| 52 | Gln Val Thr Leu Lys Glu Ser Gly Pro Gly Ile Leu Gln Pro Ser Gln Thr<br>Leu Ser Leu Thr Cys Ser Phe Ser Gly Phe Ser Leu Arg Thr Ser Gly Met<br>Gly Val Gly Trp Ile Arg Gln Pro Ser Gly Lys Gly Leu Glu Trp Leu Ala<br>His Ile Trp Trp Asp Asp Lys Arg Tyr Asn Pro Ala Leu Lys Ser Arg<br>Leu Thr Ile Ser Lys Asp Thr Ser Ser Asn Gln Val Phe Leu Lys Ile Ala<br>Ser Val Asp Thr Ala Asp Thr Ala Thr Tyr Tyr Cys Ala Gln Ile Asn Pro<br>Ala Trp Phe Ala Tyr Trp Gly Gln Gly Thr Leu Val Thr Val Ser Ser | αCD16 antibody 3G8 VH |
| 53 | Asp Ile Val Leu Thr Gln Ser Pro Ala Ser Leu Ala Val Ser Leu Gly Gln<br>Arg Ala Thr Ile Ser Cys Lys Ala Ser Gln Ser Val Asp Phe Asp Gly Asp<br>Ser Phe Met Asn Trp Tyr Gln Gln Lys Pro Gly Gln Pro Pro Lys Leu Leu<br>Ile Tyr Thr Thr Ser Asn Leu Glu Ser Gly Ile Pro Ala Arg Phe Ser Ala<br>Ser Gly Ser Gly Thr Asp Phe Thr Leu Asn Ile His Pro Val Glu Glu Glu<br>Asp Thr Ala Thr Tyr Tyr Cys Gln Gln Ser Asn Glu Asp Pro Tyr Thr Phe<br>Gly Gly Gly Thr Lys Leu Glu Ile Lys | αCD16 antibody 3G8 VL |
| 54 | YNLDVRGARSFSPPRAGRHFGYRVLQVGNGVIVGAPGEGNSTGSL<br>YQCQSGTGHCLPVTLRGSNYTSKYLGMTLATDPTDGSILACDPGL<br>SRTCDQNTYLSGLCYLFRQNLQGPMLQGRPGFQECIKGNVDLVFL<br>FDGSMSLQPDEFQKILDFMKDVMKKLSNTSYQFAAVQFSTSYKTE<br>FDFSDYVKRKDPDALLKHVKHMLLLTNTFGAINYVATEVFREELG<br>ARPDATKVLIIITDGEATDSGNIDAAKDIIRYIIGIGKHFQTKES<br>QETLHKFASKPASEFVKILDTFEKLKDLFTELQKKIYVIEGTSKQ<br>DLTSFNMELSSSGISADLSRGHAVVGAVGAKDWAGGFLDLKADLQ<br>DDTFIGNEPLTPEVRAGYLGYTVTWLPSRQKTSLLASGAPRYQHM<br>GRVLLFQEPQGGGHWSQVQTIHGTQIGSYFGGELCGVDVDQDGET<br>ELLLIGAPLFYGEQRGGRVFIYQRRQLGFEEVSELQGDPGYPLGR<br>FGEAITALTDINGDGLVDVAVGAPLEEQGAVYIFNGRHGGLSPQP<br>SQRIEGTQVLSGIQWFGRSIHGVKDLEGDGLADVAVGAESQMIVL<br>SSRPVVDMVTLMSFSPAEIPVHEVECSYSTSNKMKEGVNITICFQ<br>IKSLIPQFQGRLVANLTYTLQLDGHRTRRRGLFPGGRHELRRNIA<br>VTTSMSCTDFSFHFPVCVQDLISPINVSLNFSLWEEEGTPRDQRA<br>QGKDIPPILRPSLHSETWEIPFEKNCGEDKKCEANLRVSFSPARS<br>RALRLTAFASLSVELSLSNLEEDAYWVQLDLHFPPGLSFRKVEML<br>KPHSQIPVSCEELPEESRLLSRALSCNVSSPIFKAGHSVALQMMF<br>NTLVNSSWGDSVELHANVTCNNEDSDLLEDNSATTIIPILYPINI<br>LIQDQEDSTLYVSFTPKGPKIHQVKHMYQVRIQPSIHDHNIPTLE<br>AVVGVPQPPSEGPITHQWSVQMEPPVPCHYEDLERLPDAAEPCLP<br>GALFRCPVVFRQEILVQVIGTLELVGEIEASSMFSLCSSLSISFN<br>SSKHFHLYGSNASLAQVVMKVDVVYEKQML | LFA-1α Extracellular<br>domain (ECD) |
| 55 | QECTKFKVSSCRECIESGPGCTWCQKLNFTGPGDPDSIRCDTRPQ<br>LLMRGCAADDIMDPTSLAETQEDHNGGQKQLSPQKVTLYLRPGQA<br>AAFNVTFRRAKGYPIDLYYLMDLSYSMLDDLRNVKKLGGDLLRAL | LFA-1β Extracellular<br>Domain (ECD) |

| No. | Sequence | Description |
|---|---|---|
| | NEITESGRIGFGSFVDKTVLPFVNTHPDKLRNPCPNKEKECQPPF<br>AFRHVLKLTNNSNQFQTEVGKQLISGNLDAPEGGLDAMMQVAACP<br>EEIGWRNVTRLLVFATDDGFHFAGDGKLGAILTPNDGRCHLEDNL<br>YKRSNEFDYPSVGQLAHKLAENNIQPIFAVTSRMVKTYEKLTEII<br>PKSAVGELSEDSSNVVQLIKNAYNKLSSRVFLDHNALPDTLKVTY<br>DSFCSNGVTHRNQPRGDCDGVQINVPITFQVKVTATECIQEQSFV<br>IRALGFTDIVTVQVLPQCECRCRDQSRDRSLCHGKGFLECGICRC<br>DTGYIGKNCECQTQGRSSQELEGSCRKDNNSIICSGLGDCVCGQC<br>LCHTSDVPGKLIYGQYCECDTINCERYNGQVCGGPGRGLCFCGKC<br>RCHPGFEGSACQCERTTEGCLNPRRVECSGRGRCRCNVCECHSGY<br>QLPLCQECPGCSPCGKYISCAECLKFEKGPFGKNCSAACPGLQL<br>SNNPVKGRTCKERDSEGCWVAYTLEQQDGMDRYLIYVDESRECVA<br>GPN | |
| 56 | FKIETTPESRYLAQIGDSVSLTCSTTGCESPFFSWRTQIDSPLNG<br>KVTNEGTTSTLTMNPVSFGNEHSYLCTATCESRKLEKGIQVEIYS<br>FPKDPEIHLSGPLEAGKPITVKCSVADVYPFDRLEIDLLKGDHLM<br>KSQEFLEDADRKSLETKSLEVTFTPVIEDIGKVLVCRAKLHIDEM<br>DSVPTVRQAVKELQVYISPKNTVISVNPSTKLQEGGSVTMTCSSE<br>GLPAPEIFWSKKLDNGNLQHLSGNATLTLIAMRMEDSGIYVCEGV<br>NLIGKNRKEVELIVQEKPFTVEISPGPRIAAQIGDSVMLTCSVMG<br>CESPSFSWRTQIDSPLSGKVRSEGTNSTLTLSPVSFENEHSYLCT<br>VTCGHKKLEKGIQVELYSFPRDPEIEMSGGLVNGSSVTVSCKVPS<br>VYPLDRLEIELLKGETILENIEFLEDTDMKSLENKSLEMTFIPTI<br>EDTGKALVCQAKLHIDDMEFEPKQRQSTQTLYVNVAPRDTTVLVS<br>PSSILEEGSSVNMTCLSQGFPAPKILWSRQLPNGELQPLSENATL<br>TLISTKMEDSGVYLCEGINQAGRSRKEVELIIQVTPKDIKLTAFP<br>SESVKEGDTVIISCTCGNVPETWIILKKKAETGDTVLKSIDGAYT<br>IRKAQLKDAGVYECESKNKVGSQLRSLTLDVQGRENNKDYFSPE | VCAM-1 Extracellular<br>Domain (ECD) |
| 57 | WTYHYSEKPMNWQRARRFCRDNYTDLVAIQNKAEIEYLEKTLPFS<br>RSYYWIGIRKIGGIWTWVGTNKSLTEEAENWGDGEPNNKKNKEDC<br>VEIYIKRNKDAGKWNDDACHKLKAALCYTASCQPWSCSGHGECVE<br>IINNYTCNCDVGYYGPQCQFVIQCEPLEAPELGTMDCTHPLGNES<br>FSSQCAFSCSEGTNLTGIEETTCGPFGNWSSPEPTCQVIQCEPLS<br>APDLGIMNCSHPLASFSFTSACTFICSEGTELIGKKKTICESSGI<br>WSNPSPICQKLDKSFSMIKEGDYN | L-selectin Extracellular<br>Domain (ECD) |
| 58 | NVDTESALLYQGPHNTLFGYSVVLHSHGANRWLLVGAPTANWLAN<br>ASVINPGAIYRCRIGKNPGQTCEQLQLGSPNGEPCGKTCLEERDN<br>QWLGVTLSRQPGENGSIVTCGHRWKNIFYIKNENKLPTGGCYGVP<br>PDLRTELSKRIAPCYQDYVKKFGENFASCQAGISSFYTKDLIVMG<br>APGSSYWTGSLFVYNITTNKYKAFLDKQNQVKFGSYLGYSVGAGH<br>FRSQHTTEVVGGAPQHEQIGKAYIFSIDEKELNILHEMKGKKLGS<br>YFGASVCAVDLNADGESDLLVGAPMQSTIREEGRVFVYINSGSGA<br>VMNAMETNLVGSDKYAARFGESIVNLGDIDNDGFEDVAIGAPQED<br>DLQGAIYIYNGRADGISSTFSQRIEGLQISKSLSMFGQSISGQID<br>ADNNGYVDVAVGAFRSDSAVLLRTRPVVIVDASLSHPESVNRTKF<br>DCVENGWPSVCIDLTLCFSYKGKEVPGYIVLFYNMSLDVNRKAES<br>PPREYESSNGTSDVITGSIQVSSREANCRTHQAFMRKDVRDILTP<br>IQIEAAYHLGPHVISKRSTEEFPPLQPILQQKKEKDIMKKTINFA<br>RECAHENCSADLQVSAKIGELKPHENKTYLAVGSMKTLMLNVSLF<br>NAGDDAYETTLHVKLPVGLYFIKILELEEKQINCEVTDNSGVVQL<br>DCSIGYIYVDHLSRIDISFLLDVSSLSRAEEDLSITVHATCENEE<br>EMDNLKHSRVTVAIPLKYEVKLTVHGFVNPTSFVYGSNDENEPET<br>CMVEKMNLTFHVINTGNSMAPNVSVEIMVPNSFSPQTDKLFNILD<br>VQTTTGECHFENYQRVCALEQQKSAMQTLKGIVRFLSKTDKRLLY<br>CIKADPHCLNELCNEGKMESGKEASVHIQLEGRPSILEMDETSAL<br>KFEIRATGFPEPNPRVIELNKDENVAHVLLEGLHHQRPKRYFT | VLA-4 Extracellular Domain<br>(ECD) |
| 59 | MEAGITGTWYNQLGSTFIVTAGADGALTGTYESAVGNAES<br>RYVLTGRYDSAPATDGSGTALGWTVAWKNNYRNAHSATT<br>WSGQYVGGAEARINTQWLLTSGTTEANAWKSTLVGHDTFT | Minimal streptavidin<br>Species: *Streptomyces<br>avidinii* |
| 60 | MEAGITGTWYNQLGSTFIVTAGADGALTGTYVTARGNAES<br>RYVLTGRYDSAPATDGSGTALGWTVAWKNNYRNAHSATT<br>WSGQYVGGAEARINTQWLLTSGTTEANAWKSTLVGHDTFT<br>KVKPSAAS | Mutein Streptavidin Val44-<br>Thr45-Ala46-Arg47<br>Species: *Streptomyces<br>avidinii* |
| 61 | EAGITGTWYNQLGSTFIVTAGADGALTGTYIGARGNAESRY<br>VLTGRYDSAPATDGSGTALGWTVAWKNNYRNAHSATTWS<br>GQYVGGAEARINTQWLLTSGTTEANAWKSTLVGHDTFTKV<br>KPSAAS | Mutein Streptavidin Ile44-<br>Gly45-Ala-46-Arg47<br>Species: *Streptomyces<br>avidinii* |

| SEQUENCES | | |
|---|---|---|
| No. | Sequence | Description |
| 62 | VTAR | Streptavidin Mutein Residues |
| 62 | IGAR | Streptavidin Mutein Residues |

What is claimed:

1. A multimerized oligomeric particle reagent that is in soluble form and comprises (i) an oligomer of between 1,500 and 7,500 tetramers of a streptavidin molecule or a streptavidin mutein molecule and (ii) a receptor-binding agent that binds to a receptor expressed on the surface of a target cell, wherein:

the receptor-binding agent comprises a streptavidin-binding peptide that is reversibly bound to one or more binding sites of the streptavidin or streptavidin mutein molecules of the oligomer; and the receptor-binding agent is a stimulatory agent, wherein binding of the receptor-binding agent to the receptor induces a stimulatory signal in the target cell.

2. The multimerized oligomeric particle reagent of claim 1, wherein the oligomer is of between 1,500 and 7,500 tetramers of the streptavidin mutein molecule.

3. The multimerized oligomeric particle reagent of claim 2, wherein the streptavidin mutein molecule comprises the amino acid sequence Val$^{44}$-Thr$^{45}$-Ala$^{46}$-Arg$^{47}$ (SEQ ID NO: 62) or Ile$^{44}$-Gly$^{45}$-Ala$^{46}$-Arg$^{47}$ (SEQ ID NO: 63) at sequence positions corresponding to positions 44 to 47 of the sequence of amino acids set forth in SEQ ID NO: 1.

4. The multimerized oligomeric particle reagent of claim 2, wherein the streptavidin mutein molecule comprises a sequence of amino acids that exhibits at least 85%, sequence identity to the sequence of amino acids set forth in any of SEQ ID NOS: 3-6, 27, 28, and 60 and contains the amino acid sequence corresponding to Val$^{44}$-Thr$^{45}$-Ala$^{46}$-Arg$^{47}$ (SEQ ID NO: 62) or Ile$^{44}$-Gly$^{45}$-Ala$^{46}$-Arg$^{47}$ (SEQ ID NO: 63) at sequence positions corresponding to positions 44 to 47 of the sequence of amino acids set forth in SEQ ID NO: 1.

5. The multimerized oligomeric particle reagent of claim 2, wherein the streptavidin mutein molecule comprises the sequence of amino acids set forth in SEQ ID NO: 6.

6. The multimerized oligomeric particle reagent of claim 1, wherein the streptavidin-binding peptide comprises the sequence of amino acids set forth in any of SEQ ID NOS: 7, 8, and 15-19.

7. The multimerized oligomeric particle reagent of claim 1, wherein the receptor-binding agent comprises an antibody or an antigen-binding fragment thereof that binds to the receptor.

8. The multimerized oligomeric particle reagent of claim 1, wherein the receptor-binding agent comprises a monovalent antibody fragment that binds to the receptor.

9. The multimerized oligomeric particle reagent of claim 1, wherein the receptor-binding agent comprises each a Fab that binds to the receptor.

10. The multimerized oligomeric particle of claim 1, wherein the target cell is a T cell.

11. The multimerized oligomeric particle reagent of claim 1, wherein the stimulatory signal is a TCR/CD3 complex-associated signal in T cells.

12. The multimerized oligomeric particle reagent of claim 1, wherein the receptor-binding agent is a first receptor-binding agent, the streptavidin-binding peptide is a first streptavidin-binding peptide, and the multimerized oligomeric particle reagent comprises a second receptor-binding agent, wherein:

the second receptor-binding agent comprises a streptavidin-binding peptide that is reversibly bound to one or more binding sites of the streptavidin or streptavidin mutein molecules of the oligomer; and the second receptor-binding agent binds to a second molecule on the surface of the target cell, wherein binding to the second molecule induces a second signal in the target cell.

13. The multimerized oligomeric particle reagent of claim 12, wherein the second molecule is a costimulatory molecule, accessory molecule, immune checkpoint molecule, member of the TNF family or the TNF family receptor, cytokine receptor, chemokine receptor, or adhesion molecule.

14. The multimerized oligomeric particle reagent of claim 12, wherein the second molecule is CD28.

15. The multimerized oligomeric particle reagent of claim 12, wherein the first receptor-binding agent comprises the first streptavidin-binding peptide and an anti-CD3 antibody or antibody fragment, and the second receptor-binding agent comprises the second streptavidin-binding peptide and an anti-CD28 antibody or antibody fragment.

16. The multimerized oligomeric particle reagent of claim 1, wherein the receptor is a costimulatory molecule, accessory molecule, immune checkpoint molecule, member of the TNF family or the TNF family receptor, cytokine receptor, chemokine receptor, or adhesion molecule.

17. The multimerized oligomeric particle reagent of claim 1, wherein the multimerized oligomeric particle reagent further comprises a selection agent, wherein:

the selection agent comprises a streptavidin-binding peptide that is reversibly bound to one or more binding sites of the streptavidin or streptavidin mutein molecules of the oligomer; and the selection agent binds to a selection marker that is expressed on the surface of the target cell.

18. The multimerized oligomeric particle reagent of claim 12, wherein the target cell is a T cell.

19. The multimerized oligomeric particle reagent of claim 17, wherein the selection marker is CCR7, CD3, CD4, CD8, CD25, CD28, CD27, CD45RA, CD45RO, CD62L, or CD127.

20. The multimerized oligomeric particle reagent of claim 1, wherein the oligomer comprises a radius of between 50 nm and 150 nm, inclusive.

21. The multimerized oligomeric particle reagent of claim 1, wherein less than 20% of the lysine residues of the streptavidin or streptavidin mutein molecules comprise N-substituted iminothiolane.

22. A composition comprising a plurality of the multimerized oligomeric particle reagent of claim 1, the plurality of multimerized oligomeric particle reagents comprising (i) a plurality of the oligomers and (ii) a plurality of the receptor-binding agent.

23. The composition of claim 22, wherein the plurality of oligomers comprises an average number of streptavidin or streptavidin mutein tetramers per oligomer of at least 2,000.

24. The composition of claim 22, wherein the plurality of oligomers comprises an average radius of between 50 nm and 150 nm, inclusive.

25. The composition of claim 22, wherein the plurality of oligomers comprises an average radius of 97±10 nm.

26. The composition of claim 22, wherein at least 95% of the plurality of oligomers comprise a radius of between 50 and 150 nm.

27. The composition of claim 22, wherein the plurality of oligomers comprises an average radius of between 80 nm and 115 nm, and at least 95% of the plurality of oligomers comprises a radius between ±25% of the average radius.

28. The composition of claim 22, wherein the plurality of oligomers comprises an average number of streptavidin or streptavidin mutein tetramers per oligomer between 2,000 and 5,000, inclusive.

29. The composition of claim 22, wherein the average radius of the plurality of oligomers does not increase by more than 25% when stored at about or below 4° C. for at least 1 week.

30. The multimerized oligomeric particle reagent of claim 12, wherein the first receptor-binding agent comprises the first streptavidin-binding peptide and an anti-CD3 Fab, and the second receptor-binding agent comprises the second streptavidin-binding peptide and an anti-CD28 Fab.

31. The multimerized oligomeric particle reagent of claim 2, wherein the streptavidin mutein molecule comprises the sequence of amino acids set forth in any of SEQ ID NOS: 3-6, 27, 28, and 60.

32. The multimerized oligomeric particle reagent of claim 1, wherein the oligomer comprises a radius of between 75 nm and 125 nm, inclusive.

33. The multimerized oligomeric particle reagent of claim 1, wherein the oligomer comprises between 2,000 and 5,000 tetramers of the streptavidin or streptavidin mutein molecule.

34. The multimerized oligomeric particle reagent of claim 1, wherein the oligomer comprises between 2,000 and 4,000 tetramers of the streptavidin or streptavidin mutein molecule.

35. The multimerized oligomeric particle reagent of claim 1, wherein the oligomer comprises between 2,000 and 3,000 tetramers of the streptavidin or streptavidin mutein molecule.

36. The multimerized oligomeric particle reagent of claim 1, wherein streptavidin or streptavidin mutein molecules of the oligomer are crosslinked by a heterobifunctional crosslinker.

37. The multimerized oligomeric particle reagent of claim 12, wherein the oligomer is of between 1,500 and 7,500 tetramers of the streptavidin mutein molecule, and the streptavidin mutein molecule comprises the sequence of amino acids set forth in any of SEQ ID NOS: 3-6, 27, 28, and 60.

38. The multimerized oligomeric particle reagent of claim 37, wherein the streptavidin mutein molecule comprises the sequence of amino acids set forth in SEQ ID NO: 6.

39. The multimerized oligomeric particle reagent of claim 37, wherein the first and second streptavidin-binding peptides each comprise a sequence independently selected from the sequences of amino acids set forth in SEQ ID NOS: 7, 8, and 15-19.

40. The multimerized oligomeric particle reagent of claim 12, wherein the oligomer comprises between 2,000 and 5,000 tetramers of the streptavidin or streptavidin mutein molecule.

41. The multimerized oligomeric particle reagent of claim 12, wherein the oligomer comprises between 2,000 and 4,000 tetramers of the streptavidin or streptavidin mutein molecule.

42. The multimerized oligomeric particle reagent of claim 12, wherein the oligomer comprises between 2,000 and 3,000 tetramers of the streptavidin or streptavidin mutein molecule.

43. The multimerized oligomeric particle reagent of claim 12, wherein streptavidin or streptavidin mutein molecules of the oligomer are crosslinked by a heterobifunctional crosslinker.

44. The multimerized oligomeric particle reagent of claim 15, wherein the oligomer is of between 1,500 and 7,500 tetramers of the streptavidin mutein molecule, and the streptavidin mutein molecule comprises the sequence of amino acids set forth in any of SEQ ID NOS: 3-6, 27, 28, and 60.

45. The multimerized oligomeric particle reagent of claim 44, wherein the first and second streptavidin-binding peptides each comprise a sequence independently selected from the sequences of amino acids set forth in SEQ ID NOS: 7, 8, and 15-19.

46. The multimerized oligomeric particle reagent of claim 15, wherein the oligomer comprises between 2,000 and 5,000 tetramers of the streptavidin or streptavidin mutein molecule.

47. The multimerized oligomeric particle reagent of claim wherein the oligomer comprises between 2,000 and 4,000 tetramers of the streptavidin or streptavidin mutein molecule.

48. The multimerized oligomeric particle reagent of claim wherein the oligomer comprises between 2,000 and 3,000 tetramers of the streptavidin or streptavidin mutein molecule.

49. The multimerized oligomeric particle reagent of claim 15, wherein streptavidin or streptavidin mutein molecules of the oligomer are crosslinked by a heterobifunctional crosslinker.

50. A multimerized oligomeric particle reagent, comprising an oligomer of between 2,000 and 3,000 tetramers of a streptavidin mutein molecule, a first receptor-binding agent comprising a first streptavidin-binding peptide and an anti-CD3 Fab, and a second receptor-binding agent comprising a second streptavidin-binding peptide and an anti-CD28 Fab, wherein:
the streptavidin mutein molecule comprises the sequence of amino acids set forth in SEQ ID NO: 6;
the amino acid sequence of the first streptavidin-binding peptide is set forth in SEQ ID NO: 16, and the first streptavidin-binding peptide is reversibly bound to one or more binding sites of a streptavidin mutein molecule of the oligomer; and
the amino acid sequence of the second streptavidin-binding peptide is set forth in SEQ ID NO: 16, and the second streptavidin-binding peptide is reversibly bound to one or more binding sites of a streptavidin mutein molecule of the oligomer.

51. The multimerized oligomeric particle reagent of claim 12, wherein the second molecule is CD28, CD90 (Thy-1), CD95 (Apo-/Fas), CD137 (4-1BB), CD154 (CD40L), ICOS, LAT, CD27, OX40, or HVEM.

52. The multimerized oligomeric particle reagent of claim 4, wherein the streptavidin-binding peptide comprises the sequence of amino acids set forth in any of SEQ ID NOS: 7, 8, and 15-19.

53. The multimerized oligomeric particle reagent of claim 4, wherein the oligomer comprises between 2,000 and 5,000 tetramers of the streptavidin mutein molecule.

54. The multimerized oligomeric particle reagent of claim 4, wherein the oligomer comprises between 2,000 and 4,000 tetramers of the streptavidin mutein molecule.

55. The multimerized oligomeric particle reagent of claim 4, wherein the oligomer comprises between 2,000 and 3,000 tetramers of the streptavidin mutein molecule.

56. The multimerized oligomeric particle reagent of claim 4, wherein streptavidin mutein molecules of the oligomer are crosslinked by a heterobifunctional crosslinker.

\* \* \* \* \*

UNITED STATES PATENT AND TRADEMARK OFFICE
CERTIFICATE OF CORRECTION

PATENT NO. : 11,866,465 B2  
APPLICATION NO. : 16/608796  
DATED : January 9, 2024  
INVENTOR(S) : Thomas Schmidt Page 1 of 1

It is certified that error appears in the above-identified patent and that said Letters Patent is hereby corrected as shown below:

In the Claims

At Column 263, Claim number 4, Line number 31, please replace "85%," with --85%--.

At Column 263, Claim number 9, Line number 55, please replace "comprises each" with --comprises--.

At Column 263, Claim number 10, Line number 57, please replace "particle of" with --particle reagent of--.

At Column 266, Claim number 47, Line number 20, please replace "claim" with --claim 15--.

At Column 266, Claim number 48, Line number 24, please replace "claim" with --claim 15--.

Signed and Sealed this  
Nineteenth Day of November, 2024

Katherine Kelly Vidal  
*Director of the United States Patent and Trademark Office*